United States Patent

Mueller et al.

[11] Patent Number: 6,075,148
[45] Date of Patent: Jun. 13, 2000

[54] CARBAMATES AND CROP PROTECTION AGENTS CONTAINING THEM

[75] Inventors: Bernd Mueller, Frankenthal; Hubert Sauter, Mannheim; Franz Roehl, Schifferstadt; Reinhard Doetzer, Weinheim; Gisela Lorenz, Neustadt; Eberhard Ammermann, Heppenheim, all of Germany

[73] Assignee: BASF Aktiengesellschaft, Ludwigshafen, Germany

[21] Appl. No.: 09/275,767

[22] Filed: Mar. 25, 1999

Related U.S. Application Data

[62] Division of application No. 09/110,884, Jul. 7, 1998, Pat. No. 5,981,532, which is a continuation of application No. 08/256,628, filed as application No. PCT/EP93/00104, Jan. 18, 1993, Pat. No. 5,824,705.

[30] Foreign Application Priority Data

| Jan. 29, 1992 | [DE] | Germany | 42 02 386 |
| Jun. 26, 1992 | [DE] | Germany | 42 21 007 |
| Oct. 9, 1992 | [DE] | Germany | 42 34 081 |
| Oct. 9, 1992 | [DE] | Germany | 42 34 028 |
| Oct. 9, 1992 | [DE] | Germany | 42 34 012 |
| Oct. 9, 1992 | [DE] | Germany | 42 34 067 |

[51] Int. Cl.[7] .................................. C07D 237/16
[52] U.S. Cl. .................. 546/334; 548/189; 548/338.1; 548/366.7; 558/417; 560/24; 560/29; 560/30
[58] Field of Search ..................... 558/417; 560/24, 560/29, 30; 546/334; 548/189, 338.1, 366.7

[56] References Cited

U.S. PATENT DOCUMENTS

| 4,097,594 | 6/1978 | Peak et al. | 424/246 |
| 4,608,385 | 8/1986 | Noguchi et al. | 514/444 |
| 4,626,608 | 12/1986 | Lee | 546/288 |
| 4,666,938 | 5/1987 | Takahashi et al. | 514/578 |
| 4,752,615 | 6/1988 | Takahashi et al. | 514/479 |
| 5,100,916 | 3/1992 | Johansson et al. | 514/478 |
| 5,436,267 | 7/1995 | Komyoji et al. | 514/485 |

FOREIGN PATENT DOCUMENTS

| 612550 | 1/1962 | Belgium . |
| 59-42307 | 3/1984 | Japan . |
| 59-84804 | 5/1984 | Japan . |
| 574995 | 1/1946 | United Kingdom . |
| WO 80/00344 | 3/1980 | WIPO . |

*Primary Examiner*—Richard L. Raymond
*Attorney, Agent, or Firm*—Oblon, Spivak, McClelland, Maier & Neustadt, P.C.

[57] ABSTRACT

Carbamates of the formula I

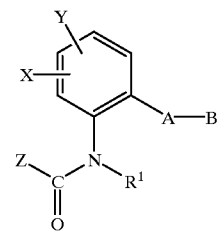

where the substituents have the following meanings:

Z is methoxy, $NH_2$, $NHCH_3$, $N(CH_3)_2$, $CH_3$, $C_2H_5$, $CF_3$ or $CCl_3$, X and Y are identical or different and each is hydrogen, F, Cl, Br, $CF_3$, CN, $NO_2$, alkoxy, alkenyloxy, alkynyloxy, alkyl, alkenyl or alkynyl or may be condensed together to form a substituted or unsubstituted aromatic or heteroaromatic, alicyclic or heterocyclic, partially or completely hydrogenated ring, $R^1$ may also be substituted or unsubstituted and is O-alkyl, O-alkenyl, O-alkynyl, O-cycloalkyl, O-cycloalkenyl or O—$CO_2$-alkyl, A is —O—, —S—, —$CR^2$=$CR^3$—, $CHR^2$—O—, —$CHR^2$—S—, —$CHR^2$—O—N=C($R^4$)—, —$CR^2$=N—O—, —O—N=C($R^4$)—, —C≡C—, —$CHR^2$—$CHR^3$—, —$CHR^2$—O—CO—, —O—$CHR^2$— or a single bond, B is substituted or unsubstituted and is alkyl, alkenyl, alkynyl, cycloalkyl, cycloalkenyl, cycloalkynyl, aryl, hetaryl, heterocyclyl, hydrogen, substituted or unsubstituted alkylaryl, substituted or unsubstituted alkylhetaryl, substituted or unsubstituted alkylcycloalkyl, substituted or unsubstituted alkylcycloalkenyl, $R^2$ and $R^3$ are identical or different and each is hydrogen, alkyl, alkenyl, alkynyl or cycloalkyl, $R^4$ is hydrogen, CN, alkyl, alkenyl, alkynyl, alkoxy or cycloalkyl, $R^5$ is alkyl, cyclopropyl, cyclopropylmethyl or cyclobutyl and plant-tolerated acid and base adducts thereof, and fungicides containing them.

7 Claims, No Drawings

CARBAMATES AND CROP PROTECTION AGENTS CONTAINING THEM

This application is a Division of application Ser. No. 09/110,884 Filed on Jul. 7, 1998, now U.S. Pat. No. 5,981, 532, which is a continuation of Ser. No. 08/256,628 Jul. 29, 1994, now U.S. Pat. No. 5,824,705, which is a continuation of International Application No. PCT/EP93/00104 filed Jan. 18, 1993.

The present invention relates to carbamates and crop protection agents, in particular for controlling fungi, insects, nematodes and spider mites.

It is known that aniline derivatives, for example isopropyl N-phenylcarbamate or the corresponding 3-chlorophenyl ester (GB 574 995) or methyl N-3,4-dichlorophenylcarbamate (BE 612 550) can be used as crop protection agents. However, their fungicidal action is unsatisfactory.

It has now been found, surprisingly, that carbamates of the formula I

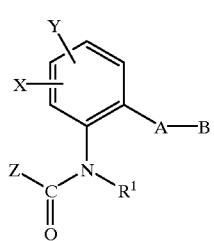

where the substituents have the following meanings:

Z is methoxy, $NH_2$, $NHCH_3$, $N(CH_3)_2$, $CH_3$, $C_2H_5$, $CF_3$ or $CCl_3$, X and Y independently of one another are each hydrogen, F, Cl, Br, $CF_3$, CN, $NO_2$, alkoxy, alkenyloxy, alkynyloxy, alkyl, alkenyl or alkynyl or X and Y may be condensed together to form an unsubstituted or substituted aromatic or heteroaromatic, alicyclic or heterocyclic, partially or completely hydrogenated ring, $R^1$ is unsubstituted or substituted alkyl, alkenyl, cyclopropyl, cyclopropylmethyl, cyclobutyl, —$CH_2$—CN, —$CH_2OCH_3$, —$CO_2CH_3$ or —S—$R^5$, O-alkyl, O-alkenyl, O-alkynyl, O-cycloalkyl, O-cycloalkenyl or O—$CO_2$-alkyl, A is —O—, —S—, —$CR^2$=$CR^3$—, $CHR^2$—O—, —$CHR^2$—S—, —$CHR^2$—O—N=$C(R^4)$—, —$CR^2$=N—O—, —O—N=$C(R^4)$—, —C≡C—, —$CHR^2$—$CHR^3$—, —$CHR^2$—O—CO—, —O—$CHR^2$— or a single bond, B can be unsubstituted or substituted and is alkyl, alkenyl, alkynyl, cycloalkyl, cycloalkenyl, cycloalkynyl, aryl, hetaryl, heterocyclyl, hydrogen, unsubstituted or substituted alkylaryl, unsubstituted or substituted alkylhetaryl, unsubstituted or substituted alkylcycloalkyl or unsubstituted or substituted alkylcycloalkenyl, $R^2$ and $R^3$ independently of one another are each hydrogen, alkyl, alkenyl, alkynyl or cycloalkyl, $R^4$ is hydrogen, CN, alkyl, alkenyl, alkynyl, alkoxy or cycloalkyl, $R^5$ is alkyl, cyclopropyl, cyclopropylmethyl or cyclobutyl, and their plant-tolerated acid addition products and base addition products have a good fungicidal, acaricidal, insecticidal and nematocidal action.

Acids for addition products are, for example, mineral acids, such as hydrochloric acid, hydrobromic acid, phosphoric acid, sulfuric acid or nitric acid, or carboxylic acids, such as formic acid, acetic acid, oxalic acid, malonic acid, lactic acid, malic acid, succinic acid, tartaric acid, citric acid, salicylic acid, p-toluenesulfonic acid or dodecylbenzenesulfonic acid, as well as proton-acidic compounds generally, for example saccharin.

Bases for base addition products are, for example, potassium hydroxide, sodium hydroxide, potassium carbonate, sodium carbonate and ammonium hydroxide.

The novel compounds of the formula I may be obtained in the preparation as mixtures of stereoisomers (E/Z isomers, diastereomers, enantiomers), which can be separated into the individual components in a conventional manner, for example by crystallization or chromatography. Both the individual isomers and mixtures thereof may be used as fungicides, acaricides, nematocides or insecticides, and form the subject of the present invention.

The abovementioned alkyl radicals may be substituted and are of 1 to 6 carbon atoms.

The abovementioned alkenyl and alkynyl radicals may be substituted and are of 2 to 6 carbon atoms.

The abovementioned cycloalkyl radicals are of 3 to 10 carbon atoms and are unsubstituted or substituted, for example by 1 to 4 identical or different substituents $R^6$.

The abovementioned aryl radicals are of 6, 10 or 14 carbon atoms and are unsubstituted or substituted, for example by 1 to 4 identical or different substituents $R^6$.

The abovementioned hetaryl radicals have 5 to 14 ring atoms, including from 1 to 4 hetero atoms selected from the group consisting of N, O and S, are unsaturated and are unsubstituted or substituted, for example by 1 to 4 identical or different substituents $R^6$.

The abovementioned heterocyclyl radicals have 5 to 14 carbon atoms, including 1 to 4 hetero atoms selected from the group consisting of N, O and S, are saturated or partially unsaturated and are unsubstituted or substituted, for example by 1 to 4 identical or different substituents $R^6$.

The abovementioned cycloalkenyl radicals are of 5 to 14 carbon atoms and are unsubstituted or substituted, for example by 1 to 4 identical or different substituents $R^6$.

Two adjacent substituents $R^6$, together with the carbon atoms of which they are substituents, may form a carbocyclic hydrogenated, partially unsaturated or aromatic ring having 3 to 14 carbon atoms or a heterocyclic hydrogenated, partially unsaturated or heteroaromatic ring having 3 to 14 carbon atoms, including 1 to 4 hetero atoms selected from the group consisting of N, O and S.

$R^6$ may be unsubstituted or substituted, for example by 1 to 4 identical or different substituents $R^7$, and $R^6$ is, for example, hydrogen, halogen, cyano, nitro, haloalkyl, alkyl, haloalkoxy, alkenyl, alkynyl, cycloalkyl, aryl, hetaryl, heterocyclyl, cycloalkenyl, alkoxy, alkenyloxy, alkynyloxy, cycloalkoxy, aryloxy, hetaryloxy, heterocyclyloxy, cycloalkenyloxy, alkoximino, alkenyloximino, alkynyloximino, cycloalkoxyimino, cycloalkenyloximino, aryloximino, hetaryloximino, heterocyclyloximino, alkoxycarbonyl, alkenyloxycarbonyl, alkynyloxycarbonyl, cycloalkyloxycarbonyl, aryloxycarbonyl, hetaryloxycarbonyl, heterocyclyloxycarbonyl, cycloalkenyloxycarbonyl, alkylaminocarbonyl, dialkylaminocarbonyl, alkenylaminocarbonyl, dialkenylaminocarbonyl, alkylthio, alkenylthio, alkynylthio, cycloalkylthio, arylthio, hetarylthio, heterocyclylthio, cycloalkenylthio, alkylamino, alkenylamino, alkynylamino, cycloalkylamino, arylamino, hetarylamino, heterocyclylamino, cycloalkenylamino, alkylcarbonyl, alkenylcarbonyl, alkynylcarbonyl, cycloalkylcarbonyl, arylcarbonyl, hetarylcarbonyl, heterocyclylcarbonyl, cycloalkenylcarbonyl, alkylsulfoxyl, alkenylsulfoxyl, alkynylsulfoxyl, cycloalkylsulfoxyl, arylsulfoxyl, hetarylsulfoxyl, heterocyclylsulfoxyl, cycloalkenylsulfoxyl, alkylsulfonyl, alkenylsulfonyl, alkynylsulfonyl, cycloalkylsulfonyl, arylsulfonyl, hetarylsulfonyl, heterocyclylsulfonyl, cycloalkenylsulfonyl, alkylsulfinyl, alkenylsulfinyl, alkynylsulfinyl, cycloalkylsulfinyl, arylsulfinyl, hetarylsulfinyl, heterocyclylsulfinyl or cycloalkenylsulfinyl.

$R^7$ is any substituent and is, for example, hydrogen, halogen, cyano, nitro, haloalkyl, alkyl, haloalkoxy, alkenyl, alkynyl, cycloalkyl, aryl, hetaryl, heterocyclyl, cycloalkenyl, alkoxy, alkenyloxy, alkynyloxy, cycloalkoxy, aryloxy, hetaryloxy, heterocyclyloxy, cycloalkenyloxy, alkoximino, alkenyloximino, alkynyloximino, cycloalkoximino, cycloalkenyloximino, aryloximino, hetaryloximino, heterocyclyloximino, alkoxycarbonyl, alkenyloxycarbonyl, alkynyloxycarbonyl, cycloalkyloxycarbonyl, aryloxycarbonyl, hetaryloxycarbonyl, heterocyclyloxycarbonyl, cycloalkenyloxycarbonyl, alkylaminocarbonyl, dialkylaminocarbonyl, alkenylaminocarbonyl, dialkenylaminocarbonyl, alkylthio, alkenylthio, alkynylthio, cycloalkylthio, arylthio, hetarylthio, heterocyclylthio, cycloalkenylthio, alkylamino, alkenylamino, alkynylamino, cycloalkylamino, arylamino, hetarylamino, heterocyclylamino, cycloalkenylamino, alkylcarbonyl, alkenylcarbonyl, alkynylcarbonyl, cycloalkylcarbonyl, arylcarbonyl, hetarylcarbonyl, heterocyclylcarbonyl, cycloalkenylcarbonyl, alkylsulfoxyl; alkenylsulfoxyl, alkynylsulfoxyl, cycloalkylsulfoxyl, arylsulfoxyl, hetarylsulfoxyl, heterocyclylsulfoxyl, cycloalkenylsulfoxyl, alkylsulfonyl, alkenylsulfonyl, alkynylsulfonyl, cycloalkylsulfonyl, arylsulfonyl, hetarylsulfonyl, heterocyclylsulfonyl, cycloalkenylsulfonyl, alkylsulfinyl, alkenylsulfinyl, alkynylsulfinyl, cycloalkylsulfinyl, arylsulfinyl, hetarylsulfinyl, heterocyclylsulfinyl or cycloalkenylsulfinyl.

The abovementioned alkyl radicals may be substituted, are preferably of 1 to 6 carbon atoms and are, in particular, methyl, ethyl, propyl, such as n-propyl or isopropyl, butyl, such as n-butyl, isobutyl, tert-butyl or sec-butyl, pentyl or hexyl.

The abovementioned alkenyl radicals may be substituted, are preferably of 2 to 6 carbon atoms and are, in particular, ethenyl, propenyl, such as prop-1-enyl, prop-2-enyl or prop-1-en-2-yl, butenyl, such as but-1-enyl, but-2-enyl, but-3-enyl, but-1-en-3-yl, but-2-en-2-yl, but-1-en-2-yl, 2-methyl-1-propenyl or 2-methyl-2-propenyl, pentenyl or hexenyl.

The abovementioned alkynyl radicals may be substituted, are preferably of 2 to 6 carbon atoms and are, in particular, ethynyl, propynyl, such as prop-1-ynyl or prop-3-ynyl, butynyl, such as but-1-ynyl, but-2-ynyl, but-3-ynyl or 1-methylprop-2-ynyl, pentynyl or hexynyl.

The abovementioned halogens are fluorine, chlorine, bromine or iodine.

The abovementioned cycloalkyl radicals are preferably cyclopropyl, cyclobutyl, cyclopentyl, cyclohexyl, cycloheptyl, cyclooctyl, cyclononyl, cyclodecyl, bornanyl, norbornanyl, dicyclohexyl, bicyclo[3.3.0]octyl, bicyclo[3.2.1]octyl, bicyclo[2.2.2]octyl or bicyclo[3.3.1]nonyl.

The abovementioned cycloalkenyl radicals are preferably cyclopropenyl, cyclobutenyl, cyclopentenyl, cyclohexenyl, cycloheptenyl, cyclooctenyl, cyclononenyl, cyclodecenyl, bornenyl, norbornenyl, bicyclo[3.3.0]octenyl, bicyclo[3.2.1]octenyl, bicyclo[2.2.2]octenyl or bicyclo[3.3.1]nonenyl.

The abovementioned haloalkyl radicals are preferably $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The abovementioned haloalkoxy radicals are preferably $C_2$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy.

The abovementioned aryl radicals are preferably phenyl, 1-naphthyl, 2-naphthyl, 1-anthracenyl, 2-anthracenyl or 9-anthracenyl.

The abovementioned hetaryl radicals are preferably furyl, such as 2-furyl or 3-furyl, thienyl, such as 2-thienyl or 3-thienyl, pyrrolyl, such as 1-pyrrolyl, 2-pyrrolyl or 3-pyrrolyl, isoxazolyl, such as 3-isoxazolyl, 4-isoxazolyl or 5-isoxazolyl, isothiazolyl, such as 3-isothiazolyl, 4-isothiazolyl or 5-isothiazolyl, pyrazolyl, such as 1-pyrazolyl, 3-pyrazolyl, 4-pyrazolyl or 5-pyrazolyl, oxazolyl, such as 2-oxazolyl, 4-oxazolyl or 5-oxazolyl, thiazolyl, such as 2-thiazolyl, 4-thiazolyl or 5-thiazolyl, imidazolyl, such as 1-imidazolyl, 2-imidazolyl, 4-imidazolyl or 5-imidazolyl, 1,2,3-thiadiazolyl, 1,2,4-thiadiazolyl, 1,2,5-thiadiazolyl, 1,3,4-thiadiazolyl, tetrazolyl, 1,2,3,4-thiatriazolyl, 1,2,3,4-oxatriazolyl, pyridyl, such as 2-pyridyl or 4-pyridyl, pyridazinyl, such as 3-pyridazinyl or 4-pyridazinyl, pyrimidinyl, such as 2-pyrimidinyl, 4-pyrimidinyl or 5-pyrimidinyl, pyrazinyl, such as 2-pyrazinyl or 3-pyrazinyl, 1,2,4-triazinyl, 1,3,5-triazinyl or 1,2,4,5-tetrazinyl.

Adjacent substituents of the hetero atoms may be condensed to form an aromatic or heteroaromatic ring, so that hetaryl also comprises fused ring systems, eg. benzofuranyl, isobenzofuranyl, 1-benzothienyl, 2-benzothienyl, indolyl, isoindolyl, benzisoxazolyl, benzoxazolyl, benzisothiazolyl, benzothiazolyl, such as 2-benzothiazolyl, 4-benzothiazolyl, 5-benzothiazolyl, 6-benzothiazolyl or 7-benzothiazolyl, indazolyl, benzimidazolyl, benzofurazanyl, dibenzofuranyl, dibenzothienyl, acridinyl, phenanthridinyl, carbazolyl, quinolyl, isoquinolyl, phthalazinyl, quinazolinyl, quinoxalinyl, cinnolinyl, 1,5-naphthyridinyl, 1,6-naphthyridinyl, 1,7-naphthyridinyl, 1,8-naphthyridinyl, pteridinyl, pyrrolopyridinyl, pyrrolopyridazinyl, pyrrolopyrimidinyl, pyrrolopyrazinyl, pyrrolotriazinyl, furopyridyl, furopyridazinyl, furopyrimidinyl, furopyrazinyl, furotriazinyl, thienopyridyl, thienopyridazinyl, thienopyrimidinyl, thienopyrazinyl, thienotriazinyl, imidazopyridazinyl, imidazopyrimidinyl, imidazopyrazinyl, pyrazolopyridyl, pyrazolopyridazinyl, pyrazolopyrimidinyl, pyrazolopyrazinyl, isoxazolopyrazinyl, oxazolopyridyl, oxazolopyridazinyl, oxazolopyrimidinyl, oxazolopyrazinyl, thiazolopyridyl, thiazolopyridazinyl, isothiazolopyrazinyl, triazolopyridyl, triazolopyridazinyl, triazolopyrimidinyl or triazolopyrazinyl.

The abovementioned heterocycyl radicals are preferably 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,5-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,5-dihydrofur-2-yl, 2,5-dihydrofur-2-yl, 2,3-dihydrofur-3-yl, 2,3-dihydrothieno-2-yl, 2,3-dihydrothien-3-yl, 2,5-dihydrothien-2-yl, 2,4-pyrrolin-2-yl, 2,3-pyrrolin-3-yl, 2,5-pyrrolin-2-yl, 2,5-pyrrolin-3-yl, 2,3-isoxazolidin-3-yl, 3,4-isoxazolin-3-yl, 4,5-isoxazolin-2-yl, 2,3-isoxazolin-4-yl, 3,4-isoxazolin-3-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-2-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 3,4-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, oxazol-2-in-2-yl, 2-tetrahydropyranyl, 1,3-dioxolan-2-yl, thiazol-2-in-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, N-morpholinyl or dihydroquinazolinyl.

The invention furthermore relates to carbamates of the formula I

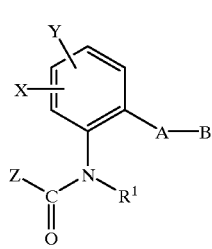

I where the substituents have the following meanings:
Z is methoxy, NH$_2$, NHCH$_3$ or CH$_3$,
X and Y independently of one another are each hydrogen, F, Cl, Br, CF$_3$, CN, NO$_2$, alkoxy, alkenyloxy, alkynyloxy, alkyl, alkenyl or alkynyl or X and Y may be condensed together to form a phenyl ring,
R$^1$ is hydrogen, alkyl, alkenyl alkynyl cyclopropyl, cyclopropylmethyl, cyclobutyl, —CH$_2$—CN, —CH$_2$—O—CH$_3$, —CO$_2$CH$_3$ or —S—R$^5$, A is —O—, —CR$^2$=CR$^3$—, —C≡C—, —CHR$^2$—O—, —CHR$^2$—S—, —CHR$^2$—O—N=C(R$^4$)—, —CR$^2$=N—O— or —O—N=C(R$^4$)—, a) B is substituted phenyl when A is —CR$^2$≡CR$^3$—, —C=C—, —CHR$^2$—O—, —CHR$^2$—S—, —CR$^2$—O—N=C(R$^4$)—, —CR$^2$=N—O— or —O—N=C(R$^4$)—, b) or B is unsubstituted or substituted cyclolalkyl, unsubstituted or substituted cycloalkenyl, unsubstituted or substituted heterocyclyl, unsubstituted or substituted hetaryl, unsubstituted or substituted naphthyl, unsubstituted or substituted arylalkyl, unsubstituted or substituted hetarylalkyl, unsubstituted or substituted cycloalkylalkyl, unsubstituted or substituted cycloalkenylalkyl or unsubstituted or substituted anthracenyl, R$^2$ and R$^3$ independently of one another are each hydrogen, alkyl, alkenyl, alkynyl or cycloalkyl, R$^4$ is CN, alkyl, alkenyl, alkynyl or cycloalkyl and R$^5$ is alkyl, cyclopropyl, cyclopropylmethyl or cyclobutyl, and their plant-tolerated acid addition products and base addition products.

The invention furthermore relates to carbamates of the formula II

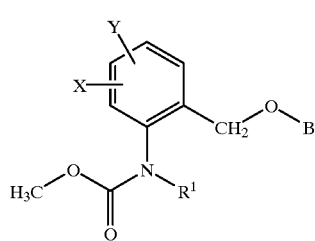

II where X, Y, R$^1$ and B have the meanings stated in claim 2.

The invention furthermore relates to carbamates of the formula III

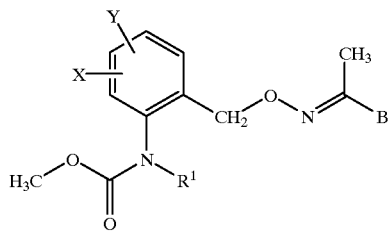

III where X, Y, R$^1$ and B have the meanings stated in claim 2.

The invention furthermore relates to carbamates of the formula I as claimed in claim 2, where A is —CH=CH— and X, Y, R$^1$ and B have the meanings stated in claim 2.

The invention furthermore relates to carbamates of the formula VII

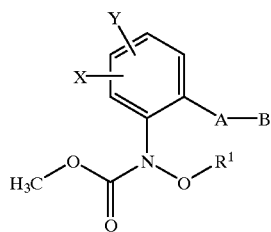

VII where the substituents have the following meanings:

X and Y independently of one another are each hydrogen, F, Cl, Br, $CF_3$, CN, $NO_2$, alkoxy, alkenyloxy, alkynyloxy, alkyl, alkenyl or alkynyl or X and Y may be condensed together to form an unsubstituted or substituted aromatic or heteroaromatic, alicyclic or heterocyclic, partially or completely hydrogenated ring, $R^1$ can be unsubstituted or substituted and is alkyl, alkenyl, alkynyl, cycloalkyl, cycloalkenyl or —$CO_2$-alkyl, A is —O—, —S—, —$CR^2$=$CR^3$—, $CHR^2$—O—, —$CHR^2$—S—, —$CHR^2$—O=N—C($R^4$)—, —$CR^2$=N—O—, —O—N=C($R^4$)—, —C≡C—, —CHR$^2$—CHR$^3$—, —CHR$^2$—O—CO—, —O—CHR$^2$— or a single bond, B can be unsubstituted or substituted and is alkyl, alkenyl, alkynyl, cycloalkyl, cycloalkenyl, cycloalkynyl, aryl, hetaryl, heterocyclyl or hydrogen, $R^2$ and $R^3$ independently of one another are each hydrogen, alkyl, alkenyl, alkynyl or cycloalkyl and $R^4$ is hydrogen, cyano, alkyl, alkenyl, alkynyl, cycloalkyl or alkoxy, and their plant-tolerated acid addition products and base addition products.

The invention furthermore relates to carbamates of the formula VIII

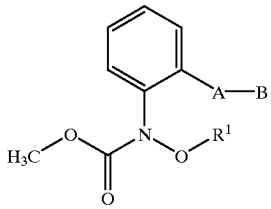

VIII where A, B and $R^1$ have the meanings stated in claim 9.

The invention furthermore relates to carbamates of the formula IX

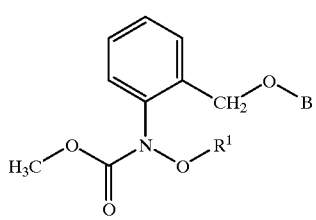

IX where $R^1$ and B have the meanings stated in claim 1.

The invention furthermore relates to carbamates of the formula X

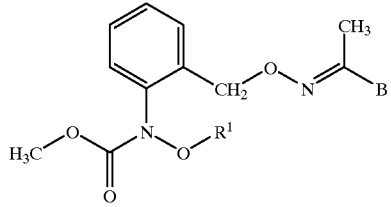

X where $R^1$ and B have the meanings stated in claim 1.

The novel compounds can be prepared, for example, by the following processes:

The nitrobenzenes 1 obtainable by standard processes are reduced to the anilines 2, for example with hydrogen or hydrogen transfer agents, such as ammonium formate, in the presence of suitable catalysts, such as Pd, Pt or Ni, with complex reducing agents, eg. Collman's reagent ($Na_2Fe(CO)_4$) or by other methods known from the literature (J. March, Advanced Organic Chemistry, 3rd Edition,. 1985, page 1103 et seq.). The anilines 2 are reacted under alkaline conditions with methyl chloroformate to give the carbamates 3. The reaction of the carbamates 3 under alkaline conditions with the corresponding alkylating agents, acylating agents or $R^5$—S—S(=O)$_2$—$R^5$ gives the derivatives 4 (Scheme 1).

Scheme 1

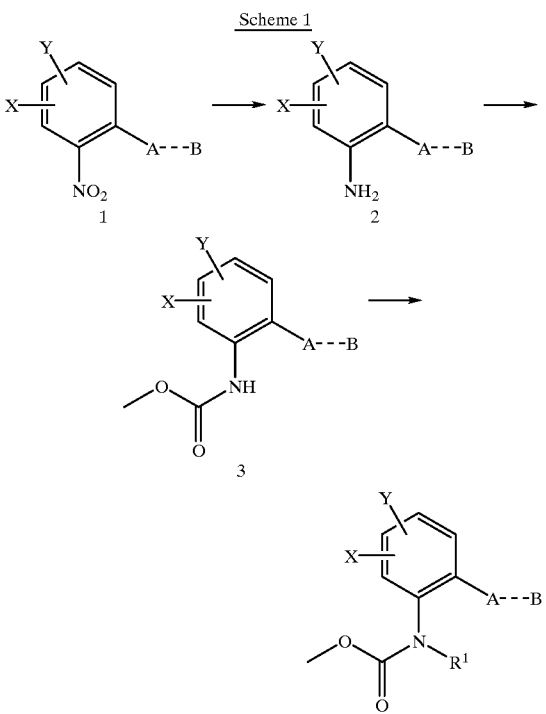

The nitrobenzenes 5 can be converted into the carbamates 6 similarly to Scheme 1. The halogen derivatives 7 (Z=Cl or Br) are obtainable by acidic cleavage of the methyl ether of 6 (Scheme 2).

Scheme 2

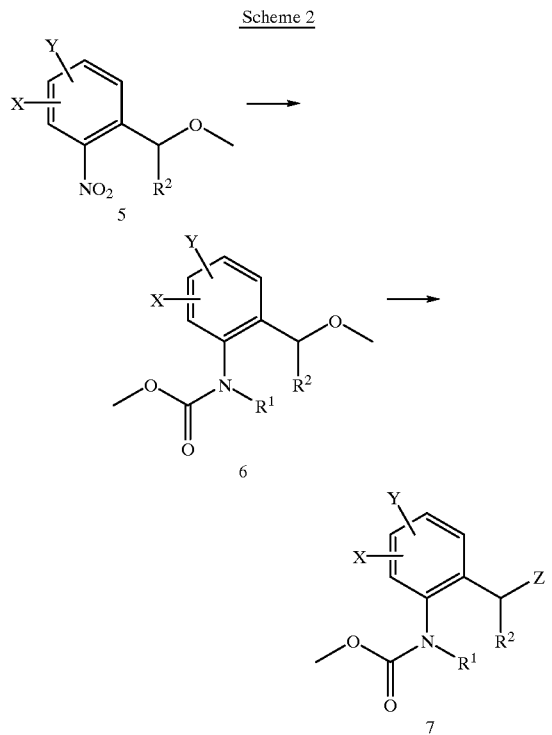

Alternatively, the halogen derivatives 7 (Z=Cl or Br) are obtainable from the derivatives 9 by free radical halogenation. The carbamates 9 are in turn prepared from the corresponding starting materials 8, similarly to Scheme 1 (Scheme 3).

Scheme 3

The halogen derivatives 7 (Z=Cl or Br) can be converted into the active ingredients 10 under alkaline conditions. Alternatively, the compounds 7 are converted into the phosphorus compounds 11a and 11b by reaction with $P(C_6H_5)_3$ or $P(O\text{-Alkyl})_3$, or into the carbonyl compounds 12 by oxidation (for example with N-methylmorpholine N-oxide) (Scheme 4).

Scheme 4

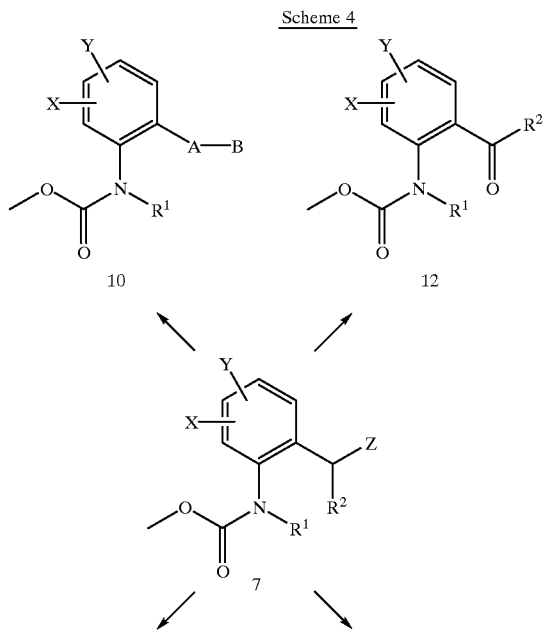

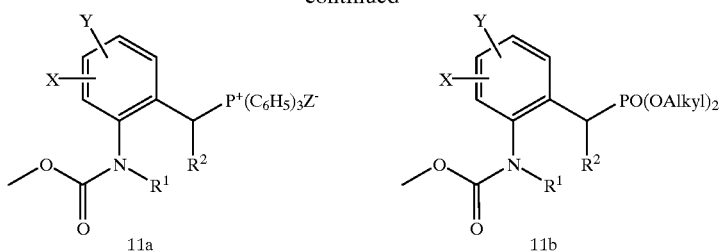

A=—CHR$^2$—O—  —CHR$^2$—S—  —CHR$^2$—O—N=C(R$^4$)—    15

The corresponding stilbenes 13 are obtainable from the phosphonium salts 11a or phosphonates 11b or carbonyl compounds 12 by a Wittig reaction (Scheme 5).

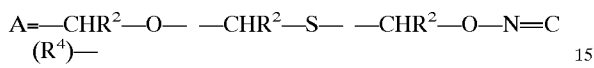

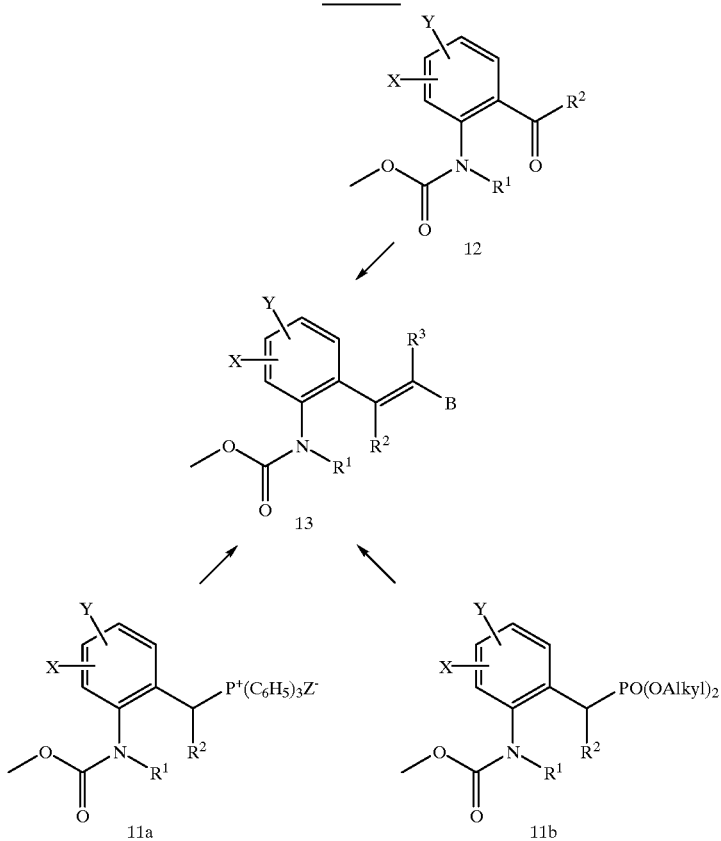

Partial reduction of the nitroaromatics 21 (for example with zinc (similarly to Bamberger et al., Ann. Chem. 316 (1901), 278) or with hydrogen in the presence of suitable catalysts such as platinum (similarly to European Patent 85,890)) gives the hydroxylamines 22, which can be reacted under alkaline conditions with an acylating agent (eg. propionyl chloride) or a carbamoylating agent (eg. methyl isocyanate) to give the compound 23 and then with an electrophile, for example with an alkylating agent, to give the active ingredients 24 (scheme 11).

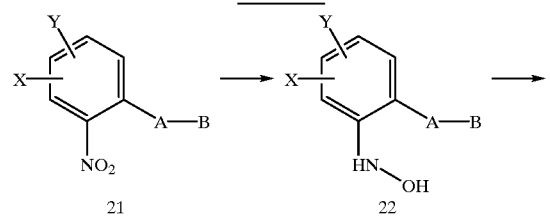

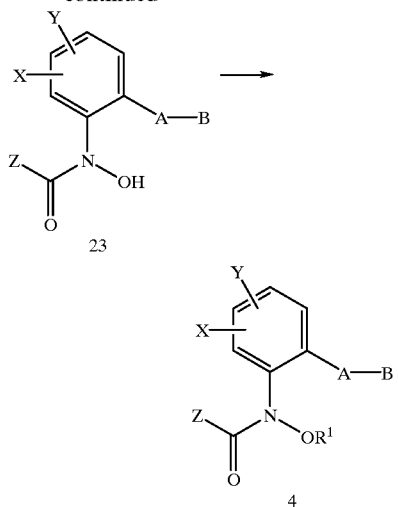

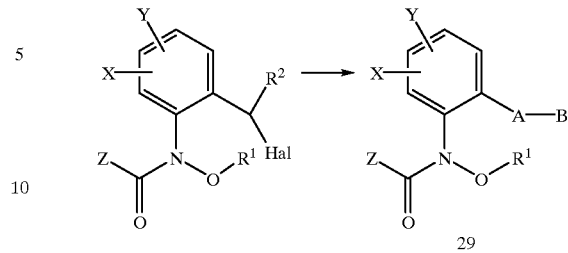

In addition, the hydroxylamine 25 can be acylated or aminoacylated (for example with methyl isocyanate) (similarly to Bamberger et al., Ann. Chem. 316 (1901), 278; European Patent 85,890) to give the compound 26, which can then be alkylated or alkoxyacylated (for example with chloroformates) to give the hydroxylamine derivative 27. The free radical halogenation of 27, for example with N-bromosuccinamide, bromine, chlorine or $SO_2Cl_2$ in the presence of free radical initiator, eg. azobisisobutyronitrile, or with exposure to UV light, then gives the halide 28 (Hal=Cl or Br; Scheme 12).

The halides 28 can then be converted into the compounds 29 with the corresponding nucelphiles (Scheme 13).

In addition, the halides 28 can be converted by free radical reaction to the dihalide 30 and then converted with $H_2O$/MeOH in the presence of $AgNO_3$ into the carbonyl compound 31 or reacted directly with N-methylmorpholine N-oxide to give the carbonyl compound 11. Furthermore, the phosphonates, phosphonium salts or phosphine oxides 32 (P is the particular organophosphorus radical) are obtainable from the halides 8 (Scheme 14).

The carbonyl compounds 31 can then be reacted with the corresponding hydroxylamines to give the oximes 33 or can be subjected to a Wittig reaction to give the olefins 34, The olefins 34 are also obtainable by a Wittig reaction starting from the phosphonates, phosphonium salts or phosphine oxides 32 (Scheme 15).

Scheme 15
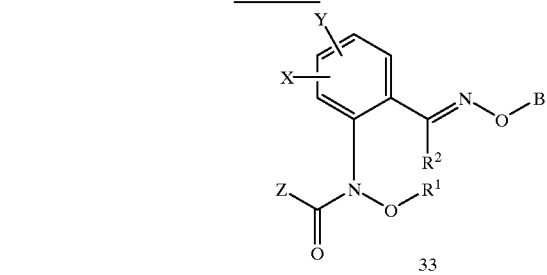
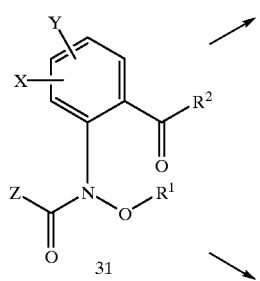
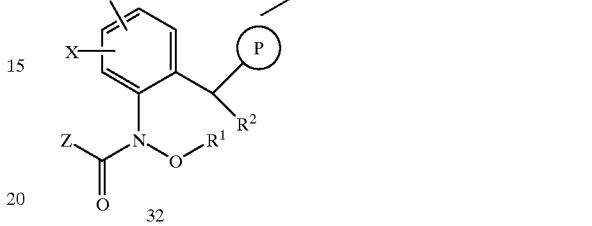
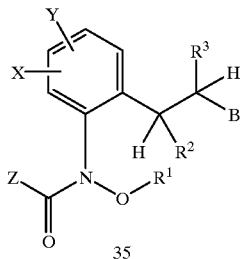
The saturated compounds 35 can be prepared from the olefins 34 by reduction or, where $R^2$ and $R^3$ are each H, the acetylenes 36 can be prepared from said olefins by halogen addition (Hal=Cl, Br or I) and subsequent two-fold elimination of hydrogen halide (Scheme 16).
Scheme 16
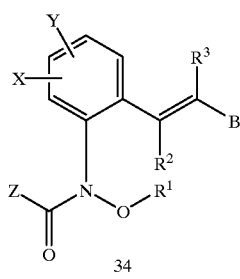
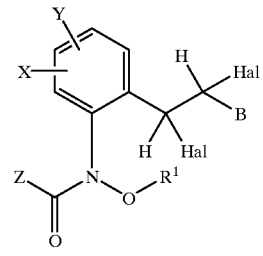

Alternatively, the ureas 39 can be synthesized by acylation of the hydroxylamines 22 to the compounds 37, subsequent alkylation or acylation to the compounds 38 and substitution of the nucleofugic leaving group V (V is, for example, $OCH_3$, $OCCl_3$, $CCl_3$, O-phenyl or O-p-nitrophenyl) by $NH_3$, $H_2N—CH_3$ or $HN(CH_3)_2$ (Scheme 17).

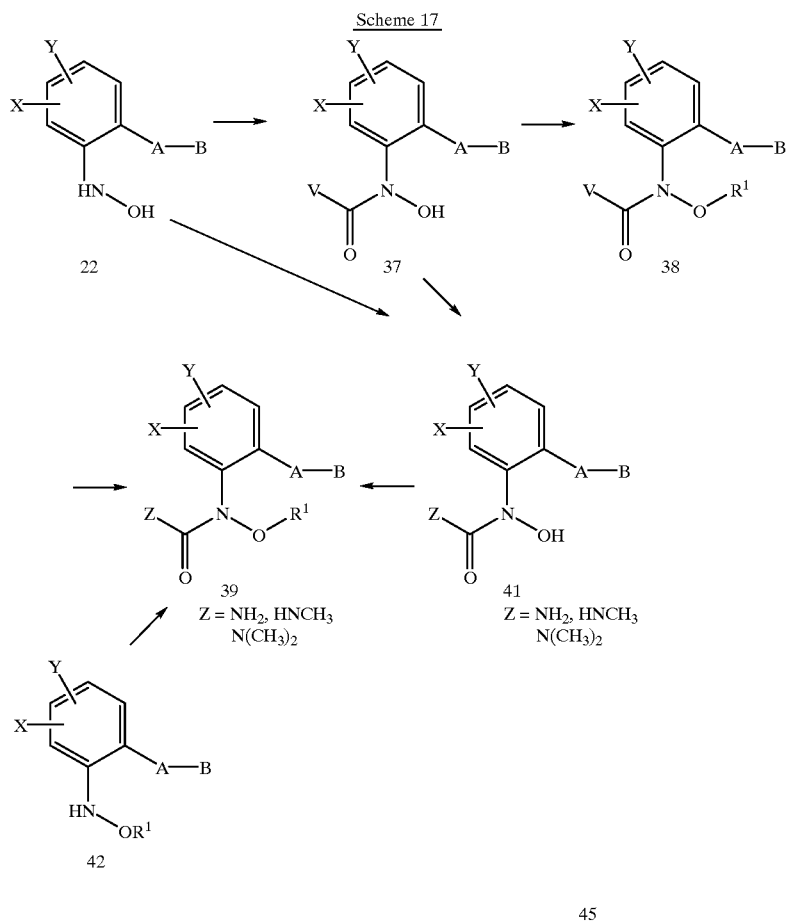

Alternatively, ureas of the formula 39 can also be obtained by alkylating ureas of the formula 41, which in turn are obtainable from 17 by reacting 17 with the corresponding amines, or directly from 22 by aminocarbonylation (for example with dimethylcarbamoyl chloride or methyl isocyanate) (cf. for example Houben-Weyl, volume E16a, page 208).

Furthermore, ureas of the formula 39 can also be obtained from the N-aryl-O-alkylhydroxylamines of the formula 42 in a similar manner by aminocarbonylation.

The compounds of the formula 42 are in turn obtainable by methods known from the literature, from hydroxylamines of the formula 2 (cf. for example Houben-Weyl, volume E16a, pages 271 and 282–289).

In addition, the hydroxylamines 22 are obtainable from the anilines 43 by formation of the imines 44, oxidation of the compounds 44 with the m-chloroperbenzoic acid and reaction of the oxaziridines 45 with hydroxylamine (Scheme 18; similarly to G. Grundke et al., Synthesis 1987, 1115).

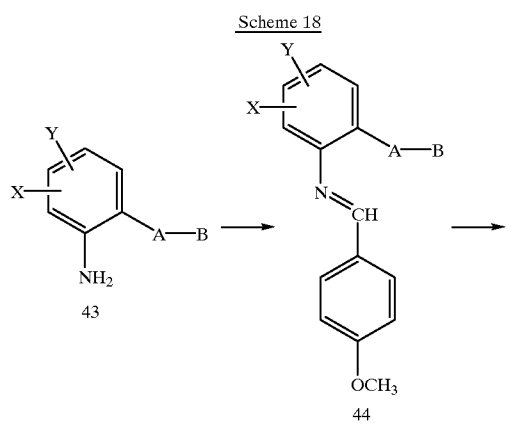

-continued

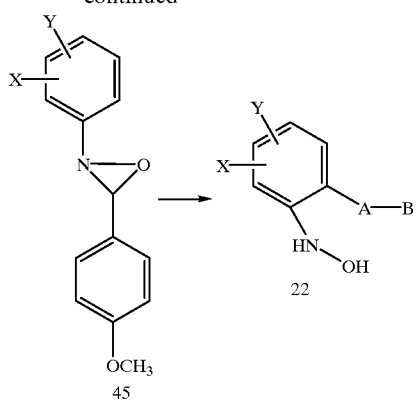

The Examples which follow illustrate the preparation of the novel compounds.

EXAMPLES

Example 1

Methyl N-ethyl-N-(2-(2'-methylphenoxymethyl)-phenyl)-carbamate (Table 7, No. 2)

a) Methyl N-(o-methylphenyl)-carbamate 50 g (0.53 mol) of methyl chloroformate are added dropwise to 53 g (0.5 mol) of o-toluidine in 500 ml of methylene chloride. During this procedure, the reaction solution heats up to the boiling point and a colorless solid is precipitated.

Stirring is carried out for one hour, after which 200 ml of 10% strength sodium hydroxide solution are added dropwise, the colorless solid going into solution. The organic phase is dried over $MgSO_4$ and evaporated down under reduced pressure. The remaining solid is stirred with n-hexane and filtered off under suction. 84 g (0.5 mol, quantitative yield) of the title compound are obtained as a colorless solid.

mp.=61–62° C.

$^1$H-NMR (DMSO-$d_6$; δ (ppm)): 8.85 (s, 1H, NH); 7.35 (d, broad, 1H, aromatic); 7.1 (m, 3H, aromatic); 3.6 (s, 3H, $OCH_3$); 2.2 (s, 3H, $CH_3$).

b) Methyl N-ethyl-N-(o-methylphenyl)-carbamate 5.1 g (0.2 mol) of sodium hydride are added a little at a time to 30 g (0.18 mol) of methyl N-(o-methylphenyl)-carbamate (Example 1a) in 200 ml of dimethylformamide. After the evolution of gas has ceased, 30 g (0.2 mol) of ethyl iodide are added dropwise, the reaction mixture being lightly cooled in a water bath. A white solid is precipitated. After about 4 hours, the reaction mixture is diluted with water and the aqueous phase is extracted three times with ether. The organic phase is dried over $MgSO_4$ and evaporated down. The residue is distilled. 32.5 g (0.17 mol=93%) of the title compound are obtained as a colorless oil.

bp.$^{0.5}$=74° C.

$^1$H-NMR (CDCl$_3$; δ (ppm): 7.2 (m, 3H, aromatic); 7.1 (m, 1H, aromatic); 3.8 (m, 1H, N—CH$_A$); 3.6 (s, 3H, OCH$_3$); 3.5 (m, 1H, N—CH$_B$); 2.2 (s, 3H, CH$_3$); 1.1 (t, 3H, CH$_3$).

c) Methyl N-ethyl-N-(o-bromomethylphenyl)-carbamate

A mixture of 30 g (0.155 mol) of methyl N-ethyl-N-(o-methylphenyl)-carbamate (Example 1b), 33 g (0.185 mol) of N-bromosuccinimide and 0.1 g of azoisobutyronitrile in 300 ml of carbon tetrachloride is exposed to a 300 W UV lamp for 6 hours. During this procedure, the contents of the flask heat up to about 70° C. Thereafter, the reaction mixture is washed four times with water, dried and evaporated down. The residue obtained comprises 41 g of a brown oil which contains the title compound in about 50% purity and is used without further purification in the next reaction.

$^1$H-NMR (CDCl$_3$; δ (ppm)): 7.2 (m, 4H, aromatic); 4.45 (s, 2H, CH$_2$—Br); 3.8 (m, 1H, N—CH$_A$); 3.6 (s, 3H, OCH$_3$); 3.5 (m, 1H, N—CH$_B$); 1.15 (t, 3H, J=8 Hz, CH$_3$).

d) Methyl N-ethyl-N-(2-(2'-methylphenoxymethyl)phenyl)-carbamate (Table 7, No. 2)

2.4 g (17 mmol) of sodium hydride are added a little at a time to 8.6 g (80 mmol) of o-cresol in 100 ml of dimethylformamide. Stirring is carried out for 30 minutes at room temperature (20° C.), after which 20.5 g of methyl N-ethyl-N-(o-bromomethylphenyl)-carbamate (Example 1c, about 50% purity, about 37 mmol) are added. Stirring is carried out overnight at room temperature, after which the reaction mixture is diluted with water and the aqueous phase is extracted three times with ether. The combined ether phases are dried over $MgSO_4$ and evaporated down. The residue is distilled in a kugelrohr (bulb tube) apparatus. 10 g of a yellow oil are obtained at 220° C. and 0.2 mbar, and the oil is then purified by chromatography with cyclohexane/ethyl acetate mixtures over silica gel and then over alumina. The product thus obtained is purified again by kugelrohr distillation. 3.6 g (12 mmol=32%) of the title compound are obtained as a colorless oil.

$^1$H-NMR (CDCl$_3$; δ (ppm)): 7.6 (m, 1H, aromatic); 7.35 (m, 2H, aromatic); 7.15 (m, 3H, aromatic); 6.85 (m, 2H, aromatic); 5.0 (dd, broad, 2H, O—CH$_2$); 3.8 (m, 1H, N—CH$_A$); 3.6 (s, 3H, O—CH$_3$); 3.5 (m, 1H, N—CH$_B$); 2.3 (s, 3H, CH$_3$); 1.15 (t, 3H, J=8 Hz, CH$_3$).

Example 2

Methyl N-[2-(2'-methylphenoxymethyl)-phenyl]-N-methylthiocarbamate (Table 7, No. 89)

a) 2-(2'-Methylphenoxymethyl)-nitrobenzene 75 g (0.347 mol) of 2-nitrobenzyl bromide, 37 g (0.342 mol) of o-cresol and 56 g (0.405 mol) of potassium carbonate in 500 ml of dimethylformamide are stirred for 5 hours at room temperature. The reaction mixture is then diluted with water and the aqueous phase is extracted three times with ether. The ether phase is dried and evaporated down. The crystalline residue is stirred with methanol and filtered off under suction. 73 g (0.300 mol=88%) of the title compound are obtained as a colorless solid.

mp.=83° C.

$^1$H-NMR (CDCl$_3$; δ (ppm)): 8.15 (d, 1H, J=8 Hz, aromatic); 7.95 (d, 1H, J=8 Hz, aromatic); 7.7 (t, 1H, J=8 Hz, aromatic); 7.45 (t, 1H, J=8 Hz, aromatic); 7.15 (m, 2H, aromatic); 6.9 (m, 2H, aromatic); 5.45 (s, 2H, O—CH$_2$); 2.35 (s, 3H, CH$_3$).

b) 2-(2'-Methylphenoxymethyl)-aniline 75 g (0.308 mol) of 2-(2'-methylphenoxymethyl) nitrobenzene (Example 2a) and 10 g of 5% strength Pt/C (platinum adsorbed onto active carbon) in 50 ml of methanol are stirred vigorously for two hours under an H$_2$ atmosphere. Thereafter, a further 2 g of 5% strength Pt/C are added and stirring is continued overnight. The catalyst is then filtered off under suction and is replaced with 10 g of fresh catalyst. Stirring is continued overnight, the mixture is filtered under suction and the filtrate is evaporated down under reduced pressure. The residue is purified by column chromatography using hexane/ethyl acetate mixtures. 61 g (0.286 mol=93%) of the title compound are obtained as a colorless solid.

mp.=56° C.

$^1$H-NMR (CDCl$_3$; δ (ppm)): 7.2 (m, 4H, aromatic); 6.95 (d, 1H, J=8 Hz, aromatic); 6.9 (t, 1H, J=6 Hz, aromatic); 6.7

(m, 2H, aromatic); 5.0 (s, 2H, O—CH$_2$); 4.05 (s, broad, 2H, NH$_2$); 2.2 (s, 3H, CH$_3$).

c) Methyl N-(2-(2'-methylphenoxymethyl)-phenyl]-carbamate (Table 7, No. 3)

6 g (63 mmol) of methyl chloroformate are added dropwise to 10 g (47 mmol) of 2-(2'-methylphenoxymethyl) aniline in 500 of methylene chloride at 20–30° C. Stirring is carried out for 3 hours at room temperature, a white solid being precipitated, and the reaction mixture is then stirred with 20 ml of 10% strength sodium hydroxide solution. The organic phase is filtered off under suction over silica gel, the filtrate is evaporated down and the remaining residue is stirred thoroughly with methanol and filtered under suction. 10.5 g (39 mmol=82%) of the title compound are obtained as a colorless solid.

mp.=111° C.

$^1$H-NMR (CDCl$_3$; δ (ppm)): 8.0 (d, broad, 1H, aromatic); 7.7 (s, broad, 1H, aromatic); 7.7 (s, broad, 1H, NH); 6.8–7.5 (m, 6H, aromatic); 5.0 (s, 2H, O—CH$_2$); 3.75 (s, 3H, O—CH$_3$); 2.25 (s, 3H, CH$_3$).

d) Methyl N-[2-(2'-methylphenoxymethyl)-phenyl]-N-methylthiocarbamate (Table 7, No. 89)

0.5 g (20.8 mmol) of sodium hydride is added a little at a time to 4.9 g (17.3 mmol) of methyl N-[2-(2'-methylphenoxymethyl)]-phenylcarbamate (Example 2c) in 80 ml of toluene. After the end of gas evolution, 2.4 g (19 mmol) of methyl methanethiosulfonate are added and stirring is carried out overnight at room temperature. Thereafter, the reaction mixture is extracted with water, dried over MgSO$_4$ and evaporated down under reduced pressure. The residue is purified by column chromatography with hexane/ethyl acetate mixtures over silica gel. 3 g (9.1 mmol=53%) of the title compound are obtained as a yellow oil.

$^1$H-NMR (CDCl$_3$; δ (ppm)): 7.65 (d, broad, 1H, aromatic); 7.35 (m, 2H, aromatic); 7.15 (m, 3H, aromatic); 6.85 (m, 2H, aromatic); 5.0 (m, 2H, O—CH$_2$); 3.75 (s, 3H, O—CH$_3$); 2.55 (s, 3H, S—CH$_3$); 2.3 (s, 3H, CH$_3$).

Example 3

Methyl N-allyl-N-[2-(3"-bromophenylmethyliminoxymethyl)phenyl]-carbamate (Table 7, No. 91)

a) o-Methoxymethylnitrobenzene 125 g of 30% strength sodium methylate solution (0.69 mol) in methanol are added dropwise to 130 g (0.6 mol) of o-nitrobenzyl bromide in 200 ml of methanol. During this procedure, the reaction mixture heats up to about 50° C. Stirring is continued for a further 3 hours, the reaction mixture being cooled to room temperature, after which ice water is added to the reaction vessel and the reaction mixture is neutralized by adding dilute hydrochloric acid. The aqueous phase is extracted with three times with ether, and the organic phase is dried over MgSO$_4$ and evaporated down. 101 g (0.6 mol, quantitative yield) of the title compound are obtained as a residue in the form of a brownish oil.

$^1$H-NMR (CDCl$_3$; δ (ppm)): 8.1 (d, broad, 1H, aromatic); 7.8 (d, broad, 1H, aromatic); 7.65 (t, broad, 1H, aromatic); 7.45 (t, broad, 1H, aromatic); 4.85 (s, 2H, O—CH$_2$); 3.5 (s, 3H, OCH$_3$).

b) Methyl N-(2-methoxymethylphenyl)-carbamate 528 g of 21.8% strength Na$_2$[Fe(CO)$_4$] solution (0.6 mol; 1 kg of the solution contains 633 g of water, 218 g of Na$_2$[Fe(CO)$_4$], 108 g of Na$_2$CO$_3$ and 41 g of NaOH) are added dropwise to 101 g (0.6 mol) of o-methoxymethylnitrobenzene (Example 3a) in 1 l of methanol at 20–30° C. Stirring is carried out for 1 hour at room temperature, after which the reaction mixture is diluted with ether. A brown oil separates out in the reaction vessel. The total reaction mixture is poured onto a silica gel column and is eluted with ether. Thereafter, the ether phase is evaporated, the residue is taken up in methylene chloride and the solution is dried over MgSO$_4$. It is filtered under suction over silica gel and the solvent is then evaporated off under reduced pressure. The residue is purified by column chromatography with hexane and methylene chloride. 83.8 g of o-methoxymethylaniline are obtained as a brown oil, which is directly reacted further.

The resulting crude product is dissolved in 700 ml of methylene chloride, 62.4 g (0.66 mol) of methyl chloroformate are added and 52.2 g (0.66 mol) of pyridine are then added dropwise. Stirring is carried out overnight at room temperature and the reaction mixture is then extracted with dilute hydrochloric acid and water. The organic phase is dried over MgSO$_4$ and evaporated down. The residue is purified by column chromatography with hexane/ethyl acetate mixtures. 89.4 g (0.41 mol=69%, based on 2-methoxymethylnitrobenzene) of the title compound are obtained as a yellow oil in a purity of about 90%.

$^1$H-NMR (CDCl$_3$; δ (ppm): 8.0 (m, 2H, 1×aromatic, NH); 7.35 (t, broad, 1H, aromatic); 7.15 (d, broad, 1H, aromatic); 7.0 (t, broad, 1H, aromatic); 4.5 (s, 2H, OCH$_2$); 3.8 (s, broad, 3H, OCH$_3$); 3.4 (s, broad, 3H, OCH$_3$).

c) Methyl N-(2-bromomethylphenyl)-carbamate 38.6 g (150 mmol) of boron tribromide are added dropwise to 10 g (51 mmol) of methyl N-(2-methoxymethylphenyl)-carbamate (Example 2b) in 100 ml of methylene chloride. Stirring is carried out for 2 hours, after which the vigorously stirred reaction mixture is added dropwise to a solution of 11.8 g (0.17 mol) of NaHCO$_3$ in water. The organic phase is separated off and the aqueous phase is extracted once with methylene chloride and once with ethyl acetate. The combined organic phases are dried over MgSO$_4$ and evaporated down. 9.5 g (39 mmol=76%) of the title compound are obtained as a colorless solid.

mp.=132° C.

$^1$H-NMR (CDCl$_3$; δ (ppm)): 7.85 (d, broad, 1H, aromatic); 7.3 (m, 2H, aromatic); 7.1 (t, broad, 1H, aromatic); 6.9 (s, broad, 1H, NH); 4.5 (s, 2H, CH$_2$—Br); 3.8 (s, 3H, OCH$_3$).

d) Methyl N-[2-(3"-bromophenylmethyliminoxymethyl)-phenyl]-carbamate (Table 7, No. 88)

0.95 g (39 mmol) of sodium hydride is added a little at a time to 7 g (33 mmol) of m-bromoacetophenone oxime in 100 ml of dimethylformamide. When the evolution of gas has ended, 8 g (33 mmol) of methyl N-(2-bromomethylphenyl)-carbamate (Example 3c), dissolved in 10 ml of dimethylformamide, are added dropwise. Stirring is carried out for 3 hours at room temperature, the reaction mixture is diluted with water and the aqueous phase is extracted three times with ether. The organic phase is washed three times with water, dried and evaporated down. The residue crystallizes and is stirred thoroughly with methanol. 5.1 g (13.5 mmol=41%) of the title compound are obtained as a colorless solid.

mp.=124–125° C.

$^1$H-NMR (CDCl$_3$; δ (ppm)): 8.6 (s, broad, 1H, NH); 7.8–8.1 (m, 2H, aromatic); 7–7.6 (m, 6H, aromatic); 5.2 (s, 2H, O—CH$_2$); 3.8 (s, 3H, O—CH$_3$); 2.2 (s, 3H, CH$_3$).

e) Methyl N-allyl-N-[2-(3"-bromophenylmethyliminoxymethyl)-phenyl]-carbamate (Table 7, No. 91)

0.1 g (4.1 mmol) of sodium hydride is added a little at a time to 1.3 g (3.5 mmol) of methyl N-[2-(3"-bromophenylmethyliminoxymethyl)-phenyl]-carbamate (Example 3d) in 20 ml of dimethylformamide. After gas evolution has ended, 0.5 g (3.8 mmol) of allyl bromide are added and stirring is carried out overnight at room temperature. Thereafter, the reaction mixture is diluted with water and extracted three times with ether. The combined ether phases are washed three times with water, dried over MgSO$_4$ and evaporated down. 1.5 g (quantitative yield) of the title compound are obtained as a residue in the form of a yellow oil.

$^1$H-NMR (CDCl$_3$; δ (ppm)):

7.8 (s, broad, 1H, aromatic); 7.1–7.6 (m, 7H, aromatic); 6.0 (m, 1H, C—CH=C); 5.1 (m, 4H, O—CH$_2$ and C=CH$_2$); 4.4 (m, 1H, N—CH$_A$); 4.0 (m, 1H, N—CH$_B$) 3.6–3.8 (2s, broad, O—CH$_3$); 2.2 (s, 3H, CH$_3$).

The compounds described in the Tables below can be prepared in a similar manner.

TABLE 1

I:   R$^1$ = H
II:  R$^1$ = CH$_3$
III: R$^1$ = Allyl
IV:  R$^1$ = Propargyl
V:   R$^1$ = S—CH$_3$
VI:  R$^1$ = CH$_2$—CN
VII: R$^1$ = CH$_2$—O—CH$_3$
VIII: R$^1$ = CO—OCH$_3$

| No. | X$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |

TABLE 1-continued

| No. | X$_m$ |
|---|---|
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |

TABLE 1-continued

| | |
|---|---|
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O-(CH$_2$)$_3$C$_6$H$_5$ |
| 181 | 3-O-(CH$_2$)$_3$C$_6$H$_5$ |
| 182 | 4-O-(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |

TABLE 1-continued

| | |
|---|---|
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |

TABLE 1-continued

| | |
|---|---|
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)—CH$_3$ |
| 333 | 3-C(=NO-Allyl)—CH$_3$ |
| 334 | 4-C(=NO-Allyl)—CH$_3$ |
| 335 | 2-C(=NO-trans-Chloroallyl)—CH$_3$ |
| 336 | 3-C(=NO-trans-Chloroallyl)—CH$_3$ |
| 337 | 4-C(=NO-trans-Chloroallyl)—CH$_3$ |
| 338 | 2-C(=NO-Propargyl)—CH$_3$ |
| 339 | 3-C(=NO-Propargyl)—CH$_3$ |
| 340 | 4-C(=NO-Propargyl)—CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl-C$_6$H$_4$) |
| 396 | 2-(3'-Cl-C$_6$H$_4$) |
| 397 | 2-(4'-Cl-C$_6$H$_4$) |
| 398 | 3-(2'-Cl-C$_6$H$_4$) |
| 399 | 3-(3'-Cl-C$_6$H$_4$) |
| 400 | 3-(4'-Cl-C$_6$H$_4$) |
| 401 | 4-(2'-Cl-C$_6$H$_4$) |
| 402 | 4-(3'-Cl-C$_6$H$_4$) |
| 403 | 4-(4'-Cl-C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))—C$_6$H$_4$) |
| 424 | 2-(3'-(CH$_3$—C(=NOAllyl))—C$_6$H$_4$) |
| 425 | 2-(4'-(CH$_3$—C(=NOAllyl))—C$_6$H$_4$) |
| 426 | 3-(2'-(CH$_3$—C(=NOAllyl))—C$_6$H$_4$) |
| 427 | 3-(3'-(CH$_3$—C(=NOAllyl))—C$_6$H$_4$) |
| 428 | 3-(4'-(CH$_3$—C(=NOAllyl))—C$_6$H$_4$) |
| 429 | 4-(2'-(CH$_3$—C(=NOAllyl))—C$_6$H$_4$) |
| 430 | 4-(3'-(CH$_3$—C(=NOAllyl))—C$_6$H$_4$) |
| 431 | 4-(4'-(CH$_3$—C(=NOAllyl))—C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |

TABLE 1-continued

| | |
|---|---|
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl-C$_6$H$_4$) |
| 488 | 2-O-(3'-Cl-C$_6$H$_4$) |
| 489 | 2-O-(4'-Cl-C$_6$H$_4$) |
| 490 | 3-O-(2'-Cl-C$_6$H$_4$) |
| 491 | 3-O-(3'-Cl-C$_6$H$_4$) |
| 492 | 3-O-(4'-Cl-C$_6$H$_4$) |
| 493 | 3-O-(4'-Cl-C$_6$H$_4$) |
| 494 | 4-O-(2'-Cl-C$_6$H$_4$) |
| 495 | 4-O-(3'-Cl-C$_6$H$_4$) |
| 496 | 4-O-(4'-Cl-C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))—C$_6$H$_4$) |
| 516 | 2-O-(3'-(CH$_3$—C(=NOAllyl))—C$_6$H$_4$) |
| 517 | 2-O-(4'-(CH$_3$—C(=NOAllyl))—C$_6$H$_4$) |
| 518 | 3-O-(2'-(CH$_3$—C(=NOAllyl))—C$_6$H$_4$) |
| 519 | 3-O-(3'-(CH$_3$—C(=NOAllyl))—C$_6$H$_4$) |
| 520 | 3-O-(4'-(CH$_3$—C(=NOAllyl))—C$_6$H$_4$) |
| 521 | 4-O-(2'-(CH$_3$—C(=NOAllyl))—C$_6$H$_4$) |
| 522 | 4-O-(3'-(CH$_3$—C(=NOAllyl))—C$_6$H$_4$) |
| 523 | 4-O-(4'-(CH$_3$—C(=NOAllyl))—C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |

TABLE 1-continued

| | |
|---|---|
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-$CH_3$-4-($CH_3$—C=N—O—$CH_2$—$CH_2$—$OCH_3$) |
| 642 | 2-$CH_3$-4-($C_2H_5$—C=N—O—$CH_2$—$CH_2$—$OCH_3$) |
| 643 | 2,5-$(CH_3)_2$-4-($CH_3$—C=N—O—$CH_2$—$CH_2$—$OCH_3$) |
| 644 | 2-$CH_3$-4-(n-$C_3H_7$—C=N—$OCH_3$) |
| 645 | 2-$CH_3$-4-(n-$C_3H_7$—C=N—$OC_2H_5$) |
| 646 | 2-$CH_3$-4-(n-$C_3H_7$—C=N—O-n-$C_3H_7$) |
| 647 | 2-$CH_3$-4-(n-$C_3H_7$—C=N—O-i-$C_3H_7$) |
| 648 | 2-$CH_3$-4-(n-$C_3H_7$—C=N—O-Allyl) |
| 649 | 2-$CH_3$-4-(n-$C_3H_7$—C=N—O-trans-Chloroallyl) |
| 650 | 2-$CH_3$-4-(n-$C_3H_7$—C=N—O-Propargyl) |
| 651 | 2-$CH_3$-4-(n-$C_3H_7$—C=N—O-n-$C_4H_9$) |
| 652 | 2-$CH_3$-4-(n-$C_3H_7$—C=N—O—$CH_2$—$C_6H_5$) |
| 653 | 2-$CH_3$-4-(i-$C_3H_7$—C=N—$OCH_3$) |
| 654 | 2-$CH_3$-4-(i-$C_3H_7$—C=N—$OC_2H_5$) |
| 655 | 2-$CH_3$-4-(i-$C_3H_7$—C=N—O-n-$C_3H_7$) |
| 656 | 2-$CH_3$-4-(i-$C_3H_7$—C=N—O-i-$C_3H_7$) |
| 657 | 2-$CH_3$-4-(i-$C_3H_7$—C=N—O-Allyl) |
| 658 | 2-$CH_3$-4-(i-$C_3H_7$—C=N—O-trans-Chloroallyl) |
| 659 | 2-$CH_3$-4-(i-$C_3H_7$—C=N—O-Propargyl) |
| 660 | 2-$CH_3$-4-(i-$C_3H_7$—C=N—O-n-$C_4H_9$) |
| 661 | 2-$CH_3$-4-(i-$C_3H_7$—C=N—O—$CH_2$—$C_6H_5$) |
| 662 | 2-O-n-$C_4H_9$ |
| 663 | 2-O-i-$C_4H_9$ |
| 664 | 2-O-s-$C_4H_9$ |
| 665 | 2-O-t-$C_4H_9$ |
| 666 | 2-Neopentyloxy |
| 667 | 3-O-n-$C_4H_9$ |
| 668 | 3-O-i-$C_4H_9$ |
| 669 | 3-O-s-$C_4H_9$ |
| 670 | 3-O-t-$C_4H_9$ |
| 671 | 3-Neopentyloxy |
| 672 | 4-O-n-$C_4H_9$ |
| 673 | 4-O-i-$C_4H_9$ |
| 674 | 4-O-s-$C_4H_9$ |
| 675 | 4-O-t-$C_4H_9$ |
| 676 | 4-Neopentyloxy |
| 677 | 3-$CH_3$-4-$OCH_3$ |
| 678 | 3-$CH_3$-4-$OC_2H_5$ |
| 679 | 3-$CH_3$-4-O-n-$C_3H_7$ |
| 680 | 3-$CH_3$-4-O-n-$C_4H_9$ |
| 681 | 3-$CH_3$-4-O-i-$C_4H_9$ |
| 682 | 3-$CH_3$-4-O-s-$C_4H_9$ |
| 683 | 3-$CH_3$-4-O-t-$C_4H_9$ |
| 684 | 3-$CH_3$-4-Neopentyloxy |
| 685 | 2-$CH_3$-3-$OCH_3$ |
| 686 | 2-$CH_3$-4-$OCH_3$ |
| 687 | 2-$CH_3$-5-$OCH_3$ |
| 688 | 2-$CH_3$-6-$OCH_3$ |
| 689 | 3-$CH_3$-4-$OCH_3$ |
| 690 | 3-$CH_3$-5-$OCH_3$ |
| 691 | 3-$CH_3$-6-$OCH_3$ |
| 692 | 4-$CH_3$-5-O—$CH_3$ |
| 693 | 4-$CH_3$-6-O—$CH_3$ |
| 694 | 4-$CH_3$-6-$OCH_3$ |
| 695 | 2-$CH_3$-3-O-i-$C_3H_7$ |
| 696 | 2-$CH_3$-4-O-i-$C_3H_7$ |
| 697 | 2-$CH_3$-5-O-i-$C_3H_7$ |
| 698 | 2-$CH_3$-6-O-i-$C_3H_7$ |
| 699 | 3-$CH_3$-4-O-i-$C_3H_7$ |
| 700 | 3-$CH_3$-5-O-i-$C_3H_7$ |
| 701 | 3-$CH_3$-6-O-i-$C_3H_7$ |
| 702 | 4-$CH_3$-5-O-i-$C_3H_7$ |
| 793 | 4-$CH_3$-6-O-i-$C_3H_7$ |
| 704 | 5-$CH_3$-6-O-i-$C_3H_7$ |
| 705 | 2-Cl-3-$OCH_3$ |
| 706 | 2-Cl-4-$OCH_3$ |
| 707 | 2-Cl-5-$OCH_3$ |
| 708 | 2-Cl-6-$OCH_3$ |
| 709 | 3-Cl-4-$OCH_3$ |
| 710 | 3-Cl-5-$OCH_3$ |
| 711 | 3-Cl-6-$OCH_3$ |
| 712 | 4-Cl-5-$OCH_3$ |
| 713 | 4-Cl-6-$OCH_3$ |
| 714 | 5-Cl-6-$OCH_3$ |

TABLE 2

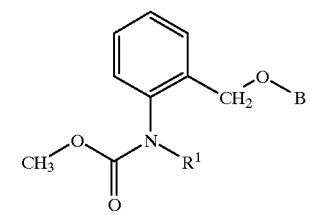

| | |
|---|---|
| I: | $R^1$ = H |
| II: | $R^1$ = $CH_3$ |
| III: | $R^1$ = Allyl |
| IV: | $R^1$ = Propargyl |
| V: | $R^1$ = S—$CH_3$ |
| VI: | $R^1$ = $CH_2$—CN |
| VII: | $R^1$ = $CH_2$—O—$CH_3$ |
| VIII: | $R^1$ = CO—$OCH_3$ |

| No. | B |
|---|---|
| 1 | Pyrrolyl-3 |
| 2 | N—$CH_3$-Pyrrolyl-3 |
| 3 | N—$C_6H_5$-Pyrrolyl-3 |
| 4 | N—(4'-$CH_3$—$C_6H_4$)-Pyrrolyl-3 |
| 5 | N—(3'-$CH_3$—$C_6H_4$)-Pyrrolyl-3 |
| 6 | N—(2'-$CH_3$—$C_6H_4$)-Pyrrolyl-3 |
| 7 | N—(4'-$CH_3O$—$C_6H_4$)-Pyrrolyl-3 |
| 8 | N—(3'-$CH_3O$—$C_6H_4$)-Pyrrolyl-3 |

TABLE 2-continued

| | |
|---|---|
| 9 | N—(2'-CH$_3$O—C$_6$H$_4$)-Pyrrolyl-3 |
| 10 | N—(4'-NO$_2$—C$_6$H$_4$)-Pyrrolyl-3 |
| 11 | N—(3'-NO$_2$—C$_6$H$_4$)-Pyrrolyl-3 |
| 12 | N—(2'-NO$_2$—C$_6$H$_4$)-Pyrrolyl-3 |
| 13 | N—(4'-CN—C$_6$H$_4$)-Pyrrolyl-3 |
| 14 | N—(3'-CN—C$_6$H$_4$)-Pyrrolyl-3 |
| 15 | N—(2'-CN—C$_6$H$_4$)-Pyrrolyl-3 |
| 16 | N—(4'-Cl—C$_6$H$_4$)-Pyrrolyl-3 |
| 17 | N—(3'-Cl—C$_6$H$_4$)-Pyrrolyl-3 |
| 18 | N—(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N—(4'-CH$_3$—C$_6$H$_4$)-Pyrrolyl-2 |
| 23 | N—(3'-CH$_3$—C$_6$H$_4$)-Pyrrolyl-2 |
| 24 | N—(2'-CH$_3$—C$_6$H$_4$)-Pyrrolyl-2 |
| 25 | N—(4'-CH$_3$O—C$_6$H$_4$)-Pyrrolyl-2 |
| 26 | N—(3'-CH$_3$O—C$_6$H$_4$)-Pyrrolyl-2 |
| 27 | N—(2'-CH$_3$O—C$_6$H$_4$)-Pyrrolyl-2 |
| 28 | N—(4'-NO$_2$—C$_6$H$_4$)-Pyrrolyl-2 |
| 29 | N—(3'-NO$_2$—C$_6$H$_4$)-Pyrrolyl-2 |
| 30 | N—(2'-NO$_2$—C$_6$H$_4$)-Pyrrolyl-2 |
| 31 | N—(4'-CN—C$_6$H$_4$)-Pyrrolyl-2 |
| 32 | N—(3'-CN—C$_6$H$_4$)-Pyrrolyl-2 |
| 33 | N—(2'-CN—C$_6$H$_4$)-Pyrrolyl-2 |
| 34 | N—(4'-Cl—C$_6$H$_4$)-Pyrrolyl-2 |
| 35 | N—(3'-Cl—C$_6$H$_4$)-Pyrrolyl-2 |
| 36 | N—(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N—(4'-CH$_3$—C$_6$H$_4$)-Pyrazolyl-4 |
| 129 | N—(3'-CH$_3$—C$_6$H$_4$)-Pyrazolyl-4 |
| 130 | N—(2'-CH$_3$—C$_6$H$_4$)-Pyrazolyl-4 |
| 131 | N—(4'-CH$_3$O—C$_6$H$_4$)-Pyrazolyl-4 |
| 132 | N—(3'-CH$_3$O—C$_6$H$_4$)-Pyrazolyl-4 |
| 133 | N—(2'-CH$_3$O—C$_6$H$_4$)-Pyrazolyl-4 |
| 134 | N—(4'-NO$_2$—C$_6$H$_4$)-Pyrazolyl-4 |
| 135 | N—(3'-NO$_2$—C$_6$H$_4$)-Pyrazolyl-4 |
| 136 | N—(2'-NO$_2$—C$_6$H$_4$)-Pyrazolyl-4 |
| 137 | N—(4'-CN—C$_6$H$_4$)-Pyrazolyl-4 |
| 138 | N—(3'-CN—C$_6$H$_4$)-Pyrazolyl-4 |
| 139 | N—(2'-CN—C$_6$H$_4$)-Pyrazolyl-4 |
| 140 | N—(4'-Cl—C$_6$H$_4$)-Pyrazolyl-4 |
| 141 | N—(3'-Cl—C$_6$H$_4$)-Pyrazolyl-4 |
| 142 | N—(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |

TABLE 2-continued

| | |
|---|---|
| 167 | 3-(3'-CH₃O—C₆H₄)-Isoxazolyl-5 |
| 168 | 3-(2'-CH₃O—C₆H₄)-Isoxazolyl-5 |
| 169 | 3-(4'-NO₂—C₆H₄)-Isoxazolyl-5 |
| 170 | 3-(3'-NO₂—C₆H₄)-Isoxazolyl-5 |
| 171 | 3-(2'-NO₂—C₆H₄)-Isoxazolyl-5 |
| 172 | 3-(4'-CN—C₆H₄)-Isoxazolyl-5 |
| 173 | 3-(3'-CN—C₆H₄)-Isoxazolyl-5 |
| 174 | 3-(2'-CN—C₆H₄)-Isoxazolyl-5 |
| 175 | 3-(4'-Cl—C₆H₄)-Isoxazolyl-5 |
| 176 | 3-(3'-Cl—C₆H₄)-Isoxazolyl-5 |
| 177 | 3-(2'-Cl—C₆H₄)-Isoxazolyl-5 |
| 178 | 4-Chloroisoxazolyl-5 |
| 179 | 3-CH₃-4-Chloroisoxazolyl-5 |
| 180 | 3-C₆H₅-4-Chloroisoxazolyl-5 |
| 181 | 3-(4'-CH₃—C₆H₄)-4-Chloroisoxazolyl-5 |
| 182 | 3-(3'-CH₃—C₆H₄)-4-Chloroisoxazolyl-5 |
| 183 | 3-(2'-CH₃—C₆H₄)-4-Chloroisoxazolyl-5 |
| 184 | 3-(4'-CH₃O—C₆H₄)-4-Chloroisoxazolyl-5 |
| 185 | 3-(3'-CH₃O—C₆H₄)-4-Chloroisoxazolyl-5 |
| 186 | 3-(2'-CH₃O—C₆H₄)-4-Chloroisoxazolyl-5 |
| 187 | 3-(4'-NO₂—C₆H₄)-4-Chloroisoxazolyl-5 |
| 188 | 3-(3'-NO₂—C₆H₄)-4-Chloroisoxazolyl-5 |
| 189 | 3-(2'-NO₂—C₆H₄)-4-Chloroisoxazolyl-5 |
| 190 | 3-(4'-CN—C₆H₄)-4-Chloroisoxazolyl-5 |
| 191 | 3-(3'-CN—C₆H₄)-4-Chloroisoxazolyl-5 |
| 192 | 3-(2'-CN—C₆H₄)-4-Chloroisoxazolyl-5 |
| 193 | 3-(4'-Cl—C₆H₄)-4-Chloroisoxazolyl-5 |
| 194 | 3-(3'-Cl—C₆H₄)-4-Chloroisoxazolyl-5 |
| 195 | 3-(2'-Cl—C₆H₄)-4-Chloroisoxazolyl-5 |
| 196 | Isoxazolyl-3 |
| 197 | 5-CH₃-Isoxazolyl-3 |
| 198 | 5-C₆H₅-Isoxazolyl-3 |
| 199 | 5-(4'-CH₃—C₆H₄)-Isoxazolyl-3 |
| 200 | 5-(3'-CH₃—C₆H₄)-Isoxazolyl-3 |
| 201 | 5-(2'-CH₃—C₆H₄)-Isoxazolyl-3 |
| 202 | 5-(4'-CH₃O—C₆H₄)-Isoxazolyl-3 |
| 203 | 5-(3'-CH₃O—C₆H₄)-Isoxazolyl-3 |
| 204 | 5-(2'-CH₃O—C₆H₄)-Isoxazolyl-3 |
| 205 | 5-(4'-NO₂—C₆H₄)-Isoxazolyl-3 |
| 206 | 5-(3'-NO₂—C₆H₄)-Isoxazolyl-3 |
| 207 | 5-(2'-NO₂—C₆H₄)-Isoxazolyl-3 |
| 208 | 5-(4'-CN—C₆H₄)-Isoxazolyl-3 |
| 209 | 5-(3'-CN—C₆H₄)-Isoxazolyl-3 |
| 210 | 5-(2'-CN—C₆H₄)-Isoxazolyl-3 |
| 211 | 5-(4'-Cl—C₆H₄)-Isoxazolyl-3 |
| 212 | 5-(3'-Cl—C₆H₄)-Isoxazolyl-3 |
| 213 | 5-(2'-Cl—C₆H₄)-Isoxazolyl-3 |
| 214 | Isothiazolyl-5 |
| 215 | 3-CH₃-Isothiazolyl-5 |
| 216 | 3-C₆H₅-Isothiazolyl-5 |
| 217 | 3-(4'-CH₃—C₆H₄)-Isothiazolyl-5 |
| 218 | 3-(3'-CH₃—C₆H₄)-Isothiazolyl-5 |
| 219 | 3-(2'-CH₃—C₆H₄)-Isothiazolyl-5 |
| 220 | 3-(4'-CH₃O—C₆H₄)-Isothiazolyl-5 |
| 221 | 3-(3'-CH₃O—C₆H₄)-Isothiazolyl-5 |
| 222 | 3-(2'-CH₃O—C₆H₄)-Isothiazolyl-5 |
| 223 | 3-(4'-NO₂—C₆H₄)-Isothiazolyl-5 |
| 224 | 3-(3'-NO₂—C₆H₄)-Isothiazolyl-5 |
| 225 | 3-(2'-NO₂—C₆H₄)-Isothiazolyl-5 |
| 226 | 3-(4'-CN—C₆H₄)-Isothiazolyl-5 |
| 227 | 3-(3'-CN—C₆H₄)-Isothiazolyl-5 |
| 228 | 3-(2'-CN—C₆H₄)-Isothiazolyl-5 |
| 229 | 3-(4'-Cl—C₆H₄)-Isothiazolyl-5 |
| 230 | 3-(3'-Cl—C₆H₄)-Isothiazolyl-5 |
| 231 | 3-(2'-Cl—C₆H₄)-Isothiazolyl-5 |
| 232 | Oxazolyl-4 |
| 233 | 3-CH₃-Oxazolyl-4 |
| 234 | 3-C₆H₅-Oxazolyl-4 |
| 235 | 3-(4'-CH₃—C₆H₄)-Oxazolyl-4 |
| 236 | 3-(3'-CH₃—C₆H₄)-Oxazolyl-4 |
| 237 | 3-(2'-CH₃—C₆H₄)-Oxazolyl-4 |
| 238 | 3-(4'-CH₃O—C₆H₄)-Oxazolyl-4 |
| 239 | 3-(3'-CH₃O—C₆H₄)-Oxazolyl-4 |
| 240 | 3-(2'-CH₃O—C₆H₄)-Oxazolyl-4 |
| 241 | 3-(4'-NO₂—C₆H₄)-Oxazolyl-4 |
| 242 | 3-(3'-NO₂—C₆H₄)-Oxazolyl-4 |
| 243 | 3-(2'-NO₂—C₆H₄)-Oxazolyl-4 |
| 244 | 3-(4'-CN—C₆H₄)-Oxazolyl-4 |
| 245 | 3-(3'-CN—C₆H₄)-Oxazolyl-4 |
| 246 | 3-(2'-CN—C₆H₄)-Oxazolyl-4 |
| 247 | 3-(4'-Cl—C₆H₄)-Oxazolyl-4 |
| 248 | 3-(3'-Cl—C₆H₄)-Oxazolyl-4 |
| 249 | 3-(2'-Cl—C₆H₄)-Oxazolyl-4 |
| 250 | Thiazolyl-4 |
| 251 | 2-CH₃-Thiazolyl-4 |
| 252 | 2-C₆H₅-Thiazolyl-4 |
| 253 | 2-(4'-CH₃—C₆H₄)-Thiazolyl-4 |
| 254 | 2-(3'-CH₃—C₆H₄)-Thiazolyl-4 |
| 255 | 2-(2'-CH₃—C₆H₄)-Thiazolyl-4 |
| 256 | 2-(4'-CH₃O—C₆H₄)-Thiazolyl-4 |
| 267 | 2-(3'-CH₃O—C₆H₄)-Thiazolyl-4 |
| 258 | 2-(2'-CH₃O—C₆H₄)-Thiazolyl-4 |
| 259 | 2-(4'-NO₂—C₆H₄)-Thiazolyl-4 |
| 260 | 2-(3'-NO₂—C₆H₄)-Thiazolyl-4 |
| 261 | 2-(2'-NO₂—C₆H₄)-Thiazolyl-4 |
| 262 | 2-(4'-CN—C₆H₄)-Thiazolyl-4 |
| 263 | 2-(3'-CN—C₆H₄)-Thiazolyl-4 |
| 264 | 2-(2'-CN—C₆H₄)-Thiazolyl-4 |
| 265 | 2-(4'-Cl—C₆H₄)-Thiazolyl-4 |
| 66 | 2-(3'-Cl—C₆H₄)-Thiazolyl-4 |
| 267 | 2-(2'-Cl—C₆H₄)-Thiazolyl-4 |
| 268 | N—CH₃-1,2,4-Triazolyl-5 |
| 269 | 3-CH₃—N—CH₃-1,2,4-Triazolyl-5 |
| 270 | 3-C₆H₅—N—CH₃-1,2,4-Triazolyl-5 |
| 271 | 3-(4'-CH₃—C₆H₄)—N—CH₃-1,2,4-Triazolyl-5 |
| 272 | 3-(3'-CH₃—C₆H₄)—N—CH₃-1,2,4-Triazolyl-5 |
| 273 | 3-(2'-CH₃—C₆H₄)—N—CH₃-1,2,4-Triazolyl-5 |
| 274 | 3-(4'-CH₃O—C₆H₄)—N—CH₃-1,2,4-Triazolyl-5 |
| 275 | 3-(3'-CH₃O—C₆H₄)—N—CH₃-1,2,4-Triazolyl-5 |
| 276 | 3-(2'-CH₃O—C₆H₄)—N—CH₃-1,2,4-Triazolyl-5 |
| 277 | 3-(4'-NO₂—C₆H₄)—N—CH₃-1,2,4-Triazolyl-5 |
| 278 | 3-(3'-NO₂—C₆H₄)—N—CH₃-1,2,4-Triazolyl-5 |
| 279 | 3-(2'-NO₂—C₆H₄)—N—CH₃-1,2,4-Triazolyl-5 |
| 280 | 3-(4'-CN—C₆H₄)—N—CH₃-1,2,4-Triazolyl-5 |
| 281 | 3-(3'-CN—C₆H₄)—N—CH₃-1,2,4-Triazolyl-5 |
| 282 | 3-(2'-CN—C₆H₄)—N—CH₃-1,2,4-Triazolyl-5 |
| 283 | 3-(4'-Cl—C₆H₄)—N—CH₃-1,2,4-Triazolyl-5 |
| 284 | 3-(3'-Cl—C₆H₄)—N—CH₃-1,2,4-Triazolyl-5 |
| 285 | 3-(2'-Cl—C₆H₄)—N—CH₃-1,2,4-Triazolyl-5 |
| 286 | 1,3,4-Oxadiazolyl-2 |
| 287 | 5-CH₃-1,3,4-Oxadiazolyl-2 |
| 288 | 5-C₆H₅-1,3,4-Oxadiazolyl-2 |
| 289 | 5-(4'-CH₃—C₆H₄)-1,3,4-Oxadiazolyl-2 |
| 290 | 5-(3'-CH₃—C₆H₄)-1,3,4-Oxadiazolyl-2 |
| 291 | 5-(2'-CH₃—C₆H₄)-1,3,4-Oxadiazolyl-2 |
| 292 | 5-(4'-CH₃O—C₆H₄)-1,3,4-Oxadiazolyl-2 |
| 293 | 5-(3'-CH₃O—C₆H₄)-1,3,4-Oxadiazolyl-2 |
| 294 | 5-(2'-CH₃O—C₆H₄)-1,3,4-Oxadiazolyl-2 |
| 295 | 5-(4'-NO₂—C₆H₄)-1,3,4-Oxadiazolyl-2 |
| 296 | 5-(3'-NO₂—C₆H₄)-1,3,4-Oxadiazolyl-2 |
| 297 | 5-(2'-NO₂—C₆H₄)-1,3,4-Oxadiazolyl-2 |
| 298 | 5-(4'-CN—C₆H₄)-1,3,4-Oxadiazolyl-2 |
| 299 | 5-(3'-CN—C₆H₄)-1,3,4-Oxadiazolyl-2 |
| 300 | 5-(2'-CN—C₆H₄)-1,3,4-Oxadiazolyl-2 |
| 301 | 5-(4'-Cl—C₆H₄)-1,3,4-Oxadiazolyl-2 |
| 302 | 5-(3'-Cl—C₆H₄)-1,3,4-Oxadiazolyl-2 |
| 303 | 5-(2'-Cl—C₆H₄)-1,3,4-Oxadiazolyl-2 |
| 304 | 1,2,4-Oxadiazolyl-3 |
| 305 | 5-CH₃-1,2,4-Oxadiazolyl-3 |
| 306 | 5-C₆H₅-1,2,4-Oxadiazolyl-3 |
| 307 | 5-(4'-CH₃—C₆H₄)-1,2,4-Oxadiazolyl-3 |
| 308 | 5-(3'-CH₃—C₆H₄)-1,2,4-Oxadiazolyl-3 |
| 309 | 5-(2'-CH₃—C₆H₄)-1,2,4-Oxadiazolyl-3 |
| 310 | 5-(4'-CH₃O—C₆H₄)-1,2,4-Oxadiazolyl-3 |
| 311 | 5-(3'-CH₃O—C₆H₄)-1,2,4-Oxadiazolyl-3 |
| 312 | 5-(2'-CH₃O—C₆H₄)-1,2,4-Oxadiazolyl-3 |
| 313 | 5-(4'-NO₂—C₆H₄)-1,2,4-Oxadiazolyl-3 |
| 314 | 5-(3'-NO₂—C₆H₄)-1,2,4-Oxadiazolyl-3 |
| 315 | 5-(2'-NO₂—C₆H₄)-1,2,4-Oxadiazolyl-3 |
| 316 | 5-(4'-CN—C₆H₄)-1,2,4-Oxadiazolyl-3 |
| 317 | 5-(3'-CN—C₆H₄)-1,2,4-Oxadiazolyl-3 |
| 318 | 5-(2'-CN—C₆H₄)-1,2,4-Oxadiazolyl-3 |
| 319 | 5-(4'-Cl—C₆H₄)-1,2,4-Oxadiazolyl-3 |
| 320 | 5-(3'-Cl—C₆H₄)-1,2,4-Oxadiazolyl-3 |
| 321 | 5-(2'-Cl—C₆H₄)-1,2,4-Oxadiazolyl-3 |
| 322 | 1,2,4-Oxadiazolyl-5 |
| 323 | 3-CH₃-1,2,4-Oxadiazolyl-5 |
| 324 | 3-C₆H₅-1,2,4-Oxadiazolyl-5 |

TABLE 2-continued

| | |
|---|---|
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | 1-Naphthyl |
| 385 | 2-Naphthyl |

TABLE 3

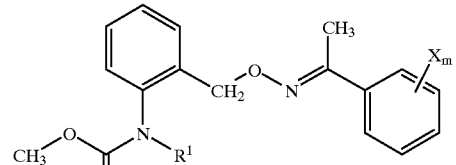

I: $R^1$ = H
II: $R^1$ = CH$_3$
III: $R^1$ = Allyl
IV: $R^1$ = Propargyl
V: $R^1$ = S—CH$_3$
VI: $R^1$ = CH$_2$—CN
VII: $R^1$ = CH$_2$—O—CH$_3$
VIII: $R^1$ = CO—OCH$_3$

| No. | X$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |

TABLE 3-continued

| | |
|---|---|
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |

TABLE 3-continued

| | |
|---|---|
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)—CH$_3$ |
| 333 | 3-C(=NO-Allyl)—CH$_3$ |
| 334 | 4-C(=NO-Allyl)—CH$_3$ |
| 335 | 2-C(=NO-trans-Chloroallyl)—CH$_3$ |
| 336 | 3-C(=NO-trans-Chloroallyl)—CH$_3$ |
| 337 | 4-C(=NO-trans-Chloroallyl)—CH$_3$ |
| 338 | 2-C(=NO-Propargyl)—CH$_3$ |
| 339 | 3-C(=NO-Propargyl)—CH$_3$ |
| 340 | 4-C(=NO-Propargyl)—CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |

TABLE 3-continued

| | |
|---|---|
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))—C$_6$H$_4$) |
| 424 | 2-(3'-(CH$_3$—C(=NOAllyl))—C$_6$H$_4$) |
| 425 | 2-(4'-(CH$_3$—C(=NOAllyl))—C$_6$H$_4$) |
| 426 | 3-(2'-(CH$_3$—C(=NOAllyl))—C$_6$H$_4$) |
| 427 | 3-(3'-(CH$_3$—C(=NOAllyl))—C$_6$H$_4$) |
| 428 | 3-(4'-(CH$_3$—C(=NOAllyl))—C$_6$H$_4$) |
| 429 | 4-(2'-(CH$_3$—C(=NOAllyl))—C$_6$H$_4$) |
| 430 | 4-(3'-(CH$_3$—C(=NOAllyl))—C$_6$H$_4$) |
| 431 | 4-(4'-(CH$_3$—C(=NOAllyl))—C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |

TABLE 3-continued

| | |
|---|---|
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))—C$_6$H$_4$) |
| 516 | 2-O-(3'-(CH$_3$—C(=NOAllyl))—C$_6$H$_4$) |
| 517 | 2-O-(4'-(CH$_3$—C(=NOAllyl))—C$_6$H$_4$) |
| 518 | 3-O-(2'-(CH$_3$—C(=NOAllyl))—C$_6$H$_4$) |
| 519 | 3-O-(3'-(CH$_3$—C(=NOAllyl))—C$_6$H$_4$) |
| 520 | 3-O-(4'-(CH$_3$—C(=NOAllyl))—C$_6$H$_4$) |
| 521 | 4-O-(2'-(CH$_3$—C(=NOAllyl))—C$_6$H$_4$) |
| 522 | 4-O-(3'-(CH$_3$—C(=NOAllyl))—C$_6$H$_4$) |
| 523 | 4-O-(4'-(CH$_3$—C(=NOAllyl))—C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |

TABLE 3-continued

| | |
|---|---|
| 528 | 3-O-(3'-$CH_3O_2C$—$C_6H_4$) |
| 529 | 3-O-(4'-$CH_3O_2C$—$C_6H_4$) |
| 530 | 4-O-(2'-$CH_3O_2C$—$C_6H_4$) |
| 531 | 4-O-(3'-$CH_3O_2C$—$C_6H_4$) |
| 532 | 4-O-(4'-$CH_3O_2C$—$C_6H_4$) |
| 533 | 2-O-(2'-$CH_3O$—$C_6H_4$) |
| 534 | 2-O-(3'-$CH_3O$—$C_6H_4$) |
| 535 | 2-O-(4'-$CH_3O$—$C_6H_4$) |
| 536 | 3-O-(2'-$CH_3O$—$C_6H_4$) |
| 537 | 3-O-(3'-$CH_3O$—$C_6H_4$) |
| 538 | 3-O-(4'-$CH_3O$—$C_6H_4$) |
| 539 | 4-O-(2'-$CH_3O$—$C_6H_4$) |
| 540 | 4-O-(3'-$CH_3O$—$C_6H_4$) |
| 541 | 4-O-(4'-$CH_3O$—$C_6H_4$) |
| 542 | 2-O-(2'-$O_2N$—$C_6H_4$) |
| 543 | 2-O-(3'-$O_2N$—$C_6H_4$) |
| 544 | 2-O-(4'-$O_2N$—$C_6H_4$) |
| 545 | 3-O-(2'-$O_2N$—$C_6H_4$) |
| 546 | 3-O-(3'-$O_2N$—$C_6H_4$) |
| 547 | 3-O-(4'-$O_2N$—$C_6H_4$) |
| 548 | 4-O-(2'-$O_2N$—$C_6H_4$) |
| 549 | 4-O-(3'-$O_2N$—$C_6H_4$) |
| 550 | 4-O-(4'-$O_2N$—$C_6H_4$) |
| 551 | 2-O-(2'-NC—$C_6H_4$) |
| 552 | 2-O-(3'-NC—$C_6H_4$) |
| 553 | 2-O-(4'-NC—$C_6H_4$) |
| 554 | 3-O-(2'-NC—$C_6H_4$) |
| 555 | 3-O-(3'-NC—$C_6H_4$) |
| 556 | 3-O-(4'-NC—$C_6H_4$) |
| 557 | 4-O-(2'-NC—$C_6H_4$) |
| 558 | 4-O-(3'-NC—$C_6H_4$) |
| 559 | 4-O-(4'-NC—$C_6H_4$) |
| 560 | 2-O-(2'-$CF_3$—$C_6H_4$) |
| 561 | 2-O-(3'-$CF_3$—$C_6H_4$) |
| 562 | 2-O-(4'-$CF_3$—$C_6H_4$) |
| 563 | 3-O-(2'-$CF_3$—$C_6H_4$) |
| 564 | 3-O-(3'-$CF_3$—$C_6H_4$) |
| 565 | 3-O-(4'-$CF_3$—$C_6H_4$) |
| 566 | 4-O-(2'-$CF_3$—$C_6H_4$) |
| 567 | 4-O-(3'-$CF_3$—$C_6H_4$) |
| 568 | 4-O-(4'-$CF_3$—$C_6H_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-$CH_3$-4-($CH_3$—C=N—O—$CH_2$—$CH_2$—$OCH_3$) |
| 642 | 2-$CH_3$-4-($C_2H_5$—C=N—O—$CH_2$—$CH_2$—$OCH_3$) |
| 643 | 2,5-$(CH_3)_2$-4-($CH_3$—C=N—O—$CH_2$—$CH_2$—$OCH_3$) |
| 644 | 2-$CH_3$-4-(n-$C_3H_7$—C=N—$OCH_3$) |
| 645 | 2-$CH_3$-4-(n-$C_3H_7$—C=N—$OC_2H_5$) |
| 646 | 2-$CH_3$-4-(n-$C_3H_7$—C=N—O-n-$C_3H_7$) |
| 647 | 2-$CH_3$-4-(n-$C_3H_7$—C=N—O-i-$C_3H_7$) |
| 648 | 2-$CH_3$-4-(n-$C_3H_7$—C=N—O-Allyl) |
| 649 | 2-$CH_3$-4-(n-$C_3H_7$—C=N—O-trans-Chloroallyl) |
| 650 | 2-$CH_3$-4-(n-$C_3H_7$—C=N—O-Propargyl) |
| 651 | 2-$CH_3$-4-(n-$C_3H_7$—C=N—O-n-$C_4H_9$) |
| 652 | 2-$CH_3$-4-(n-$C_3H_7$—C=N—O—$CH_2$—$C_6H_5$) |
| 653 | 2-$CH_3$-4-(i-$C_3H_7$—C=N—$OCH_3$) |
| 654 | 2-$CH_3$-4-(i-$C_3H_7$—C=N—$OC_2H_5$) |
| 655 | 2-$CH_3$-4-(i-$C_3H_7$—C=N—O-n-$C_3H_7$) |
| 656 | 2-$CH_3$-4-(i-$C_3H_7$—C=N—O-i-$C_3H_7$) |
| 657 | 2-$CH_3$-4-(i-$C_3H_7$—C=N—O-Allyl) |
| 658 | 2-$CH_3$-4-(i-$C_3H_7$—C=N—O-trans-Chloroallyl) |
| 659 | 2-$CH_3$-4-(i-$C_3H_7$—C=N—O-Propargyl) |
| 660 | 2-$CH_3$-4-(i-$C_3H_7$—C=N—O-n-$C_4H_9$) |
| 661 | 2-$CH_3$-4-(i-$C_3H_7$—C=N—O—$CH_2$—$C_6H_5$) |
| 662 | 2-O-n-$C_4H_9$ |
| 663 | 2-O-i-$C_4H_9$ |
| 664 | 2-O-s-$C_4H_9$ |
| 665 | 2-O-t-$C_4H_9$ |
| 666 | 2-Neopentyloxy |
| 667 | 3-O-n-$C_4H_9$ |
| 668 | 3-O-i-$C_4H_9$ |
| 669 | 3-O-s-$C_4H_9$ |
| 670 | 3-O-t-$C_4H_9$ |
| 671 | 3-Neopentyloxy |
| 672 | 4-O-n-$C_4H_9$ |
| 673 | 4-O-i-$C_4H_9$ |
| 674 | 4-O-s-$C_4H_9$ |
| 675 | 4-O-t-$C_4H_9$ |
| 676 | 4-Neopentyloxy |
| 677 | 3-$CH_3$-4-$OCH_3$ |
| 678 | 3-$CH_3$-4-$OC_2H_5$ |
| 679 | 3-$CH_3$-4-O-n-$C_3H_7$ |
| 680 | 3-$CH_3$-4-O-n-$C_4H_9$ |
| 681 | 3-$CH_3$-4-O-i-$C_4H_9$ |
| 682 | 3-$CH_3$-4-O-s-$C_4H_9$ |
| 683 | 3-$CH_3$-4-O-t-$C_4H_9$ |
| 684 | 2-$CH_3$-4-Neopentyloxy |
| 685 | 2-$CH_3$-3-$OCH_3$ |

TABLE 3-continued

| | |
|---|---|
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 4

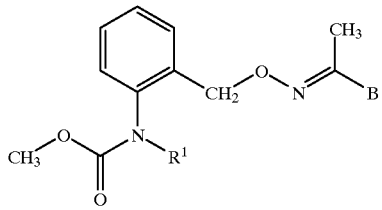

| | |
|---|---|
| I: | R$^1$ = H |
| II: | R$^1$ = CH$_3$ |
| III: | R$^1$ = Allyl |
| IV: | R$^1$ = Propargyl |
| V: | R$^1$ = S—CH$_3$ |
| VI: | R$^1$ = CH$_2$—CN |
| VII: | R$^1$ = CH$_2$—O—CH$_3$ |
| VIII: | R$^1$ = CO—OCH$_3$ |

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |

TABLE 4-continued

| | |
|---|---|
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |

TABLE 4-continued

| | |
|---|---|
| 102 | 4-(3'-CN—C₆H₄)-Thienyl-2 |
| 103 | 4-(2'-CN—C₆H₄)-Thienyl-2 |
| 104 | 4-(4'-CN—C₆H₄)-Thienyl-2 |
| 105 | 4-(3'-Cl—C₆H₄)-Thienyl-2 |
| 106 | 4-(2'-Cl—C₆H₄)-Thienyl-2 |
| 107 | Thienyl-3 |
| 108 | 5-CH₃-Thienyl-3 |
| 109 | 5-C₆H₅-Thienyl-3 |
| 110 | 5-(4'-CH₃—C₆H₄)-Thienyl-3 |
| 111 | 5-(3'-CH₃—C₆H₄)-Thienyl-3 |
| 112 | 5-(2'-CH₃—C₆H₄)-Thienyl-3 |
| 113 | 5-(4'-CH₃O—C₆H₄)-Thienyl-3 |
| 114 | 5-(3'-CH₃O—C₆H₄)-Thienyl-3 |
| 115 | 5-(2'-CH₃O—C₆H₄)-Thienyl-3 |
| 116 | 5-(4'-NO₂—C₆H₄-)-Thienyl-3 |
| 117 | 5-(3'-NO₂—C₆H₄)-Thienyl-3 |
| 118 | 5-(2'-NO₂—C₆H₄)-Thienyl-3 |
| 119 | 5-(4'-CN—C₆H₄)-Thienyl-3 |
| 120 | 5-(3'-CN—C₆H₄)-Thienyl-3 |
| 121 | 5-(2'-CN—C₆H₄)-Thienyl-3 |
| 122 | 5-(4'-Cl—C₆H₄)-Thienyl-3 |
| 123 | 5-(3'-Cl—C₆H₄)-Thienyl-3 |
| 124 | 5-(2'-Cl—C₆H₄)-Thienyl-3 |
| 125 | Pyrazolyl-4 |
| 126 | N—CH₃-Pyrazolyl-4 |
| 127 | N—C₆H₅-Pyrazolyl-4 |
| 128 | N-(4'-CH₃—C₆H₄)-Pyrazolyl-4 |
| 129 | N-(3'-CH₃—C₆H₄)-Pyrazolyl-4 |
| 130 | N-(2'-CH₃—C₆H₄)-Pyrazolyl-4 |
| 131 | N-(4'-CH₃O—C₆H₄)-Pyrazolyl-4 |
| 132 | N-(3'-CH₃O—C₆H₄)-Pyrazolyl-4 |
| 133 | N-(2'-CH₃O—C₆H₄)-Pyrazolyl-4 |
| 134 | N-(4'-NO₂—C₆H₄)-Pyrazolyl-4 |
| 135 | N-(3'-NO₂—C₆H₄)-Pyrazolyl-4 |
| 136 | N-(2'-NO₂—C₆H₄)-Pyrazolyl-4 |
| 137 | N-(4'-CN—C₆H₄)-Pyrazolyl-4 |
| 138 | N-(3'-CN—C₆H₄)-Pyrazolyl-4 |
| 139 | N-(2'-CN—C₆H₄)-Pyrazolyl-4 |
| 140 | N-(4'-Cl—C₆H₄)-Pyrazolyl-4 |
| 141 | N-(3'-Cl—C₆H₄)-Pyrazolyl-4 |
| 142 | N-(2'-Cl—C₆H₄)-Pyrazolyl-4 |
| 143 | 3-CH₃—N-Methylpyrazolyl-4 |
| 144 | 3-C₆H₅—N-Methylpyrazolyl-4 |
| 145 | 3-(4'-CH₃—C₆H₄)-N-Methylpyrazolyl-4 |
| 146 | 3-(3'-CH₃—C₆H₄)-N-Methylpyrazolyl-4 |
| 147 | 3-(2'-CH₃—C₆H₄)-N-Methylpyrazolyl-4 |
| 148 | 3-(4'-CH₃O—C₆H₄)-N-Methylpyrazolyl-4 |
| 149 | 3-(3'-CH₃O—C₆H₄)-N-Methylpyrazolyl-4 |
| 150 | 3-(2'-CH₃O—C₆H₄)-N-Methylpyrazolyl-4 |
| 151 | 3-(4'-NO₂—C₆H₄)-N-Methylpyrazolyl-4 |
| 152 | 3-(3'-NO₂—C₆H₄)-N-Methylpyrazolyl-4 |
| 153 | 3-(2'-NO₂—C₆H₄)-N-Methylpyrazolyl-4 |
| 154 | 3-(4'-CN—C₆H₄)-N-Methylpyrazolyl-4 |
| 155 | 3-(3'-CN—C₆H₄)-N-Methylpyrazolyl-4 |
| 156 | 3-(2'-CN—C₆H₄)-N-Methylpyrazolyl-4 |
| 157 | 3-(4'-Cl—C₆H₄)-N-Methylpyrazolyl-4 |
| 158 | 3-(3'-Cl—C₆H₄)-N-Methylpyrazolyl-4 |
| 159 | 3-(2'-Cl—C₆H₄)-N-Methylpyrazolyl-4 |
| 160 | Isoxazolyl-5 |
| 161 | 3-CH₃-Isoxazolyl-5 |
| 162 | 3-C₆H₅-Isoxazolyl-5 |
| 163 | 3-(4'-CH₃—C₆H₄)-Isoxazolyl-5 |
| 164 | 3-(3'-CH₃—C₆H₄)-Isoxazolyl-5 |
| 165 | 3-(2'-CH₃—C₆H₄)-Isoxazolyl-5 |
| 166 | 3-(4'-CH₃O—C₆H₄)-Isoxazolyl-5 |
| 167 | 3-(3'-CH₃O—C₆H₄)-Isoxazolyl-5 |
| 168 | 3-(2'-CH₃O—C₆H₄)-Isoxazolyl-5 |
| 169 | 3-(4'-NO₂—C₆H₄)-Isoxazolyl-5 |
| 170 | 3-(3'-NO₂—C₆H₄)-Isoxazolyl-5 |
| 171 | 3-(2'-NO₂—C₆H₄)-Isoxazolyl-5 |
| 172 | 3-(4'-CN—C₆H₄)-Isoxazolyl-5 |
| 173 | 3-(3'-CN—C₆H₄)-Isoxazolyl-5 |
| 174 | 3-(2'-CN—C₆H₄)-Isoxazolyl-5 |
| 175 | 3-(4'-Cl—C₆H₄)-Isoxazolyl-5 |
| 176 | 3-(3'-Cl—C₆H₄)-Isoxazolyl-5 |
| 177 | 3-(2'-Cl—C₆H₄)-Isoxazolyl-5 |
| 178 | 4-Chloroisoxazolyl-5 |
| 179 | 3-CH₃-4-Chloroisoxazolyl-5 |
| 180 | 3-C₆H₅-4-Chloroisoxazolyl-5 |
| 181 | 3-(4'-CH₃—C₆H₄)-4-Chloroisoxazolyl-5 |
| 182 | 3-(3'-CH₃—C₆H₄)-4-Chloroisoxazolyl-5 |
| 183 | 3-(2'-CH₃—C₆H₄)-4-Chloroisoxazolyl-5 |
| 184 | 3-(4'-CH₃O—C₆H₄)-4-Chloroisoxazolyl-5 |
| 185 | 3-(3'-CH₃O—C₆H₄)-4-Chloroisoxazolyl-5 |
| 186 | 3-(2'-CH₃O—C₆H₄)-4-Chloroisoxazolyl-5 |
| 187 | 3-(4'-NO₂—C₆H₄)-4-Chloroisoxazolyl-5 |
| 188 | 3-(3'-NO₂—C₆H₄)-4-Chloroisoxazolyl-5 |
| 189 | 3-(2'-NO₂—C₆H₄)-4-Chloroisoxazolyl-5 |
| 190 | 3-(4'-CN—C₆H₄)-4-Chloroisoxazolyl-5 |
| 191 | 3-(3'-CN—C₆H₄)-4-Chloroisoxazolyl-5 |
| 192 | 3-(2'-CN—C₆H₄)-4-Chloroisoxazolyl-5 |
| 193 | 3-(4'-Cl—C₆H₄)-4-Chloroisoxazolyl-5 |
| 194 | 3-(3'-Cl—C₆H₄)-4-Chloroisoxazolyl-5 |
| 195 | 3-(2'-Cl—C₆H₄)-4-Chloroisoxazolyl-5 |
| 196 | Isoxazolyl-3 |
| 197 | 5-CH₃-Isoxazolyl-3 |
| 198 | 5-C₆H₅-Isoxazolyl-3 |
| 199 | 5-(4'-CH₃—C₆H₄)-Isoxazolyl-3 |
| 200 | 5-(3'-CH₃—C₆H₄)-Isoxazolyl-3 |
| 201 | 5-(2'-CH₃—C₆H₄)-Isoxazolyl-3 |
| 202 | 5-(4'-CH₃O—C₆H₄)-Isoxazolyl-3 |
| 203 | 5-(3'-CH₃O—C₆H₄)-Isoxazolyl-3 |
| 204 | 5-(2'-CH₃O—C₆H₄)-Isoxazolyl-3 |
| 205 | 5-(4'-NO₂—C₆H₄)-Isoxazolyl-3 |
| 206 | 5-(3'-NO₂—C₆H₄)-Isoxazolyl-3 |
| 207 | 5-(2'-NO₂—C₆H₄)-Isoxazolyl-3 |
| 208 | 5-(4'-CN—C₆H₄)-Isoxazolyl-3 |
| 209 | 5-(3'-CN—C₆H₄)-Isoxazolyl-3 |
| 210 | 5-(2'-CN—C₆H₄)-Isoxazolyl-3 |
| 211 | 5-(4'-Cl—C₆H₄)-Isoxazolyl-3 |
| 212 | 5-(3'-Cl—C₆H₄)-Isoxazolyl-3 |
| 213 | 5-(2'-Cl—C₆H₄)-Isoxazolyl-3 |
| 214 | Isothiazolyl-5 |
| 215 | 3-CH₃-Isothiazolyl-5 |
| 216 | 3-C₆H₅-Isothiazolyl-5 |
| 217 | 3-(4'-CH₃—C₆H₄)-Isothiazolyl-5 |
| 218 | 3-(3'-CH₃—C₆H₄)-Isothiazolyl-5 |
| 219 | 3-(2'-CH₃—C₆H₄)-Isothiazolyl-5 |
| 220 | 3-(4'-CH₃O—C₆H₄)-Isothiazolyl-5 |
| 221 | 3-(3'-CH₃O—C₆H₄)-Isothiazolyl-5 |
| 222 | 3-(2'-CH₃O—C₆H₄)-Isothiazolyl-5 |
| 223 | 3-(4'-NO₂—C₆H₄)-Isothiazolyl-5 |
| 224 | 3-(3'-NO₂—C₆H₄)-Isothiazolyl-5 |
| 225 | 3-(2'-NO₂—C₆H₄)-Isothiazolyl-5 |
| 226 | 3-(4'-CN—C₆H₄)-Isothiazolyl-5 |
| 227 | 3-(3'-CN—C₆H₄)-Isothiazolyl-5 |
| 228 | 3-(2'-CN—C₆H₄)-Isothiazolyl-5 |
| 229 | 3-(4'-Cl—C₆H₄)-Isothiazolyl-5 |
| 230 | 3-(3'-Cl—C₆H₄)-Isothiazolyl-5 |
| 231 | 3-(2'-Cl—C₆H₄)-Isothiazolyl-5 |
| 232 | Oxazolyl-4 |
| 233 | 2-CH₃-Oxazolyl-4 |
| 234 | 2-C₆H₅-Oxazolyl-4 |
| 235 | 2-(4'-CH₃—C₆H₄)-Oxazolyl-4 |
| 236 | 2-(3'-CH₃—C₆H₄)-Oxazolyl-4 |
| 237 | 2-(2'-CH₃—C₆H₄)-Oxazolyl-4 |
| 238 | 2-(4'-CH₃O—C₆H₄)-Oxazolyl-4 |
| 239 | 2-(3'-CH₃O—C₆H₄)-Oxazolyl-4 |
| 240 | 2-(2'-CH₃O—C₆H₄)-Oxazolyl-4 |
| 241 | 2-(4'-NO₂—C₆H₄)-Oxazolyl-4 |
| 242 | 2-(3'-NO₂—C₆H₄)-Oxazolyl-4 |
| 243 | 2-(2'-NO₂—C₆H₄)-Oxazolyl-4 |
| 244 | 2-(4'-CN—C₆H₄)-Oxazolyl-4 |
| 245 | 2-(3'-CN—C₆H₄)-Oxazolyl-4 |
| 246 | 2-(2'-CN—C₆H₄)-Oxazolyl-4 |
| 247 | 2-(4'-Cl—C₆H₄)-Oxazolyl-4 |
| 248 | 2-(3'-Cl—C₆H₄)-Oxazolyl-4 |
| 249 | 2-(2'-Cl—C₆H₄)-Oxazolyl-4 |
| 250 | Thiazolyl-4 |
| 251 | 2-CH₃-Thiazolyl-4 |
| 252 | 2-C₆H₅-Thiazolyl-4 |
| 253 | 2-(4'-CH₃—C₆H₄)-Thiazolyl-4 |
| 254 | 2-(3'-CH₃—C₆H₄)-Thiazolyl-4 |
| 255 | 2-(2'-CH₃—C₆H₄)-Thiazolyl-4 |
| 256 | 2-(4'-CH₃O—C₆H₄)-Thiazolyl-4 |
| 257 | 2-(3'-CH₃O—C₆H₄)-Thiazolyl-4 |
| 258 | 2-(2'-CH₃O—C₆H₄)-Thiazolyl-4 |
| 259 | 2-(4'-NO₂—C₆H₄)-Thiazolyl-4 |

TABLE 4-continued

| No. | |
|---|---|
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,2,3-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |
| 385 | 1-Naphthyl |
| 386 | 2-Naphthyl |

TABLE 5

[Structure: a benzene ring connected via a —CH=CH— (trans-alkene) to another benzene ring bearing substituent X$_m$; the first benzene also bears a —N(R$^1$)—C(=O)—OCH$_3$ group]

I: R$^1$ = H
II: R$^1$ = CH$_3$
III: R$^1$ = Allyl
IV: R$^1$ = Propargyl
V: R$^1$ = S—CH$_3$
VI: R$^1$ = CH$_2$—CN
VII: R$^1$ = CH$_2$—O—CH$_3$
VIII: R$^1$ = CO—OCH$_3$

| No. | X$_m$ |
|---|---|
| 1 | H |
| 2 | 2-F |

TABLE 5-continued

| | |
|---|---|
| 3 | 3-F |
| 4 | 4-F |
| 5 | 2,4-$F_2$ |
| 6 | 2,4,6-$F_3$ |
| 7 | 2,3,4,5,6-$F_5$ |
| 8 | 2,3-$F_2$ |
| 9 | 2-Cl |
| 10 | 3-Cl |
| 11 | 4-Cl |
| 12 | 2,3-$Cl_2$ |
| 13 | 2,4-$Cl_2$ |
| 14 | 2,5-$Cl_2$ |
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |
| 37 | 4-I |
| 38 | 2,4-$I_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-$Cl_2$, 4-Br |
| 66 | 2-$CH_3$ |
| 67 | 3-$CH_3$ |
| 68 | 4-$CH_3$ |
| 69 | 2,3-$(CH_3)_2$ |
| 70 | 2,4-$(CH_3)_2$ |
| 71 | 2,5-$(CH_3)_2$ |
| 72 | 2,6-$(CH_3)_2$ |
| 73 | 3,4-$(CH_3)_2$ |
| 74 | 3,5-$(CH_3)_2$ |
| 75 | 2,3,5-$(CH_3)_3$ |
| 76 | 2,3,4-$(CH_3)_3$ |
| 77 | 2,3,6-$(CH_3)_3$ |
| 78 | 2,4,5-$(CH_3)_3$ |
| 79 | 2,4,6-$(CH_3)_3$ |

TABLE 5-continued

| | |
|---|---|
| 80 | 3,4,5-$(CH_3)_3$ |
| 81 | 2,3,4,6-$(CH_3)_4$ |
| 82 | 2,3,5,6-$(CH_3)_4$ |
| 83 | 2,3,4,5,6-$(CH_3)_5$ |
| 84 | 2-$C_2H_5$ |
| 85 | 3-$C_2H_5$ |
| 86 | 4-$C_2H_5$ |
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C_2H_5)_3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7)_2$ |
| 98 | 2,6-(i-$C_3H_7)_2$ |
| 99 | 3,5-(i-$C_3H_7)_2$ |
| 100 | 2,4,6-(i-$C_3H_7)_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9)_2$ |
| 108 | 2,4-(t-$C_4H_9)_2$ |
| 109 | 2,5-(t-$C_4H_9)_2$ |
| 110 | 2,6-(t-$C_4H_9)_2$ |
| 111 | 3,4-(t-$C_4H_9)_2$ |
| 112 | 2,4,6-(t-$C_4H_9)_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-$C_4H_9$, 4-$CH_3$ |
| 119 | 2-t-$C_4H_9$, 5-$CH_3$ |
| 120 | 2,6-(t-$C_4H_9)_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9)_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11})_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-$(CH_3)_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |

TABLE 5-continued

| | |
|---|---|
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O-(CH$_2$)$_3$C$_6$H$_5$ |
| 181 | 3-O-(CH$_2$)$_3$C$_6$H$_5$ |
| 182 | 4-O-(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$C(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |

TABLE 5-continued

| | |
|---|---|
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$——CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$ |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |

TABLE 5-continued

| | |
|---|---|
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-CH$_3$—C(=NOAllyl))-C$_6$H$_4$) |
| 516 | 2-O-(3'-CH$_3$—C(=NOAllyl))-C$_6$H$_4$) |
| 517 | 2-O-(4'-CH$_3$—C(=NOAllyl))-C$_6$H$_4$) |
| 518 | 3-O-(2'-CH$_3$—C(=NOAllyl))-C$_6$H$_4$) |
| 519 | 3-O-(3'-CH$_3$—C(=NOAllyl))-C$_6$H$_4$) |
| 520 | 3-O-(4'-CH$_3$—C(=NOAllyl))-C$_6$H$_4$) |
| 521 | 4-O-(2'-CH$_3$—C(=NOAllyl))-C$_6$H$_4$) |
| 522 | 4-O-(3'-CH$_3$—C(=NOAllyl))-C$_6$H$_4$) |
| 523 | 4-O-(4'-CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_5$) |
| 561 | 2-O-(3'-CF$_3$—C$_6$H$_5$) |
| 562 | 2-O-(4'-CF$_3$—C$_6$H$_5$) |
| 563 | 3-O-(2'-CF$_3$—C$_6$H$_5$) |
| 564 | 3-O-(3'-CF$_3$—C$_6$H$_5$) |
| 565 | 3-O-(4'-CF$_3$—C$_6$H$_5$) |
| 566 | 4-O-(2'-CF$_3$—C$_6$H$_5$) |
| 567 | 4-O-(3'-CF$_3$—C$_6$H$_5$) |
| 568 | 4-O-(4'-CF$_3$—C$_6$H$_5$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |

TABLE 5-continued

| | |
|---|---|
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |

TABLE 6

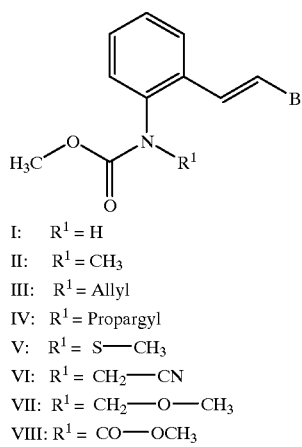

I: $R^1 = H$
II: $R^1 = CH_3$
III: $R^1 = $ Allyl
IV: $R^1 = $ Propargyl
V: $R^1 = S-CH_3$
VI: $R^1 = CH_2-CN$
VII: $R^1 = CH_2-O-CH_3$
VIII: $R^1 = CO-OCH_3$

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |

TABLE 6-continued

| | |
|---|---|
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-2 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |

TABLE 6-continued 120 5-(3'-CN—C$_6$H$_4$)-Thienyl-3
121 5-(2'-CN—C$_6$H$_4$)-Thienyl-3
122 5-(4'-Cl—C$_6$H$_4$)-Thienyl-3
123 5-(3'-Cl—C$_6$H$_4$)-Thienyl-3
124 5-(2'-Cl—C$_6$H$_4$)-Thienyl-3
125 Pyrazolyl-4
126 N—CH$_3$-Pyrazolyl-4
127 N—C$_6$H$_5$-Pyrazolyl-4
128 N-(4'-CH$_3$—C$_6$H$_4$)-Pyrazolyl-4
129 N-(3'-CH$_3$—C$_6$H$_4$)-Pyrazolyl-4
130 N-(2'-CH$_3$—C$_6$H$_4$)-Pyrazolyl-4
131 N-(4'-CH$_3$O—C$_6$H$_4$)-Pyrazolyl-4
132 N-(3'-CH$_3$O—C$_6$H$_4$)-Pyrazolyl-4
133 N-(2'-CH$_3$O—C$_6$H$_4$)-Pyrazolyl-4
134 N-(4'-NO$_2$—C$_6$H$_4$)-Pyrazolyl-4
135 N-(3'-NO$_2$—C$_6$H$_4$)-Pyrazolyl-4
136 N-(2'-NO$_2$—C$_6$H$_4$)-Pyrazolyl-4
137 N-(4'-CN—C$_6$H$_4$)-Pyrazolyl-4
138 N-(3'-CN—C$_6$H$_4$)-Pyrazolyl-4
139 N-(2'-CN—C$_6$H$_4$)-Pyrazolyl-4
140 N-(4'-Cl—C$_6$H$_4$)-Pyrazolyl-4
141 N-(3'-Cl—C$_6$H$_4$)-Pyrazolyl-4
142 N-(2'-Cl—C$_6$H$_4$)-Pyrazolyl-4
143 3-CH$_3$—N-Methylpyrazolyl-4
144 3-C$_5$H$_5$—N-Methylpyrazolyl-4
145 3-(4'-CH$_3$—C$_6$H$_4$)-N-Methylpyrazolyl-4
146 3-(3'-CH$_3$—C$_6$H$_4$)-N-Methylpyrazolyl-4
147 3-(2'-CH$_3$—C$_6$H$_4$)-N-Methylpyrazolyl-4
148 3-(4'-CH$_3$O—C$_6$H$_4$)-N-Methylpyrazolyl-4
149 3-(3'-CH$_3$O—C$_6$H$_4$)-N-Methylpyrazolyl-4
150 3-(2'-CH$_3$O—C$_6$H$_4$)-N-Methylpyrazolyl-4
151 3-(4'-NO$_2$—C$_6$H$_4$)-N-Methylpyrazolyl-4
152 3-(3'-NO$_2$—C$_6$H$_4$)-N-Methylpyrazolyl-4
153 3-(2'-NO$_2$—C$_6$H$_4$)-N-Methylpyrazolyl-4
154 3-(4'-CN—C$_6$H$_4$)-N-Methylpyrazolyl-4
155 3-(3'-CN—C$_6$H$_4$)-N-Methylpyrazolyl-4
156 3-(2'-CN—C$_6$H$_4$)-N-Methylpyrazolyl-4
157 3-(4'-Cl—C$_6$H$_4$)-N-Methylpyrazolyl-4
158 3-(3'-Cl—C$_6$H$_4$)-N-Methylpyrazolyl-4
159 3-(2'-Cl—C$_6$H$_4$)-N-Methylpyrazolyl-4
160 Isoxazolyl-5
161 3-CH$_3$-Isoxazolyl-5
162 3-C$_6$H$_5$-Isoxazolyl-5
163 3-(4'-CH$_3$—C$_6$H$_4$)-Isoxazolyl-5
164 3-(3'-CH$_3$—C$_6$H$_4$)-Isoxazolyl-5
165 3-(2'-CH$_3$—C$_6$H$_4$)-Isoxazolyl-5
166 3-(4'-CH$_3$O—C$_6$H$_4$)-Isoxazolyl-5
167 3-(3'-CH$_3$O—C$_6$H$_4$)-Isoxazolyl-5
168 3-(2'-CH$_3$O—C$_6$H$_4$)-Isoxazolyl-5
169 3-(4'-NO$_2$—C$_6$H$_4$)-Isoxazolyl-5
170 3-(3'-NO$_2$—C$_6$H$_4$)-Isoxazolyl-5
171 3-(2'-NO$_2$—C$_6$H$_4$)-Isoxazolyl-5
172 3-(4'-CN—C$_6$H$_4$)-Isoxazolyl-5
173 3-(3'-CN—C$_6$H$_4$)-Isoxazolyl-5
174 3-(2'-CN—C$_6$H$_4$)-Isoxazolyl-5
175 3-(4'-Cl—C$_6$H$_4$)-Isoxazolyl-5
176 3-(3'-Cl—C$_6$H$_4$)-Isoxazolyl-5
177 3-(2'-Cl—C$_6$H$_4$)-Isoxazolyl-5
178 4-Chloroisoxazolyl-5
179 3-CH$_3$-4-Chloroisoxazolyl-5
180 3-C$_6$H$_5$-4-Chloroisoxazolyl-5
181 3-(4'-CH$_3$—C$_6$H$_4$)-4-Chloroisoxazolyl-5
182 3-(3'-CH$_3$—C$_6$H$_4$)-4-Chloroisoxazolyl-5
183 3-(2'-CH$_3$—C$_6$H$_4$)-4-Chloroisoxazolyl-5
184 3-(4'-CH$_3$O—C$_6$H$_4$)-4-Chloroisoxazolyl-5
185 3-(3'-CH$_3$O—C$_6$H$_4$)-4-Chloroisoxazolyl-5
186 3-(2'-CH$_3$O—C$_6$H$_4$)-4-Chloroisoxazolyl-5
187 3-(4'-NO$_2$—C$_6$H$_4$)-4-Chloroisoxazolyl-5
188 3-(3'-NO$_2$—C$_6$H$_4$)-4-Chloroisoxazolyl-5
189 3-(2'-NO$_2$—C$_6$H$_4$)-4-Chloroisoxazolyl-5
190 3-(4'-CN—C$_6$H$_4$)-4-Chloroisoxazolyl-5
191 3-(3'-CN—C$_6$H$_4$)-4-Chloroisoxazolyl-5
192 3-(2'-CN—C$_6$H$_4$)-4-Chloroisoxazolyl-5
193 3-(4'-Cl—C$_6$H$_4$)-4-Chloroisoxazolyl-5
194 3-(3'-Cl—C$_6$H$_4$)-4-Chloroisoxazolyl-5
195 3-(2'-Cl—C$_6$H$_4$)-4-Chloroisoxazolyl-5
196 Isoxazolyl-3
197 5-CH$_3$-Isoxazolyl-3
198 5-C$_6$H$_5$-Isoxazolyl-3

TABLE 6-continued 199 5-(4'-CH$_3$—C$_6$H$_4$)-Isoxazolyl-3
200 5-(3'-CH$_3$—C$_6$H$_4$)-Isoxazolyl-3
201 5-(2'-CH$_3$—C$_6$H$_4$)-Isoxazolyl-3
202 5-(4'-CH$_3$—C$_6$H$_4$)-Isoxazolyl-3
203 5-(3'-CH$_3$O—C$_6$H$_4$)-Isoxazolyl-3
204 5-(2'-CH$_3$O—C$_6$H$_4$)-Isoxazolyl-3
205 5-(4'-NO$_2$—C$_6$H$_4$)-Isoxazolyl-3
206 5-(3'-NO$_2$—C$_6$H$_4$)-Isoxazolyl-3
207 5-(2'-NO$_2$—C$_6$H$_4$)-Isoxazolyl-3
208 5-(4'-CN—C$_6$H$_4$)-Isoxazolyl-3
209 5-(3'-CN—C$_6$H$_4$)-Isoxazolyl-3
210 5-(2'-CN—C$_6$H$_4$)-Isoxazolyl-3
211 5-(4'-Cl—C$_6$H$_4$)-Isoxazolyl-3
212 5-(3'-Cl—C$_6$H$_4$)-Isoxazolyl-3
213 5-(2'-Cl—C$_6$H$_4$)-Isoxazolyl-3
214 Isothiazolyl-5
215 3-CH$_3$-Isothiazolyl-5
216 3-C$_6$H$_5$-Isothiazolyl-5
217 3-(4'-CH$_3$—C$_6$H$_4$)-Isothiazolyl-5
218 3-(3'-CH$_3$—C$_6$H$_4$)-Isothiazolyl-5
219 3-(2'-CH$_3$—C$_6$H$_4$)-Isothiazolyl-5
220 3-(4'-CH$_3$O—C$_6$H$_4$)-Isothiazolyl-5
221 3-(3'-CH$_3$O—C$_6$H$_4$)-Isothiazolyl-5
222 3-(2'-CH$_3$O—C$_6$H$_4$)-Isothiazolyl-5
223 3-(4'-NO$_2$—C$_6$H$_4$)-Isothiazolyl-5
224 3-(3'-NO$_2$—C$_6$H$_4$)-Isothiazolyl-5
225 3-(2'-NO$_2$—C$_6$H$_4$)-Isothiazolyl-5
226 3-(4'-CN—C$_6$H$_4$)-Isothiazolyl-5
227 3-(3'-CN—C$_6$H$_4$)-Isothiazolyl-5
228 3-(2'-CN—C$_6$H$_4$)-Isothiazolyl-5
229 3-(4'-Cl—C$_6$H$_4$)-Isothiazolyl-5
230 3-(3'-Cl—C$_6$H$_4$)-Isothiazolyl-5
231 3-(2'-Cl—C$_6$H$_4$)-Isothiazolyl-5
232 Oxazolyl-4
233 2-CH$_3$-Oxazolyl-4
234 2-C$_6$H$_5$-Oxazolyl-4
235 2-(4'-CH$_3$—C$_6$H$_4$)-Oxazolyl-4
236 2-(3'-CH$_3$—C$_6$H$_4$)-Oxazolyl-4
237 2-(2'-CH$_3$—C$_6$H$_4$)-Oxazolyl-4
238 2-(4'-CH$_3$O—C$_6$H$_4$)-Oxazolyl-4
239 2-(3'-CH$_3$O—C$_6$H$_4$)-Oxazolyl-4
240 2-(2'-CH$_3$O—C$_6$H$_4$)-Oxazolyl-4
241 2-(4'-NO$_2$—C$_6$H$_4$)-Oxazolyl-4
242 2-(3'-NO$_2$—C$_6$H$_4$)-Oxazolyl-4
243 2-(2'-NO$_2$—C$_6$H$_4$)-Oxazolyl-4
244 2-(4'-CN—C$_6$H$_4$)-Oxazolyl-4
245 2-(3'-CN—C$_6$H$_4$)-Oxazolyl-4
246 2-(2'-CN—C$_6$H$_4$)-Oxazolyl-4
247 2-(4'-Cl—C$_6$H$_4$)-Oxazolyl-4
248 2-(3'-Cl—C$_6$H$_4$)-Oxazolyl-4
249 2-(2'-Cl—C$_6$H$_4$)-Oxazolyl-4
250 Thiazolyl-4
251 2-CH$_3$-Thiazolyl-4
252 2-C$_6$H$_5$-Thiazolyl-4
253 2-(4'-CH$_3$—C$_6$H$_4$)-Thiazolyl-4
254 2-(3'-CH$_3$—C$_6$H$_4$)-Thiazolyl-4
255 2-(2'-CH$_3$—C$_6$H$_4$)-Thiazolyl-4
256 2-(4'-CH$_3$O—C$_6$H$_4$)-Thiazolyl-4
267 2-(3'-CH$_3$O—C$_6$H$_4$)-Thiazolyl-4
258 2-(2'-CH$_3$O—C$_6$H$_4$)-Thiazolyl-4
259 2-(4'-NO$_2$—C$_6$H$_4$)-Thiazolyl-4
260 2-(3'-NO$_2$—C$_6$H$_4$)-Thiazolyl-4
261 2-(2'-NO$_2$—C$_6$H$_4$)-Thiazolyl-4
262 2-(4'-CN—C$_6$H$_4$)-Thiazolyl-4
263 2-(3'-CN—C$_6$H$_4$)-Thiazolyl-4
264 2-(2'-CN—C$_6$H$_4$)-Thiazolyl-4
265 2-(4'-Cl—C$_6$H$_4$)-Thiazolyl-4
266 2-(3'-Cl—C$_6$H$_4$)-Thiazolyl-4
267 2-(2'-Cl—C$_6$H$_4$)-Thiazolyl-4
268 N—CH$_3$-1,2,4-Triazolyl-5
269 3-CH$_3$—N—CH$_3$-1,2,4-Triazolyl-5
270 3-C$_6$H$_5$—N—CH$_3$-1,2,4-Triazolyl-5
271 3-(4'-CH$_3$—C$_6$H$_4$)—N—CH$_3$-1,2,4-Triazolyl-5
272 3-(3'-CH$_3$—C$_6$H$_4$)—N—CH$_3$-1,2,4-Triazolyl-5
273 3-(2'-CH$_3$—C$_6$H$_4$)—N—CH$_3$-1,2,4-Triazolyl-5
274 3-(4'-CH$_3$O—C$_6$H$_4$)—N—CH$_3$-1,2,4-Triazolyl-5
275 3-(3'-CH$_3$O—C$_6$H$_4$)—N—CH$_3$-1,2,4-Triazolyl-5
276 3-(2'-CH$_3$O—C$_6$H$_4$)—N—CH$_3$-1,2,4-Triazolyl-5
277 3-(4'-NO$_2$—C$_6$H$_4$)—N—CH$_3$-1,2,4-Triazolyl-5

TABLE 6-continued 278 3-(3'-NO₂—C₆H₄)—N—CH₃-1,2,4-Triazolyl-5
279 3-(2'-NO₂—C₆H₄)—N—CH₃-1,2,4-Triazolyl-5
280 3-(4'-CN—C₆H₄)—N—CH₃-1,2,4-Triazolyl-5
281 3-(3'-CN—C₆H₄)—N—CH₃-1,2,4-Triazolyl-5
282 3-(2'-CN—C₆H₄)—N—CH₃-1,2,4-Triazolyl-5
283 3-(4'-Cl—C₆H₄)—N—CH₃-1,2,4-Triazolyl-5
284 3-(3'-Cl—C₆H₄)—N—CH₃-1,2,4-Triazolyl-5
285 3-(2'-Cl—C₆H₄)—N—CH₃-1,2,4-Triazolyl-5
286 1,3,4-Oxadiazolyl-2
287 5-CH₃-1,3,4-Oxadiazolyl-2
288 5-C₆H₅-1,3,4-Oxadiazolyl-2
289 5-(4'-CH₃—C₆H₄)-1,3,4-Oxadiazolyl-2
290 5-(3'-CH₃—C₆H₄)-1,3,4-Oxadiazolyl-2
291 5-(2'-CH₃—C₆H₄)-1,3,4-Oxadiazolyl-2
292 5-(4'-CH₃O—C₆H₄)-1,3,4-Oxadiazolyl-2
293 5-(3'-CH₃O—C₆H₄)-1,3,4-Oxadiazolyl-2
294 5-(2'-CH₃O—C₆H₄)-1,3,4-Oxadiazolyl-2
295 5-(4'-NO₂—C₆H₄)-1,3,4-Oxadiazolyl-2
296 5-(3'-NO₂—C₆H₄)-1,3,4-Oxadiazolyl-2
297 5-(2'-NO₂—C₆H₄)-1,3,4-Oxadiazolyl-2
298 5-(4'-CN—C₆H₄)-1,3,4-Oxadiazolyl-2
299 5-(3'-CN—C₆H₄)-1,3,4-Oxadiazolyl-2
300 5-(2'-CN—C₆H₄)-1,3,4-Oxadiazolyl-2
301 5-(4'-Cl—C₆H₄)-1,3,4-Oxadiazolyl-2
302 5-(3'-Cl—C₆H₄)-1,3,4-Oxadiazolyl-2
303 5-(2'-Cl—C₆H₄)-1,3,4-Oxadiazolyl-2
304 1,2,4-Oxadiazolyl-3
305 5-CH₃-1,2,4-Oxadiazolyl-3
306 5-C₆H₅-1,2,4-Oxadiazolyl-3
307 5-(4'-CH₃—C₆H₄)-1,2,4-Oxadiazolyl-3
308 5-(3'-CH₃—C₆H₄)-1,2,4-Oxadiazolyl-3
309 5-(2'-CH₃—C₆H₄)-1,2,4-Oxadiazolyl-3
310 5-(4'-CH₃O—C₆H₄)-1,2,4-Oxadiazolyl-3
311 5-(3'-CH₃O—C₆H₄)-1,2,4-Oxadiazolyl-3
312 5-(2'-CH₃O—C₆H₄)-1,2,4-Oxadiazolyl-3
313 5-(4'-NO₂—C₆H₄)-1,2,4-Oxadiazolyl-3
314 5-(3'-NO₂—C₆H₄)-1,2,4-Oxadiazolyl-3
315 5-(2'-NO₂—C₆H₄)-1,2,4-Oxadiazolyl-3
316 5-(4'-CN—C₆H₄)-1,2,4-Oxadiazolyl-3
317 5-(3'-CN—C₆H₄)-1,2,4-Oxadiazolyl-3
318 5-(2'-CN—C₆H₄)-1,2,4-Oxadiazolyl-3
319 5-(4'-Cl—C₆H₄)-1,2,4-Oxadiazolyl-3
320 5-(3'-Cl—C₆H₄)-1,2,4-Oxadiazolyl-3
321 5-(2'-Cl—C₆H₄)-1,2,4-Oxadiazolyl-3
322 1,2,4-Oxadiazolyl-5
323 3-CH₃-1,2,4-Oxadiazolyl-5
324 3-C₆H₅-1,2,4-Oxadiazolyl-5
325 3-(4'-CH₃—C₆H₄)-1,2,4-Oxadiazolyl-5
326 3-(3'-CH₃—C₆H₄)-1,2,4-Oxadiazolyl-5
327 3-(2'-CH₃—C₆H₄)-1,2,4-Oxadiazolyl-5
328 3-(4'-CH₃O—C₆H₄)-1,2,4-Oxadiazolyl-5
329 3-(3'-CH₃O—C₆H₄)-1,2,4-Oxadiazolyl-5
330 3-(2'-CH₃O—C₆H₄)-1,2,4-Oxadiazolyl-5
331 3-(4'-NO₂—C₆H₄)-1,2,4-Oxadiazolyl-5
332 3-(3'-NO₂—C₆H₄)-1,2,4-Oxadiazolyl-5
333 3-(2'-NO₂—C₆H₄)-1,2,4-Oxadiazolyl-5
334 3-(4'-CN—C₆H₄)-1,2,4-Oxadiazolyl-5
335 3-(3'-CN—C₆H₄)-1,2,4-Oxadiazolyl-5
336 3-(2'-CN—C₆H₄)-1,2,4-Oxadiazolyl-5
337 3-(4'-Cl—C₆H₄)-1,2,4-Oxadiazolyl-5
338 3-(3'-Cl—C₆H₄)-1,2,4-Oxadiazolyl-5
339 3-(2'-Cl—C₆H₄)-1,2,4-Oxadiazolyl-5

TABLE 6-continued 340 1,2,4-Thiadiazolyl-3
341 5-CH₃-1,2,4-Thiadiazolyl-3
342 5-C₆H₅-1,2,4-Thiadiazolyl-3
343 5-(4'-CH₃—C₆H₄)-1,2,4-Thiadiazolyl-3
344 5-(3'-CH₃—C₆H₄)-1,2,4-Thiadiazolyl-3
345 5-(2'-CH₃—C₆H₄)-1,2,4-Thiadiazolyl-3
346 5-(4'-CH₃O—C₆H₄)-1,2,4-Thiadiazolyl-3
347 5-(3'-CH₃O—C₆H₄)-1,2,4-Thiadiazolyl-3
348 5-(2'-CH₃O—C₆H₄)-1,2,4-Thiadiazolyl-3
349 5-(4'-NO₂—C₆H₄)-1,2,4-Thiadiazolyl-3
350 5-(3'-NO₂—C₆H₄)-1,2,4-Thiadiazolyl-3
351 5-(2'-NO₂—C₆H₄)-1,2,4-Thiadiazolyl-3
352 5-(4'-CN—C₆H₄)-1,2,4-Thiadiazolyl-3
353 5-(3'-CN—C₆H₄)-1,2,4-Thiadiazolyl-3
354 5-(2'-CN—C₆H₄)-1,2,4-Thiadiazolyl-3
355 5-(4'-Cl—C₆H₄)-1,2,4-Thiadiazolyl-3
356 5-(3'-Cl—C₆H₄)-1,2,4-Thiadiazolyl-3
357 5-(2'-Cl—C₆H₄)-1,2,4-Thiadiazolyl-3
358 1,3,4-Thiadiazolyl-2
359 5-CH₃-1,3,4-Thiadiazolyl-2
360 5-C₆H₅-1,3,4-Thiadiazolyl-2
361 5-(4'-CH₃—C₆H₄)-1,3,4-Thiadiazolyl-2
362 5-(3'-CH₃—C₆H₄)-1,3,4-Thiadiazolyl-2
363 5-(2'-CH₃—C₆H₄)-1,3,4-Thiadiazolyl-2
364 5-(4'-CH₃O—C₆H₄)-1,3,4-Thiadiazolyl-2
365 5-(3'-CH₃O—C₆H₄)-1,3,4-Thiadiazolyl-2
366 5-(2'-CH₃—C₆H₄)-1,3,4-Thiadiazolyl-2
367 5-(4'-NO₂—C₆H₄)-1,3,4-Thiadiazolyl-2
368 5-(3'-NO₂—C₆H₄)-1,3,4-Thiadiazolyl-2
369 5-(2'-NO₂—C₆H₄)-1,3,4-Thiadiazolyl-2
370 5-(4'-CN—C₆H₄)-1,3,4-Thiadiazolyl-2
371 5-(3'-CN—C₆H₄)-1,3,4-Thiadiazolyl-2
372 5-(2'-CN—C₆H₄)-1,3,4-Thiadiazolyl-2
373 5-(4'-Cl—C₆H₄)-1,3,4-Thiadiazolyl-2
374 5-(3'-Cl—C₆H₄)-1,3,4-Thiadiazolyl-2
375 5-(2'-Cl—C₆H₄)-1,3,4-Thiadiazolyl-2
376 Pyridinyl-2
377 Pyridinyl-4
378 Pyridazinyl-3
379 Pyridazinyl-4
380 Pyridazinyl-2
381 Pyrimidinyl-4
382 Pyrimidinyl-5
383 Pyrimidinyl-2

TABLE 7
Selected physical data of some compounds
| No. | Compound | mp/° C. | IR/cm$^{-1}$ |
|---|---|---|---|
| 1 | 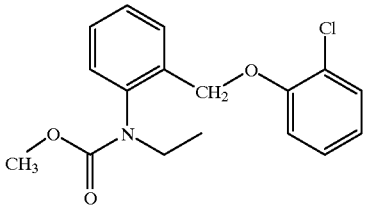 | — | 1707, 1484, 1457 1447, 1303, 1277 |
| 2 | 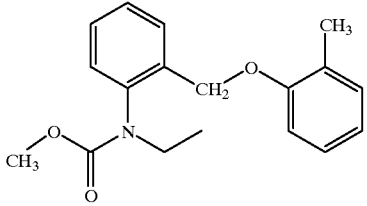 | — | 1708, 1495, 1457 1449, 1304, 1241 |
| 3 | 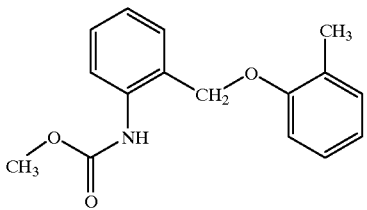 | 111 | |
| 4 | 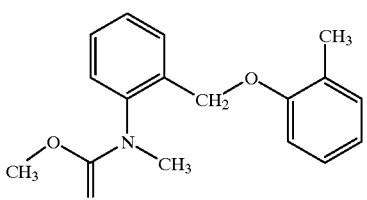 | 73 | |
| 5 | 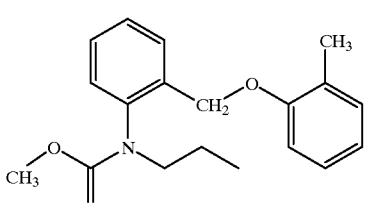 | 54 | |
| 6 | 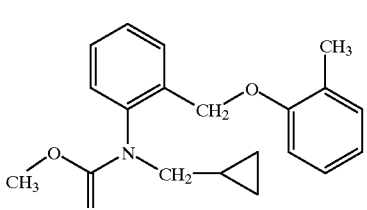 | — | 1706, 1496, 1456 1447, 1294, 1243 |

TABLE 7-continued

Selected physical data of some compounds

| No. | Compound | mp/° C. | IR/cm$^{-1}$ |
|---|---|---|---|
| 7 | | 73 | |
| 8 | | 57 | |
| 9 | | 86 | |
| 10 | | — | 1709, 1599, 1497 1453, 1346, 1241 |
| 11 | | — | 1708, 1599, 1497 1455, 1447, 1397 1238 |
| 12 | | — | 1740, 1593, 1527 1489, 1456, 1252 1225 |

TABLE 7-continued

Selected physical data of some compounds

| No. | Compound | mp/° C. | IR/cm$^{-1}$ |
|---|---|---|---|
| 13 | | — | 1710, 1603, 1584 1490, 1451, 1364 1254 |
| 14 | | — | 1709, 1490, 1456 1447, 1379, 1300 1258 |
| 15 | | — | 1712, 1490, 1456 1447, 1378, 1298 1259 |
| 16 | | 88 | |
| 17 | | — | 1710, 1511, 1451 1364, 1302, 1238 |
| 18 | | — | 1709, 1511, 1456 1447, 1379, 1301 1236 |

TABLE 7-continued

Selected physical data of some compounds

| No. | Compound | mp/° C. | IR/cm⁻¹ |
|-----|----------|---------|---------|
| 19 | [methyl N-(2-((4-methylphenoxy)methyl)phenyl)-N-(prop-2-ynyl)carbamate] | — | 1712, 1511, 1447 1378, 1298, 1233 |
| 20 | [methyl N-(2-((E)-2-(2-methylphenyl)ethenyl)phenyl)carbamate] | — | 1738, 1723, 1582 1522, 1452, 1223 |
| 21 | [methyl N-methyl-N-(2-(2-(2-methylphenyl)ethenyl)phenyl)carbamate] (2 isomers approx. 4:3) | — | 1711, 1492, 1480 1447, 1362, 1303 1192, 1159 |
| 22 | [methyl N-allyl-N-(2-(2-(2-methylphenyl)ethenyl)phenyl)carbamate] (2 isomers approx. 4:3) | — | 1708, 1491, 1479 1446, 1376, 1300 1277, 1150 |
| 23 | [methyl N-(2-(2-(2-methylphenyl)ethenyl)phenyl)-N-(prop-2-ynyl)carbamate] (2 isomers approx. 4:3) | — | 1712, 1511, 1447 1378, 1298, 1233 |

TABLE 7-continued
Selected physical data of some compounds
| No. | Compound | mp/° C. | IR/cm$^{-1}$ |
|---|---|---|---|
| 24 | 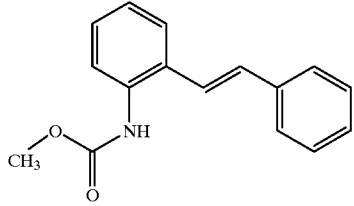 (2 isomers approx. 4:3) | — | 1736, 1582, 1523 1453, 1221 |
| 25 | 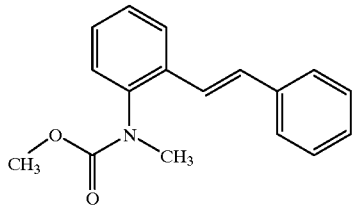 (2 isomers approx. 4:3) | — | 1706, 1495, 1485 1363, 1303, 1193 1160 |
| 26 | 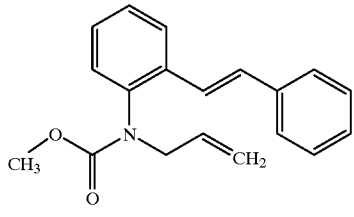 (2 isomers approx. 4:3) | — | 1706, 1484, 1447 1377, 1301, 1280 1150 |
| 27 | 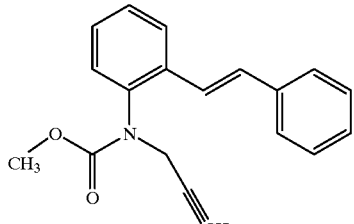 (2 isomers approx. 4:3) | — | 1710, 1495, 1483 1446, 1376, 1299 1233 |
| 28 | 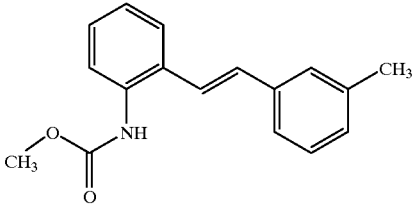 (2 isomers approx. 4:1) | 92 | |

TABLE 7-continued
Selected physical data of some compounds
| No. | Compound | mp/° C. | IR/cm$^{-1}$ |
|---|---|---|---|
| 29 | 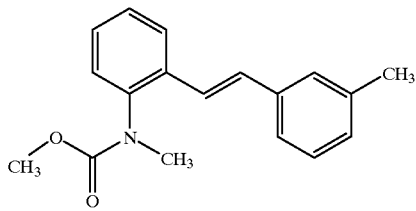 (2 isomers approx. 4:1) | — | 1709, 1489, 1447 1362, 1303, 1192 1159 |
| 30 | 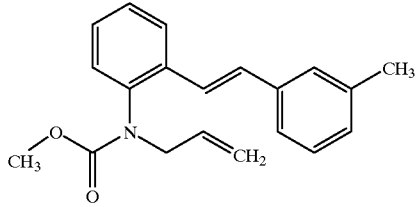 (2 isomers approx. 4:1) | — | 1706, 1484, 1447 1377, 1301, 1280 1150 |
| 31 | 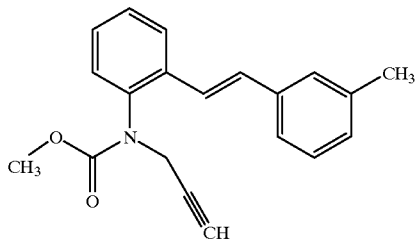 (2 isomers approx. 4:1) | — | 1711, 1488, 1446 1375, 1299, 1232 |
| 32 | 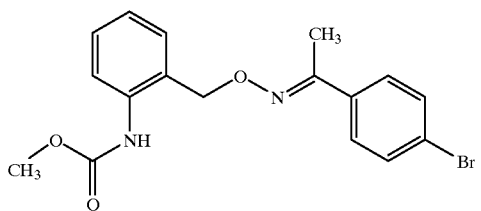 | 132 | |
| 33 | 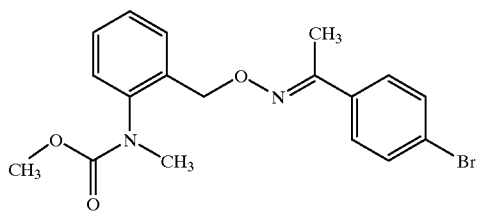 | — | 1709, 1495, 1486 1451, 1366, 1161 1008 |
| 34 | 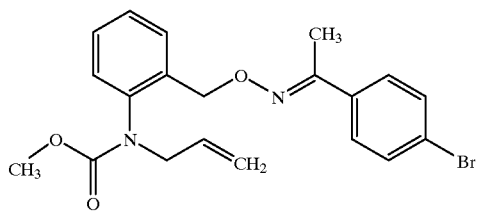 | — | 1708, 1487, 1455 1447, 1379, 1300 1009 |

TABLE 7-continued

Selected physical data of some compounds

| No. | Compound | mp/° C. | IR/cm⁻¹ |
|---|---|---|---|
| 35 | (structure: methyl N-(2-((E)-1-(4-bromophenyl)ethylideneaminooxymethyl)phenyl)-N-propargylcarbamate) | — | 1711, 1488, 1447, 1378, 1297, 1232, 1023, 1008 |
| 36 | (structure: methyl N-(2-((E)-2-(4-methylphenyl)vinyl)phenyl)carbamate) | — | 1696, 1532, 1515, 1453, 1267, 1245, 1069 |
| 37 | (structure: methyl N-methyl-N-(2-((E)-2-(4-methylphenyl)vinyl)phenyl)carbamate) | — | 1712, 1486, 1447, 1361, 1303, 1191, 1160 |
| 38 | (structure: methyl N-allyl-N-(2-((E)-2-(4-methylphenyl)vinyl)phenyl)carbamate) | — | 1708, 1485, 1446, 1376, 1300, 1274 |
| 39 | (structure: methyl N-(2-((E)-2-(4-methylphenyl)vinyl)phenyl)-N-propargylcarbamate) | — | 1709, 1484, 1446, 1374, 1297, 1277, 1232 |
| 40 | (structure: methyl N-(2-((4-methylphenoxy)methyl)phenyl)-N-propargylcarbamate) | — | 1712, 1495, 1457, 1447, 1378, 1298, 1237 |

TABLE 7-continued

Selected physical data of some compounds

| No. | Compound | mp/° C. | IR/cm⁻¹ |
|-----|----------|---------|---------|
| 41 | | 110 | |
| 42 | | — | 1739, 1593, 1528, 1511, 1457, 1226, 1035 |
| 43 | | 102 | |
| 44 | | — | 1708, 1513, 1457, 1447, 1378, 1302, 1246, 1035 |
| 45 | | 102 | |
| 46 | | 74 | |

TABLE 7-continued
Selected physical data of some compounds
| No. | Compound | mp/° C. | IR/cm⁻¹ |
|---|---|---|---|
| 47 | 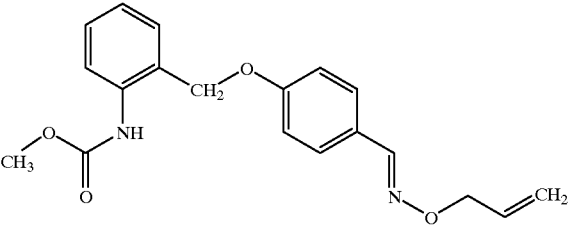 | — | 1709, 1606, 1512 1364, 1245, 1228 1171, 1162, 1033 1005 |
| 48 | 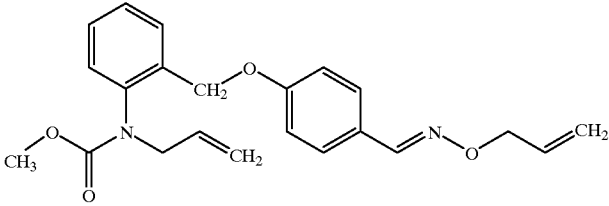 | 59 | |
| 49 | 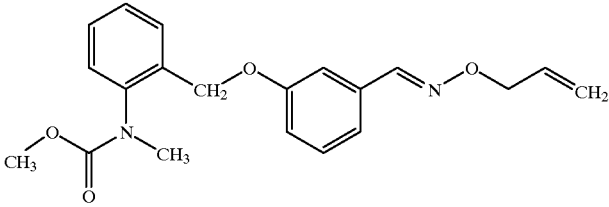 | — | 1709, 1447, 1364 1261, 1157, 1034 1007 |
| 50 | 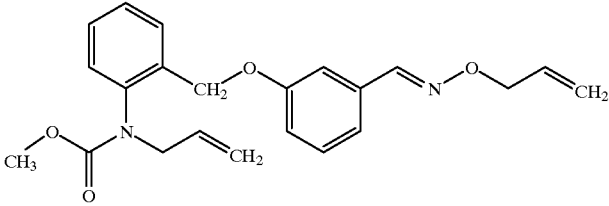 | — | 1709, 1576, 1446 1379, 1300, 1260 1239, 1156, 1037 |
| 51 | 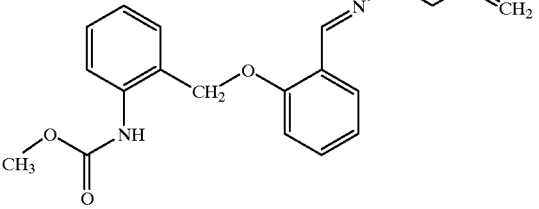 | 89 | |
| 52 | 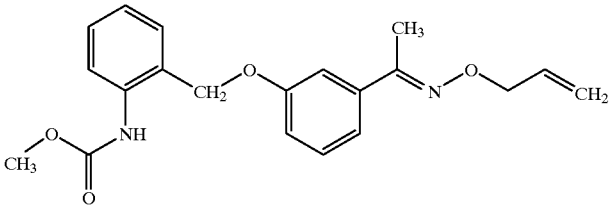 | — | 1740, 1593, 1575 1527, 1457, 1316 1300, 1224, 1067 1029 |

TABLE 7-continued

Selected physical data of some compounds

| No. | Compound | mp/° C. | IR/cm⁻¹ |
|---|---|---|---|
| 53 | | 81 | |
| 54 | | — | 1711, 1574, 1447 1365, 1322, 1303 1213, 1160, 1033 1008 |
| 55 | | — | 1709, 1574, 1446 1378, 1321, 1301 1284, 1213, 1034 |
| 56 | | — | 1711, 1505, 1451 1365, 1304, 1245 1160, 1143, 1035 1007 |
| 57 | | 63 | |
| 58 | | — | 1710, 1487, 1450 1364, 1301, 1246 1160, 1030, 1006 |

TABLE 7-continued

Selected physical data of some compounds

| No. | Compound | mp/° C. | IR/cm$^{-1}$ |
|---|---|---|---|
| 59 | | — | 1708, 1487, 1449 1378, 1300, 1247 1030, 1009 |
| 60 | | — | 1743, 1593, 1528 1502, 1457, 1301 1255, 1190, 1066 1006 |
| 61 | | 77 | |
| 62 | | — | 1712, 1503, 1453 1363, 1303, 1259 1244, 1160, 1136 1006 |
| 63 | | — | 1711, 1503, 1457 1447, 1380, 1301 1258, 1239, 1136 1015 |
| 64 | | 92 | 1743, 1593, 1528 1502, 1457, 1301 1255, 1190, 1066 1006 |

TABLE 7-continued

Selected physical data of some compounds

| No. | Compound | mp/° C. IR/cm$^{-1}$ |
|---|---|---|
| 65 | | 90 |
| 66 | | 70 |
| 67 | | 75 |
| 68 | | 108 |
| 69 | | 93 |
| 70 | | 74 |

TABLE 7-continued

Selected physical data of some compounds

| No. | Compound | mp/° C. | IR/cm$^{-1}$ |
|---|---|---|---|
| 71 | | — | 1712, 1504, 1450 1363, 1303, 1255 1222, 1159, 1134 |
| 72 | | — | 1712, 1510, 1498 1450, 1365, 1327 1246, 1150, 1035 1005 |
| 73 | | 60 | |
| 74 | | — | 1711, 1509, 1497 1451, 1363, 1302 1264, 1193, 1156 1129 |
| 75 | | — | 1710, 1496, 1475 1149, 1365, 1301 1263, 1195, 1159 |
| 76 | | 66 | |

TABLE 7-continued

Selected physical data of some compounds

| No. | Compound | mp/° C. | IR/cm$^{-1}$ |
|---|---|---|---|
| 77 | (structure) | 86 | |
| 78 | (structure) | 91 | |
| 79 | (structure) | 100 | |
| 80 | (structure) | — | 1710, 1593, 1497 1452, 1364, 1323 1297, 1193, 1165 1153 |
| 81 | (structure) | — | 1715, 1510, 1447 1367, 1324, 1299 1243, 1149, 1027 996 |
| 82 | (structure) | — | 1710, 1509, 1456 1446, 1377, 1326 1300, 1241, 1149 1306 |

TABLE 7-continued

Selected physical data of some compounds

| No. | Compound | mp/° C. | IR/cm⁻¹ |
|---|---|---|---|
| 83 | | — | 1723, 1509, 1453 1437, 1316, 1292 1241, 1149, 1064 1036 |
| 84 | | — | 1738, 1611, 1581 1539, 1446, 1312 1301, 1231, 1201 1067 |
| 85 | | — | 1713, 1504, 1447 1375, 1313, 1300 1233, 1143, 1027 |
| 86 | | — | 1711, 1486, 1447 1376, 1300, 1281 1150, 1034, 1013 |
| 87 | | — | 1714, 1487, 1447 1376, 1300, 1231 1023, 999 |
| 88 | | — | 1733, 1594, 1533 1457, 1306, 1231 1013, 984 |

TABLE 7-continued

Selected physical data of some compounds

| No. | Compound | mp/° C. | IR/cm$^{-1}$ |
|---|---|---|---|
| 89 | | — | 1721, 1495, 1453<br>1437, 1313, 1290<br>1239, 1123 |
| 90 | | — | 1709, 1453, 1366<br>1303, 1228, 1160<br>1014 |
| 91 | | — | 1708, 1455, 1447<br>1378, 1299, 1282<br>1015, 996 |
| 92 | | — | 1710, 1447, 1378<br>1296, 1232, 1045<br>1023, 995 |
| 93 | | 108 | |
| 94 | | — | 1717, 1495, 1457<br>1444, 1376, 1298<br>1241, 1228, 1193 |

TABLE 7-continued

Selected physical data of some compounds

| No. | Compound | mp/° C. | IR/cm⁻¹ |
|---|---|---|---|
| 95 | | — | 1739, 1614, 1603 1542, 1450, 1262 129, 1179 |
| 96 | | 170 | |
| 97 | | 180 | |
| 98 | | 173 | |
| 99 | | 150 | |
| 100 | | 129 | |

TABLE 7-continued

Selected physical data of some compounds

| No. | Compound | mp/° C. | IR/cm⁻¹ |
|-----|----------|---------|---------|
| 101 | | 112 | |
| 102 | | 116 | |
| 103 | | 127 | |
| 104 | | 108 | |
| 105 | | — | 1710, 1486, 1447 1363, 1307, 1193 1159, 1031, 1006 919 |
| 106 | | — | 1706, 1484, 1447 1376, 1302, 1279 1150, 1031, 1011 923 |

TABLE 7-continued

Selected physical data of some compounds

| No. | Compound | mp/° C. | IR/cm⁻¹ |
|---|---|---|---|
| 107 | | — | 1711, 1484, 1446 1376, 1298, 1232 1144, 1024, 995, 922 |
| 108 | | 147 | |
| 109 | | — | 1716, 1455, 1445 1376, 1297, 1279 1097, 1069, 1017 1008 |
| 110 | | — | 1718, 1487, 1447 1394, 1374, 1306 1232, 1025, 1008 |
| 111 | | 109 | |
| 112 | | — | 1706, 1487, 1450 1387, 1304, 1276 1155, 1022, 1009 769 |

TABLE 7-continued

Selected physical data of some compounds

| No. | Compound | mp/° C. | IR/cm$^{-1}$ |
|---|---|---|---|
| 113 | | — | 1706, 1487, 1453 1383, 1312, 1301 1274, 1155, 1033 1008 |
| 114 | | 115 | |
| 115 | | 167 | |
| 116 | | — | 1729, 1575, 1565 1545, 1523, 1445 1434, 1224, 1060 |
| 117 | | 110 | |
| 118 | | 77 | |

TABLE 7-continued

Selected physical data of some compounds

| No. | Compound | mp/° C. | IR/cm⁻¹ |
|---|---|---|---|
| 119 | | — | 1712, 1494, 1447 1378, 1298, 1232 1045, 1024, 818, 771 |
| 120 | | 115 | |
| 121 | | — | 1717, 1455, 1445 1376, 1298, 1278 1097, 1068, 1016 999 |
| 122 | | 81 | |
| 123 | | — | 1712, 1493, 1447 1378, 1297, 1232 1047, 1024, 998, 772 |
| 124 | | 107 | |

TABLE 7-continued

Selected physical data of some compounds

| No. | Compound | mp/° C. | IR/cm$^{-1}$ |
|---|---|---|---|
| 125 | | — | 1717, 1455, 1445 1376, 1298, 1279 1096, 1068, 1017 999 |
| 126 | | 128 | |
| 127 | | — | 1712, 1492, 1447 1378, 1298, 1232 1096, 1044, 1023 |
| 128 | | 119 | |
| 129 | | — | 1717, 1492, 1455 1445, 1376, 1298 1096, 1068, 1012 1000 |
| 130 | | 133 | |

TABLE 7-continued

Selected physical data of some compounds

| No. | Compound | mp/°C. | IR/cm⁻¹ |
|---|---|---|---|
| 131 | | — | 1712, 1511, 1494 1447, 1378, 1298 1232, 1045, 1024 837 |
| 132 | | 113 | |
| 133 | | — | 1716, 1511, 1455 1445, 1376, 1298 1228, 1097, 1068 999 |
| 134 | | — | 1737, 1592, 1529 1509, 1489, 1455 1303, 1231, 1067 1014 |
| 135 | | — | 1712, 1586, 1507 1489, 1454, 1378 1297, 1239, 1023 |
| 136 | | 148 | |

TABLE 7-continued

Selected physical data of some compounds

| No. | Compound | mp/° C. | IR/cm$^{-1}$ |
|---|---|---|---|
| 137 | | — | 1716, 1587, 1507 1490, 1455, 1375 1298, 1240, 1068 |
| 138 | | 90 | |
| 139 | | — | 1719, 1495, 1464 1446, 1375, 1295 1239, 1104, 1075 1014 |
| 140 | | — | 1715, 1495, 1463 1448, 1376, 1298 1239 |
| 141 | | 134 | |
| 142 | | — | 1744, 1583, 1522 1503, 1458, 1442 1223, 1304, 1035 1004 |

TABLE 7-continued

Selected physical data of some compounds

| No. | Compound | mp/° C. | IR/cm⁻¹ |
|---|---|---|---|
| 143 | | — | 1720, 1465, 1446 1372, 1296, 1280 1243, 1144, 1035 1014 |
| 144 | | — | 1716, 1505, 1465 1448, 1374, 1298 1279, 1241, 1141 999 |
| 145 | | 109 | |
| 146 | | 158 | |
| 147 | | — | 1718, 1463, 1445 1376, 1294, 1104 1073, 1024, 1010 |
| 148 | | — | 1714, 1462, 1447 1377, 1297, 1238 1025, 1009 |

TABLE 7-continued

Selected physical data of some compounds

| No. | Compound | mp/° C. | IR/cm$^{-1}$ |
|---|---|---|---|
| 149 | (structure: 2-chloro-6-[N,N-bis(methoxycarbonyl)amino]benzyl O-methyl ketoxime ether with 4-bromophenyl) | 140 | |

Example 4

Methyl N-(2-methylphenyl)-N-methoxy-carbamate (Table 14, No. 1)

a) Methyl N-(2-methylphenyl)-N-hydroxy-carbamate

At 25–30° C., 14.0 g (0.148 mol) of methyl Chloroocarbonate is added dropwise to 16.4 g of N-(2-methylphenyl)-hydroxylamine (crude product, obtained according to Bamberger et al., Ann. Chem. 316 (1901), 278) and 12.9 g (0.163 mol) of pyridine in 100 ml of methylene Chloroide. The mixture is stirred overnight at room temperature (20° C.) and is then extracted with dilute hydrochloroic acid and water. The organic phase is dried over MgSO$_4$ and evaporated down. The residue is purified by column chromatography with mixtures of hexane and ethyl acetate. There is obtained 7 g (39 mmol) of the title compound as a yellow oil.

$^1$H-NMR (CDCl$_3$; δ in ppm): 8.6 (s, broad, OH); 7.3 (m, 4H, phenyl); 3.75 (s, 3H, OCH$_3$); 2.3 (s, 3H, CH$_3$).

b) Methyl N-(2-methylphenyl)-N-methoxy-carbamate (Table 14, No. 1)

At 20–30° C., 1.1 g (44.1 mmol) of sodium hydride is added in portions to 6.6 g (36.5 mmol) of the hydroxyl compound from Example 4a in 50 ml of dimethylformamide. Upon conclusion of gas evolution 5.7 g (40.1 mmol) of methyl iodide is added and the mixture is stirred overnight at room temperature. The reaction mixture is then diluted with water and the aqueous phase is extracted three times with methyl-t-butyl ether. The combined organic phases are dried over MgSO$_4$ and evaporated down. The residue is purified by column chromatography with mixtures of hexane and ethyl acetate. There is obtained 5.2 g (27mmol=73%) of the title compound as a yellow oil.

$^1$H-NMR (CDCl$_3$; δ in ppm): 7.25 (m, 4H, phenyl); 3.8; 3.75 (s, 3H, OCH$_3$; 3.75 (s, 3H, OCH$_3$); 2.3 (s, 3H, CH$_3$).

Example 5

Methyl N-(2-bromomethylphenyl)-N-methoxy-carbamate (Table 14, No. 2)

2.5 g (12.8 mmol) of the N-methoxycarbamate from Example 4b, 2.5 g (14.1 mmol) of N-bromosuccinimide and a spatula-tip (1 g) of azoisobutyrodinitrile in 20 ml of carbon tetraChloroide were irradiated with a 300 W UV lamp; the reaction mixture heated up to 30–40° C. After three hours the reaction mixture is extracted twice with water. The organic phase is dried over MgSO$_4$ and evaporated down. The residue is purified by column chromatography with mixtures of hexane and ethyl acetate. There is obtained 1.4 g (5.1 mmol 40%) of the title compound as a yellow oil.

$^1$H-NMR (CDCl$_3$; δ in ppm): 7.5 (m, 1H, phenyl); 7.35 (m, 3H, phenyl); 4.55 (s, 2H, CH$_2$—Br); 3.8 (2s, 6H, 2× OCH$_3$).

Example 6

Methyl N-[2-(2'-methylphenoxymethyl)-phenyl]-N-methoxy-carbamate (Table 14, No. 3)

1.2 g (4.4 mmol) of the methyl bromide from Example 5, 0.45 g (4.2 mmol) o-cresol and 0.7 g (4.8 mmol) of K$_2$CO$_3$ in 30 ml of dimethylformamide are stirred overnight at room temperature. The reaction mixture is then diluted with water and the aqueous phase is extracted three times with methyl-t-butyl ether. The combined organic phases are dried over MgSO$_4$ and evaporated down. The residue is purified by column chromatography with mixtures of hexane and ethyl acetate. There is obtained 1.2 g of the title compound containing o-cresol as impurity. The mixture is heated in a furnace at about 1 mbar for about 1 hour at 125° C. The residue obtained is 0.9 g (3 mmol=68%) of the title compound as a yellow oil.

$^1$H-NMR (CDCl$_3$; δ in ppm): 7.7 (m, 1H, phenyl); 7.4 (m, 3H, phenyl); 7.15 (m, 2H, phenyl); 6.9 (t, broad, 2H, phenyl); 5.15 (s, 2H, O—CH$_2$); 3.8 (s, 3H, OCH$_3$), 3.75 (s, 3H, OCH$_3$); 2.3 (s, 3H, CH$_3$).

TABLE 8

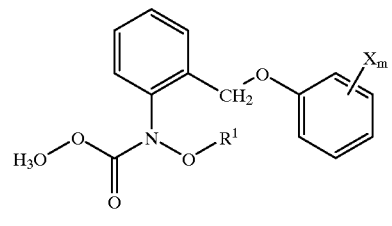

I: R$^1$ = CH$_3$
II: R$^1$ = CH$_2$—CH$_3$

| No | Xm |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F5 |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |

TABLE 8-continued

| | |
|---|---|
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |
| 37 | 4-I |
| 38 | 2,4-$I_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-$Cl_2$, 4-Br |
| 66 | 2-$CH_3$ |
| 67 | 3-$CH_3$ |
| 68 | 4-$CH_3$ |
| 69 | 2,3-$(CH_3)_2$ |
| 70 | 2,4-$(CH_3)_2$ |
| 71 | 2,5-$(CH_3)_2$ |
| 72 | 2,6-$(CH_3)_2$ |
| 73 | 3,4-$(CH_3)_2$ |
| 74 | 3,5-$(CH_3)_2$ |
| 75 | 2,3,5-$(CH_3)_3$ |
| 76 | 2,3,4-$(CH_3)_3$ |
| 77 | 2,3,6-$(CH_3)_3$ |
| 78 | 2,4,5-$(CH_3)_3$ |
| 79 | 2,4,6-$(CH_3)_3$ |
| 80 | 3,4,5-$(CH_3)_3$ |
| 81 | 2,3,4,6-$(CH_3)_4$ |
| 82 | 2,3,5,6-$(CH_3)_4$ |
| 83 | 2,3,4,5,6-$(CH_3)_5$ |
| 84 | 2-$C_2H_5$ |
| 85 | 3-$C_2H_5$ |
| 86 | 4-$C_2H_5$ |
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C_2H_5)_3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7)_2$ |
| 98 | 2,6-(i-$C_3H_7)_2$ |
| 99 | 3,5-(i-$C_3H_7)_2$ |
| 100 | 2,4,6-(i-$C_3H_7)_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9)_2$ |
| 108 | 2,4-(t-$C_4H_9)_2$ |
| 109 | 2,5-(t-$C_4H_9)_2$ |
| 110 | 2,6-(t-$C_4H_9)_2$ |
| 111 | 3,4-(t-$C_4H_9)_2$ |
| 112 | 2,4,6-(t-$C_4H_9)_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-$C_4H_9$, 4-$CH_3$ |
| 119 | 2-t-$C_4H_9$, 5-$CH_3$ |
| 120 | 2,6-(t-$C_4H_9)_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9)_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11})_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-$(CH_3)_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$OCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |

TABLE 8-continued

| | |
|---|---|
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH3 |
| 250 | 2-Cl, 4-NO$_2$ |
| 251 | 2-NO2, 4-Cl |
| 252 | 2-OCH$_3$, 5-NO$_2$ |
| 253 | 2,4-Cl2, 5-NO2 |
| 254 | 2,4-Cl2, 6-NO2 |
| 255 | 2,6-Cl2, 4-NO2 |
| 256 | 2,6-Br2, 4-NO2 |
| 257 | 2,6-I2, 4-NO2 |
| 258 | 2-CH3, 5-i-C3H7, 4-Cl |
| 259 | 2-CO$_2$CH$_3$ |
| 260 | 3-CO2CH3 |
| 261 | 4-CO2CH3 |
| 262 | 2-CO2(C2H5) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$——CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |

TABLE 8-continued

| | |
|---|---|
| 331 | 4-C(=NO-i-$C_3H_7$)—$CH_3$ |
| 332 | 2-C(=NO-Allyl)—$CH_3$ |
| 333 | 3-C(=NO-Allyl)—$CH_3$ |
| 334 | 4-C(=NO-Allyl)—$CH_3$ |
| 335 | 2-C(=NO-trans-Chloroallyl)—$CH_3$ |
| 336 | 3-C(=NO-trans-Chloroallyl)—$CH_3$ |
| 337 | 4-C(=NO-trans-Chloroallyl)—$CH_3$ |
| 338 | 2-C(=NO-Propargyl)—$CH_3$ |
| 339 | 3-C(=NO-Propargyl)—$CH_3$ |
| 340 | 4-C(=NO-Propargyl)—$CH_3$ |
| 341 | 2-C(=NO-n-$C_4H_9$)—$CH_3$ |
| 342 | 3-C(=NO-n-$C_4H_9$)—$CH_3$ |
| 343 | 4-C(=NO-n-$C_4H_9$)—$CH_3$ |
| 344 | 2-C(=NO—$CH_2$—$C_6H_5$)—$CH_3$ |
| 345 | 3-C(=NO—$CH_2$—$C_6H_5$)—$CH_3$ |
| 346 | 4-C(=NO—$CH_2$—$C_6H_5$)—$CH_3$ |
| 347 | 2-$CH_3$-4-CH=NO$CH_3$ |
| 348 | 2-$CH_3$-4-CH=NO$C_2H_5$ |
| 349 | 2-$CH_3$-4-CH=NO-n-$C_3H_7$ |
| 350 | 2-$CH_3$-4-CH=NO-i-$C_3H_7$ |
| 351 | 2-$CH_3$-4-CH=NO-Allyl |
| 352 | 2-$CH_3$-4-CH=NO—(trans-Chloroallyl) |
| 353 | 2-$CH_3$-4-CH=NO-Propargyl |
| 354 | 2-$CH_3$-4-CH=NO-n-$C_4H_9$ |
| 355 | 2-$CH_3$-4-CH=NO—$CH_2$—$C_6H_5$ |
| 356 | 2-$CH_3$-4-($CH_3$—C=NO$CH_3$) |
| 357 | 2-$CH_3$-4-($CH_3$—C=NO$C_2H_5$) |
| 358 | 2-$CH_3$-4-($CH_3$—C=NO-n-$C_3H_7$) |
| 359 | 2-$CH_3$-4-($CH_3$—C=NO-i-$C_3H_7$) |
| 360 | 2-$CH_3$-4-($CH_3$—C=NO-Allyl) |
| 361 | 2-$CH_3$-4-($CH_3$—C=NO-trans-Chloroallyl) |
| 362 | 2-$CH_3$-4-($CH_3$—C=NO-Propargyl) |
| 363 | 2-$CH_3$-4-($CH_3$—C=NO-n-$C_4H_9$) |
| 364 | 2-$CH_3$-4-($CH_3$—C=NO—$CH_2$—$C_6H_5$) |
| 365 | 2-$CH_3$-4-($C_2H_5$—C=NO—$CH_3$) |
| 366 | 2-$CH_3$-4-($C_2H_5$—C=NO—$C_2H_5$) |
| 367 | 2-$CH_3$-4-($C_2H_5$—C=NO-n-$C_3H_7$ |
| 368 | 2-$CH_3$-4-($C_2H_5$—C=NO-i-$C_3H_7$ |
| 369 | 2-$CH_3$-4-($C_2H_5$—C=NO-Allyl) |
| 370 | 2-$CH_3$-4-($C_2H_5$—C=NO-trans-Chloroallyl) |
| 371 | 2-$CH_3$-4-($C_2H_5$—C=NO-Propargyl) |
| 372 | 2-$CH_3$-4-($C_2H_5$—C=NO-n-$C_4H_9$) |
| 373 | 2-$CH_3$-4-($C_2H_5$—C=NO—$CH_2$—$C_6H_5$) |
| 374 | 2,5-($CH_3$)$_2$-4-($CH_3$—C=NO$CH_3$) |
| 375 | 2,5-($CH_3$)$_2$-4-($CH_3$—C=NO$C_2H_5$) |
| 376 | 2,5-($CH_3$)$_2$-4-($CH_3$—C=NO-n-$C_3H_7$) |
| 377 | 2,5-($CH_3$)$_2$-4-($CH_3$—C=NO-i-$C_3H_7$) |
| 378 | 2,5-($CH_3$)$_2$-4-($CH_3$—C=NO-Allyl) |
| 379 | 2,5-($CH_3$)$_2$-4-($CH_3$—C=NO-trans-Chloroallyl) |
| 380 | 2,5-($CH_3$)$_2$-4-($CH_3$—C=NO-Proparyl) |
| 381 | 2,5-($CH_3$)$_2$-4-($CH_3$—C=NO-n-$C_4H_9$) |
| 382 | 2,5-($CH_3$)$_2$-4-($CH_3$—C=NO—$CH_2$—$C_6H_5$) |
| 383 | 2-$C_6H_5$ |
| 384 | 3-$C_6H_5$ |
| 385 | 4-$C_6H_5$ |
| 386 | 2-(2'-F—$C_6H_4$) |
| 387 | 2-(3'-F—$C_6H_4$) |
| 388 | 2-(4'-F—$C_6H_4$) |
| 389 | 3-(2'-F—$C_6H_4$) |
| 390 | 3-(3'-F—$C_6H_4$) |
| 391 | 3-(4'-F—$C_6H_4$) |
| 392 | 4-(2'-F—$C_6H_4$) |
| 393 | 4-(3'-F—$C_6H_4$) |
| 394 | 4-(4'-F—$C_6H_4$) |
| 395 | 2-(2'-Cl—$C_6H_4$) |
| 396 | 2-(3'-Cl—$C_6H_4$) |
| 397 | 2-(4'-Cl—$C_6H_4$) |
| 398 | 3-(2'-Cl—$C_6H_4$) |
| 399 | 3-(3'-Cl—$C_6H_4$) |
| 400 | 3-(4'-Cl—$C_6H_4$) |
| 401 | 4-(2'-Cl—$C_6H_4$) |
| 402 | 4-(3'-Cl—$C_6H_4$) |
| 403 | 4-(4'-Cl—$C_6H_4$) |
| 405 | 2-(2'-$CH_3$—$C_6H_4$) |
| 406 | 2-(3'-$CH_3$—$C_6H_4$) |
| 407 | 2-(4'-$CH_3$—$C_6H_4$) |
| 408 | 3-(2'-$CH_3$—$C_6H_4$) |
| 409 | 3-(3'-$CH_3$—$C_6H_4$) |
| 410 | 3-(4'-$CH_3$—$C_6H_4$) |
| 411 | 4-(2'-$CH_3$—$C_6H_4$) |
| 412 | 4-(3'-$CH_3$—$C_6H_4$) |
| 413 | 4-(4'-$CH_3$—$C_6H_4$) |
| 414 | 2-(2'-$CH_3$—CO—$C_6H_4$) |
| 415 | 2-(3'-$CH_3$—CO—$C_6H_4$) |
| 416 | 2-(4'-$CH_3$—CO—$C_6H_4$) |
| 417 | 3-(2'-$CH_3$—CO—$C_6H_4$) |
| 418 | 3-(3'-$CH_3$—CO—$C_6H_4$) |
| 419 | 3-(4'-$CH_3$—CO—$C_6H_4$) |
| 420 | 4-(2'-$CH_3$—CO—$C_6H_4$) |
| 421 | 4-(3'-$CH_3$—CO—$C_6H_4$) |
| 422 | 4-(4'-$CH_3$—CO—$C_6H_4$) |
| 423 | 2-(2'-($CH_3$—C(=NOAllyl))—$C_6H_4$) |
| 424 | 2-(3'-($CH_3$—C(=NOAllyl))—$C_6H_4$) |
| 425 | 2-(4'-($CH_3$—C(=NOAllyl))—$C_6H_4$) |
| 426 | 3-(2'-($CH_3$—C(=NOAllyl))—$C_6H_4$) |
| 427 | 3-(3'-($CH_3$—C(=NOAllyl))—$C_6H_4$) |
| 428 | 3-(4'-($CH_3$—C(=NOAllyl))—$C_6H_4$) |
| 429 | 4-(2'-($CH_3$—C(=NOAllyl))—$C_6H_4$) |
| 430 | 4-(3'-($CH_3$—C(=NOAllyl))—$C_6H_4$) |
| 431 | 4-(4'-($CH_3$—C(=NOAllyl))—$C_6H_4$) |
| 432 | 2-(2'-$CH_3O_2C$—$C_6H_4$) |
| 433 | 2-(3'-$CH_3O_2C$—$C_6H_4$) |
| 434 | 2-(4'-$CH_3O_2C$—$C_6H_4$) |
| 435 | 3-(2'-$CH_3O_2C$—$C_6H_4$) |
| 436 | 3-(3'-CH3O2C—C6H4) |
| 437 | 3-(4'-$CH_3O_2C$—$C_6H_4$) |
| 438 | 4-(2'-$CH_3O_2C$—$C_6H_4$) |
| 439 | 4-(3'-$CH_3O_2C$—$C_6H_4$) |
| 440 | 4-(4'-$CH_3O_2C$—$C_6H_4$) |
| 441 | 2-(2'-$CH_3O$—$C_6H_4$) |
| 442 | 2-(3'-$CH_3O$—$C_6H_4$) |
| 443 | 2-(4'-$CH_3O$—$C_6H_4$) |
| 444 | 3-(2'-$CH_3O$—$C_6H_4$) |
| 445 | 3-(3'-$CH_3O$—$C_6H_4$) |
| 446 | 3-(4'-$CH_3O$—$C_6H_4$) |
| 447 | 4-(2'-$CH_3O$—$C_6H_4$) |
| 448 | 4-(3'-$CH_3O$—$C_6H_4$) |
| 449 | 4-(4'-$CH_3O$—$C_6H_4$) |
| 450 | 2-(2'-$O_2N$—$C_6H_4$) |
| 451 | 2-(3'-$O_2N$—$C_6H_4$) |
| 452 | 2-(4'-$O_2N$—$C_6H_4$) |
| 453 | 3-(2'-$O_2N$—$C_6H_4$) |
| 454 | 3-(3'-$O_2N$—$C_6H_4$) |
| 455 | 3-(4'-$O_2N$—$C_6H_4$) |
| 456 | 4-(2'-$O_2N$—$C_6H_4$) |
| 457 | 4-(3'-$O_2N$—$C_6H_4$) |
| 458 | 4-(4'-$O_2N$—$C_6H_4$) |
| 459 | 2-(2'-NC—$C_6H_4$) |
| 460 | 2-(3'-NC—$C_6H_4$) |
| 461 | 2-(4'-NC—$C_6H_4$) |
| 462 | 3-(2'-NC—$C_6H_4$) |
| 463 | 3-(3'-NC—$C_6H_4$) |
| 464 | 3-(4'-NC—$C_6H_4$) |
| 465 | 4-(2'-NC—$C_6H_4$) |
| 466 | 4-(3'-NC—$C_6H_4$) |
| 467 | 4-(4'-NC—$C_6H_4$) |
| 468 | 2-(2'-$CF_3$—$C_6H_4$) |
| 469 | 2-(3'-$CF_3$—$C_6H_4$) |
| 470 | 2-(4'-$CF_3$—$C_6H_4$) |
| 471 | 3-(2'-$CF_3$—$C_6H_4$) |
| 472 | 3-(3'-$CF_3$—$C_6H_4$) |
| 473 | 3-(4'-$CF_3$—$C_6H_4$) |
| 474 | 4-(2'-$CF_3$—$C_6H_4$) |
| 475 | 4-(3'-$CF_3$—$C_6H_4$) |
| 476 | 4-(4'-$CF_3$—$C_6H_4$) |
| 477 | 2-O—$C_6H_5$ |
| 475 | 3-O—C6H5 |
| 476 | 4-O—C6H5 |
| 478 | 2-O—(2'-F—$C_6H_4$) |
| 479 | 2-O—(3'-F—$C_6H_4$) |
| 480 | 2-O—(4'-F—$C_6H_4$) |
| 481 | 3-O—(2'-F—$C_6H_4$) |
| 482 | 3-O—(3'-F—$C_6H_4$) |
| 483 | 3-O—(4'-F—$C_6H_4$) |
| 484 | 4-O—(2'-F—$C_6H_4$) |
| 485 | 4-O—(3'-F—$C_6H_4$) |
| 486 | 4-O—(4'-F—$C_6H_4$) |
| 487 | 2-O—(2'-Cl—$C_6H_4$) |

TABLE 8-continued

| | |
|---|---|
| 488 | 2-O—(3'-Cl—C$_6$H$_4$) |
| 489 | 2-O—(4'-Cl—C$_6$H$_4$) |
| 490 | 3-O—(2'-Cl—C$_6$H$_4$) |
| 491 | 3-O—(3'-Cl—C$_6$H$_4$) |
| 492 | 3-O—(4'-Cl—C$_6$H$_4$) |
| 493 | 3-O—(4'-Cl—C$_6$H$_4$) |
| 494 | 4-O—(2'-Cl—C$_6$H$_4$) |
| 495 | 4-O—(3'-Cl—C$_6$H$_4$) |
| 496 | 4-O—(4'-Cl—C$_6$H$_4$) |
| 497 | 2-O—(2'-CH$_3$—C$_6$H$_4$) |
| 498 | 2-O—(3'-CH$_3$—C$_6$H$_4$) |
| 499 | 2-O—(4'-CH$_3$—C$_6$H$_4$) |
| 500 | 3-O—(2'-CH$_3$—C$_6$H$_4$) |
| 501 | 3-O—(3'-CH$_3$—C$_6$H$_4$) |
| 502 | 3-O—(4'-CH$_3$—C$_6$H$_4$) |
| 503 | 4-O—(2'-CH$_3$—C$_6$H$_4$) |
| 504 | 4-O—(3'-CH$_3$—C$_6$H$_4$) |
| 505 | 4-O—(4'-CH$_3$—C$_6$H$_4$) |
| 506 | 2-O—(2'-CH$_3$—CO—C$_6$H$_4$) |
| 507 | 2-O—(3'-CH$_3$—CO—C$_6$H$_4$) |
| 508 | 2-O—(4'-CH$_3$—CO—C6H4) |
| 509 | 3-O—(2'-CH$_3$—CO—C$_6$H$_4$) |
| 510 | 3-O—(3'-CH$_3$—CO—C$_6$H$_4$) |
| 511 | 3-O—(4'-CH$_3$—CO—C$_6$H$_4$) |
| 512 | 4-O—(2'-CH$_3$—CO—C$_6$H$_4$) |
| 513 | 4-O—(3'-CH$_3$—CO—C$_6$H$_4$) |
| 514 | 4-O—(4'-CH$_3$—CO—C$_6$H$_4$) |
| 515 | 2-O—(2'-(CH$_3$—C(=NOAllyl))—C$_6$H$_4$) |
| 516 | 2-O—(3'-(CH$_3$—C(=NOAllyl))—C$_6$H$_4$) |
| 517 | 2-O—(4'-(CH$_3$—C(=NOAllyl))—C$_6$H$_4$) |
| 518 | 3-O—(2'-(CH$_3$—C(=NOAllyl))—C$_6$H$_4$) |
| 519 | 3-O—(3'-(CH$_3$—C(=NOAllyl))—C$_6$H$_4$) |
| 520 | 3-O—(4'-(CH$_3$—C(=NOAllyl))—C$_6$H$_4$) |
| 521 | 4-O—(2'-(CH$_3$—C(=NOAllyl))—C$_6$H$_4$) |
| 522 | 4-O—(3'-(CH$_3$—C(=NOAllyl))—C$_6$H$_4$) |
| 523 | 4-O—(4'-(CH$_3$—C(=NOAllyl))—C$_6$H$_4$) |
| 524 | 2-O—(2'-CH$_3$O$_2$C—C$_6$H$_4$) |
| 525 | 2-O—(3'-CH$_3$O$_2$C—C$_6$H$_4$) |
| 526 | 2-O—(4'-CH$_3$O$_2$C—C$_6$H$_4$) |
| 527 | 3-O—(2'-CH$_3$O$_2$C—C$_6$H$_4$) |
| 528 | 3-O—(3'-CH$_3$O$_2$C—C$_6$H$_4$) |
| 529 | 3-O—(4'-CH$_3$O$_2$C—C$_6$H$_4$) |
| 530 | 4-O—(2'-CH$_3$O$_2$C—C$_6$H$_4$) |
| 531 | 4-O—(3'-CH$_3$O$_2$C—C$_6$H$_4$) |
| 532 | 4-O—(4'-CH$_3$O$_2$C—C$_6$H$_4$) |
| 533 | 2-O—(2'-CH$_3$O—C$_6$H$_4$) |
| 534 | 2-O—(3'-CH$_3$O—C$_6$H$_4$) |
| 535 | 2-O—(4'-CH$_3$O—C$_6$H$_4$) |
| 536 | 3-O—(2'-CH$_3$O—C$_6$H$_4$) |
| 537 | 3-O—(3'-CH$_3$O—C$_6$H$_4$) |
| 538 | 3-O—(4'-CH$_3$O—C$_6$H$_4$) |
| 539 | 4-O—(2'-CH$_3$O—C$_6$H$_4$) |
| 540 | 4-O—(3'-CH$_3$O—C$_6$H$_4$) |
| 541 | 4-O—(4'-CH$_3$O—C$_6$H$_4$) |
| 542 | 2-O—(2'-O$_2$N—C$_6$H$_4$) |
| 543 | 2-O—(3'-O$_2$N—C$_6$H$_4$) |
| 544 | 2-O—(4'-O$_2$N—C$_6$H$_4$) |
| 545 | 3-O—(2'-O$_2$N—C$_6$H$_4$) |
| 546 | 3-O—(3'-O$_2$N—C$_6$H$_4$) |
| 547 | 3-O—(4'-O$_2$N—C$_6$H$_4$) |
| 548 | 4-O—(2'-O$_2$N—C$_6$H$_4$) |
| 549 | 4-O—(3'-O$_2$N—C$_6$H$_4$) |
| 550 | 4-O—(4'-O$_2$N—C$_6$H$_4$) |
| 551 | 2-O—(2'-NC—C$_6$H$_4$) |
| 552 | 2-O—(3'-NC—C$_6$H$_4$) |
| 553 | 2-O—(4'-NC—C$_6$H$_4$) |
| 554 | 3-O—(2'-NC—C$_6$H$_4$) |
| 555 | 3-O—(3'-NC—C$_6$H$_4$) |
| 556 | 3-O—(4'-NC—C$_6$H$_4$) |
| 557 | 4-O—(2'-NC—C$_6$H$_4$) |
| 558 | 4-O—(3'-NC—C$_6$H$_4$) |
| 559 | 4-O—(4'-NC—C$_6$H$_4$) |
| 560 | 2-O—(2'-CF$_3$—C$_6$H$_4$) |
| 561 | 2-O—(3'-CF$_3$—C$_6$H$_4$) |
| 562 | 2-O—(4'-CF$_3$—C$_6$H$_4$) |
| 563 | 3-O—(2'-CF$_3$—C$_6$H$_4$) |
| 564 | 3-O—(3'-CF$_3$—C$_6$H$_4$) |
| 565 | 3-O—(4'-CF$_3$—C$_6$H$_4$) |
| 566 | 4-O—(2'-CF$_3$—C$_6$H$_4$) |
| 567 | 4-O—(3'-CF$_3$—C$_6$H$_4$) |
| 568 | 4-O—(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 666 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-CH$_3$-4-(CH$_3$—C=N—O—CH$_2$—CH$_2$—OCH$_3$) |
| 642 | 2-CH$_3$-4-(C$_2$H$_5$—C=N—O—CH$_2$—CH$_2$—OCH$_3$) |
| 643 | 2,5-(CH$_3$)$_2$-4-(CH$_3$—C=N—O—CH$_2$—CH$_2$—OCH$_3$) |
| 644 | 2-CH$_3$-4-(n-C$_3$H$_7$—C=N—OCH$_3$) |
| 645 | 2-CH$_3$-4-(n-C$_3$H$_7$—C=N—OC$_2$H$_5$) |

TABLE 8-continued

| | |
|---|---|
| 646 | 2-CH$_3$-4-(n-C$_3$H$_7$—C=N—O-n-C$_3$H$_7$) |
| 647 | 2-CH$_3$-4-(n-C$_3$H$_7$—C=N—O-i-C$_3$H$_7$) |
| 648 | 2-CH$_3$-4-(n-C$_3$H$_7$—C=N—O-Allyl) |
| 649 | 2-CH$_3$-4-(n-C$_3$H$_7$—C=N—O-trans-Chloroallyl) |
| 650 | 2-CH$_3$-4-(n-C$_3$H$_7$—C=N—O-Propargyl) |
| 651 | 2-CH$_3$-4-(n-C$_3$H$_7$—C=N—O-n-C$_4$H$_9$) |
| 652 | 2-CH$_3$-4-(n-C$_3$H$_7$—C=N—O—CH$_2$—C$_6$H$_5$) |
| 653 | 2-CH$_3$-4-(i-C$_3$H$_7$—C=N—OCH$_3$) |
| 654 | 2-CH$_3$-4-(i-C$_3$H$_7$—C=N—OC$_2$H$_5$) |
| 655 | 2-CH$_3$-4-(i-C$_3$H$_7$—C=N—O-n-C$_3$H$_7$) |
| 656 | 2-CH$_3$-4-(i-C$_3$H$_7$—C=N—O-i-C$_3$H$_7$) |
| 657 | 2-CH$_3$-4-(i-C$_3$H$_7$—C=N—O-Allyl) |
| 658 | 2-CH$_3$-4-(i-C$_3$H$_7$—C=N—O-trans-Chloroallyl) |
| 659 | 2-CH$_3$-4-(i-C$_3$H$_7$—C=N—O-Propargyl) |
| 660 | 2-CH$_3$-4-(i-C$_3$H$_7$—C=N—O-n-C$_4$H$_9$) |
| 661 | 2-CH$_3$-4-(i-C$_3$H$_7$—C=N—O—CH$_2$—C$_6$H$_5$) |
| 662 | 2-O-n-C$_4$H$_9$ |
| 663 | 2-O-i-C$_4$H$_9$ |
| 664 | 2-O-s-C$_4$H$_9$ |
| 665 | 2-O-t-C$_4$H$_9$ |
| 666 | 2-Neopentyloxy |
| 667 | 3-O-n-C$_4$H$_9$ |
| 668 | 3-O-i-C$_4$H$_9$ |
| 669 | 3-O-s-C$_4$H$_9$ |
| 670 | 3-O-t-C$_4$H$_9$ |
| 671 | 3-Neopentyloxy |
| 672 | 4-O-n-C$_4$H$_9$ |
| 673 | 4-O-i-C$_4$H$_9$ |
| 674 | 4-O-s-C$_4$H$_9$ |
| 675 | 4-O-t-C$_4$H$_9$ |
| 676 | 4-Neopentyloxy |
| 677 | 3-CH$_3$-4-OCH$_3$ |
| 678 | 3-CH$_3$-4-OC$_2$H$_5$ |
| 679 | 3-CH$_3$-4-O-n-C$_3$H$_7$ |
| 680 | 3-CH$_3$-4-O-n-C$_4$H$_9$ |
| 681 | 3-CH$_3$-4-O-i-C$_4$H$_9$ |
| 682 | 3-CH$_3$-4-O-s-C$_4$H$_9$ |
| 683 | 3-CH$_3$-4-O-t-C$_4$H$_9$ |
| 684 | 3-CH$_3$-4-Neopentyloxy |
| 685 | 2-CH$_3$-3-OCH$_3$ |
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 9

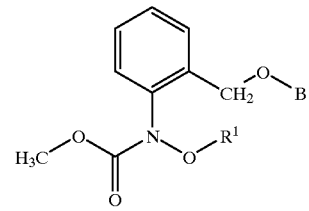

I: $R^1 = CH_3$

II: $R^1 = CH_2$—$CH_3$

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N—(4'-CH$_3$—C$_6$H$_4$)-Pyrrolyl-3 |
| 5 | N—(3'-CH$_3$—C$_6$H$_4$)-Pyrrolyl-3 |
| 6 | N—(2'-CH$_3$—C$_6$H$_4$)-Pyrrolyl-3 |
| 7 | N—(4'-CH$_3$O—C$_6$H$_4$)-Pyrrolyl-3 |
| 8 | N—(3'-CH$_3$O—C$_6$H$_4$)-Pyrrolyl-3 |
| 9 | N—(2'-CH$_3$O—C$_6$H$_4$)-Pyrrolyl-3 |
| 10 | N—(4'-NO$_2$—C$_6$H$_4$)-Pyrrolyl-3 |
| 11 | N—(3'-NO$_2$—C$_6$H$_4$)-Pyrrolyl-3 |
| 12 | N—(2'-NO$_2$—C$_6$H$_4$)-Pyrrolyl-3 |
| 13 | N—(4'-CN—C$_6$H$_4$)-Pyrrolyl-3 |
| 14 | N—(3'-CN—C$_6$H$_4$)-Pyrrolyl-3 |
| 15 | N—(2'-CN—C$_6$H$_4$)-Pyrrolyl-3 |
| 16 | N—(4'-Cl—C$_6$H$_4$)-Pyrrolyl-3 |
| 17 | N—(3'-Cl—C$_6$H$_4$)-Pyrrolyl-3 |
| 18 | N—(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N—(4'-CH$_3$—C$_6$H$_4$)-Pyrrolyl-2 |
| 23 | N—(3'-CH$_3$—C$_6$H$_4$)-Pyrrolyl-2 |
| 24 | N—(2'-CH$_3$—C$_6$H$_4$)-Pyrrolyl-2 |
| 25 | N—(4'-CH$_3$O—C$_6$H$_4$)-Pyrrolyl-2 |
| 26 | N—(3'-CH$_3$O—C$_6$H$_4$)-Pyrrolyl-2 |
| 27 | N—(2'-CH$_3$O—C$_6$H$_4$)-Pyrrolyl-2 |
| 28 | N—(4'-NO$_2$—C$_6$H$_4$)-Pyrrolyl-2 |
| 29 | N—(3'-NO$_2$—C$_6$H$_4$)-Pyrrolyl-2 |
| 30 | N—(2'-NO$_2$—C$_6$H$_4$)-Pyrrolyl-2 |
| 31 | N—(4'-CN—C$_6$H$_4$)-Pyrrolyl-2 |
| 32 | N—(3'-CN—C$_6$H$_4$)-Pyrrolyl-2 |
| 33 | N—(2'-CN—C$_6$H$_4$)-Pyrrolyl-2 |
| 34 | N—(4'-Cl—C$_6$H$_4$)-Pyrrolyl-2 |
| 35 | N—(3'-Cl—C$_6$H$_4$)-Pyrrolyl-2 |
| 36 | N—(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 44 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |

TABLE 9-continued

| | |
|---|---|
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N—(4'-CH$_3$—C$_6$H$_4$)-Pyrazolyl-4 |
| 129 | N—(3'-CH$_3$—C$_6$H$_4$)-Pyrazolyl-4 |
| 130 | N—(2'-CH$_3$—C$_6$H$_4$)-Pyrazolyl-4 |
| 131 | N—(4'-CH$_3$O—C$_6$H$_4$)-Pyrazolyl-4 |
| 132 | N—(3'-CH$_3$O—C$_6$H$_4$)-Pyrazolyl-4 |
| 133 | N—(2'-CH$_3$O—C$_6$H$_4$)-Pyrazolyl-4 |
| 134 | N—(4'-NO$_2$—C$_6$H$_4$)-Pyrazolyl-4 |
| 135 | N—(3'-NO$_2$—C$_6$H$_4$)-Pyrazolyl-4 |
| 136 | N—(2'-NO$_2$—C$_6$H$_4$)-Pyrazolyl-4 |
| 137 | N—(4'-CN—C$_6$H$_4$)-Pyrazolyl-4 |
| 138 | N—(3'-CN—C$_6$H$_4$)-Pyrazolyl-4 |
| 139 | N—(2'-CN—C$_6$H$_4$)-Pyrazolyl-4 |
| 140 | N—(4'-Cl—C$_6$H$_4$)-Pyrazolyl-4 |
| 141 | N—(3'-Cl—C$_6$H$_4$)-Pyrazolyl-4 |

TABLE 9-continued

| | |
|---|---|
| 142 | N—(2'-Cl—C$_6$H$_4$)-Pyrazolyl-4 |
| 143 | 3-CH$_3$-N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(4'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(3'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |

TABLE 9-continued

| | |
|---|---|
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 2-CH$_3$-Oxazolyl-4 |
| 234 | 2-C$_6$H$_5$-Oxazolyl-4 |
| 235 | 2-(4'-CH$_3$—C$_6$H$_4$)-Oxazolyl-4 |
| 236 | 2-(3'-CH$_3$—C$_6$H$_4$)-Oxazolyl-4 |
| 237 | 2-(2'-CH$_3$—C$_6$H$_4$)-Oxazolyl-4 |
| 238 | 2-(4'-CH$_3$O—C$_6$H$_4$)-Oxazolyl-4 |
| 239 | 2-(3'-CH$_3$O—C$_6$H$_4$)-Oxazolyl-4 |
| 240 | 2-(2'-CH$_3$O—C$_6$H$_4$)-Oxazolyl-4 |
| 241 | 2-(4'-NO$_2$—C$_6$H$_4$)-Oxazolyl-4 |
| 242 | 2-(3'-NO$_2$—C$_6$H$_4$)-Oxazolyl-4 |
| 243 | 2-(2'-NO$_2$—C$_6$H$_4$)-Oxazolyl-4 |
| 244 | 2-(4'-CN—C$_6$H$_4$)-Oxazolyl-4 |
| 245 | 2-(3'-CN—C$_6$H$_4$)-Oxazolyl-4 |
| 246 | 2-(2'-CN—C$_6$H$_4$)-Oxazolyl-4 |
| 247 | 2-(4'-Cl—C$_6$H$_4$)-Oxazolyl-4 |
| 248 | 2-(3'-Cl—C$_6$H$_4$)-Oxazolyl-4 |
| 249 | 2-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 257 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2-4-Triazolyl-5 |
| 281 | 3-(3'-CN—C$_6$H$_4$)—N—CH$_3$-1,2-4-Triazolyl-5 |
| 282 | 3-(2'-CN—C$_6$H$_4$)—N—CH$_3$-1,2-4-Triazolyl-5 |
| 283 | 3-(4'-Cl—C$_6$H$_4$)—N—CH$_3$-1,2-4-Triazolyl-5 |
| 284 | 3-(3'-Cl—C$_6$H$_4$)—N—CH$_3$-1,2-4-Triazolyl-5 |
| 285 | 3-(2'-Cl—C$_6$H$_4$)—N—CH$_3$-1,2-4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,3,4-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(4'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |

TABLE 9-continued

| | |
|---|---|
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |
| 385 | 1-Naphthyl |
| 386 | 2-Naphthyl |

TABLE 10

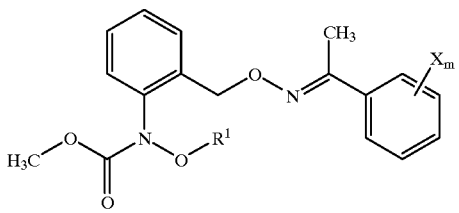

I: $R^1 = CH_3$
II: $R^1 = CH_2-CH_3$

| No. | $X_m$ |
|---|---|
| 1 | H |
| 2 | 2-F |
| 3 | 3-F |
| 4 | 4-F |
| 5 | 2,4-$F_2$ |
| 6 | 2,4,6-$F_3$ |
| 7 | 2,3,4,5,6-$F_5$ |
| 8 | 2,3-$F_2$ |
| 9 | 2-Cl |
| 10 | 3-Cl |
| 11 | 4-Cl |
| 12 | 2,3-$Cl_2$ |
| 13 | 2,4-$Cl_2$ |
| 14 | 2,5-$Cl_2$ |
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |
| 37 | 4-I |
| 38 | 2,4-$I_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |

TABLE 10-continued

| | |
|---|---|
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-$Cl_2$, 4-Br |
| 66 | 2-$CH_3$ |
| 67 | 3-$CH_3$ |
| 68 | 4-$CH_3$ |
| 69 | 2,3-$(CH_3)_2$ |
| 70 | 2,4-$(CH_3)_2$ |
| 71 | 2,5-$(CH_3)_2$ |
| 72 | 2,6-$(CH_3)_2$ |
| 73 | 3,4-$(CH_3)_2$ |
| 74 | 3,5-$(CH_3)_2$ |
| 75 | 2,3,5-$(CH_3)_3$ |
| 76 | 2,3,4-$(CH_3)_3$ |
| 77 | 2,3,6-$(CH_3)_3$ |
| 78 | 2,4,5-$(CH_3)_3$ |
| 79 | 2,4,6-$(CH_3)_3$ |
| 80 | 3,4,5-$(CH_3)_3$ |
| 81 | 2,3,4,6-$(CH_3)_4$ |
| 82 | 2,3,5,6-$(CH_3)_4$ |
| 83 | 2,3,4,5,6-$(CH_3)_5$ |
| 84 | 2-$C_2H_5$ |
| 85 | 3-$C_2H_5$ |
| 86 | 4-$C_2H_5$ |
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C2H5)3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7)_2$ |
| 98 | 2,6-(i-$C_3H_7)_2$ |
| 99 | 3,5-(i-$C_3H_7)_2$ |
| 100 | 2,4,6-(i-$C_3H_7)_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9)_2$ |
| 108 | 2,4-(t-$C_4H_9)_2$ |
| 109 | 2,5-(t-$C_4H_9)_2$ |
| 110 | 2,6-(t-$C_4H_9)_2$ |
| 111 | 3,4-(t-$C_4H_9)_2$ |
| 112 | 2,4,6-(t-$C_4H_9)_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-$C_4H_9$, 4-$CH_3$ |
| 119 | 2-t-$C_4H_9$, 5-$CH_3$ |
| 120 | 2,6-(t-$C_4H_9)_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9)_2$, 6-i-$C_3H_7$ |

TABLE 10-continued

| | |
|---|---|
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O-(CH$_2$)$_3$C$_6$H$_5$ |
| 181 | 3-O-(CH$_2$)$_3$C$_6$H$_5$ |
| 182 | 4-O-(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |

TABLE 10-continued

| | |
|---|---|
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)-CH$_3$ |
| 299 | 3-CO—CH(CH$_3$)-CH$_3$ |
| 300 | 4-CO—CH(CH$_3$)-CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)-CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)-CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)-CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$——CH(CH$_3$)-CO |
| 320 | 2-C(=NOCH$_3$)-CH$_3$ |
| 321 | 3-C(=NOCH$_3$)-CH$_3$ |
| 322 | 4-C(=NOCH$_3$)-CH$_3$ |
| 323 | 2-C(=NOC$_2$H$_5$)-CH$_3$ |
| 324 | 3-C(=NOC$_2$H$_5$)-CH$_3$ |
| 325 | 4-C(=NOC$_2$H$_5$)-CH$_3$ |
| 326 | 2-C(=NO-n-C$_3$H$_7$)-CH$_3$ |
| 327 | 3-C(=NO-n-C$_3$H$_7$)-CH$_3$ |
| 328 | 4-C(=NO-n-C$_3$H$_7$)-CH$_3$ |
| 329 | 2-C(=NO-i-C$_3$H$_7$)-CH$_3$ |
| 330 | 3-C(=NO-i-C$_3$H$_7$)-CH$_3$ |
| 331 | 4-C(=NO-i-C$_3$H$_7$)-CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)-CH$_3$ |
| 342 | 3-C(=NO-n-C$_4$H$_9$)-CH$_3$ |
| 343 | 4-C(=NO-n-C$_4$H$_9$)-CH$_3$ |
| 344 | 2-C(=NO—CH$^2$—C$_6$H$_5$)-CH$_3$ |
| 345 | 3-C(=NO—CH$_2$—C$_6$H$_5$)-CH$_3$ |
| 346 | 4-C(=NO—CH$_2$—C$_6$H$_5$)-CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C-C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH3O2C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |

TABLE 10-continued

| | |
|---|---|
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF3—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH3—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O2N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |

TABLE 10-continued

| | |
|---|---|
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-CH$_3$-4-(CH$_3$—C=N—O—CH$_2$—CH$_2$—OCH$_3$) |
| 642 | 2-CH$_3$-4-(C$_2$H$_5$—C=N—O—CH$_2$—CH$_2$—OCH$_3$) |
| 643 | 2,5-(CH$_3$)$_2$-4-(CH$_3$—C=N—O—CH$_2$—CH$_2$—OCH$_3$) |
| 644 | 2-CH$_3$-4-(n-C$_3$H$_7$—C=N—OCH$_3$) |
| 645 | 2-CH$_3$-4-(n-C$_3$H$_7$—C=N—OC$_2$H$_5$) |
| 646 | 2-CH$_3$-4-(n-C$_3$H$_7$—C=N—O-n-C$_3$H$_7$) |
| 647 | 2-CH$_3$-4-(n-C$_3$H$_7$—C=N—O-i-C$_3$H$_7$) |
| 648 | 2-CH$_3$-4-(n-C$_3$H$_7$—C=N—O-Allyl) |
| 649 | 2-CH$_3$-4-(n-C$_3$H$_7$—C=N—O-trans-Chloroallyl) |
| 650 | 2-CH$_3$-4-(n-C$_3$H$_7$—C=N—O-Propargyl) |
| 651 | 2-CH$_3$-4-(n-C$_3$H$_7$—C=N—O-n-C$_4$H$_9$) |
| 652 | 2-CH$_3$-4-(n-C$_3$H$_7$—C=N—O—CH$_2$—C$_6$H$_5$) |
| 653 | 2-CH$_3$-4-(i-C$_3$H$_7$—C=N—OCH$_3$) |
| 654 | 2-CH$_3$-4-(i-C$_3$H$_7$—C=N—OC$_2$H$_5$) |
| 655 | 2-CH$_3$-4-(i-C$_3$H$_7$—C=N—O-n-C$_3$H$_7$) |
| 656 | 2-CH$_3$-4-(i-C$_3$H$_7$—C=N—O-i-C$_3$H$_7$) |
| 657 | 2-CH$_3$-4-(i-C$_3$H$_7$—C=N—O-Allyl) |
| 658 | 2-CH$_3$-4-(i-C$_3$H$_7$—C=N—O-trans-Chloroallyl) |
| 659 | 2-CH$_3$-4-(i-C$_3$H$_7$—C=N—O-Propargyl) |
| 660 | 2-CH$_3$-4-(i-C$_3$H$_7$—C=N—O-n-C$_4$H$_9$) |
| 661 | 2-CH$_3$-4-(i-C$_3$H$_7$—C=N—O—CH$_2$—C$_6$H$_5$) |
| 662 | 2-O-n-C$_4$H$_9$ |
| 663 | 2-O-i-C$_4$H$_9$ |
| 664 | 2-O-s-C$_4$H$_9$ |
| 665 | 2-O-t-C$_4$H$_9$ |
| 666 | 2-Neopentyloxy |
| 667 | 3-O-n-C$_4$H$_9$ |
| 668 | 3-O-i-C$_4$H$_9$ |
| 669 | 3-O-s-C$_4$H$_9$ |
| 670 | 3-O-t-C$_4$H$_9$ |
| 671 | 3-Neopentyloxy |
| 672 | 4-O-n-C$_4$H$_9$ |
| 673 | 4-O-i-C$_4$H$_9$ |
| 674 | 4-O-s-C$_4$H$_9$ |
| 675 | 4-O-t-C$_4$H$_9$ |
| 676 | 4-Neopentyloxy |
| 677 | 3-CH$_3$-4-OCH$_3$ |
| 678 | 3-CH$_3$-4-OC$_2$H$_5$ |
| 679 | 3-CH$_3$-4-O-n-C$_3$H$_7$ |

TABLE 10-continued

| | |
|---|---|
| 680 | 3-CH$_3$-4-O-n-C$_4$H$_9$ |
| 681 | 3-CH$_3$-4-O-i-C$_4$H$_9$ |
| 682 | 3-CH$_3$-4-O-s-C$_4$H$_9$ |
| 683 | 3-CH$_3$-4-O-t-C$_4$H$_9$ |
| 684 | 3-CH$_3$-4-Neopentyloxy |
| 685 | 2-CH$_3$-3-OCH$_3$ |
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 793 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 11

I: R$^1$ = CH$_3$

II: R$^1$ = CH$_2$—CH$_3$

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |

TABLE 11-continued

| | |
|---|---|
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-CN—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$-)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)-N-Methylpyrazolyl-4 |
| 146 | 3-(3'-CH$_3$—C$_6$H$_4$)-N-Methylpyrazolyl-4 |
| 147 | 3-(2'-CH$_3$—C$_6$H$_4$)-N-Methylpyrazolyl-4 |
| 148 | 3-(4'-CH$_3$O—C$_6$H$_4$)-N-Methylpyrazolyl-4 |
| 149 | 3-(3'-CH$_3$O—C$_6$H$_4$)-N-Methylpyrazolyl-4 |
| 150 | 3-(2'-CH$_3$O—C$_6$H$_4$)-N-Methylpyrazolyl-4 |
| 151 | 3-(4'-NO$_2$—C$_6$H$_4$)-N-Methylpyrazolyl-4 |
| 152 | 3-(3'-NO$_2$—C$_6$H$_4$)-N-Methylpyrazolyl-4 |
| 153 | 3-(2'-NO$_2$—C$_6$H$_4$)-N-Methylpyrazolyl-4 |
| 154 | 3-(4'-CN—C$_6$H$_4$)-N-Methylpyrazolyl-4 |
| 155 | 3-(3'-CN—C$_6$H$_4$)-N-Methylpyrazolyl-4 |
| 156 | 3-(2'-CN—C$_6$H$_4$)-N-Methylpyrazolyl-4 |
| 157 | 3-(4'-Cl—C$_6$H$_4$)-N-Methylpyrazolyl-4 |
| 158 | 3-(3'-Cl—C$_6$H$_4$)-N-Methylpyrazolyl-4 |
| 159 | 3-(2'-Cl—C$_6$H$_4$)-N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |

TABLE 11-continued

| | |
|---|---|
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 2-CH$_3$-Oxazolyl-4 |
| 234 | 2-C$_6$H$_5$-Oxazolyl-4 |
| 235 | 2-(4'-CH$_3$—C$_6$H$_4$)-Oxazolyl-4 |
| 236 | 2-(3'-CH$_3$—C$_6$H$_4$)-Oxazolyl-4 |
| 237 | 2-(2'-CH$_3$—C$_6$H$_4$)-Oxazolyl-4 |
| 238 | 2-(4'-CH$_3$O—C$_6$H$_4$)-Oxazolyl-4 |
| 239 | 2-(3'-CH$_3$O—C$_6$H$_4$)-Oxazolyl-4 |
| 240 | 2-(2'-CH$_3$O—C$_6$H$_4$)-Oxazolyl-4 |
| 241 | 2-(4'-NO$_2$—C$_6$H$_4$)-Oxazolyl-4 |
| 242 | 2-(3'-NO$_2$—C$_6$H$_4$)-Oxazolyl-4 |
| 243 | 2-(2'-NO$_2$—C$_6$H$_4$)-Oxazolyl-4 |
| 244 | 2-(4'-CN—C$_6$H$_4$)-Oxazolyl-4 |
| 245 | 2-(3'-CN—C$_6$H$_4$)-Oxazolyl-4 |
| 246 | 2-(2'-CN—C$_6$H$_4$)-Oxazolyl-4 |
| 247 | 2-(4'-Cl—C$_6$H$_4$)-Oxazolyl-4 |
| 248 | 2-(3'-Cl—C$_6$H$_4$)-Oxazolyl-4 |
| 249 | 2-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 257 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,2,3-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |

TABLE 11-continued

| | |
|---|---|
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |
| 385 | 1-Naphthyl |
| 386 | 2-Naphthyl |

TABLE 12

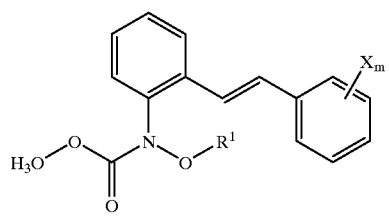

I: R$^1$ = CH$_3$
II: R$^1$ = CH$_2$—CH$_3$

| No. | X$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |

TABLE 12-continued

| | |
|---|---|
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |

TABLE 12-continued

| | |
|---|---|
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C_2H_5)_3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7)_2$ |
| 98 | 2,6-(i-$C_3H_7)_2$ |
| 99 | 3,5-(i-$C_3H_7)_2$ |
| 100 | 2,4,6-(i-$C_3H_7)_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9)_2$ |
| 108 | 2,4-(t-$C_4H_9)_2$ |
| 109 | 2,5-(t-$C_4H_9)_2$ |
| 110 | 2,6-(t-$C_4H_9)_2$ |
| 111 | 3,4-(t-$C_4H_9)_2$ |
| 112 | 2,4,6-(t-$C_4H_9)_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-$C_4H_9$, 4-$CH_3$ |
| 119 | 2-t-$C_4H_9$, 5-$CH_3$ |
| 120 | 2,6-(t-C4H9)2, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9)_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11})_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-$(CH_3)_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-C6H11 |
| 159 | 2-$OCH_3$ |
| 160 | 3-$OCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-$C_6H_{13}$ |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—$(CH_2)_3C_6H_5$ |
| 181 | 3-O—$(CH_2)_3C_6H_5$ |
| 182 | 4-O—$(CH_2)_3C_6H_5$ |
| 183 | 2,4-$(OCH_3)_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 3-$CH_3$, 4-Cl |
| 199 | 4-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-$CH_3$, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-$(CH_3)_2$ |
| 228 | 2-Br, 4,5-$(CH_3)_2$ |
| 229 | 2-Cl, 3,5-$(CH_3)_2$ |
| 230 | 2-Br, 3,5-$(CH_3)_2$ |
| 231 | 2,6-$Cl_2$, 4-$CH_3$ |
| 232 | 2,6-$F_2$, 4-$CH_3$ |
| 233 | 2,6-$Br_2$, 4-$CH_3$ |
| 234 | 2,4-$Br_2$, 6-$CH_3$ |
| 235 | 2,4-$F_2$, 6-$CH_3$ |
| 236 | 2,4-$Br_2$, 6-$CH_3$ |
| 237 | 2,6-$(CH_3)_2$, 4-F |
| 238 | 2,6-$(CH_3)_2$, 4-Cl |
| 239 | 2,6-$(CH_3)_2$, 4-Br |
| 240 | 3,5-$(CH_3)_2$, 4-F |
| 241 | 3,5-$(CH_3)_2$, 4-Cl |
| 242 | 3,5-$(CH_3)_2$, 4-Br |
| 243 | 2,3,6-$(CH_3)_3$, 4-F |
| 244 | 2,3,6-$(CH_3)_3$, 4-Cl |

TABLE 12-continued

| | |
|---|---|
| 245 | 2,3,6-$(CH_3)_3$, 4-Br |
| 246 | 2,4-$(CH_3)_2$, 6-F |
| 247 | 2,4-$(CH_3)_2$, 6-Cl |
| 248 | 2,4-$(CH_3)_2$, 6-Br |
| 249 | 2-i-$C_3H_7$, 4-Cl, 5-$CH_3$ |
| 250 | 2-Cl, 4-$NO_2$ |
| 251 | 2-$NO_2$, 4-Cl |
| 252 | 2-$OCH_3$, 5-$NO_2$ |
| 253 | 2,4-$Cl_2$, 5-$NO_2$ |
| 254 | 2,4-$Cl_2$, 6-$NO_2$ |
| 255 | 2,6-$Cl_2$, 4-$NO_2$ |
| 256 | 2,6-$Br_2$, 4-$NO_2$ |
| 257 | 2,6-$I_2$, 4-$NO_2$ |
| 258 | 2-$CH_3$, 5-i-$C_3H_7$, 4-Cl |
| 259 | 2-$CO_2CH_3$ |
| 260 | 3-$CO_2CH_3$ |
| 261 | 4-$CO_2CH_3$ |
| 262 | 2-$CO_2(C_2H_5)$ |
| 263 | 3-$CO_2(C_2H_5)$ |
| 264 | 4-$CO_2(C_2H_5)$ |
| 265 | 2-$CO_2$(n-$C_3H_7$) |
| 266 | 3-$CO_2$(n-$C_3H_7$) |
| 267 | 4-$CO_2$(n-$C_3H_7$) |
| 268 | 2-$CO_2$(i-$C_3H_7$) |
| 269 | 3-$CO_2$(i-$C_3H_7$) |
| 270 | 4-$CO_2$(i-$C_3H_7$) |
| 271 | 2-$CO_2$(n-$C_6H_{13}$) |
| 272 | 3-$CO_2$(n-$C_6H_{13}$) |
| 273 | 4-$CO_2$(n-$C_6H_{13}$) |
| 274 | 2-$CH_2$—$OCH_3$ |
| 275 | 3-$CH_2$—$OCH_3$ |
| 276 | 4-$CH_2$—$OCH_3$ |
| 277 | 2-$CH_2O(C_2H_5)$ |
| 278 | 3-$CH_2O(C_2H_5)$ |
| 279 | 4-$CH_2O(C_2H_5)$ |
| 280 | 2-$CH_2O$(n-$C_3H_7$) |
| 281 | 3-$CH_2O$(n-$C_3H_7$) |
| 282 | 4-$CH_2O$(n-$C_3H_7$) |
| 283 | 2-$CH_2O$(i-$C_3H_7$) |
| 284 | 3-$CH_2O$(i-$C_3H_7$) |
| 285 | 4-$CH_2O$(i-$C_3H_7$) |
| 286 | 2-CHO |
| 287 | 3-CHO |
| 288 | 4-CHO |
| 289 | 2-CO—$CH_3$ |
| 290 | 3-CO—$CH_3$ |
| 291 | 4-CO—$CH_3$ |
| 292 | 2-CO—$CH_2$—$CH_3$ |
| 293 | 3-CO—$CH_2$—$CH_3$ |
| 294 | 4-CO—$CH_2$—$CH_3$ |
| 295 | 2-CO—$CH_2$—$CH_2$—$CH_3$ |
| 296 | 3-CO—$CH_2$—$CH_2$—$CH_3$ |
| 297 | 4-CO—$CH_2$—$CH_2$—$CH_3$ |
| 298 | 2-CO—$CH(CH_3)$—$CH_3$ |
| 299 | 3-CO—$CH(CH_3)$—$CH_3$ |
| 300 | 4-CO—$CH(CH_3)$—$CH_3$ |
| 301 | 2-Me-4-CHO |
| 302 | 2-Me-4-$CH_3$—CO |
| 303 | 2-Me-4-$CH_3$—$CH_2$—CO |
| 304 | 2-Me-4-$CH_3$—$CH_2$—$CH_2$—CO |
| 305 | 2-Me-4-$CH_3$—$CH(CH_3)$—CO |
| 306 | 2,5-$Me_2$-4-CHO |
| 307 | 2,5-$Me_2$-4-$CH_3$—CO |
| 308 | 2,5-$Me_2$-4-$CH_3$—$CH_2$—CO |
| 309 | 2,5-$Me_2$-4-$CH_3$—$CH_2$—$CH_2$—CO |
| 310 | 2,5-$Me_2$-4-$CH_3$—$CH(CH_3)$—CO |
| 311 | 2-Cl-4-CHO |
| 312 | 2-Cl-4-$CH_3$—CO |
| 313 | 2-Cl-4-$CH_3$—$CH_2$—CO |
| 314 | 2-Cl-4-$CH_3$—$CH(CH_3)$—CO |
| 315 | 2,5-$Cl_2$-4-CHO |
| 316 | 2,5-$Cl_2$-4-$CH_3$—CO |
| 317 | 2,5-$Cl_2$-4-$CH_3$—$CH_2$—CO |
| 318 | 2,5-$Cl_2$-4-$CH_3$—$CH_2$—$CH_2$—CO |
| 319 | 2,5-$Cl_2$-4-$CH_3$—$CH(CH_3)$—CO |
| 320 | 2-C(=$NOCH_3$)—$CH_3$ |
| 321 | 3-C(=$NOCH_3$)—$CH_3$ |
| 322 | 4-C(=$NOCH_3$)—$CH_3$ |
| 323 | 2-C(=$NOC_2H_5$)—$CH_3$ |
| 324 | 3-C(=$NOC_2H_5$)—$CH_3$ |
| 325 | 4-C(=$NOC_2H_5$)—$CH_3$ |
| 326 | 2-C(=NO-n-$C_3H_7$)—$CH_3$ |
| 327 | 3-C(=NO-n-$C_3H_7$)—$CH_3$ |
| 328 | 4-C(=NO-n-$C_3H_7$)—$CH_3$ |
| 329 | 2-C(=NO-i-$C_3H_7$)—$CH_3$ |
| 330 | 3-C(=NO-i-$C_3H_7$)—$CH_3$ |
| 331 | 4-C(=NO-i-$C_3H_7$)—$CH_3$ |
| 332 | 2-C(=NO-Allyl)—$CH_3$ |
| 333 | 3-C(=NO-Allyl)—$CH_3$ |
| 334 | 4-C(=NO-Allyl)—$CH_3$ |
| 335 | 2-C(=NO-trans-Chloroallyl)—$CH_3$ |
| 336 | 3-C(=NO-trans-Chloroallyl)—$CH_3$ |
| 337 | 4-C(=NO-trans-Chloroallyl)—$CH_3$ |
| 338 | 2-C(=NO-Propargyl)—$CH_3$ |
| 339 | 3-C(=NO-Propargyl)—$CH_3$ |
| 340 | 4-C(=NO-Propargyl)—$CH_3$ |
| 341 | 2-C(=NO-n-$C_4H_9$)—$CH_3$ |
| 342 | 3-C(=NO-n-$C_4H_9$)—$CH_3$ |
| 343 | 4-C(=NO-n-$C_4H_9$)—$CH_3$ |
| 344 | 2-C(=NO—$CH_2$—$C_6H_5$)—$CH_3$ |
| 345 | 3-C(=NO—$CH_2$—$C_6H_5$)—$CH_3$ |
| 346 | 4-C(=NO—$CH_2$—$C_6H_5$)—$CH_3$ |
| 347 | 2-$CH_3$-4-CH=$NOCH_3$ |
| 348 | 2-$CH_3$-4-CH=$NOC_2H_5$ |
| 349 | 2-$CH_3$-4-CH=NO-n-$C_3H_7$ |
| 350 | 2-$CH_3$-4-CH=NO-i-$C_3H_7$ |
| 351 | 2-$CH_3$-4-CH=NO-Allyl |
| 352 | 2-$CH_3$-4-CH=NO-(trans-Chloroallyl) |
| 353 | 2-$CH_3$-4-CH=NO-Propargyl |
| 354 | 2-$CH_3$-4-CH=NO-n-$C_4H_9$ |
| 355 | 2-$CH_3$-4-CH=NO—$CH_2$—$C_6H_5$ |
| 356 | 2-$CH_3$-4-($CH_3$—C=$NOCH_3$) |
| 357 | 2-$CH_3$-4-($CH_3$—C=$NOC_2H_5$) |
| 358 | 2-$CH_3$-4-($CH_3$—C=NO-n-$C_3H_7$) |
| 359 | 2-$CH_3$-4-($CH_3$—C=NO-i-$C_3H_7$) |
| 360 | 2-$CH_3$-4-($CH_3$—C=NO-Allyl) |
| 361 | 2-$CH_3$-4-($CH_3$—C=NO-trans-Chloroallyl) |
| 362 | 2-$CH_3$-4-($CH_3$—C=NO-Propargyl) |
| 363 | 2-$CH_3$-4-($CH_3$—C=NO-n-$C_4H_9$) |
| 364 | 2-$CH_3$-4-($CH_3$—C=NO—$CH_2$—$C_6H_5$) |
| 365 | 2-$CH_3$-4-($C_2H_5$—C=NO—$CH_3$) |
| 366 | 2-$CH_3$-4-($C_2H_5$—C=NO—$C_2H_5$) |
| 367 | 2-$CH_3$-4-($C_2H_5$—C=NO-n-$C_3H_7$) |
| 368 | 2-$CH_3$-4-($C_2H_5$—C=NO-i-$C_3H_7$) |
| 369 | 2-$CH_3$-4-($C_2H_5$—C=NO-Allyl) |
| 370 | 2-$CH_3$-4-($C_2H_5$—C=NO-trans-Chloroallyl) |
| 371 | 2-$CH_3$-4-($C_2H_5$—C=NO-Propargyl) |
| 372 | 2-$CH_3$-4-($C_2H_5$—C=NO-n-$C_4H_9$) |
| 373 | 2-$CH_3$-4-($C_2H_5$—C=NO—$CH_2$—$C_6H_5$) |
| 374 | 2,5-$(CH_3)_2$-4-($CH_3$—C=$NOCH_3$) |
| 375 | 2,5-$(CH_3)_2$-4-($CH_3$—C=$NOC_2H_5$) |
| 376 | 2,5-$(CH_3)_2$-4-($CH_3$—C=NO-n-$C_3H_7$) |
| 377 | 2,5-$(CH_3)_2$-4-($CH_3$—C=NO-i-$C_3H_7$) |
| 378 | 2,5-$(CH_3)_2$-4-($CH_3$—C=NO-Allyl) |
| 379 | 2,5-$(CH_3)_2$-4-($CH_3$—C=NO-trans-Chloroallyl) |
| 380 | 2,5-$(CH_3)_2$-4-($CH_3$—C=NO-Proparyl) |
| 381 | 2,5-$(CH_3)_2$-4-($CH_3$—C=NO-n-$C_4H_9$) |
| 382 | 2,5-$(CH_3)_2$-4-($CH_3$—C=NO—$CH_2$—$C_6H_5$) |
| 383 | 2-$C_6H_5$ |
| 384 | 3-C6H5 |
| 385 | 4-C6H5 |
| 386 | 2-(2'-F—$C_6H_4$) |
| 387 | 2-(3'-F—$C_6H_4$) |
| 388 | 2-(4'-F—$C_6H_4$) |
| 389 | 3-(2'-F—$C_6H_4$) |
| 390 | 3-(3'-F—$C_6H_4$) |
| 391 | 3-(4'-F—$C_6H_4$) |
| 392 | 4-(2'-F—$C_6H_4$) |
| 393 | 4-(3'-F—$C_6H_4$) |
| 394 | 4-(4'-F—$C_6H_4$) |
| 395 | 2-(2'-Cl—$C_6H_4$) |
| 396 | 2-(3'-Cl—$C_6H_4$) |
| 397 | 2-(4'-Cl—$C_6H_4$) |
| 398 | 3-(2'-Cl—$C_6H_4$) |
| 399 | 3-(3'-Cl—$C_6H_4$) |
| 400 | 3-(4'-Cl—$C_6H_4$) |
| 401 | 4-(2'-Cl—$C_6H_4$) |
| 402 | 4-(3'-Cl—$C_6H_4$) |

TABLE 12-continued

| | |
|---|---|
| 403 | 4-(4'-Cl—$C_6H_4$) |
| 405 | 2-(2'-$CH_3$—$C_6H_4$) |
| 406 | 2-(3'-$CH_3$—$C_6H_4$) |
| 407 | 2-(4'-$CH_3$—$C_6H_4$) |
| 408 | 3-(2'-$CH_3$—$C_6H_4$) |
| 409 | 3-(3'-$CH_3$—$C_6H_4$) |
| 410 | 3-(4'-$CH_3$—$C_6H_4$) |
| 411 | 4-(2'-$CH_3$—$C_6H_4$) |
| 412 | 4-(3'-$CH_3$—$C_6H_4$) |
| 413 | 4-(4'-$CH_3$—$C_6H_4$) |
| 414 | 2-(2'-$CH_3$—CO—$C_6H_4$) |
| 415 | 2-(3'-$CH_3$—CO—$C_6H_4$) |
| 416 | 2-(4'-$CH_3$—CO—$C_6H_4$) |
| 417 | 3-(2'-$CH_3$—CO—$C_6H_4$) |
| 418 | 3-(3'-$CH_3$—CO—$C_6H_4$) |
| 419 | 3-(4'-$CH_3$—CO—$C_6H_4$) |
| 420 | 4-(2'-$CH_3$—CO—$C_6H_4$) |
| 421 | 4-(3'-$CH_3$—CO—$C_6H_4$) |
| 422 | 4-(4'-$CH_3$—CO—$C_6H_4$) |
| 423 | 2-(2'-($CH_3$—C(=NOAllyl))—$C_6H_4$) |
| 424 | 2-(3'-($CH_3$—C(=NOAllyl))—$C_6H_4$) |
| 425 | 2-(4'-($CH_3$—C(=NOAllyl))—$C_6H_4$) |
| 426 | 3-(2'-($CH_3$—C(=NOAllyl))—$C_6H_4$) |
| 427 | 3-(3'-($CH_3$—C(=NOAllyl))—$C_6H_4$) |
| 428 | 3-(4'-($CH_3$—C(=NOAllyl))—$C_6H_4$) |
| 429 | 4-(2'-($CH_3$—C(=NOAllyl))—$C_6H_4$) |
| 430 | 4-(3'-($CH_3$—C(=NOAllyl))—$C_6H_4$) |
| 431 | 4-(4'-($CH_3$—C(=NOAllyl))—$C_6H_4$) |
| 432 | 2-(2'-$CH_3O_2C$—$C_6H_4$) |
| 433 | 2-(3'-$CH_3O_2C$—$C_6H_4$) |
| 434 | 2-(4'-$CH_3O_2C$—$C_6H_4$) |
| 435 | 3-(2'-$CH_3O_2C$—$C_6H_4$) |
| 436 | 3-(3'-$CH_3O_2C$—$C_6H_4$) |
| 437 | 3-(4'-$CH_3O_2C$—$C_6H_4$) |
| 438 | 4-(2'-$CH_3O_2C$—$C_6H_4$) |
| 439 | 4-(3'-$CH_3O_2C$—$C_6H_4$) |
| 440 | 4-(4'-$CH_3O_2C$—$C_6H_4$) |
| 441 | 2-(2'-$CH_3O$—$C_6H_4$) |
| 442 | 2-(3'-$CH_3O$—$C_6H_4$) |
| 443 | 2-(4'-$CH_3O$—$C_6H_4$) |
| 444 | 3-(2'-$CH_3O$—$C_6H_4$) |
| 445 | 3-(3'-$CH_3O$—$C_6H_4$) |
| 446 | 3-(4'-$CH_3O$—$C_6H_4$) |
| 447 | 4-(2'-$CH_3O$—$C_6H_4$) |
| 448 | 4-(3'-$CH_3O$—$C_6H_4$) |
| 449 | 4-(4'-$CH_3O$—$C_6H_4$) |
| 450 | 2-(2'-$O_2N$—$C_6H_4$) |
| 451 | 2-(3'-$O_2N$—$C_6H_4$) |
| 452 | 2-(4'-$O_2N$—$C_6H_4$) |
| 453 | 3-(2'-$O_2N$—$C_6H_4$) |
| 454 | 3-(3'-$O_2N$—$C_6H_4$) |
| 455 | 3-(4'-$O_2N$—$C_6H_4$) |
| 456 | 4-(2'-$O_2N$—$C_6H_4$) |
| 457 | 4-(3'-$O_2N$—$C_6H_4$) |
| 458 | 4-(4'-$O_2N$—$C_6H_4$) |
| 459 | 2-(2'-NC—$C_6H_4$) |
| 460 | 2-(3'-NC—$C_6H_4$) |
| 461 | 2-(4'-NC—$C_6H_4$) |
| 462 | 3-(2'-NC—$C_6H_4$) |
| 463 | 3-(3'-NC—$C_6H_4$) |
| 464 | 3-(4'-NC—$C_6H_4$) |
| 465 | 4-(2'-NC—$C_6H_4$) |
| 466 | 4-(3'-NC—$C_6H_4$) |
| 467 | 4-(4'-NC—$C_6H_4$) |
| 468 | 2-(2'-$CF_3$—$C_6H_4$) |
| 469 | 2-(3'-$CF_3$—$C_6H_4$) |
| 470 | 2-(4'-$CF_3$—$C_6H_4$) |
| 471 | 3-(2'-$CF_3$—$C_6H_4$) |
| 472 | 3-(3'-$CF_3$—$C_6H_4$) |
| 473 | 3-(4'-$CF_3$—$C_6H_4$) |
| 474 | 4-(2'-$CF_3$—$C_6H_4$) |
| 475 | 4-(3'-$CF_3$—$C_6H_4$) |
| 476 | 4-(4'-$CF_3$—$C_6H_4$) |
| 477 | 2-O—$C_6H_5$ |
| 475 | 3-O—C6H5 |
| 476 | 4-O—C6H5 |
| 478 | 2-O—(2'-F—$C_6H_4$) |
| 479 | 2-O—(3'-F—$C_6H_4$) |
| 480 | 2-O—(4'-F—$C_6H_4$) |
| 481 | 3-O—(2'-F—$C_6H_4$) |
| 482 | 3-O—(3'-F—$C_6H_4$) |
| 483 | 3-O—(4'-F—$C_6H_4$) |
| 484 | 4-O—(2'-F—$C_6H_4$) |
| 485 | 4-O—(3'-F—$C_6H_4$) |
| 486 | 4-O—(4'-F—$C_6H_4$) |
| 487 | 2-O—(2'-Cl—$C_6H_4$) |
| 488 | 2-O—(3'-Cl—$C_6H_4$) |
| 489 | 2-O—(4'-Cl—$C_6H_4$) |
| 490 | 3-O—(2'-Cl—$C_6H_4$) |
| 491 | 3-O—(3'-Cl—$C_6H_4$) |
| 492 | 3-O—(4'-Cl—$C_6H_4$) |
| 493 | 3-O—(4'-Cl—$C_6H_4$) |
| 494 | 4-O—(2'-Cl—$C_6H_4$) |
| 495 | 4-O—(3'-Cl—$C_6H_4$) |
| 496 | 4-O—(4'-Cl—$C_6H_4$) |
| 497 | 2-O—(2'-$CH_3$—$C_6H_4$) |
| 498 | 2-O—(3'-$CH_3$—$C_6H_4$) |
| 499 | 2-O—(4'-$CH_3$—$C_6H_4$) |
| 500 | 3-O—(2'-$CH_3$—$C_6H_4$) |
| 501 | 3-O—(3'-$CH_3$—$C_6H_4$) |
| 502 | 3-O—(4'-$CH_3$—$C_6H_4$) |
| 503 | 4-O—(2'-$CH_3$—$C_6H_4$) |
| 504 | 4-O—(3'-$CH_3$—$C_6H_4$) |
| 505 | 4-O—(4'-$CH_3$—$C_6H_4$) |
| 506 | 2-O—(2'-$CH_3$—CO—$C_6H_4$) |
| 507 | 2-O—(3'-$CH_3$—CO—$C_6H_4$) |
| 508 | 2-O—(4'-$CH_3$—CO—$C_6H_4$) |
| 509 | 3-O—(2'-$CH_3$—CO—$C_6H_4$) |
| 510 | 3-O—(3'-$CH_3$—CO—$C_6H_4$) |
| 511 | 3-O—(4'-$CH_3$—CO—$C_6H_4$) |
| 512 | 4-O—(2'-$CH_3$—CO—$C_6H_4$) |
| 513 | 4-O—(3'-$CH_3$—CO—$C_6H_4$) |
| 514 | 4-O—(4'-$CH_3$—CO—$C_6H_4$) |
| 515 | 2-O—(2'-($CH_3$—C(=NOAllyl))—$C_6H_4$) |
| 516 | 2-O—(3'-($CH_3$—C(=NOAllyl))—$C_6H_4$) |
| 517 | 2-O—(4'-($CH_3$—C(=NOAllyl))—$C_6H_4$) |
| 518 | 3-O—(2'-($CH_3$—C(=NOAllyl))—$C_6H_4$) |
| 519 | 3-O—(3'-($CH_3$—C(=NOAllyl))—$C_6H_4$) |
| 520 | 3-O—(4'-($CH_3$—C(=NOAllyl))—$C_6H_4$) |
| 521 | 4-O—(2'-($CH_3$—C(=NOAllyl))—$C_6H_4$) |
| 522 | 4-O—(3'-($CH_3$—C(=NOAllyl))—$C_6H_4$) |
| 523 | 4-O—(4'-($CH_3$—C(=NOAllyl))—$C_6H_4$) |
| 524 | 2-O—(2'-$CH_3O_2C$—$C_6H_4$) |
| 525 | 2-O—(3'-$CH_3O_2C$—$C_6H_4$) |
| 526 | 2-O—(4'-$CH_3O_2C$—$C_6H_4$) |
| 527 | 3-O—(2'-$CH_3O_2C$—$C_6H_4$) |
| 528 | 3-O—(3'-$CH_3O_2C$—$C_6H_4$) |
| 529 | 3-O—(4'-$CH_3O_2C$—$C_6H_4$) |
| 530 | 4-O—(2'-$CH_3O_2C$—$C_6H_4$) |
| 531 | 4-O—(3'-$CH_3O_2C$—$C_6H_4$) |
| 532 | 4-O—(4'-$CH_3O_2C$—$C_6H_4$) |
| 533 | 2-O—(2'-$CH_3O$—$C_6H_4$) |
| 534 | 2-O—(3'-$CH_3O$—$C_6H_4$) |
| 535 | 2-O—(4'-$CH_3O$—$C_6H_4$) |
| 536 | 3-O—(2'-$CH_3O$—$C_6H_4$) |
| 537 | 3-O—(3'-$CH_3O$—$C_6H_4$) |
| 538 | 3-O—(4'-$CH_3O$—$C_6H_4$) |
| 539 | 4-O—(2'-$CH_3O$—$C_6H_4$) |
| 540 | 4-O—(3'-$CH_3O$—$C_6H_4$) |
| 541 | 4-O—(4'-$CH_3O$—$C_6H_4$) |
| 542 | 2-O—(2'-$O_2N$—$C_6H_4$) |
| 543 | 2-O—(3'-$O_2N$—$C_6H_4$) |
| 544 | 2-O—(4'-$O_2N$—$C_6H_4$) |
| 545 | 3-O—(2'-$O_2N$—$C_6H_4$) |
| 546 | 3-O—(3'-$O_2N$—$C_6H_4$) |
| 547 | 3-O—(4'-$O_2N$—$C_6H_4$) |
| 548 | 4-O—(2'-$O_2N$—$C_6H_4$) |
| 549 | 4-O—(3'-$O_2N$—$C_6H_4$) |
| 550 | 4-O—(4'-$O_2N$—$C_6H_4$) |
| 551 | 2-O—(2'-NC—$C_6H_4$) |
| 552 | 2-O—(3'-NC—$C_6H_4$) |
| 553 | 2-O—(4'-NC—$C_6H_4$) |
| 554 | 3-O—(2'-NC—$C_6H_4$) |
| 555 | 3-O—(3'-NC—$C_6H_4$) |
| 556 | 3-O—(4'-NC—$C_6H_4$) |
| 557 | 4-O—(2'-NC—$C_6H_4$) |
| 558 | 4-O—(3'-NC—$C_6H_4$) |
| 559 | 4-O—(4'-NC—$C_6H_4$) |

TABLE 12-continued

| | |
|---|---|
| 560 | 2-O—(2'-CF$_3$—C$_6$H$_4$) |
| 561 | 2-O—(3'-CF$_3$—C$_6$H$_4$) |
| 562 | 2-O—(4'-CF$_3$—C$_6$H$_4$) |
| 563 | 3-O—(2'-CF$_3$—C$_6$H$_4$) |
| 564 | 3-O—(3'-CF$_3$—C$_6$H$_4$) |
| 565 | 3-O—(4'-CF$_3$—C$_6$H$_4$) |
| 566 | 4-O—(2'-CF$_3$—C$_6$H$_4$) |
| 567 | 4-O—(3'-CF$_3$—C$_6$H$_4$) |
| 568 | 4-O—(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |

TABLE 12-continued

| | |
|---|---|
| 639 | 4-Thiazolyl-4' |
| 640 | 4-Thiazolyl-5' |

TABLE 13

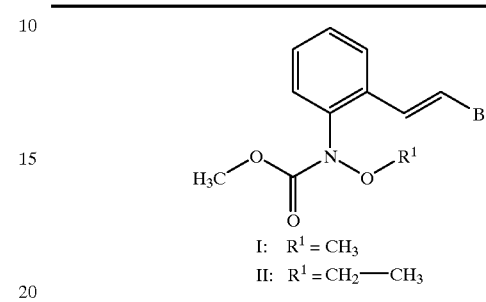

I:  $R^1 = CH_3$
II: $R^1 = CH_2$—$CH_3$

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |

TABLE 13-continued

I: $R^1 = CH_3$
II: $R^1 = CH_2-CH_3$

| No. | B |
|---|---|
| 56 | 4-$C_6H_5$-Furyl-2 |
| 57 | 4-(4'-$CH_3$—$C_6H_4$)-Furyl-2 |
| 58 | 4-(3'-$CH_3$—$C_6H_4$)-Furyl-2 |
| 59 | 4-(2'-$CH_3$—$C_6H_4$)-Furyl-2 |
| 60 | 4-(4'-$CH_3O$—$C_6H_4$)-Furyl-2 |
| 61 | 4-(3'-$CH_3O$—$C_6H_4$)-Furyl-2 |
| 62 | 4-(2'-$CH_3O$—$C_6H_4$)-Furyl-2 |
| 63 | 4-(4'-$NO_2$—$C_6H_4$)-Furyl-2 |
| 64 | 4-(3'-$NO_2$—$C_6H_4$)-Furyl-2 |
| 65 | 4-(2'-$NO_2$—$C_6H_4$)-Furyl-2 |
| 66 | 4-(4'-CN—$C_6H_4$)-Furyl-2 |
| 67 | 4-(3'-CN—$C_6H_4$)-Furyl-2 |
| 68 | 4-(2'-CN—$C_6H_4$)-Furyl-2 |
| 69 | 4-(4'-Cl—$C_6H_4$)-Furyl-2 |
| 70 | 4-(3'-Cl—$C_6H_4$)-Furyl-2 |
| 71 | 4-(2'-Cl—$C_6H_4$)-Furyl-2 |
| 72 | Thienyl-2 |
| 73 | 5-$CH_3$-Thienyl-2 |
| 74 | 5-$C_6H_5$-Thienyl-2 |
| 75 | 5-(4'-$CH_3$—$C_6H_4$)-Thienyl-2 |
| 76 | 5-(3'-$CH_3$—$C_6H_4$)-Thienyl-2 |
| 77 | 5-(2'-$CH_3$—$C_6H_4$)-Thienyl-2 |
| 78 | 5-(4'-$CH_3O$—$C_6H_4$)-Thienyl-2 |
| 79 | 5-(3'-$CH_3O$—$C_6H_4$)-Thienyl-2 |
| 80 | 5-(2'-$CH_3O$—$C_6H_4$)-Thienyl-2 |
| 81 | 5-(4'-$NO_2$—$C_6H_4$)-Thienyl-2 |
| 82 | 5-(3'-$NO_2$—$C_6H_4$)-Thienyl-2 |
| 83 | 5-(2'-$NO_2$—$C_6H_4$)-Thienyl-2 |
| 84 | 5-(4'-CN—$C_6H_4$)-Thienyl-2 |
| 85 | 5-(3'-CN—$C_6H_4$)-Thienyl-2 |
| 86 | 5-(2'-CN—$C_6H_4$)-Thienyl-2 |
| 87 | 5-(4'-Cl—$C_6H_4$)-Thienyl-2 |
| 88 | 5-(3'-Cl—$C_6H_4$)-Thienyl-2 |
| 89 | 5-(2'-Cl—$C_6H_4$)-Thienyl-2 |
| 90 | 4-$CH_3$-Thienyl-2 |
| 91 | 4-$C_6H_5$-Thienyl-2 |
| 92 | 4-(4'-$CH_3$—$C_6H_4$)-Thienyl-2 |
| 93 | 4-(3'-$CH_3$—$C_6H_4$)-Thienyl-2 |
| 94 | 4-(2'-$CH_3$—$C_6H_4$)-Thienyl-2 |
| 95 | 4-(4'-$CH_3O$—$C_6H_4$)-Thienyl-2 |
| 96 | 4-(3'-$CH_3O$—$C_6H_4$)-Thienyl-2 |
| 97 | 4-(2'-$CH_3O$—$C_6H_4$)-Thienyl-2 |
| 98 | 4-(4'-$NO_2$—$C_6H_4$)-Thienyl-2 |
| 99 | 4-(3'-$NO_2$—$C_6H_4$)-Thienyl-2 |
| 100 | 4-(2'-$NO_2$—$C_6H_4$)-Thienyl-2 |
| 101 | 4-(4'-CN—$C_6H_4$)-Thienyl-2 |
| 102 | 4-(3'-CN—$C_6H_4$)-Thienyl-2 |
| 103 | 4-(2'-CN—$C_6H_4$)-Thienyl-2 |
| 104 | 4-(4'-Cl—$C_6H_4$)-Thienyl-2 |
| 105 | 4-(3'-Cl—$C_6H_4$)-Thienyl-2 |
| 106 | 4-(2'-Cl—$C_6H_4$)-Thienyl-2 |
| 107 | Thienyl-3 |
| 108 | 5-$CH_3$-Thienyl-3 |
| 109 | 5-$C_6H_5$-Thienyl-3 |
| 110 | 5-(4'-$CH_3$—$C_6H_4$)-Thienyl-3 |
| 111 | 5-(3'-$CH_3$—$C_6H_4$)-Thienyl-3 |
| 112 | 5-(2'-$CH_3$—$C_6H_4$)-Thienyl-3 |
| 113 | 5-(4'-$CH_3O$—$C_6H_4$)-Thienyl-3 |
| 114 | 5-(3'-$CH_3O$—$C_6H_4$)-Thienyl-3 |
| 115 | 5-(2'-$CH_3O$—$C_6H_4$)-Thienyl-3 |
| 116 | 5-(4'-$NO_2$—$C_6H_4$)-Thienyl-3 |
| 117 | 5-(3'-$NO_2$—$C_6H_4$)-Thienyl-3 |
| 118 | 5-(2'-$NO_2$—$C_6H_4$)-Thienyl-3 |
| 119 | 5-(4'-CN—$C_6H_4$)-Thienyl-3 |
| 120 | 5-(3'-CN—$C_6H_4$)-Thienyl-3 |
| 121 | 5-(2'-CN—$C_6H_4$)-Thienyl-3 |
| 122 | 5-(4'-Cl—$C_6H_4$)-Thienyl-3 |
| 123 | 5-(3'-Cl—$C_6H_4$)-Thienyl-3 |
| 124 | 5-(2'-Cl—$C_6H_4$)-Thienyl-3 |
| 125 | Pyrazolyl-4 |
| 126 | N—$CH_3$-Pyrazolyl-4 |
| 127 | N—$C_6H_5$-Pyrazolyl-4 |
| 128 | N-(4'-$CH_3$—$C_6H_4$)-Pyrazolyl-4 |
| 129 | N-(3'-$CH_3$—$C_6H_4$)-Pyrazolyl-4 |
| 130 | N-(2'-$CH_3$—$C_6H_4$)-Pyrazolyl-4 |
| 131 | N-(4'-$CH_3O$—$C_6H_4$)-Pyrazolyl-4 |
| 132 | N-(3'-$CH_3O$—$C_6H_4$)-Pyrazolyl-4 |
| 133 | N-(2'-$CH_3O$—$C_6H_4$)-Pyrazolyl-4 |
| 134 | N-(4'-$NO_2$—$C_6H_4$)-Pyrazolyl-4 |
| 135 | N-(3'-$NO_2$—$C_6H_4$)-Pyrazolyl-4 |
| 136 | N-(2'-$NO_2$—$C_6H_4$)-Pyrazolyl-4 |
| 137 | N-(4'-CN—$C_6H_4$)-Pyrazolyl-4 |
| 138 | N-(3'-CN—$C_6H_4$)-Pyrazolyl-4 |
| 139 | N-(2'-CN—$C_6H_4$)-Pyrazolyl-4 |
| 140 | N-(4'-Cl—$C_6H_4$)-Pyrazolyl-4 |
| 141 | N-(3'-Cl—$C_6H_4$)-Pyrazolyl-4 |
| 142 | N-(2'-Cl—$C_6H_4$)-Pyrazolyl-4 |
| 143 | 3-$CH_3$—N-Methylpyrazolyl-4 |
| 144 | 3-$C_6H_5$—N-Methylpyrazolyl-4 |
| 145 | 3-(4'-$CH_3$—$C_6H_4$)-N-Methylpyrazolyl-4 |
| 146 | 3-(3'-$CH_3$—$C_6H_4$)-N-Methylpyrazolyl-4 |
| 147 | 3-(2'-$CH_3$—$C_6H_4$)-N-Methylpyrazolyl-4 |
| 148 | 3-(4'-$CH_3O$—$C_6H_4$)-N-Methylpyrazolyl-4 |
| 149 | 3-(3'-$CH_3O$—$C_6H_4$)-N-Methylpyrazolyl-4 |
| 150 | 3-(2'-$CH_3O$—$C_6H_4$)-N-Methylpyrazolyl-4 |
| 151 | 3-(4'-$NO_2$—$C_6H_4$)-N-Methylpyrazolyl-4 |
| 152 | 3-(3'-$NO_2$—$C_6H_4$)-N-Methylpyrazolyl-4 |
| 153 | 3-(2'-$NO_2$—$C_6H_4$)-N-Methylpyrazolyl-4 |
| 154 | 3-(4'-CN—$C_6H_4$)-N-Methylpyrazolyl-4 |
| 155 | 3-(3'-CN—$C_6H_4$)-N-Methylpyrazolyl-4 |
| 156 | 3-(2'-CN—$C_6H_4$)-N-Methylpyrazolyl-4 |
| 157 | 3-(4'-Cl—$C_6H_4$)-N-Methylpyrazolyl-4 |
| 158 | 3-(3'-Cl—$C_6H_4$)-N-Methylpyrazolyl-4 |
| 159 | 3-(2'-Cl—$C_6H_4$)-N-Methylpyrazolyl-4 |
| 160 | Isoxazolyl-5 |
| 161 | 3-$CH_3$-Isoxazolyl-5 |
| 162 | 3-$C_6H_5$-Isoxazolyl-5 |
| 163 | 3-(4'-$CH_3$—$C_6H_4$)-Isoxazolyl-5 |
| 164 | 3-(3'-$CH_3$—$C_6H_4$)-Isoxazolyl-5 |
| 165 | 3-(2'-$CH_3$—$C_6H_4$)-Isoxazolyl-5 |
| 166 | 3-(4'-$CH_3O$—$C_6H_4$)-Isoxazolyl-5 |
| 167 | 3-(3'-$CH_3O$—$C_6H_4$)-Isoxazolyl-5 |
| 168 | 3-(2'-$CH_3O$—$C_6H_4$)-Isoxazolyl-5 |
| 169 | 3-(4'-$NO_2$—$C_6H_4$)-Isoxazolyl-5 |
| 170 | 3-(3'-$NO_2$—$C_6H_4$)-Isoxazolyl-5 |
| 171 | 3-(2'-$NO_2$—$C_6H_4$)-Isoxazolyl-5 |
| 172 | 3-(4'-CN—$C_6H_4$)-Isoxazolyl-5 |
| 173 | 3-(3'-CN—$C_6H_4$)-Isoxazolyl-5 |
| 174 | 3-(2'-CN—$C_6H_4$)-Isoxazolyl-5 |
| 175 | 3-(4'-Cl—$C_6H_4$)-Isoxazolyl-5 |
| 176 | 3-(3'-Cl—$C_6H_4$)-Isoxazolyl-5 |
| 177 | 3-(2'-Cl—$C_6H_4$)-Isoxazolyl-5 |
| 178 | 4-Chloroisoxazolyl-5 |
| 179 | 3-$CH_3$-4-Chloroisoxazolyl-5 |
| 180 | 3-$C_6H_5$-4-Chloroisoxazolyl-5 |
| 181 | 3-(4'-$CH_3$—$C_6H_4$)-Chloroisoxazolyl-5 |

TABLE 13-continued

I: $R^1 = CH_3$
II: $R^1 = CH_2-CH_3$

| No. | B |
|---|---|
| 182 | 3-(3'-CH$_3$—C$_6$H$_4$)-Chloroisoxazolyl-5 |
| 183 | 3-(2'-CH$_3$—C$_6$H$_4$)-Chloroisoxazolyl-5 |
| 184 | 3-(4'-CH$_3$O—C$_6$H$_4$)-Chloroisoxazolyl-5 |
| 185 | 3-(3'-CH$_3$O—C$_6$H$_4$)-Chloroisoxazolyl-5 |
| 186 | 3-(2'-CH$_3$O—C$_6$H$_4$)-Chloroisoxazolyl-5 |
| 187 | 3-(4'-NO$_2$—C$_6$H$_4$)-Chloroisoxazolyl-5 |
| 188 | 3-(3'-NO$_2$—C$_6$H$_4$)-Chloroisoxazolyl-5 |
| 189 | 3-(2'-NO$_2$—C$_6$H$_4$)-Chloroisoxazolyl-5 |
| 190 | 3-(4'-CN—C$_6$H$_4$)-Chloroisoxazolyl-5 |
| 191 | 3-(3'-CN—C$_6$H$_4$)-Chloroisoxazolyl-5 |
| 192 | 3-(2'-CN—C$_6$H$_4$)-Chloroisoxazolyl-5 |
| 193 | 3-(4'-Cl—C$_6$H$_4$)-Chloroisoxazolyl-5 |
| 194 | 3-(3'-Cl—C$_6$H$_4$)-Chloroisoxazolyl-5 |
| 195 | 3-(2'-Cl—C$_6$H$_4$)-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 2-CH$_3$-Oxazolyl-4 |
| 234 | 2-C$_6$H$_5$-Oxazolyl-4 |
| 235 | 2-(4'-CH$_3$—C$_6$H$_4$)-Oxazolyl-4 |
| 236 | 2-(3'-CH$_3$—C$_6$H$_4$)-Oxazolyl-4 |
| 237 | 2-(2'-CH$_3$—C$_6$H$_4$)-Oxazolyl-4 |
| 238 | 2-(4'-CH$_3$O—C$_6$H$_4$)-Oxazolyl-4 |
| 239 | 2-(3'-CH$_3$O—C$_6$H$_4$)-Oxazolyl-4 |
| 240 | 2-(2'-CH$_3$O—C$_6$H$_4$)-Oxazolyl-4 |
| 241 | 2-(4'-NO$_2$—C$_6$H$_4$)-Oxazolyl-4 |
| 242 | 2-(3'-NO$_2$—C$_6$H$_4$)-Oxazolyl-4 |
| 243 | 2-(2'-NO$_2$—C$_6$H$_4$)-Oxazolyl-4 |
| 244 | 2-(4'-CN—C$_6$H$_4$)-Oxazolyl-4 |
| 245 | 2-(3'-CN—C$_6$H$_4$)-Oxazolyl-4 |
| 246 | 2-(2'-CN—C$_6$H$_4$)-Oxazolyl-4 |
| 247 | 2-(4'-Cl—C$_6$H$_4$)-Oxazolyl-4 |
| 248 | 2-(3'-Cl—C$_6$H$_4$)-Oxazolyl-4 |
| 249 | 2-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 257 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N-CH$_3$-1,2,4-Triazolyl-5 |
| 269 | 3-CH$_3$-N-CH$_3$-1,2,4-Triazolyl-5 |
| 270 | 3-C$_6$H$_5$-N-CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,2,3-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |

TABLE 13-continued

Structure:
- Phenyl ring with ortho substituent: –CH=CH–B
- N-substituent on phenyl: N(OR¹)C(=O)OCH₃

I: R¹ = CH₃
II: R¹ = CH₂—CH₃

| No. | B |
|---|---|
| 308 | 5-(3'-CH₃—C₆H₄)-1,2,4-Oxadiazolyl-3 |
| 309 | 5-(2'-CH₃—C₆H₄)-1,2,4-Oxadiazolyl-3 |
| 310 | 5-(4'-CH₃O—C₆H₄)-1,2,4-Oxadiazolyl-3 |
| 311 | 5-(3'-CH₃O—C₆H₄)-1,2,4-Oxadiazolyl-3 |
| 312 | 5-(2'-CH₃O—C₆H₄)-1,2,4-Oxadiazolyl-3 |
| 313 | 5-(4'-NO₂—C₆H₄)-1,2,4-Oxadiazolyl-3 |
| 314 | 5-(3'-NO₂—C₆H₄)-1,2,4-Oxadiazolyl-3 |
| 315 | 5-(2'-NO₂—C₆H₄)-1,2,4-Oxadiazolyl-3 |
| 316 | 5-(4'-CN—C₆H₄)-1,2,4-Oxadiazolyl-3 |
| 317 | 5-(3'-CN—C₆H₄)-1,2,4-Oxadiazolyl-3 |
| 318 | 5-(2'-CN—C₆H₄)-1,2,4-Oxadiazolyl-3 |
| 319 | 5-(4'-Cl—C₆H₄)-1,2,4-Oxadiazolyl-3 |
| 320 | 5-(3'-Cl—C₆H₄)-1,2,4-Oxadiazolyl-3 |
| 321 | 5-(2'-Cl—C₆H₄)-1,2,4-Oxadiazolyl-3 |
| 322 | 1,2,4-Oxadiazolyl-5 |
| 323 | 3-CH₃-1,2,4-Oxadiazolyl-5 |
| 324 | 3-C₆H₅-1,2,4-Oxadiazolyl-5 |
| 325 | 3-(4'-CH₃—C₆H₄)-1,2,4-Oxadiazolyl-5 |
| 326 | 3-(3'-CH₃—C₆H₄)-1,2,4-Oxadiazolyl-5 |
| 327 | 3-(2'-CH₃—C₆H₄)-1,2,4-Oxadiazolyl-5 |
| 328 | 3-(4'-CH₃O—C₆H₄)-1,2,4-Oxadiazolyl-5 |
| 329 | 3-(3'-CH₃O—C₆H₄)-1,2,4-Oxadiazolyl-5 |
| 330 | 3-(2'-CH₃O—C₆H₄)-1,2,4-Oxadiazolyl-5 |
| 331 | 3-(4'-NO₂—C₆H₄)-1,2,4-Oxadiazolyl-5 |
| 332 | 3-(3'-NO₂—C₆H₄)-1,2,4-Oxadiazolyl-5 |
| 333 | 3-(2'-NO₂—C₆H₄)-1,2,4-Oxadiazolyl-5 |
| 334 | 3-(4'-CN—C₆H₄)-1,2,4-Oxadiazolyl-5 |
| 335 | 3-(3'-CN—C₆H₄)-1,2,4-Oxadiazolyl-5 |
| 336 | 3-(2'-CN—C₆H₄)-1,2,4-Oxadiazolyl-5 |
| 337 | 3-(4'-Cl—C₆H₄)-1,2,4-Oxadiazolyl-5 |
| 338 | 3-(3'-Cl—C₆H₄)-1,2,4-Oxadiazolyl-5 |
| 339 | 3-(2'-Cl—C₆H₄)-1,2,4-Oxadiazolyl-5 |
| 340 | 1,2,4-Thiadiazolyl-3 |
| 341 | 5-CH₃-1,2,4-Thiadiazolyl-3 |
| 342 | 5-C₆H₅-1,2,4-Thiadiazolyl-3 |
| 343 | 5-(4'-CH₃—C₆H₄)-1,2,4-Thiadiazolyl-3 |
| 344 | 5-(3'-CH₃—C₆H₄)-1,2,4-Thiadiazolyl-3 |
| 345 | 5-(2'-CH₃—C₆H₄)-1,2,4-Thiadiazolyl-3 |
| 346 | 5-(4'-CH₃O—C₆H₄)-1,2,4-Thiadiazolyl-3 |
| 347 | 5-(3'-CH₃O—C₆H₄)-1,2,4-Thiadiazolyl-3 |
| 348 | 5-(2'-CH₃O—C₆H₄)-1,2,4-Thiadiazolyl-3 |
| 349 | 5-(4'-NO₂—C₆H₄)-1,2,4-Thiadiazolyl-3 |
| 350 | 5-(3'-NO₂—C₆H₄)-1,2,4-Thiadiazolyl-3 |
| 351 | 5-(2'-NO₂—C₆H₄)-1,2,4-Thiadiazolyl-3 |
| 352 | 5-(4'-CN—C₆H₄)-1,2,4-Thiadiazolyl-3 |
| 353 | 5-(3'-CN—C₆H₄)-1,2,4-Thiadiazolyl-3 |
| 354 | 5-(2'-CN—C₆H₄)-1,2,4-Thiadiazolyl-3 |
| 355 | 5-(4'-Cl—C₆H₄)-1,2,4-Thiadiazolyl-3 |
| 356 | 5-(3'-Cl—C₆H₄)-1,2,4-Thiadiazolyl-3 |
| 357 | 5-(2'-Cl—C₆H₄)-1,2,4-Thiadiazolyl-3 |
| 358 | 1,3,4-Thiadiazolyl-2 |
| 359 | 5-CH₃-1,3,4-Thiadiazolyl-2 |
| 360 | 5-C₆H₅-1,3,4-Thiadiazolyl-2 |
| 361 | 5-(4'-CH₃—C₆H₄)-1,3,4-Thiadiazolyl-2 |
| 362 | 5-(3'-CH₃—C₆H₄)-1,3,4-Thiadiazolyl-2 |
| 363 | 5-(2'-CH₃—C₆H₄)-1,3,4-Thiadiazolyl-2 |
| 364 | 5-(4'-CH₃O—C₆H₄)-1,3,4-Thiadiazolyl-2 |
| 365 | 5-(3'-CH₃O—C₆H₄)-1,3,4-Thiadiazolyl-2 |
| 366 | 5-(2'-CH₃O—C₆H₄)-1,3,4-Thiadiazolyl-2 |
| 367 | 5-(4'-NO₂—C₆H₄)-1,3,4-Thiadiazolyl-2 |
| 368 | 5-(3'-NO₂—C₆H₄)-1,3,4-Thiadiazolyl-2 |
| 369 | 5-(2'-NO₂—C₆H₄)-1,3,4-Thiadiazolyl-2 |
| 370 | 5-(4'-CN—C₆H₄)-1,3,4-Thiadiazolyl-2 |
| 371 | 5-(3'-CN—C₆H₄)-1,3,4-Thiadiazolyl-2 |
| 372 | 5-(2'-CN—C₆H₄)-1,3,4-Thiadiazolyl-2 |
| 373 | 5-(4'-Cl—C₆H₄)-1,3,4-Thiadiazolyl-2 |
| 374 | 5-(3'-Cl—C₆H₄)-1,3,4-Thiadiazolyl-2 |
| 375 | 5-(2'-Cl—C₆H₄)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |

TABLE 14

Selected physical data of some compounds

| No. | Compound | ¹H-NMR (ppm) |
|---|---|---|
| 1 | 2-methylphenyl-N-methoxy-N-(methoxycarbonyl)amine | 3.8 (s, 3H); 3.75 (s, 3H) |
| 2 | 2-(bromomethyl)phenyl-N-methoxy-N-(methoxycarbonyl)amine | 3.8 (2s, 2 × 3H) |
| 3 | 2-[(2-methylphenoxy)methyl]phenyl-N-methoxy-N-(methoxycarbonyl)amine | 3.8 (s, 3H); 3.75 (s, 3H) |
| 4 | 2-methylphenyl-N-ethoxy-N-(methoxycarbonyl)amine | 3.95 (q, 2H, I = 7.5 Hz); 3.8 (s, 3H) |
| 5 | 2-(bromomethyl)phenyl-N-ethoxy-N-(methoxycarbonyl)amine | 4.05 (q, 2H, I = 7.5 Hz); 3.85 (s, 3H) |
| 6 | 2-[(2-methylphenoxy)methyl]phenyl-N-ethoxy-N-(methoxycarbonyl)amine | 4.0 (q, 2H, I = 7.5 Hz); 3.8 (s, 3H) |

TABLE 14-continued

Selected physical data of some compounds

| No. | Compound | ¹H-NMR (ppm) |
|---|---|---|
| 7 | (structure) | 3.8 (s, 3H); 3.75 (s, 3H) |
| 8 | (structure) | 3.8 (s, 3H); 3.75 (s, 3H) |
| 9 | (structure) | 3.85 (s, 3H); 3.8 (s, 3H) |
| 10 | (structure) | 4.0 (s, 3H); 3.8 (s, 3H), 3.75 (s, 3H) |
| 11 | (structure) | 3.8 (s, 3H); 3.75 (s, 3H) |
| 12 | (structure) | 3.8 (s, 3H); 3.75 (s, 3H) |

TABLE 14-continued

Selected physical data of some compounds

| No. | Compound | $^1$H-NMR (ppm) |
|---|---|---|
| 13 | (structure: 2-[(methoxycarbonyl)(methoxy)amino]benzyl O-[1-(3,5-dichlorophenyl)ethylidene] oxime) | 3.8 (s, 3H); 3.75 (s, 3H) |
| 14 | (structure: 2-[(methoxycarbonyl)(methoxy)amino]benzyl O-[1-(4-chlorophenyl)ethylidene] oxime) | 3.8 (s, 3H); 3.75 (s, 3H) 66 |
| 15 | (structure: 2-[(methoxycarbonyl)(methoxy)amino]benzyl O-[1-(4-methylphenyl)ethylidene] oxime) | 3.8 (s, 3H); 3.75 (s, 3H) |
| 16 | (structure: 2-[(methoxycarbonyl)(ethoxy)amino]benzyl O-[1-(4-methylphenyl)ethylidene] oxime) | 4.0 (q, 2H, I = 7.5 Hz); 3.8 (s, 3H) |
| 17 | (structure: 2-[(methoxycarbonyl)(methoxy)amino]benzyl 6-methylpyridin-2-yl ether) | 3.8 (2s, each 3H) |
| 18 | (structure: 2-[(methoxycarbonyl)(methoxy)amino]benzyl O-[1-(naphthalen-2-yl)ethylidene] oxime) | 3.8 (2s, each 3H) |

TABLE 14-continued

Selected physical data of some compounds

| No. | Compound | $^1$H-NMR (ppm) |
|---|---|---|
| 19 | (structure) | 3.8 (s, 3H); 3.75 (s, 3H) |
| 20 | (structure) | 3.8 (s, 3H); 3.75 (s, 3H) |
| 21 | (structure) | 3.8 (s, 3H); 3.75 (s, 3H) |
| 22 | (structure) | 3.8 (s, 3H); 3.75 (s, 3H) |
| 23 | (structure) | 3.8 (s, 3H); 3.75 (s, 3H) |
| 24 | (structure) | 3.8 (s, 6H) |
| 25 | (structure) | 3.75 (2s, each 3H) |

TABLE 14-continued

Selected physical data of some compounds

| No. | Compound | $^1$H-NMR (ppm) |
|---|---|---|
| 26 | (2-propyl-6-trifluoromethyl-pyrimidin-4-yloxymethyl-phenyl) structure with H₃CO₂C-N(OCH₃)- group | 3.8 (s, 3H); 3.75 (s, 3H) |
| 27 | (2-chlorophenylthiomethyl-phenyl) structure with H₃CO₂C-N(OCH₃)- group | 3.8 (s, 3H); 3.75 (s, 3H) |
| 28 | (1-phenyl-pyrazol-4-yloxymethyl-phenyl) structure with H₃CO₂C-N(OCH₃)- group | 3.8 (s, 3H); 3.75 (s, 3H) |
| 29 | (4-(4-chlorophenyl)-thiazol-2-yloxymethyl-phenyl) structure with H₃CO₂C-N(OCH₃)- group | 3.8 (s, 3H); 3.75 (s, 3H) |
| 30 | (6-methyl-pyridin-2-yloxymethyl-phenyl) structure with H₃CO₂C-N(OCH₃)- group | 3.8 (s, 6H) |

TABLE 52

Selected physical data of some compounds

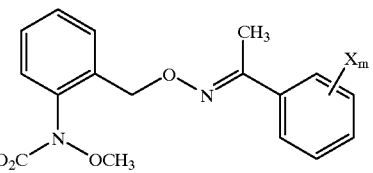

| No. | $X_m$ | mp (°C.) | $^1$H-NMR (ppm) or IR (cm$^{-1}$) |
|---|---|---|---|
| 1 | H | | 3.75(2s, each 3H) |
| 2 | 2-CH$_3$ | | 3.75(2s, each 3H) |
| 3 | 3-CH$_3$ | | 3.75(2s, each 3H) |
| 4 | 2,4-(CH$_3$)$_2$ | | 3.75(2s, each 3H) |
| 5 | 4-C$_2$H$_5$ | | 3.75(2s, each 3H) |
| 6 | 4-i-C$_3$H$_7$ | | 3.75(2s, each 3H) |
| 7 | 4-t-C$_4$H$_9$ | | 3.75(2s, each 3H) |
| 8 | 3,4-(CH$_3$)$_2$ | | 3.75(2s, each 3H) |
| 9 | 3-Cl | | 3.75(2s, each 3H) |
| 10 | 3-Br | | 3.75(2s, each 3H) |
| 11 | 3-CF$_3$ | | 3.75(2s, each 3H) |
| 12 | 4-Br | | 3.75(2s, each 3H) |
| 13 | 4-F | | 3.75(2s, each 3H) |
| 14 | 4-CF$_3$ | | 3.75(2s, each 3H) |
| 15 | 4-OCH$_3$ | | 3.8(s, 3H); 3.75(2s, each 3H) |
| 16 | 4-CN | | 3.75(2s, each 3H) |
| 17 | 3-CH$_3$-4-O-i-C$_3$H$_7$ | | 3.75(2s, each 3H) |
| 18 | 3,4-Cl$_2$ | | 3.75(2s, each 3H) |
| 19 | 3-CH$_3$-4-OCH$_3$ | | 3.85(s, 3H); 3.75(2s, each 3H) |
| 20 | 4-NO$_2$ | 112 | |
| 21 | 3,5-(CH$_3$)$_2$ | | 3.75(2s, each 3H) |
| 22 | 3-CH$_3$-4-Cl | | 3.75(2s, each 3H) |
| 23 | 3-Cl-4-CH$_3$ | | 3.75(2s, each 3H) |

TABLE 53

Selected physical data of some compounds

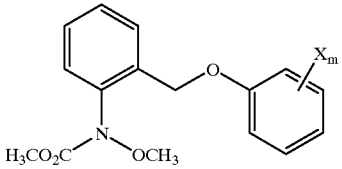

| No. | $X_m$ | mp (°C.) | $^1$H-NMR (ppm) or IR (cm$^{-1}$) |
|---|---|---|---|
| 1 | 2-CH$_3$-4-C(CH$_3$)=N—O—C$_2$H$_5$ | | 3.8(s, 3H); 3.75(s, 3H) |
| 2 | 2-CH$_3$-4-C(CH$_3$)=N—O-(trans-CH$_2$—CH=CHCl) | | 3.8(s, 3H); 3.75(s, 3H) |
| 3 | 2,5-(CH$_3$)$_2$-4-C(CH$_3$)=N—OCH$_3$ | | 3.95(s, 3H); 3.8(s, 3H); 3.75(s, 3H) |
| 4 | 2,5-(CH$_3$)$_2$-4-C(CH$_3$)=N—OC$_2$H$_5$ | | 3.8(s, 3H); 3.75(s, 3H) |
| 5 | 2,5-(CH$_3$)$_2$-4-C(CH$_3$)=N—O-(trans-CH$_2$—CH=CHCl) | | 3.85(s, 3H); 3.75(s, 3H) |
| 6 | 2-CH$_3$-4-C(C$_2$H$_5$)=N—OCH$_3$ | | 3.95(s, 3H); 3.8(s, 3H); 3.75(s, 3H) |
| 7 | 2-CH$_3$-4-C(C$_2$H$_5$)=N—O—C$_2$H$_5$ | | 3.8(s, 3H); 3.75(s, 3H) |
| 8 | 2-CH$_3$-4-C(C$_2$H$_5$)=N—O-Allyl | | 3.8(s, 3H); 3.75(s, 3H) |
| 9 | 2-CH$_3$-4-C(C$_2$H$_5$)=N—O-(trans-CH$_2$—CH=CHCl) | | 3.8(s, 3H); 3.75(s, 3H) |
| 10 | 2,5-(CH$_3$)$_2$-4-C(C$_2$H$_5$)=N—OCH$_3$ | | 3.95(S, 3H); 3.8(s, 3H); 3.75(s, 3H) |

TABLE 53-continued

Selected physical data of some compounds

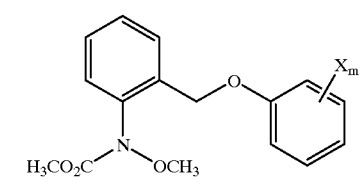

| No. | $X_m$ | mp (°C.) | $^1$H-NMR (ppm) or IR (cm$^{-1}$) |
|---|---|---|---|
| 11 | 2,5-(CH$_3$)$_2$-4-C(C$_2$H$_5$)=N—O—C$_2$H$_5$ | | 3.8(s, 3H); 3.75(s, 3H) |
| 12 | 2,5-(CH$_3$)$_2$-4-C(C$_2$H$_5$)=N—O-Allyl | | 3.8(s, 3H); 3.75(s, 3H) |
| 13 | 2-Cl | | 3.8(s, 3H); 3.75(s, 3H) |
| 14 | 4-Cl | | 3.8(s, 3H); 3.75(s, 3H) |
| 15 | 2-CH$_3$-4-Cl | | 3.8(s, 3H); 3.75(s, 3H) |
| 16 | 2-Cl-4-CH$_3$ | | 3.8(s, 3H); 3.75(s, 3H) |
| 17 | 2-Cl-5-CH$_3$ | | 3.8(s, 3H); 3.75(s, 3H) |
| 18 | 2,5-(CH$_3$)$_2$-4-C(CH$_3$)=N—O-Allyl | | 3.8(s, 3H); 3.75(s, 3H) |
| 19 | 2,5-(CH$_3$)$_2$-4-C(C$_2$H$_5$)=N—O-(trans-CH$_2$—CH=CHCl) | | 3.8(s, 3H); 3.75(s, 3H) |

TABLE 54

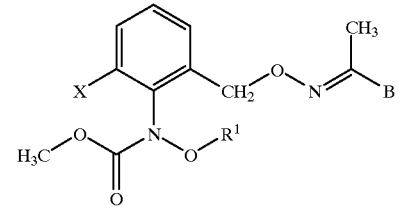

| No. | B |
|---|---|
| 1 | 2-Pyridyl |
| 2 | 3-Trifluoromethyl-2-pyridyl |
| 3 | 5-Trifluoromethyl-2-pyridyl |
| 4 | 3,5-Bis-(trifluoromethyl)-2-pyridyl |
| 5 | 3,5-Dichloro-2-pyridyl |
| 6 | 3-Chloro-5-trifluoromethyl-2-pyridyl |
| 7 | 3,5-Dichloro-2-pyridyl |
| 8 | 2-Chloro-4-trifluoromethylphenyl |
| 9 | 2-Benzothiazolyl |
| 10 | 5-Chloro-4-methyl-2-benzimidazolyl |
| 11 | 2-Benzoxazolyl |
| 12 | 1-Methyl-5-trifluoromethylimidazo[5,4-a]-pyridin-2-yl |
| 13 | 5-Chloro-2-pyrimidinyl |
| 14 | 4-Methyl-5-phenyl-2-thiazolin-2-yl |
| 15 | 4-Methyl-5-phenyl-2-oxazolin-2-yl |
| 16 | 7-Trifluoromethyl-4-quinolinyl |

TABLE 55

Selected physical data of some compounds

| No. | $X_m$ | mp (° C.) | $^1$H-NMR (ppm) or IR (cm$^{-1}$) |
|---|---|---|---|
| 1 | H | | 3.75(s, 3H); 3.65(s, 3H) |
| 2 | 4-OCH$_3$ | | 3.8(s, 3H); 3.75(s, 3H); 3.65(s, 3H) |
| 3 | 4-CH$_3$ | | 3.75(s, 3H); 3.65(s, 3H) |
| 4 | 4-Cl | | 3.75(s, 3H); 3.65(s, 3H) |
| 5 | 4-CF$_3$ | | 3.75(s, 3H); 3.65(s, 3H) |
| 6 | 3,5-(CF$_3$)$_2$ | | 3.75(s, 3H); 3.65(s, 3H) |
| 7 | 2,4-Cl$_2$ | | 3.75(s, 3H); 3.65(s, 3H) |
| 8 | 3,4-Cl$_2$ | | 3.75(s, 3H); 3.65(s, 3H) |

Example 6

O-Methyl-N-(2-methylphenyl)-N-propionyl-hydroxylamine (Table 21, No. 1)

a) N-(2-Methylphenyl)-N-propionyl-hydroxylamine

At 25 to 30° C., 12,5 g (0.135 mol) of propionyl Chloroide and then 10.7 g (0.135 mol) of pyridine are dripped into 30 g of N-(2-methylphenyl)-hydroxylamine (crude product, prepared according to Bamberger et al., Anm. Chem. 316 (1901), 278; content approx. 80%=0.2 mol) in 500 ml of methylene Chloroide. The mixture is stirred for 30 minutes at room temperature, and is then extracted with dilute hydrochloroic acid and water. The organic phase is dried over MgSO$_4$ and evaporated down. The residue is purified by column chromatography with mixtures of cyclohexane and ethyl acetate. There is obtained 22.7 g (0.127 mol=63%) of the title compound as a yellow oil.

$^1$H-NMR (COCl$_3$; δ in ppm): 9.4 (s, broad, 1H, OH); 7.2 (m, 4H, phenyl); 2.4 (s, 3H, CH$_3$); 2.1 (q, broad, 2H, CH$_2$); 1.1 (t, 3H, I=7 Hz, CH$_3$).

b) O-Methyl-N-(2-methylphenyl)-N-propionyl-hydroxylamine (Table 21, No. 1)

At 25 to 30° C., a solution of 22.7 g (0.127 mol) (Example 6a) of N-(2-methylphenyl)-N-propionyl-hydroxylamine in 50 ml of dimethylformamide is dripped into a stirred mixture of 3.4 g (0.14 mol) of NaH in 150 ml of dimethylformamide. After completion of gas evolution (15 mins) 18.4 g (0.13 mol) of methyl iodide is added and the mixture is stirred overnight at room temperature. The reaction mixture is then diluted with water and the aqueous phase is extracted three times with methyl tert-butyl ether. The combined organic phases are extracted with water, dried over MgSO$_4$ and evaporated down. The residue is purified by column chromatography with mixtures of cyclohexane and ethyl acetate. There is obtained 18 g (0.081 mol=64%) of the title compound as a yellow oil.

$^1$H-NMR (COCl$_3$; δ in ppm): 7.2 (m, 4H, phenyl); 3.7 (s, broad, 3H, OCH$_3$); 2.6 (s, very broad, 2H, CH$_2$); 2.3 (s, 3H, CH$_3$); 1.2 (s, broad, 3H, CH$_3$).

Example 7

O-Methyl-N-(2-bromomethylphenyl)-N-propionyl-hydroxylamine (Table 21, No. 2)

A mixture of 10 g (51.8 mmol) of the hydroxylamine derivative from Example 1, 11 g (61 mmol) of N-bromosuccinimide and 0.1 g of azoisobutyrodinitrile in 100 ml of CCl$_4$ is refluxed. One drop of bromine is added and the mixture is refluxed for a further 2.5 hours. The reaction mixture is cooled to room temperature, washed with water, dried over MgSO$_4$ and evaporated down. The residue is purified by column chromatography with mixtures of cyclohexane and ethyl acetate. There is obtained in this sequence 3.4 g (7.9 mmol=15%) of O-methyl-N-(2-bromomethylphenyl)-d-(α,α-dibromopropionyl)-hydroxylamine, 3.8 g (10.8 mmol=21%) of O-methyl-N-(2-bromomethylphenyl)-N-(α-bromopropionyl)-hydroxylamine, 2.3 g (8.5 g (8.5 mmol=16%) of the title compound and 3.5 g of starting material, each as brown oils.

a) O-Methyl-N-(2-bromomethylphenyl)-N-(α,α-dibromopropionyl)-hydroxylamine 7.55 (m, 1H, phenyl); 7.4 (m, 3H, phenyl); 4.5 (s, 2H, CH$_2$, Br); 3.8 (s, 3H, OCH$_3$); 2.75 (s, 3H, CH$_3$).

b) O-Methyl-N-(2-bromomethylphenyl)-N-(α-bromopropionyl)-hydroxylamine 7.5 (s, broad, 1H, phenyl); 7.4 (s, broad, 3H, phenyl); 5.15 (s, broad, 1H, CH—Br); 4.5 (dd, broad, 2H, CH$_2$—Br); 3.8 (s, 3H, OCH$_3$); 1.85 (s, broad, 3H, CH$_3$).

c) O-Methyl-N-(2-bromomethylphenyl)-N-propionyl-hydroxylamine 7.5 (m, 1H, phenyl); 7.35 (m, 3H, phenyl); 4.5 (s, broad, 2H, CH$_2$—Br); 3.75 (s, 3H, OCH$_3$); 2.55 (s, very broad, CH$_2$); 1.2 (t, 3H, I=7 Hz, CH$_3$).

Example 8

O-Methyl-N-(2-(2'-methylphenyloxymethyl)-phenyl)-N-propionyl-hydroxylamine (Table 21, No. 3)

0.12 g (5 mmol) of sodium hydride is added to a solution of 0.4 g (3.7 mmol) of o-cresol in 5 ml of dimethylformamide. Upon completion of gas evolution, 1 g (3.6 mmol) of the benzyl bromide from Example 2c is added and the mixture is stirred for 2 hours at room temperature. The reaction mixture is diluted with water and extracted three times with methyl tert-butyl ether. The combined organic phases are washed with water, dried over MgSO$_4$ and evaporated down. The residue is chromatographed with mixtures of cyclohexane and ethyl acetate using Al$_2$O$_3$ and silica gel. There is obtained 0.4 g (1.33 mmol=37%) of the title compound as a yellow oil.

$^1$H-NMR (COCl$_3$; δ in ppm): 7.7 (d, broad, 1H, phenyl); 7.35 (m, 3H, phenyl); 7.1 (m, 2H, phenyl); 6.85 (t, broad, 2H, phenyl); 5.05 (s, 2H, OCH$_3$); 3.7 (s, 3H, OCH$_3$); 2.55 (s, very broad, 2H, CH$_2$); 2.3 (s, 3H, CH$_3$); 1.2 (t, broad, 3H, CH$_3$).

Example 9

N-Methyl-N'-methoxy-N'-2-methylphenylurea (Table 21, No. 5)

a) Phenyl N-hydroxy-N-(2-methylphenyl)-carbamate

A mixture of 2.5 g (20 mmol) of N-(2-methylphenyl)-hydroxylamine (crude product, obtained according to Bamberger et al., Anm. Chem. 316 (1901), 278), 3.5 g (25 mmol) of K$_2$CO$_3$ and 3.5 g (22 mmol) of phenyl Chlorooformate in 20 ml of CH$_2$Cl$_2$ is stirred for 2 hours at room temperature. The reaction mixture is then extracted with water, dried over MgSO$_4$ and evaporated down. The residue is purified by column chromatography with mixtures of cyclohexane and ethyl acetate. There is obtained 2.0 g (8.2 mmol=42%) of the title compound as a colorless solid (mp=98° C.).

$^1$H-NMR (COCl$_3$; δ in ppm): 7–7.6 (m, 10H, phenyl, OH); 2.35 (s, 3H, CH$_3$).

b) Phenyl N-methoxy-N-(2-methylphenyl)-carbamate

A mixture of 2.0 g (8.2 mmol) of the phenyl carbamate from Example 4a, 2 g (15 mmol) of $K_2CO_3$ and 1.3 g (10 mmol) of dimethyl sulfate in 20 ml of acetone is stirred for 3 hours at room temperature. The reaction mixture is then filtered and evaporated down, and the residue is purified by column chromatography with mixtures of cyclohexane and ethyl acetate. There is obtained 1.5 g (5.8 mmol≙71%) of the title compound as a colorless oil, which slowly crystallizes (mp=60° C.).

$^1$H-NMR (COCl$_3$; δ in ppm): 7.1–7.5 (m, 9H, phenyl); 3.8 (s, 3H, OCH$_3$); 2.4 (s, 3H, CH$_3$).

c) N-Methyl-N'-methoxy-N'-2-methylphenylurea (Table 21, No. 5)

1.5 g (5.8 mmol) of the phenyl carbamate from Example 4b in 20 ml of 40% strength aqueous methylamine solution is stirred for 1 hour at 50° C. The reaction mixture is then cooled and extracted with $CH_2Cl_2$. The combined organic phases are dried over $MgCO_4$ and evaporated down. The residue is purified by column chromatography with mixtures of cyclohexane and ethyl acetate. There is obtained 0.6 g (3.1 mol≙53%) of the title compound as a colorless solid (mp 99° C.).

$^1$H-NMR (COCl$_3$; δ in ppm): 7.2 (m, 4H, phenyl); 5.9 (s, broad, 1H, NH); 3.6 (s, 3H, OCH$_3$); 2.9 (d, 3H, I=approx. 2 Hz, N—CH$_3$); 2.3 (s, 3H, CH$_3$).

Example 18

N-Methyl-N'-methoxy-N'-(2-2',5'-dimethylphenoxymethyl)-phenyl)-urea a) Phenyl N-methoxy-N-(2-bromomethylphenyl)-carbamate A mixture of 125 g (0.486 mol) of methyl N-methoxy-N-(2-methylphenyl)-carbamate (Example 4b), 88 g (0.494 mol) of N-bromosuccinimide and 1 g of azoisobutyrodinitrile (AIBN) in 800 ml of $CCl_4$ is refluxed for about 12 hours. 10 g of N-bromosuccinimide is then added and the mixture is refluxed for about 4 hours. The reaction mixture is extracted with water and sodium thiosulfate solution, and the organic phase is dried over $MgSO_4$ and evaporated down under reduced pressure. The residue crystallizes, is stirred with hexane/methyl tert-butyl ether and suction dried. There is obtained 107 g (63%) of the title compound as a colorless solid.

$^1$H-NMR (CDCl$_3$; δ in ppm): 7.1–7.6 (m, 9H, phenyl); 4.65 (s, 2H, CH$_2$Br); 3.9 (s, 3H, OCH$_3$).

b) Phenyl N-methoxy-N-(2-(2',5'-dimethylphenoxymethyl)-phenyl)-carbamate

A mixture of 7 g (20 mmol) of the bromide of Example 5a and 3.3 g (22 mmol) of sodium iodide in 50 ml of acetone is refluxed for 30 minutes. The precipitated solid is then filtered off and the organic phase is evaporated down under reduced pressure. The crude product obtained is the iodide corresponding to Example 5a, which is used in the next reaction without any further purification.

The crude product obtained above is dissolved in 100 ml of dimethylformamide, 3 g (21.6 mmol) of $K_2CO_3$ and 7.3 g (60 mmol) of 2,5-dimethylphenol are added and the mixture is stirred overnight at room temperature. The reaction mixture is then diluted with water and the aqueous phase is extracted three times with methyl tert-butyl ether. The combined organic phases are extracted with water, dried over $MgSO_4$ and evaporated down. The residue is purified by column chromatography using methylene chloride/cyclohexane (1:2) over $Al_2O_3$. There is obtained 7.3 g (94%) of the title compound as a yellow oil.

$^1$H-NMR (CDCl$_3$; δ in PPM): 7.7 (d, broad, 1H, phenyl); 7–7.6 (m, 9H, phenyl); 6.7 (m, 2H, phenyl); 5.2 (s, 2H, OCH$_2$); 3.85 (s, 3H, OCH$_3$); 2.3 (s, 6H, 2×CH$_3$).

c) N-Methyl-N'-methoxy-N'-(2-(2',5'-dimethylphenoxymethyl)-phenyl)-urea (Table 1, No. V.71)

A mixture of 3.4 g (8.8 mmol) of the phenyl carbamate of Example 5b and 20 ml of 40% strength aqueous methylamine solution is stirred for 2 hours at 50° C. The mixture is allowed to cool and is then extracted with methylene chloride. The organic phase is evaporated down and the residue is purified by column chromatography with mixtures of cyclohexane/ethyl acetate. There is obtained 1 g (36%) of the title compound as a colorless solid (mp=101° C.).

$^1$H-NMR (CDCl$_3$; δ in PPM): 7.75 (m, 1H, phenyl); 6.6–7.4 (m, 6H, phenyl); 6.0 (s, broad, NH); 5.15 (s, 2H, OCH$_2$); 3.65 (s, 3H, OCH$_3$); 2.9 (d, 3H, N—CH$_3$); 2.3 (s, 3H, CH$_3$); 2.25 (s, 3H, CH$_3$).

The compounds listed in the tables below may be prepared analogously. Compound I.1 from Table 15 has for instance the following formula

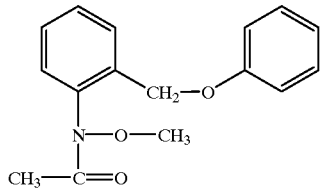

TABLE 15

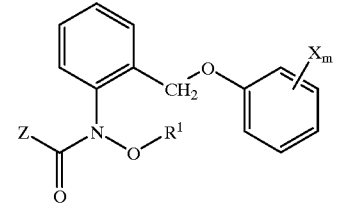

I: $R^1 = CH_3$, $Z = CH_3$
II: $R^1 = CH_2$—$CH_3$, $Z = CH_3$
III: $R^1 = CH_3$, $Z = C_2H_5$
IV: $R^1 = CH_2$—$CH_3$, $Z = C_2H_5$
V: $R^1 = CH_3$, $Z = NHCH_3$
VI: $R^1 = CH_2$—$CH_3$, $Z = NHCH_3$

| No. | Xm |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |

TABLE 15-continued

| | |
|---|---|
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_2$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C6H13 |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O-(CH$_2$)$_3$C$_6$H$_5$ |

TABLE 15-continued

| | |
|---|---|
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH3, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO2 |
| 251 | 2-NO2, 4-Cl |
| 252 | 2-OCH$_3$, 5-NO$_2$ |
| 253 | 2,4-Cl2, 5-NO2 |
| 254 | 2,3-Cl2, 6-NO2 |
| 255 | 2,6-Cl2, 4-NO2 |
| 256 | 2,6-Br2, 4-NO2 |
| 257 | 2,6-I2, 4-NO2 |
| 258 | 2-CH3, 5-i-C3H7, 4-Cl |
| 259 | 2-CO$_2$CH$_3$ |
| 260 | 3-CO2CH3 |
| 261 | 4-CO2CH3 |
| 262 | 2-CO2(C2H5) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$——CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |

TABLE 15-continued

| | |
|---|---|
| 341 | 2-C(=NO-n-$C_4H_9$)—$CH_3$ |
| 342 | 3-C(=NO-n-$C_4H_9$)—$CH_3$ |
| 343 | 4-C(=NO-n-$C_4H_9$)—$CH_3$ |
| 344 | 2-C(=NO—$CH_2$—$C_6H_5$)—$CH_3$ |
| 345 | 3-C(=NO—$CH_2$—$C_6H_5$)—$CH_3$ |
| 346 | 4-C(=NO—$CH_2$—$C_6H_5$)—$CH_3$ |
| 347 | 2-$CH_3$-4-CH=$NOCH_3$ |
| 348 | 2-$CH_3$-4-CH=$NOC_2H_5$ |
| 349 | 2-$CH_3$-4-CH=NO-n-$C_3H_7$ |
| 350 | 2-$CH_3$-4-CH=NO-i-$C_3H_7$ |
| 351 | 2-$CH_3$-4-CH=NO-Allyl |
| 352 | 2-$CH_3$-4-CH=NO-(trans-Chloroallyl) |
| 353 | 2-$CH_3$-4-CH=NO-Propargyl |
| 354 | 2-$CH_3$-4-CH=NO-n-$C_4H_9$ |
| 355 | 2-$CH_3$-4-CH=NO—$CH_2$—$C_6H_5$ |
| 356 | 2-$CH_3$-4-($CH_3$—C=$NOCH_3$) |
| 357 | 2-$CH_3$-4-($CH_3$—C=$NOC_2H_5$) |
| 358 | 2-$CH_3$-4-($CH_3$—C=NO-n-$C_3H_7$) |
| 359 | 2-$CH_3$-4-($CH_3$—C=NO-i-$C_3H_7$) |
| 360 | 2-$CH_3$-4-($CH_3$—C=NO-Allyl) |
| 361 | 2-CH3-4-(CH3-C=NO-trans-Chloroallyl) |
| 362 | 2-$CH_3$-4-($CH_3$—C=NO-Propargyl) |
| 363 | 2-$CH_3$-4-($CH_3$—C=NO-n-$C_4H_9$) |
| 364 | 2-$CH_3$-4-($CH_3$—C=NO—$CH_2$—$C_6H_5$) |
| 365 | 2-$CH_3$-4-($C_2H_5$—C=NO—$CH_3$) |
| 366 | 2-$CH_3$-4-($C_2H_5$—C=NO—$C_2H_5$) |
| 367 | 2-$CH_3$-4-($C_2H_5$—C=NO-n-$C_3H_7$) |
| 368 | 2-$CH_3$-4-($C_2H_5$—C=NO-i-$C_3H_7$) |
| 369 | 2-CH3-4-(C2H5—C=NO-Allyl) |
| 370 | 2-$CH_3$-4-($C_2H_5$—C=NO-trans-Chloroallyl) |
| 371 | 2-$CH_3$-4-($C_2H_5$—C=NO-Propargyl) |
| 372 | 2-$CH_3$-4-($C_2H_5$—C=NO-n-$C_4H_9$) |
| 373 | 2-$CH_3$-4-($C_2H_5$—C=NO—$CH_2$—$C_6H_5$) |
| 374 | 2,5-$(CH_3)_2$-4-($CH_3$—C=$NOCH_3$) |
| 375 | 2,5-$(CH_3)_2$-4-($CH_3$—C=$NOC_2H_5$) |
| 376 | 2,5-$(CH_3)_2$-4-($CH_3$—C=NO-n-$C_3H_7$) |
| 377 | 2,5-$(CH_3)_2$-4-($CH_3$—C=NO-i-$C_3H_7$) |
| 378 | 2,5-$(CH_3)_2$-4-($CH_3$—C=NO-Allyl) |
| 379 | 2,5-$(CH_3)_2$-4-($CH_3$—C=NO-trans-Chloroallyl) |
| 380 | 2,5-$(CH_3)_2$-4-($CH_3$—C=NO-Proparyl) |
| 381 | 2,5-$(CH_3)_2$-4-($CH_3$—C=NO-n-$C_4H_9$) |
| 382 | 2,5-$(CH_3)_2$-4-($CH_3$C=NO—$CH_2$—$C_6H_5$) |
| 383 | 2-$C_6H_5$ |
| 384 | 3-$C_6H_5$ |
| 385 | 4-$C_6H_5$ |
| 386 | 2-(2'-F—$C_6H_4$) |
| 387 | 2-(3'-F—$C_6H_4$) |
| 388 | 2-(4'-F—$C_6H_4$) |
| 389 | 3-(2'-F—$C_6H_4$) |
| 390 | 3-(3'-F—$C_6H_4$) |
| 391 | 3-(4'-F—$C_6H_4$) |
| 392 | 4-(2'-F—$C_6H_4$) |
| 393 | 4-(3'-F—$C_6H_4$) |
| 394 | 4-(4'-F—$C_6H_4$) |
| 395 | 2-(2'-Cl—$C_6H_4$) |
| 396 | 2-(3'-Cl—$C_6H_4$) |
| 397 | 2-(4'-Cl—$C_6H_4$) |
| 398 | 3-(2'-Cl—$C_6H_4$) |
| 399 | 3-(3'-Cl—$C_6H_4$) |
| 400 | 3-(4'-Cl—$C_6H_4$) |
| 401 | 4-(2'-Cl—$C_6H_4$) |
| 402 | 4-(3'-Cl—$C_6H_4$) |
| 403 | 4-(4'-Cl—$C_6H_4$) |
| 405 | 2-(2'-$CH_3$—$C_6H_4$) |
| 406 | 2-(3'-$CH_3$—$C_6H_4$) |
| 407 | 2-(4'-$CH_3$—$C_6H_4$) |
| 408 | 3-(2'-$CH_3$—$C_6H_4$) |
| 409 | 3-(3'-$CH_3$—$C_6H_4$) |
| 410 | 3-(4'-$CH_3$—$C_6H_4$) |
| 411 | 4-(2'-$CH_3$—$C_6H_4$) |
| 412 | 4-(3'-$CH_3$—$C_6H_4$) |
| 413 | 4-(4'-$CH_3$—$C_6H_4$) |
| 414 | 2-(2'-$CH_3$—CO—$C_6H_4$) |
| 415 | 2-(3'-$CH_3$—CO—$C_6H_4$) |
| 416 | 2-(4'-$CH_3$—CO—$C_6H_4$) |
| 417 | 3-(2'-$CH_3$—CO—$C_6H_4$) |
| 418 | 3-(3'-$CH_3$—CO—$C_6H_4$) |
| 419 | 3-(4'-$CH_3$—CO—$C_6H_4$) |

TABLE 15-continued

| | |
|---|---|
| 420 | 4-(2'-$CH_3$—CO—$C_6H_4$) |
| 421 | 4-(3'-$CH_3$—CO—$C_6H_4$) |
| 422 | 4-(4'-$CH_3$—CO—$C_6H_4$) |
| 423 | 2-(2'-($CH_3$—C(=NOAllyl))-$C_6H_4$) |
| 424 | 2-(3'-($CH_3$—C(=NOAllyl))-$C_6H_4$) |
| 425 | 2-(4'-($CH_3$—C(=NOAllyl))-$C_6H_4$) |
| 426 | 3-(2'-($CH_3$—C(=NOAllyl))-$C_6H_4$) |
| 427 | 3-(3'-($CH_3$—C(=NOAllyl))-$C_6H_4$) |
| 428 | 3-(4'-($CH_3$—C(=NOAllyl))-$C_6H_4$) |
| 429 | 4-(2'-($CH_3$—C(=NOAllyl))-$C_6H_4$) |
| 430 | 4-(3'-($CH_3$—C(=NOAllyl))-$C_6H_4$) |
| 431 | 4-(4'-($CH_3$—C(=NOAllyl))-$C_6H_4$) |
| 432 | 2-(2'-$CH_3O_2$C—$C_6H_4$) |
| 433 | 2-(3'-$CH_3O_2$C—$C_6H_4$) |
| 434 | 2-(4'-$CH_3O_2$C—$C_6H_4$) |
| 435 | 3-(2'-$CH_3O_2$C—$C_6H_4$) |
| 436 | 3-(3'-CH3O2C—$C_6H_4$) |
| 437 | 3-(4'-$CH_3O_2$C—$C_6H_4$) |
| 438 | 4-(2'-$CH_3O_2$C—$C_6H_4$) |
| 439 | 4-(3'-$CH_3O_2$C—$C_6H_4$) |
| 440 | 4-(4'-$CH_3O_2$C—$C_6H_4$) |
| 441 | 2-(2'-$CH_3$O—$C_6H_4$) |
| 442 | 2-(3'-$CH_3$O—$C_6H_4$) |
| 443 | 2-(4'-$CH_3$O—$C_6H_4$) |
| 444 | 3-(2'-$CH_3$O—$C_6H_4$) |
| 445 | 3-(3'-$CH_3$O—$C_6H_4$) |
| 446 | 3-(4'-$CH_3$O—$C_6H_4$) |
| 447 | 4-(2'-$CH_3$O—$C_6H_4$) |
| 448 | 4-(3'-$CH_3$O—$C_6H_4$) |
| 449 | 4-(4'-$CH_3$O—$C_6H_4$) |
| 450 | 2-(2'-$O_2$N—$C_6H_4$) |
| 451 | 2-(3'-$O_2$N—$C_6H_4$) |
| 452 | 2-(4'-$O_2$N—$C_6H_4$) |
| 453 | 3-(2'-$O_2$N—$C_6H_4$) |
| 454 | 3-(3'-$O_2$N—$C_6H_4$) |
| 455 | 3-(4'-$O_2$N—$C_6H_4$) |
| 456 | 4-(2'-$O_2$N—$C_6H_4$) |
| 457 | 4-(3'-$O_2$N—$C_6H_4$) |
| 458 | 4-(4'-$O_2$N—$C_6H_4$) |
| 459 | 2-(2'-NC—$C_6H_4$) |
| 460 | 2-(3'-NC—$C_6H_4$) |
| 461 | 2-(4'-NC—$C_6H_4$) |
| 462 | 3-(2'-NC—$C_6H_4$) |
| 463 | 3-(3'-NC—$C_6H_4$) |
| 464 | 3-(4'-NC—$C_6H_4$) |
| 465 | 4-(2'-NC—$C_6H_4$) |
| 466 | 4-(3'-NC—$C_6H_4$) |
| 467 | 4-(4'-NC—$C_6H_4$) |
| 468 | 2-(2'-$CF_3$—$C_6H_4$) |
| 469 | 2-(3'-$CF_3$—$C_6H_4$) |
| 470 | 2-(4'-$CF_3$—$C_6H_4$) |
| 471 | 3-(2'-$CF_3$—$C_6H_4$) |
| 472 | 3-(3'-$CF_3$—$C_6H_4$) |
| 473 | 3-(4'-$CF_3$—$C_6H_4$) |
| 474 | 4-(2'-$CF_3$—$C_6H_4$) |
| 475 | 4-(3'-$CF_3$—$C_6H_4$) |
| 476 | 4-(4'-$CF_3$—$C_6H_4$) |
| 477 | 2-O—$C_6H_5$ |
| 475 | 3-O—C6H5 |
| 476 | 4-O—C6H5 |
| 478 | 2-O-(2'-F—$C_6H_4$) |
| 479 | 2-O-(3'-F—$C_6H_4$) |
| 480 | 2-O-(4'-F—$C_6H_4$) |
| 481 | 3-O-(2'-F—$C_6H_4$) |
| 482 | 3-O-(3'-F—$C_6H_4$) |
| 483 | 3-O-(4'-F—$C_6H_4$) |
| 484 | 4-O-(2'-F—$C_6H_4$) |
| 485 | 4-O-(3'-F—$C_6H_4$) |
| 486 | 4-O-(4'-F—$C_6H_4$) |
| 487 | 2-O-(2'-Cl—$C_6H_4$) |
| 488 | 2-O-(3'-Cl—$C_6H_4$) |
| 489 | 2-O-(4'-Cl—$C_6H_4$) |
| 490 | 3-O-(2'-Cl—$C_6H_4$) |
| 491 | 3-O-(3'-Cl—$C_6H_4$) |
| 492 | 3-O-(4'-Cl—$C_6H_4$) |
| 493 | 3-O-(4'-Cl—$C_6H_4$) |
| 494 | 4-O-(2'-Cl—$C_6H_4$) |
| 495 | 4-O-(3'-Cl—$C_6H_4$) |
| 496 | 4-O-(4'-Cl—$C_6H_4$) |

TABLE 15-continued

| | |
|---|---|
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(3'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH3—CO—C6H4) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O2N—C6H4) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-CH$_3$-4-(CH$_3$—C=N—O—CH$_2$—CH$_2$—OCH$_3$) |
| 642 | 2-CH$_3$-4-(C$_2$H$_5$—C=N—O—CH$_2$—CH$_2$—OCH$_3$ |
| 643 | 2,5-(CH$_3$)$_2$-4-(CH$_3$—C=N—O—CH$_2$—CH$_2$—OCH$_3$) |
| 644 | 2-CH$_3$-4-(n-C$_3$H$_7$—C=N—OCH$_3$) |
| 645 | 2-CH$_3$-4-(n-C$_3$H$_7$—C=N—OC$_2$H$_5$) |
| 646 | 2-CH$_3$-4-(n-C$_3$H$_7$—C=N—O-n-C$_3$H$_7$) |
| 647 | 2-CH$_3$-4-(n-C$_3$H$_7$—C=N—O-i-C$_3$H$_7$) |
| 648 | 2-CH$_3$-4-(n-C$_3$H$_7$—C=N—O-Allyl) |
| 649 | 2-CH$_3$-4-(n-C$_3$H$_7$—C=N—O-trans-Chloroallyl) |
| 650 | 2-CH$_3$-4-(n-C$_3$H$_7$—C=N—O-Propargyl) |
| 651 | 2-CH$_3$-4-(n-C$_3$H$_7$—C=N—O-n-C$_4$H$_9$) |
| 652 | 2-CH$_3$-4-(n-C$_3$H$_7$—C=N—O—CH$_2$—C$_6$H$_5$) |
| 653 | 2-CH$_3$-4-(i-C$_3$H$_7$—C=N—OCH$_3$) |
| 654 | 2-CH$_3$-4-(i-C$_3$H$_7$—C=N—OC$_2$H$_5$) |

TABLE 15-continued

| | |
|---|---|
| 655 | 2-CH$_3$-4-(i-C$_3$H$_7$—C=N—O-n-C$_3$H$_7$) |
| 656 | 2-CH$_3$-4-(i-C$_3$H$_7$—C=N—O-i-C$_3$H$_7$) |
| 657 | 2-CH$_3$-4-(i-C$_3$H$_7$—C=N—O-Allyl) |
| 658 | 2-CH$_3$-4-(i-C$_3$H$_7$—C=N—O-trans-Chloroallyl) |
| 659 | 2-CH$_3$-4-(i-C$_3$H$_7$—C=N—O-Propargyl) |
| 660 | 2-CH$_3$-4-(i-C$_3$H$_7$—C=N—O-n-C$_4$H$_9$) |
| 661 | 2-CH$_3$-4-(i-C$_3$H$_7$—C=N—O—CH$_2$—C$_6$H$_5$) |
| 662 | 2-O-n-C$_4$H$_9$ |
| 663 | 2-O-i-C$_4$H$_9$ |
| 664 | 2-O-s-C$_4$H$_9$ |
| 665 | 2-O-t-C$_4$H$_9$ |
| 666 | 2-Neopentyloxy |
| 667 | 3-O-n-C$_4$H$_9$ |
| 668 | 3-O-i-C$_4$H$_9$ |
| 669 | 3-O-s-C$_4$H$_9$ |
| 670 | 3-O-t-C$_4$H$_9$ |
| 671 | 3-Neopentyloxy |
| 672 | 4-O-n-C$_4$H$_9$ |
| 673 | 4-O-i-C$_4$H$_9$ |
| 674 | 4-O-s-C$_4$H$_9$ |
| 675 | 4-O-t-C$_4$H$_9$ |
| 676 | 4-Neopentyloxy |
| 677 | 3-CH$_3$-4-OCH$_3$ |
| 678 | 3-CH$_3$-4-OC$_2$H$_5$ |
| 679 | 3-CH$_3$-4-O-n-C$_3$H$_7$ |
| 680 | 3-CH$_3$-4-O-n-C$_4$H$_9$ |
| 681 | 3-CH$_3$-4-O-i-C$_4$H$_9$ |
| 682 | 3-CH$_3$-4-O-s-C$_4$H$_9$ |
| 683 | 3-CH$_3$-4-O-t-C$_4$H$_9$ |
| 684 | 3-CH$_3$-4-Neopentyloxy |
| 685 | 2-CH$_3$-3-OCH$_3$ |
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 16

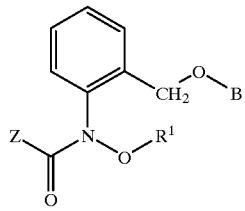

I: R$^1$ = CH$_3$, Z = CH$_3$
II: R$^1$ = CH$_2$—CH$_3$, Z = CH$_3$
III: R$^1$ = CH$_3$, Z = C$_2$H$_5$
IV: R$^1$ = CH$_2$—CH$_3$, Z = C$_2$H$_5$
V: R$^1$ = CH$_3$, Z = NHCH$_3$
VI: R$^1$ = CH$_2$—CH$_3$, Z = NHCH$_3$

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |

TABLE 16-continued

| | |
|---|---|
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |

TABLE 16-continued

| | |
|---|---|
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 2-CH$_3$-Oxazolyl-4 |
| 234 | 2-C$_6$H$_5$-Oxazolyl-4 |
| 235 | 2-(4'-CH$_3$—C$_6$H$_4$)-Oxazolyl-4 |
| 236 | 2-(3'-CH$_3$—C$_6$H$_4$)-Oxazolyl-4 |
| 237 | 2-(2'-CH$_3$—C$_6$H$_4$)-Oxazolyl-4 |
| 238 | 2-(4'-CH$_3$O—C$_6$H$_4$)-Oxazolyl-4 |
| 239 | 2-(3'-CH$_3$O—C$_6$H$_4$)-Oxazolyl-4 |
| 240 | 2-(2'-CH$_3$O—C$_6$H$_4$)-Oxazolyl-4 |
| 241 | 2-(4'-NO$_2$—C$_6$H$_4$)-Oxazolyl-4 |
| 242 | 2-(3'-NO$_2$—C$_6$H$_4$)-Oxazolyl-4 |
| 243 | 2-(2'-NO$_2$—C$_6$H$_4$)-Oxazolyl-4 |
| 244 | 2-(4'-CN—C$_6$H$_4$)-Oxazolyl-4 |
| 245 | 2-(3'-CN—C$_6$H$_4$)-Oxazolyl-4 |
| 246 | 2-(2'-CN—C$_6$H$_4$)-Oxazolyl-4 |
| 247 | 2-(4'-Cl—C$_6$H$_4$)-Oxazolyl-4 |
| 248 | 2-(3'-Cl—C$_6$H$_4$)-Oxazolyl-4 |
| 249 | 2-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 257 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,3,4-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |

TABLE 16-continued

| | |
|---|---|
| 374 | 5-(3'-Cl—$C_6H_4$)-1,3,4-Thiadiazolyl-2 |
| 375 | 5-(2'-Cl—$C_6H_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |
| 385 | 1-Naphthyl |
| 386 | 2-Naphthyl |

TABLE 17

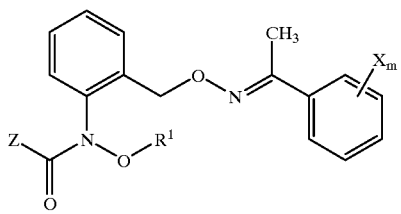

I: $R^1 = CH_3$, $Z = CH_3$
II: $R^1 = CH_2$—$CH_3$, $Z = CH_3$
III: $R^1 = CH_3$, $Z = C_2H_5$
IV: $R^1 = CH_2$—$CH_3$, $Z = C_2H_5$
V: $R^1 = CH_3$, $Z = NHCH_3$
VI: $R^1 = CH_2$—$CH_3$, $Z = NHCH_3$

| No. | $X_m$ |
|---|---|
| 1 | H |
| 2 | 2-F |
| 3 | 3-F |
| 4 | 4-F |
| 5 | 2,4-$F_2$ |
| 6 | 2,4,6-$F_3$ |
| 7 | 2,3,4,5,6-$F_5$ |
| 8 | 2,3-$F_2$ |
| 9 | 2-Cl |
| 10 | 3-Cl |
| 11 | 4-Cl |
| 12 | 2,3-$Cl_2$ |
| 13 | 2,4-$Cl_2$ |
| 14 | 2,5-$Cl_2$ |
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |
| 37 | 4-I |
| 38 | 2,4-$I_2$ |
| 39 | 2-Cl, 3-F |

TABLE 17-continued

| No. | $X_m$ |
|---|---|
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-$Cl_2$, 4-Br |
| 66 | 2-$CH_3$ |
| 67 | 3-$CH_3$ |
| 68 | 4-$CH_3$ |
| 69 | 2,3-$(CH_3)_2$ |
| 70 | 2,4-$(CH_3)_2$ |
| 71 | 2,5-$(CH_3)_2$ |
| 72 | 2,6-$(CH_3)_2$ |
| 73 | 3,4-$(CH_3)_2$ |
| 74 | 3,5-$(CH_3)_2$ |
| 75 | 2,3,5-$(CH_3)_3$ |
| 76 | 2,3,4-$(CH_3)_3$ |
| 77 | 2,3,6-$(CH_3)_3$ |
| 78 | 2,4,5-$(CH_3)_3$ |
| 79 | 2,4,6-$(CH_3)_3$ |
| 80 | 3,4,5-$(CH_3)_3$ |
| 81 | 2,3,4,6-$(CH_3)_4$ |
| 82 | 2,3,5,6-$(CH_3)_4$ |
| 83 | 2,3,4,5,6-$(CH_3)_5$ |
| 84 | 2-$C_2H_5$ |
| 85 | 3-$C_2H_5$ |
| 86 | 4-$C_2H_5$ |
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C_2H_5)_3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7$)$_2$ |
| 98 | 2,6-(i-$C_3H_7$)$_2$ |
| 99 | 3,5-(i-$C_3H_7$)$_2$ |
| 100 | 2,4,6-(i-$C_3H_7$)$_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9$)$_2$ |
| 108 | 2,4-(t-$C_4H_9$)$_2$ |
| 109 | 2,5-(t-$C_4H_9$)$_2$ |
| 110 | 2,6-(t-$C_4H_9$)$_2$ |
| 111 | 3,4-(t-$C_4H_9$)$_2$ |
| 112 | 2,4,6-(t-$C_4H_9$)$_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-$C_4H_9$, 4-$CH_3$ |

TABLE 17-continued

| | |
|---|---|
| 119 | 2-t-$C_4H_9$, 5-$CH_3$ |
| 120 | 2,6-(t-$C_4H_9$)$_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9$)$_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11}$)$_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-($CH_3$)$_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$OCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-$C_6H_{13}$ |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—($CH_2$)$_3C_6H_5$ |
| 181 | 3-O—($CH_2$)$_3C_6H_5$ |
| 182 | 4-O—($CH_2$)$_3C_6H_5$ |
| 183 | 2,4-($OCH_3$)$_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 2-$CH_3$, 4-Cl |
| 199 | 2-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-$CH_3$, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-($CH_3$)$_2$ |
| 228 | 2-Br, 4,5-($CH_3$)$_2$ |
| 229 | 2-Cl, 3,5-($CH_3$)$_2$ |
| 230 | 2-Br, 3,5-($CH_3$)$_2$ |
| 231 | 2,6-Cl$_2$, 4-$CH_3$ |
| 232 | 2,6-F$_2$, 4-$CH_3$ |
| 233 | 2,6-Br$_2$, 4-$CH_3$ |
| 234 | 2,4-Br$_2$, 6-$CH_3$ |
| 235 | 2,4-F$_2$, 6-$CH_3$ |
| 236 | 2,4-Br$_2$, 6-$CH_3$ |
| 237 | 2,6-($CH_3$)$_2$, 4-F |
| 238 | 2,6-($CH_3$)$_2$, 4-Cl |
| 239 | 2,6-($CH_3$)$_2$, 4-Br |
| 240 | 3,5-($CH_3$)$_2$, 4-F |
| 241 | 3,5-($CH_3$)$_2$, 4-Cl |
| 242 | 3,5-($CH_3$)$_2$, 4-Br |
| 243 | 2,3,6-($CH_3$)$_3$, 4-F |
| 244 | 2,3,6-($CH_3$)$_3$, 4-Cl |
| 245 | 2,3,6-($CH_3$)$_3$, 4-Br |
| 246 | 2,4-($CH_3$)$_2$, 6-F |
| 247 | 2,4-($CH_3$)$_2$, 6-Cl |
| 248 | 2,4-($CH_3$)$_2$, 6-Br |
| 249 | 2-i-$C_3H_7$, 4-Cl, 5-$CH_3$ |
| 250 | 2-Cl, 4-$NO_2$ |
| 251 | 2-$NO_2$, 4-Cl |
| 252 | 2-$OCH_3$, 5-$NO_2$ |
| 253 | 2,4-Cl$_2$, 5-$NO_2$ |
| 254 | 2,4-Cl$_2$, 6-$NO_2$ |
| 255 | 2,6-Cl$_2$, 4-$NO_2$ |
| 256 | 2,6-Br$_2$, 4-$NO_2$ |
| 257 | 2,6-I$_2$, 4-$NO_2$ |
| 258 | 2-$CH_3$, 5-i-$C_3H_7$, 4-Cl |
| 259 | 2-$CO_2CH_3$ |
| 260 | 3-$CO_2CH_3$ |
| 261 | 4-$CO_2CH_3$ |
| 262 | 2-$CO_2$($C_2H_5$) |
| 263 | 3-$CO_2$($C_2H_5$) |
| 264 | 4-$CO_2$($C_2H_5$) |
| 265 | 2-$CO_2$(n-$C_3H_7$) |
| 266 | 3-$CO_2$(n-$C_3H_7$) |
| 267 | 4-$CO_2$(n-$C_3H_7$) |
| 268 | 2-$CO_2$(i-$C_3H_7$) |
| 269 | 3-$CO_2$(i-$C_3H_7$) |
| 270 | 4-$CO_2$(i-$C_3H_7$) |
| 271 | 2-$CO_2$(n-$C_6H_{13}$) |
| 272 | 3-$CO_2$(n-$C_6H_{13}$) |
| 273 | 4-$CO_2$(n-$C_6H_{13}$) |
| 274 | 2-$CH_2$—$OCH_3$ |
| 275 | 3-$CH_2$—$OCH_3$ |
| 276 | 4-$CH_2$—$OCH_3$ |

TABLE 17-continued

| | |
|---|---|
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |

TABLE 17-continued

| | |
|---|---|
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |

TABLE 17-continued

| | |
|---|---|
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-$CH_3$-4-($CH_3$—C=N—O—$CH_2$—$CH_2$—$OCH_3$) |
| 642 | 2-$CH_3$-4-($C_2H_5$—C=N—O—$CH_2$—$CH_2$—$OCH_3$) |
| 643 | 2,5-$(CH_3)_2$-4-($CH_3$—C=N—O—$CH_2$—$CH_2$—$OCH_3$) |
| 644 | 2-$CH_3$-4-(n-$C_3H_7$—C=N—$OCH_3$) |
| 645 | 2-$CH_3$-4-(n-$C_3H_7$—C=N—$OC_2H_5$) |
| 646 | 2-$CH_3$-4-(n-$C_3H_7$—C=N—O-n-$C_3H_7$) |
| 647 | 2-$CH_3$-4-(n-$C_3H_7$—C=N—O-i-$C_3H_7$) |
| 648 | 2-$CH_3$-4-(n-$C_3H_7$—C=N—O-Allyl) |
| 649 | 2-$CH_3$-4-(n-$C_3H_7$—C=N—O-trans-Chloroallyl) |
| 650 | 2-$CH_3$-4-(n-$C_3H_7$—C=N—O-Propargyl) |
| 651 | 2-$CH_3$-4-(n-$C_3H_7$—C=N—O-n-$C_4H_9$) |
| 652 | 2-$CH_3$-4-(n-$C_3H_7$—C=N—O—$CH_2$—$C_6H_5$) |
| 653 | 2-$CH_3$-4-(i-$C_3H_7$—C=N—$OCH_3$) |
| 654 | 2-$CH_3$-4-(i-$C_3H_7$—C=N—$OC_2H_5$) |
| 655 | 2-$CH_3$-4-(i-$C_3H_7$—C=N—O-n-$C_3H_7$) |
| 656 | 2-$CH_3$-4-(i-$C_3H_7$—C=N—O-i-$C_3H_7$) |
| 657 | 2-$CH_3$-4-(i-$C_3H_7$—C=N—O-Allyl) |
| 658 | 2-$CH_3$-4-(i-$C_3H_7$—C=N—O-trans-Chloroallyl) |
| 659 | 2-$CH_3$-4-(i-$C_3H_7$—C=N—O-Propargyl) |
| 660 | 2-$CH_3$-4-(i-$C_3H_7$—C=N—O-n-$C_4H_9$) |
| 661 | 2-$CH_3$-4-(i-$C_3H_7$—C=N—O—$CH_2$—$C_6H_5$) |
| 662 | 2-O-n-$C_4H_9$ |
| 663 | 2-O-i-$C_4H_9$ |
| 664 | 2-O-s-$C_4H_9$ |
| 665 | 2-O-t-$C_4H_9$ |
| 666 | 2-Neopentyloxy |
| 667 | 3-O-n-$C_4H_9$ |
| 668 | 3-O-i-$C_4H_9$ |
| 669 | 3-O-s-$C_4H_9$ |
| 670 | 3-O-t-$C_4H_9$ |
| 671 | 3-Neopentyloxy |
| 672 | 4-O-n-$C_4H_9$ |
| 673 | 4-O-i-$C_4H_9$ |
| 674 | 4-O-s-$C_4H_9$ |
| 675 | 4-O-t-$C_4H_9$ |
| 676 | 4-Neopentyloxy |
| 677 | 3-$CH_3$-4-$OCH_3$ |
| 678 | 3-$CH_3$-4-$OC_2H_5$ |
| 679 | 3-$CH_3$-4-O-n-$C_3H_7$ |
| 680 | 3-$CH_3$-4-O-n-$C_4H_9$ |
| 681 | 3-$CH_3$-4-O-i-$C_4H_9$ |
| 682 | 3-$CH_3$-4-O-s-$C_4H_9$ |
| 683 | 3-$CH_3$-4-O-t-$C_4H_9$ |
| 684 | 3-$CH_3$-4-Neopentyloxy |
| 685 | 2-$CH_3$-3-$OCH_3$ |
| 686 | 2-$CH_3$-4-$OCH_3$ |
| 687 | 2-$CH_3$-5-$OCH_3$ |
| 688 | 2-$CH_3$-6-$OCH_3$ |
| 689 | 3-$CH_3$-4-$OCH_3$ |
| 690 | 3-$CH_3$-5-$OCH_3$ |
| 691 | 3-$CH_3$-6-$OCH_3$ |
| 692 | 4-$CH_3$-5-O—$CH_3$ |
| 693 | 4-$CH_3$-6-O—$CH_3$ |
| 694 | 4-$CH_3$-6-$OCH_3$ |
| 695 | 2-$CH_3$-3-O-i-$C_3H_7$ |
| 696 | 2-$CH_3$-4-O-i-$C_3H_7$ |
| 697 | 2-$CH_3$-5-O-i-$C_3H_7$ |
| 698 | 2-$CH_3$-6-O-i-$C_3H_7$ |
| 699 | 3-$CH_3$-4-O-i-$C_3H_7$ |
| 700 | 3-$CH_3$-5-O-i-$C_3H_7$ |
| 701 | 3-$CH_3$-6-O-i-$C_3H_7$ |
| 702 | 4-$CH_3$-5-O-i-$C_3H_7$ |
| 703 | 4-$CH_3$-6-O-i-$C_3H_7$ |
| 704 | 5-$CH_3$-6-O-i-$C_3H_7$ |
| 705 | 2-Cl-3-$OCH_3$ |
| 706 | 2-Cl-4-$OCH_3$ |
| 707 | 2-Cl-5-$OCH_3$ |
| 708 | 2-Cl-6-$OCH_3$ |
| 709 | 3-Cl-4-$OCH_3$ |
| 710 | 3-Cl-5-$OCH_3$ |
| 711 | 3-Cl-6-$OCH_3$ |
| 712 | 4-Cl-5-$OCH_3$ |
| 713 | 4-Cl-6-$OCH_3$ |
| 714 | 5-Cl-6-$OCH_3$ |

TABLE 18

I: $R^1 = CH_3$, $Z = CH_3$

II: $R^1 = CH_2$—$CH_3$, $Z = CH_3$

III: $R^1 = CH_3$, $Z = C_2H_5$

IV: $R^1 = CH_2$—$CH_3$, $Z = C_2H_5$

V: $R^1 = CH_3$, $Z = NHCH_3$

VI: $R^1 = CH_2$—$CH_3$, $Z = NHCH_3$

| No. | B |
|---|---|
| 1 | Pyrrolyl-3 |
| 2 | N—$CH_3$-Pyrrolyl-3 |
| 3 | N—$C_6H_5$-Pyrrolyl-3 |
| 4 | N-(4'-$CH_3$—$C_6H_4$)-Pyrrolyl-3 |
| 5 | N-(3'-$CH_3$—$C_6H_4$)-Pyrrolyl-3 |
| 6 | N-(2'-$CH_3$—$C_6H_4$)-Pyrrolyl-3 |
| 7 | N-(4'-$CH_3O$—$C_6H_4$)-Pyrrolyl-3 |

TABLE 18-continued

| | |
|---|---|
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |

TABLE 18-continued

| | |
|---|---|
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 2-CH$_3$-Oxazolyl-4 |
| 234 | 2-C$_6$H$_5$-Oxazolyl-4 |
| 235 | 2-(4'-CH$_3$—C$_6$H$_4$)-Oxazolyl-4 |
| 236 | 2-(3'-CH$_3$—C$_6$H$_4$)-Oxazolyl-4 |
| 237 | 2-(2'-CH$_3$—C$_6$H$_4$)-Oxazolyl-4 |
| 238 | 2-(4'-CH$_3$O—C$_6$H$_4$)-Oxazolyl-4 |
| 239 | 2-(3'-CH$_3$O—C$_6$H$_4$)-Oxazolyl-4 |
| 240 | 2-(2'-CH$_3$O—C$_6$H$_4$)-Oxazolyl-4 |
| 241 | 2-(4'-NO$_2$—C$_6$H$_4$)-Oxazolyl-4 |
| 242 | 2-(3'-NO$_2$—C$_6$H$_4$)-Oxazolyl-4 |
| 243 | 2-(2'-NO$_2$—C$_6$H$_4$)-Oxazolyl-4 |
| 244 | 2-(4'-CN—C$_6$H$_4$)-Oxazolyl-4 |
| 245 | 2-(3'-CN—C$_6$H$_4$)-Oxazolyl-4 |
| 246 | 2-(2'-CN—C$_6$H$_4$)-Oxazolyl-4 |
| 247 | 2-(4'-Cl—C$_6$H$_4$)-Oxazolyl-4 |
| 248 | 2-(3'-Cl—C$_6$H$_4$)-Oxazolyl-4 |
| 249 | 2-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 267 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,2,3-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |

TABLE 18-continued

| | |
|---|---|
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyrimidinyl-2 |
| 381 | Pyrimidinyl-4 |
| 382 | Pyrimidinyl-5 |
| 383 | Pyrimidinyl-2 |
| 384 | Pyridinyl-3 |
| 385 | 1-Naphthyl |
| 386 | 2-Naphthyl |

TABLE 19

| I: | R$^1$ = CH$_3$, | Z = CH$_3$ |
|---|---|---|
| II: | R$^1$ = CH$_2$—CH$_3$, | Z = CH$_3$ |
| III: | R$^1$ = CH$_3$, | Z = C$_2$H$_5$ |
| IV: | R$^1$ = CH$_2$—CH$_3$, | Z = C$_2$H$_5$ |
| V: | R$^1$ = CH$_3$, | Z = NHCH$_3$ |
| VI: | R$^1$ = CH$_2$—CH$_3$, | Z = NHCH$_3$ |

| No. | X$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |

TABLE 19-continued

| | |
|---|---|
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C4H9)2, 4-CH3 |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C6H11 |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH3 |
| 211 | 2-Cl, 5-CH3 |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |

TABLE 19-continued

| | |
|---|---|
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH2—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 3-CH3-4-(CH3—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH3-4-(C2H5—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |

TABLE 19-continued

| | |
|---|---|
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C6H5 |
| 385 | 4-C6H5 |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C6H4) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH3O2C—C6H4) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF3—C6H4) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C6H5 |
| 476 | 4-O—C6H5 |
| 478 | 2-O-(2'-F—C6H4) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 3-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C6H4) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |

TABLE 19-continued

| | |
|---|---|
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O2N—C6H4) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |

TABLE 19-continued

| | |
|---|---|
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |

TABLE 20

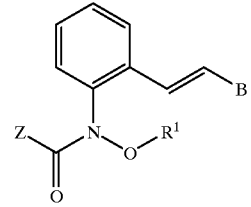

I: R$^1$ = CH$_3$, Z = CH$_3$

II: R$^1$ = CH$_2$—CH$_3$, Z = CH$_3$

III: R$^1$ = CH$_3$, Z = C$_2$H$_5$

IV: R$^1$ = CH$_2$—CH$_3$, Z = C$_2$H$_5$

V: R$^1$ = CH$_3$, Z = NHCH$_3$

VI: R$^1$ = CH$_2$—CH$_3$, Z = NHCH$_3$

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |

TABLE 20-continued

| | |
|---|---|
| 23 | N-(3'-CH₃—C₆H₄)-Pyrrolyl-2 |
| 24 | N-(2'-CH₃—C₆H₄)-Pyrrolyl-2 |
| 25 | N-(4'-CH₃O—C₆H₄)-Pyrrolyl-2 |
| 26 | N-(3'-CH₃O—C₆H₄)-Pyrrolyl-2 |
| 27 | N-(2'-CH₃O—C₆H₄)-Pyrrolyl-2 |
| 28 | N-(4'-NO₂—C₆H₄)-Pyrrolyl-2 |
| 29 | N-(3'-NO₂—C₆H₄)-Pyrrolyl-2 |
| 30 | N-(2'-NO₂—C₆H₄)-Pyrrolyl-2 |
| 31 | N-(4'-CN—C₆H₄)-Pyrrolyl-2 |
| 32 | N-(3'-CN—C₆H₄)-Pyrrolyl-2 |
| 33 | N-(2'-CN—C₆H₄)-Pyrrolyl-2 |
| 34 | N-(4'-Cl—C₆H₄)-Pyrrolyl-2 |
| 35 | N-(3'-Cl—C₆H₄)-Pyrrolyl-2 |
| 36 | N-(2'-Cl—C₆H₄)-Pyrrolyl-2 |
| 37 | Furyl-2 |
| 38 | 5-CH₃-Furyl-2 |
| 39 | 5-C₆H₅-Furyl-2 |
| 40 | 5-(4'-CH₃—C₆H₄)-Furyl-2 |
| 41 | 5-(3'-CH₃—C₆H₄)-Furyl-2 |
| 42 | 5-(2'-CH₃—C₆H₄)-Furyl-2 |
| 43 | 5-(4'-CH₃O—C₆H₄)-Furyl-2 |
| 44 | 5-(3'-CH₃O—C₆H₄)-Furyl-2 |
| 45 | 5-(2'-CH₃O—C₆H₄)-Furyl-2 |
| 46 | 5-(4'-NO₂—C₆H₄)-Furyl-2 |
| 47 | 5-(3'-NO₂—C₆H₄)-Furyl-2 |
| 48 | 5-(2'-NO₂—C₆H₄)-Furyl-2 |
| 49 | 5-(4'-CN—C₆H₄)-Furyl-2 |
| 50 | 5-(3'-CN—C₆H₄)-Furyl-2 |
| 51 | 5-(2'-CN—C₆H₄)-Furyl-2 |
| 52 | 5-(4'-Cl—C₆H₄)-Furyl-2 |
| 53 | 5-(3'-Cl—C₆H₄)-Furyl-2 |
| 54 | 5-(2'-Cl—C₆H₄)-Furyl-2 |
| 55 | 4-CH₃-Furyl-2 |
| 56 | 4-C₆H₅-Furyl-2 |
| 57 | 4-(4'-CH₃—C₆H₄)-Furyl-2 |
| 58 | 4-(3'-CH₃—C₆H₄)-Furyl-2 |
| 59 | 4-(2'-CH₃—C₆H₄)-Furyl-2 |
| 60 | 4-(4'-CH₃O—C₆H₄)-Furyl-2 |
| 61 | 4-(3'-CH₃O—C₆H₄)-Furyl-2 |
| 62 | 4-(2'-CH₃O—C₆H₄)-Furyl-2 |
| 63 | 4-(4'-NO₂—C₆H₄)-Furyl-2 |
| 64 | 4-(3'-NO₂—C₆H₄)-Furyl-2 |
| 65 | 4-(2'-NO₂—C₆H₄)-Furyl-2 |
| 66 | 4-(4'-CN—C₆H₄)-Furyl-2 |
| 67 | 4-(3'-CN—C₆H₄)-Furyl-2 |
| 68 | 4-(2'-CN—C₆H₄)-Furyl-2 |
| 69 | 4-(4'-Cl—C₆H₄)-Furyl-2 |
| 70 | 4-(3'-Cl—C₆H₄)-Furyl-2 |
| 71 | 4-(2'-Cl—C₆H₄)-Furyl-2 |
| 72 | Thienyl-2 |
| 73 | 5-CH₃-Thienyl-2 |
| 74 | 5-C₆H₅-Thienyl-2 |
| 75 | 5-(4'-CH₃—C₆H₄)-Thienyl-2 |
| 76 | 5-(3'-CH₃—C₆H₄)-Thienyl-2 |
| 77 | 5-(2'-CH₃—C₆H₄)-Thienyl-2 |
| 78 | 5-(4'-CH₃O—C₆H₄)-Thienyl-2 |
| 79 | 5-(3'-CH₃O—C₆H₄)-Thienyl-2 |
| 80 | 5-(2'-CH₃O—C₆H₄)-Thienyl-2 |
| 81 | 5-(4'-NO₂—C₆H₄)-Thienyl-2 |
| 82 | 5-(3'-NO₂—C₆H₄)-Thienyl-2 |
| 83 | 5-(2'-NO₂—C₆H₄)-Thienyl-2 |
| 84 | 5-(4'-CN—C₆H₄)-Thienyl-2 |
| 85 | 5-(3'-CN—C₆H₄)-Thienyl-2 |
| 86 | 5-(2'-CN—C₆H₄)-Thienyl-2 |
| 87 | 5-(4'-Cl—C₆H₄)-Thienyl-2 |
| 88 | 5-(3'-Cl—C₆H₄)-Thienyl-2 |
| 89 | 5-(2'-Cl—C₆H₄)-Thienyl-2 |
| 90 | 4-CH₃-Thienyl-2 |
| 91 | 4-C₆H₅-Thienyl-2 |
| 92 | 4-(4'-CH₃—C₆H₄)-Thienyl-2 |
| 93 | 4-(3'-CH₃—C₆H₄)-Thienyl-2 |
| 94 | 4-(2'-CH₃—C₆H₄)-Thienyl-2 |
| 95 | 4-(4'-CH₃O—C₆H₄)-Thienyl-2 |
| 96 | 4-(3'-CH₃O—C₆H₄)-Thienyl-2 |
| 97 | 4-(2'-CH₃O—C₆H₄)-Thienyl-2 |
| 98 | 4-(4'-NO₂—C₆H₄)-Thienyl-2 |
| 99 | 4-(3'-NO₂—C₆H₄)-Thienyl-2 |
| 100 | 4-(2'-NO₂—C₆H₄)-Thienyl-2 |
| 101 | 4-(4'-CN—C₆H₄)-Thienyl-2 |
| 102 | 4-(3'-CN—C₆H₄)-Thienyl-2 |
| 103 | 4-(2'-CN—C₆H₄)-Thienyl-2 |
| 104 | 4-(4'-Cl—C₆H₄)-Thienyl-2 |
| 105 | 4-(3'-Cl—C₆H₄)-Thienyl-2 |
| 106 | 4-(2'-Cl—C₆H₄)-Thienyl-2 |
| 107 | Thienyl-3 |
| 108 | 5-CH₃-Thienyl-3 |
| 109 | 5-C₆H₅-Thienyl-3 |
| 110 | 5-(4'-CH₃—C₆H₄)-Thienyl-3 |
| 111 | 5-(3'-CH₃—C₆H₄)-Thienyl-3 |
| 112 | 5-(2'-CH₃—C₆H₄)-Thienyl-3 |
| 113 | 5-(4'-CH₃O—C₆H₄)-Thienyl-3 |
| 114 | 5-(3'-CH₃O—C₆H₄)-Thienyl-3 |
| 115 | 5-(2'-CH₃O—C₆H₄)-Thienyl-3 |
| 116 | 5-(4'-NO₂—C₆H₄)-Thienyl-3 |
| 117 | 5-(3'-NO₂—C₆H₄)-Thienyl-3 |
| 118 | 5-(2'-NO₂—C₆H₄)-Thienyl-3 |
| 119 | 5-(4'-CN—C₆H₄)-Thienyl-3 |
| 120 | 5-(3'-CN—C₆H₄)-Thienyl-3 |
| 121 | 5-(2'-CN—C₆H₄)-Thienyl-3 |
| 122 | 5-(4'-Cl—C₆H₄)-Thienyl-3 |
| 123 | 5-(3'-Cl—C₆H₄)-Thienyl-3 |
| 124 | 5-(2'-Cl—C₆H₄)-Thienyl-3 |
| 125 | Pyrazolyl-4 |
| 126 | N—CH₃-Pyrazolyl-4 |
| 127 | N—C₆H₅-Pyrazolyl-4 |
| 128 | N-(4'-CH₃—C₆H₄)-Pyrazolyl-4 |
| 129 | N-(3'-CH₃—C₆H₄)-Pyrazolyl-4 |
| 130 | N-(2'-CH₃—C₆H₄)-Pyrazolyl-4 |
| 131 | N-(4'-CH₃O—C₆H₄)-Pyrazolyl-4 |
| 132 | N-(3'-CH₃O—C₆H₄)-Pyrazolyl-4 |
| 133 | N-(2'-CH₃O—C₆H₄)-Pyrazolyl-4 |
| 134 | N-(4'-NO₂—C₆H₄)-Pyrazolyl-4 |
| 135 | N-(3'-NO₂—C₆H₄)-Pyrazolyl-4 |
| 136 | N-(2'-NO₂—C₆H₄)-Pyrazolyl-4 |
| 137 | N-(4'-CN—C₆H₄)-Pyrazolyl-4 |
| 138 | N-(3'-CN—C₆H₄)-Pyrazolyl-4 |
| 139 | N-(2'-CN—C₆H₄)-Pyrazolyl-4 |
| 140 | N-(4'-Cl—C₆H₄)-Pyrazolyl-4 |
| 141 | N-(3'-Cl—C₆H₄)-Pyrazolyl-4 |
| 142 | N-(2'-Cl—C₆H₄)-Pyrazolyl-4 |
| 143 | 3-CH₃—N-Methylpyrazolyl-4 |
| 144 | 3-C₆H₅—N-Methylpyrazolyl-4 |
| 145 | 3-(4'-CH₃—C₆H₄)—N-Methylpyrazolyl-4 |
| 146 | 3-(3'-CH₃—C₆H₄)—N-Methylpyrazolyl-4 |
| 147 | 3-(2'-CH₃—C₆H₄)—N-Methylpyrazolyl-4 |
| 148 | 3-(4'-CH₃O—C₆H₄)—N-Methylpyrazolyl-4 |
| 149 | 3-(3'-CH₃O—C₆H₄)—N-Methylpyrazolyl-4 |
| 150 | 3-(2'-CH₃O—C₆H₄)—N-Methylpyrazolyl-4 |
| 151 | 3-(4'-NO₂—C₆H₄)—N-Methylpyrazolyl-4 |
| 152 | 3-(3'-NO₂—C₆H₄)—N-Methylpyrazolyl-4 |
| 153 | 3-(2'-NO₂—C₆H₄)—N-Methylpyrazolyl-4 |
| 154 | 3-(4'-CN—C₆H₄)—N-Methylpyrazolyl-4 |
| 155 | 3-(3'-CN—C₆H₄)—N-Methylpyrazolyl-4 |
| 156 | 3-(2'-CN—C₆H₄)—N-Methylpyrazolyl-4 |
| 157 | 3-(4'-Cl—C₆H₄)—N-Methylpyrazolyl-4 |
| 158 | 3-(3'-Cl—C₆H₄)—N-Methylpyrazolyl-4 |
| 159 | 3-(2'-Cl—C₆H₄)—N-Methylpyrazolyl-4 |
| 160 | Isoxazolyl-5 |
| 161 | 3-CH₃-Isoxazolyl-5 |
| 162 | 3-C₆H₅-Isoxazolyl-5 |
| 163 | 3-(4'-CH₃—C₆H₄)-Isoxazolyl-5 |
| 164 | 3-(3'-CH₃—C₆H₄)-Isoxazolyl-5 |
| 165 | 3-(2'-CH₃—C₆H₄)-Isoxazolyl-5 |
| 166 | 3-(4'-CH₃O—C₆H₄)-Isoxazolyl-5 |
| 167 | 3-(3'-CH₃O—C₆H₄)-Isoxazolyl-5 |
| 168 | 3-(2'-CH₃O—C₆H₄)-Isoxazolyl-5 |
| 169 | 3-(4'-NO₂—C₆H₄)-Isoxazolyl-5 |
| 170 | 3-(3'-NO₂—C₆H₄)-Isoxazolyl-5 |
| 171 | 3-(2'-NO₂—C₆H₄)-Isoxazolyl-5 |
| 172 | 3-(4'-CN—C₆H₄)-Isoxazolyl-5 |
| 173 | 3-(3'-CN—C₆H₄)-Isoxazolyl-5 |
| 174 | 3-(2'-CN—C₆H₄)-Isoxazolyl-5 |
| 175 | 3-(4'-Cl—C₆H₄)-Isoxazolyl-5 |
| 176 | 3-(3'-Cl—C₆H₄)-Isoxazolyl-5 |
| 177 | 3-(2'-Cl—C₆H₄)-Isoxazolyl-5 |
| 178 | 4-Chloroisoxazolyl-5 |
| 179 | 3-CH₃-4-Chloroisoxazolyl-5 |
| 180 | 3-C₆H₅-4-Chloroisoxazolyl-5 |

TABLE 20-continued

| | |
|---|---|
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 2-CH$_3$-Oxazolyl-4 |
| 234 | 2-C$_6$H$_5$-Oxazolyl-4 |
| 235 | 2-(4'-CH$_3$—C$_6$H$_4$)-Oxazolyl-4 |
| 236 | 2-(3'-CH$_3$—C$_6$H$_4$)-Oxazolyl-4 |
| 237 | 2-(2'-CH$_3$—C$_6$H$_4$)-Oxazolyl-4 |
| 238 | 2-(4'-CH$_3$O—C$_6$H$_4$)-Oxazolyl-4 |
| 239 | 2-(3'-CH$_3$O—C$_6$H$_4$)-Oxazolyl-4 |
| 240 | 2-(2'-CH$_3$O—C$_6$H$_4$)-Oxazolyl-4 |
| 241 | 2-(4'-NO$_2$—C$_6$H$_4$)-Oxazolyl-4 |
| 242 | 2-(3'-NO$_2$—C$_6$H$_4$)-Oxazolyl-4 |
| 243 | 2-(2'-NO$_2$—C$_6$H$_4$)-Oxazolyl-4 |
| 244 | 2-(4'-CN—C$_6$H$_4$)-Oxazolyl-4 |
| 245 | 2-(3'-CN—C$_6$H$_4$)-Oxazolyl-4 |
| 246 | 2-(2'-CN—C$_6$H$_4$)-Oxazolyl-4 |
| 247 | 2-(4'-Cl—C$_6$H$_4$)-Oxazolyl-4 |
| 248 | 2-(3'-Cl—C$_6$H$_4$)-Oxazolyl-4 |
| 249 | 2-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 257 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,2,3-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadizolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |

TABLE 20-continued

| | |
|---|---|
| 339 | 3-(2'-Cl—$C_6H_4$)-1,2,4-Oxadiazolyl-5 |
| 340 | 1,2,4-Thiadiazolyl-3 |
| 341 | 5-$CH_3$-1,2,4-Thiadiazolyl-3 |
| 342 | 5-$C_6H_5$-1,2,4-Thiadiazolyl-3 |
| 343 | 5-(4'-$CH_3$—$C_6H_4$)-1,2,4-Thiadiazolyl-3 |
| 344 | 5-(3'-$CH_3$—$C_6H_4$)-1,2,4-Thiadiazolyl-3 |
| 345 | 5-(2'-$CH_3$—$C_6H_4$)-1,2,4-Thiadiazolyl-3 |
| 346 | 5-(4'-$CH_3O$—$C_6H_4$)-1,2,4-Thiadiazolyl-3 |
| 347 | 5-(3'-$CH_3O$—$C_6H_4$)-1,2,4-Thiadiazolyl-3 |
| 348 | 5-(2'-$CH_3O$—$C_6H_4$)-1,2,4-Thiadiazolyl-3 |
| 349 | 5-(4'-$NO_2$—$C_6H_4$)-1,2,4-Thiadiazolyl-3 |
| 350 | 5-(3'-$NO_2$—$C_6H_4$)-1,2,4-Thiadiazolyl-3 |
| 351 | 5-(2'-$NO_2$—$C_6H_4$)-1,2,4-Thiadiazolyl-3 |
| 352 | 5-(4'-CN—$C_6H_4$)-1,2,4-Thiadiazolyl-3 |
| 353 | 5-(3'-CN—$C_6H_4$)-1,2,4-Thiadiazolyl-3 |
| 354 | 5-(2'-CN—$C_6H_4$)-1,2,4-Thiadiazolyl-3 |
| 355 | 5-(4'-Cl—$C_6H_4$)-1,2,4-Thiadiazolyl-3 |
| 356 | 5-(3'-Cl—$C_6H_4$)-1,2,4-Thiadiazolyl-3 |
| 357 | 5-(2'-Cl—$C_6H_4$)-1,2,4-Thiadiazolyl-3 |
| 358 | 1,3,4-Thiadiazolyl-2 |
| 359 | 5-$CH_3$-1,3,4-Thiadiazolyl-2 |
| 360 | 5-$C_6H_5$-1,3,4-Thiadiazolyl-2 |
| 361 | 5-(4'-$CH_3$—$C_6H_4$)-1,3,4-Thiadiazolyl-2 |
| 362 | 5-(3'-$CH_3$—$C_6H_4$)-1,3,4-Thiadiazolyl-2 |
| 363 | 5-(2'-$CH_3$—$C_6H_4$)-1,3,4-Thiadiazolyl-2 |
| 364 | 5-(4'-$CH_3O$—$C_6H_4$)-1,3,4-Thiadiazolyl-2 |
| 365 | 5-(3'-$CH_3O$—$C_6H_4$)-1,3,4-Thiadiazolyl-2 |
| 366 | 5-(2'-$CH_3O$—$C_6H_4$)-1,3,4-Thiadiazolyl-2 |
| 367 | 5-(4'-$NO_2$—$C_6H_4$)-1,3,4-Thiadiazolyl-2 |
| 368 | 5-(3'-$NO_2$—$C_6H_4$)-1,3,4-Thiadiazolyl-2 |
| 369 | 5-(2'-$NO_2$—$C_6H_4$)-1,3,4-Thiadiazolyl-2 |
| 370 | 5-(4'-CN—$C_6H_4$)-1,3,4-Thiadiazolyl-2 |
| 371 | 5-(3'-CN—$C_6H_4$)-1,3,4-Thiadiazolyl-2 |
| 372 | 5-(2'-CN—$C_6H_4$)-1,3,4-Thiadiazolyl-2 |
| 373 | 5-(4'-Cl—$C_6H_4$)-1,3,4-Thiadiazolyl-2 |
| 374 | 5-(3'-Cl—$C_6H_4$)-1,3,4-Thiadiazolyl-2 |
| 375 | 5-(2'-Cl—$C_6H_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |

TABLE 21

Selected physical data of some compounds

| No. | Compound | $^1$H-NMR (ppm) | m.p. |
|---|---|---|---|
| 1 | [structure: N-methoxy-N-(2-methylphenyl)propanamide] | 3.7(s, broad, 3H); 1.2(s, broad, 3H) | |
| 2 | [structure: N-(2-(bromomethyl)phenyl)-N-methoxypropanamide] | 3.75(s, 3H); 1.2(t, 3H) | |

TABLE 21-continued

Selected physical data of some compounds

| No. | Compound | $^1$H-NMR (ppm) | m.p. |
|---|---|---|---|
| 3 | | 3.7(s, 3H); 1.2(t, 3H) | |
| 4 | | 3.95(s, 3H); 3.7(s, 3H); 1.2(t, 3H) | |
| 5 | | 3.6(s, 3H); 2.9(d, 3H) | |
| 6 | | | 123 |
| 7 | | | 118 |
| 8 | | 3.7(s, 3H); 2.55 (s, very broad, 2H) | |

TABLE 56

Selected physical data of some compounds

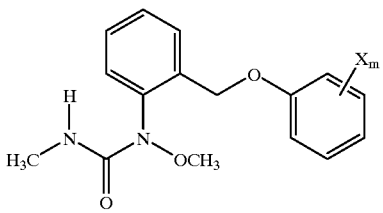

| No. | $X_m$ | mp (° C.) | $^1$H-NMR (ppm) or IR (cm$^{-1}$) |
|---|---|---|---|
| 1 | H | 90 | |
| 2 | 2-CH$_3$ | 80 | |
| 3 | 2,5-(CH$_3$)$_2$ | 101 | |
| 4 | 2-CH$_3$-4-C(CH$_3$)=N—OCH$_3$ | | 3.95(s, 3H); 3.65(s, 3H); 2.9(d, 3H) |
| 5 | 2,5-(CH$_3$)$_2$-4-C(CH$_3$)=N—O-Allyl | | 3.65(s, 3H); 2.9(d, 3H) |

TABLE 22

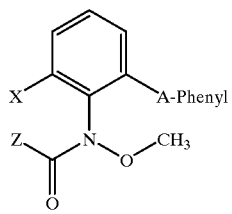

| No. | X | Z | A |
|---|---|---|---|
| 1 | H | CH$_3$ | —CH$_2$O— |
| 2 | H | CH$_3$ | —CH$_2$O—N=C(CH$_3$)— |
| 3 | H | CH$_3$ | —CH=CH— |
| 4 | H | NH$_2$ | —CH$_2$O— |
| 5 | H | NH$_2$ | —CH$_2$O—N=C(CH$_3$)— |
| 6 | H | NH$_2$ | —CH=CH— |
| 7 | H | N(CH$_3$)$_2$ | —CH$_2$O— |
| 8 | H | N(CH$_3$)$_2$ | —CH$_2$O—N=C(CH$_3$)— |
| 9 | H | N(CH$_3$)$_2$ | —CH=CH— |
| 10 | H | CCl$_3$ | —CH$_2$O— |
| 11 | H | CCl$_3$ | —CH$_2$O—N=C(CH$_3$)— |
| 12 | H | CCl$_3$ | —CH=CH— |
| 13 | H | CF$_3$ | —CH$_2$O— |
| 14 | H | CF$_3$ | —CH$_2$O—N=C(CH$_3$)— |
| 15 | H | CF$_3$ | —CH=CH— |
| 16 | CH$_3$ | CH$_3$ | —CH$_2$O— |
| 17 | CH$_3$ | CH$_3$ | —CH$_2$O—N=C(CH$_3$)— |
| 18 | CH$_3$ | CH$_3$ | —CH=CH— |
| 19 | CH$_3$ | NH$_2$ | —CH$_2$O— |
| 20 | CH$_3$ | NH$_2$ | —CH$_2$O—N=C(CH$_3$)— |
| 21 | CH$_3$ | NH$_2$ | —CH=CH— |
| 22 | CH$_3$ | N(CH$_3$)$_2$ | —CH$_2$O— |
| 23 | CH$_3$ | N(CH$_3$)$_2$ | —CH$_2$O—N=C(CH$_3$)— |
| 24 | CH$_3$ | N(CH$_3$)$_2$ | —CH=CH— |
| 25 | CH$_3$ | CCl$_3$ | —CH$_2$O— |
| 26 | CH$_3$ | CCl$_3$ | —CH$_2$O—N=C(CH$_3$)— |
| 27 | CH$_3$ | CCl$_3$ | —CH=CH— |
| 28 | CH$_3$ | CF$_3$ | —CH$_2$O— |
| 29 | CH$_3$ | CF$_3$ | —CH$_2$O—N=C(CH$_3$)— |
| 30 | CH$_3$ | CF$_3$ | —CH=CH— |
| 31 | Cl | CH$_3$ | —CH$_2$O— |
| 32 | Cl | CH$_3$ | —CH$_2$O—N=C(CH$_3$)— |
| 33 | Cl | CH$_3$ | —CH=CH— |
| 34 | Cl | NH$_2$ | —CH$_2$O— |
| 35 | Cl | NH$_2$ | —CH$_2$O—N=C(CH$_3$)— |
| 36 | Cl | NH$_2$ | —CH=CH— |
| 37 | Cl | N(CH$_3$)$_2$ | —CH$_2$O— |

TABLE 22-continued

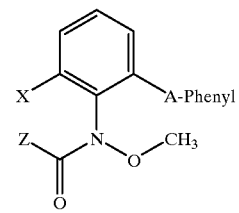

| No. | X | Z | A |
|---|---|---|---|
| 38 | Cl | N(CH$_3$)$_2$ | —CH$_2$O—N=C(CH$_3$)— |
| 39 | Cl | N(CH$_3$)$_2$ | —CH=CH— |
| 40 | Cl | CCl$_3$ | —CH$_2$O— |
| 41 | Cl | CCl$_3$ | —CH$_2$O—N=C(CH$_3$)— |
| 42 | Cl | CCl$_3$ | —CH=CH— |
| 43 | Cl | CF$_3$ | —CH$_2$O— |
| 44 | Cl | CF$_3$ | —CH$_2$O—N=C(CH$_3$)— |
| 45 | Cl | CF$_3$ | —CH=CH— |

TABLE 23

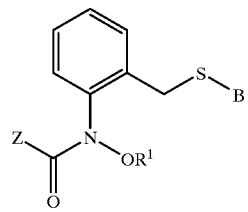

I: $R^1$ = CH$_3$, Z = CH$_3$
II: $R^1$ = CH$_2$—CH$_3$, Z = CH$_3$
III: $R^1$ = CH$_3$, Z = C$_2$H$_5$
IV: $R^1$ = CH$_2$—CH$_3$, Z = C$_2$H$_5$
V: $R^1$ = CH$_3$, Z = NHCH$_3$
VI: $R^1$ = CH$_2$—CH$_3$, Z = NHCH$_3$

| No. | B |
|---|---|
| 1 | 2-Pyridyl |
| 2 | 3-Trifluoromethyl-2-pyridyl |
| 3 | 5-Trifluoromethyl-2-pyridyl |
| 4 | 3,5-Bis-(trifluoromethyl)-2-pyridyl |
| 5 | 3,5-Dichloro-2-pyridyl |
| 6 | 3-Chloro-5-trifluoromethyl-2-pyridyl |
| 7 | 3,5-Dichloro-2-pyridyl |
| 8 | 2-Chloro-4-trifluormethylphenyl |
| 9 | 2-Benzothiazolyl |
| 10 | 5-Chloro-4-methyl-2-benzimidazolyl |
| 11 | 2-Benzoxazolyl |
| 12 | 1-Methyl-5-trifluoromethylimidazo[5,4-a]-pyridin-2-yl |
| 13 | 5-Chloro-2-pyrimidinyl |
| 14 | 4-Methyl-5-phenyl-2-thiazolin-2-yl |
| 15 | 4-Methyl-5-phenyl-2-oxazolin-2-yl |
| 16 | 7-Trifluoromethyl-4-quinolinyl |

Example 10

N-(2,6-Dimethylphenyl)-N-methoxycarbonyl-O-methyl-hydroxylamine (Table 30, No. 1)

a) N-(2,6-Dimethylphenyl)-N-methoxycarbonyl-hydroxylamine

At 0 to 5° C., 7.0 g (70 mmol) of methyl chloroformate is added dropwise to 11.3 g (80 mmol) of N-2,6-dimethylphenyl-hydroxylamine (prepared analogously to Bamberger et al., Ann. Chem. 316 (1901), 278) and 12.5 g (90 mmol) of $K_2CO_3$ in 30 ml of methylene chloride. The mixture is stirred for 30 mins at 0–5° C., the insoluble solid is filtered off and the filtrate is evaporated down under reduced pressure. The residue is purified by column chromatography with mixtures of cyclohexand and ethyl acetate. There is obtained 1.4 g (7.2 mmol 9%) of the title compound as a dark oil.

$^1$H-NMR (CDCl$_3$; δ in ppm): 8.85 (s, broad, 1H, OH); 7.1 (m, 3H, phenyl); 3.75 (s, 3H, OCH$_3$); 2.3 (s, 6H, 2×CH$_3$).

b) N-(2,6-Dimethylphenyl)-N-methoxycarbonyl-O-methylhydroxylamine (Table 7, No. 1)

A mixture of 1.4 g (7.2 mmol) of N-(2,6-dimethylphenyl)-N-methoxycarbonyl-hydroxylamine (Example 1a), 1.3 g (9 mmol) of $K_2CO_3$ and 10 g (8 mmol) of dimethyl sulfate in 10 ml of acetone is stirred overnight at room temperature. The reaction mixture is then diluted with $CH_2Cl_2$ and stirred with dilute $NH_3$ solution. The phases are then separated and the organic phase is extracted another twice with water. The organic phase is dried over $MgSO_4$ and evaporated down, and the residue is purified by column chromatography with mixtures of cyclohexane and ethyl acetate. There is obtained 1.2 g (6 mmol=83%) of the title compound as a colorless solid (mp=81° C.).

$^1$H-NMR (CDCl$_3$; δ in ppm): 7.1 (m, 3H, phenyl); 3.75 (s, broad, 6H, 2×OCH$_3$); 2.3 (s, 3H, CH$_3$).

The compounds listed in the following tables may be prepared similarly. Compound I, No. 1 from Table 24, No. 1 has for example the following formula:

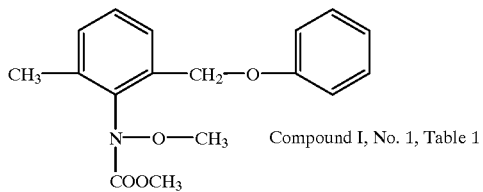

Compound I, No. 1, Table 1

TABLE 24

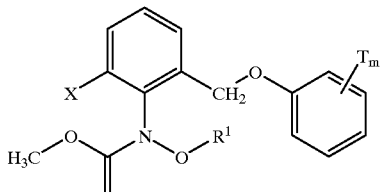

a I: $R^1 = CH_3$, X = $CH_3$
b II: $R^1 = CH_2$—$CH_3$, X = $CH_3$
c III: $R^1 = CH_3$, X = Cl
b IV: $R^1 = CH_2$—$CH_3$, X = Cl

| No. | $T_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F5 |
| 8 | 2,3-F$_2$ |
| 9 | 2-Cl |
| 10 | 3-Cl |
| 11 | 4-Cl |
| 12 | 2,3-Cl$_2$ |

TABLE 24-continued

| 13 | 2,4-Cl$_2$ |
|---|---|
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C2H5)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |

TABLE 24-continued

| | |
|---|---|
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7$)$_2$ |
| 98 | 2,6-(i-$C_3H_7$)$_2$ |
| 99 | 3,5-(i-$C_3H_7$)$_2$ |
| 100 | 2,4,6-(i-$C_3H_7$)$_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9$)$_2$ |
| 108 | 2,4-(t-$C_4H_9$)$_2$ |
| 109 | 2,5-(t-$C_4H_9$)$_2$ |
| 110 | 2,6-(t-$C_4H_9$)$_2$ |
| 111 | 3,4-(t-$C_4H_9$)$_2$ |
| 112 | 2,4,6-(t-$C_4H_9$)$_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-($C_4H_9$, 4-$CH_3$) |
| 119 | 2-t-($C_4H_9$, 5-$CH_3$) |
| 120 | 2,6-(t-$C_4H_9$)$_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9$)$_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11}$)$_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-($C_6H_5$, 2,6-($CH_3$)$_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$OCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-C6H13 |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—($CH_2$)$_3C_6H_5$ |
| 181 | 3-O—($CH_2$)$_3C_6H_5$ |
| 182 | 4-O—($CH_2$)$_3C_6H_5$ |
| 183 | 2,4-($OCH_3$)$_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 2-$CH_3$, 4-Cl |
| 199 | 2-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-CH3, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-($CH_3$)$_2$ |
| 228 | 2-Br, 4,5-($CH_3$)$_2$ |
| 229 | 2-Cl, 3,5-($CH_3$)$_2$ |
| 230 | 2-Br, 3,5-($CH_3$)$_2$ |
| 231 | 2,6-$Cl_2$, 4-$CH_3$ |
| 232 | 2,6-$F_2$, 4-$CH_3$ |
| 233 | 2,6-$Br_2$, 4-$CH_3$ |
| 234 | 2,4-$Br_2$, 6-$CH_3$ |
| 235 | 2,4-$F_2$, 6-$CH_3$ |
| 236 | 2,4-$Br_2$, 6-$CH_3$ |
| 237 | 2,6-($CH_3$)$_2$, 4-F |
| 238 | 2,6-($CH_3$)$_2$, 4-Cl |
| 239 | 2,6-($CH_3$)$_2$, 4-Br |
| 240 | 3,5-($CH_3$)$_2$, 4-F |
| 241 | 3,5-($CH_3$)$_2$, 4-Cl |
| 242 | 3,5-($CH_3$)$_2$, 4-Br |
| 243 | 2,3,6-($CH_3$)$_3$, 4-F |
| 244 | 2,3,6-($CH_3$)$_3$, 4-Cl |
| 245 | 2,3,6-($CH_3$)$_3$, 4-Br |
| 246 | 2,4-($CH_3$)$_2$, 6-F |
| 247 | 2,4-($CH_3$)$_2$, 6-Cl |
| 248 | 2,4-($CH_3$)$_2$, 6-Br |
| 249 | 2-i-$C_3H_7$, 4-Cl, 5-$CH_3$ |

TABLE 24-continued

| | |
|---|---|
| 250 | 2-Cl, 4-NO2 |
| 251 | 2-NO2, 4-Cl |
| 252 | 2-OCH$_3$, 5-NO$_2$ |
| 253 | 2,4-Cl2, 5-NO2 |
| 254 | 2,4-Cl2, 6-NO2 |
| 255 | 2,6-Cl2, 4-NO2 |
| 256 | 2,6-Br2, 4-NO2 |
| 257 | 2,6-I2, 4-NO2 |
| 258 | 2-CH3, 5-i-C3H7, 4-Cl |
| 259 | 2-CO$_2$CH$_3$ |
| 260 | 3-CO2CH3 |
| 261 | 4-CO2CH3 |
| 262 | 2-CO2(C2H5) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—Ch$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$— —CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_6$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH3-4-(CH3—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH3-4-(C2H5—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |

TABLE 24-continued

| | |
|---|---|
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |

TABLE 24-continued

| | |
|---|---|
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-CH$_3$-4-(CH$_3$—C=N—O—CH$_2$—CH$_2$—OCH$_3$) |
| 642 | 2-CH$_3$-4-(C$_2$H$_5$—C=N—O—CH$_2$—CH$_2$—OCH$_3$) |
| 643 | 2,5-(CH$_3$)$_2$-4-(CH$_3$—C=N—O—CH$_2$—CH$_2$—OCH$_3$) |
| 644 | 2-CH$_3$-4-(n-C$_3$H$_7$—C=N—OCH$_3$) |
| 645 | 2-CH$_3$-4-(n-C$_3$H$_7$—C=N—OC$_2$H$_5$) |
| 646 | 2-CH$_3$-4-(n-C$_3$H$_7$—C=N—O-n-C$_3$H$_7$) |
| 647 | 2-CH$_3$-4-(n-C$_3$H$_7$—C=N—O-i-C$_3$H$_7$) |
| 648 | 2-CH$_3$-4-(n-C$_3$H$_7$—C=N—O-Allyl) |
| 649 | 2-CH$_3$-4-(n-C$_3$H$_7$—C=N—O-trans-Chloroallyl) |
| 650 | 2-CH$_3$-4-(n-C$_3$H$_7$—C=N—O-Propargyl) |
| 651 | 2-CH$_3$-4-(n-C$_3$H$_7$—C=N—O-n-C$_4$H$_9$) |
| 652 | 2-CH$_3$-4-(n-C$_3$H$_7$—C=N—O—CH$_2$—C$_6$H$_5$) |
| 653 | 2-CH$_3$-4-(i-C$_3$H$_7$—C=N—OCH$_3$) |
| 654 | 2-CH$_3$-4-(i-C$_3$H$_7$—C=N—OC$_2$H$_5$) |
| 655 | 2-CH$_3$-4-(i-C$_3$H$_7$—C=N—O-n-C$_3$H$_7$) |
| 656 | 2-CH$_3$-4-(i-C$_3$H$_7$—C=N—O-i-C$_3$H$_7$) |
| 657 | 2-CH$_3$-4-(i-C$_3$H$_7$—C=N—O-Allyl) |
| 658 | 2-CH$_3$-4-(i-C$_3$H$_7$—C=N—O-trans-Chloroallyl) |
| 659 | 2-CH$_3$-4-(i-C$_3$H$_7$—C=N—O-Propargyl) |
| 660 | 2-CH$_3$-4-(i-C$_3$H$_7$—C=N—O-n-C$_4$H$_9$) |
| 661 | 2-CH$_3$-4-(i-C$_3$H$_7$—C=N—O—CH$_2$—C$_6$H$_5$) |
| 662 | 2-O-n-C$_4$H$_9$ |
| 663 | 2-O-i-C$_4$H$_9$ |
| 664 | 2-O-s-C$_4$H$_9$ |
| 665 | 2-O-t-C$_4$H$_9$ |
| 666 | 2-Neopentyloxy |
| 667 | 3-O-n-C$_4$H$_9$ |
| 668 | 3-O-i-C$_4$H$_9$ |
| 669 | 3-O-s-C$_4$H$_9$ |
| 670 | 3-O-t-C$_4$H$_9$ |
| 671 | 3-Neopentyloxy |
| 672 | 4-O-n-C$_4$H$_9$ |
| 673 | 4-O-i-C$_4$H$_9$ |
| 674 | 4-O-s-C$_4$H$_9$ |
| 675 | 4-O-t-C$_4$H$_9$ |
| 676 | 4-Neopentyloxy |
| 677 | 3-CH$_3$-4-OCH$_3$ |
| 678 | 3-CH$_3$-4-OC$_2$H$_5$ |
| 679 | 3-CH$_3$-4-O-n-C$_3$H$_7$ |
| 680 | 3-CH$_3$-4-O-n-C$_4$H$_9$ |
| 681 | 3-CH$_3$-4-O-i-C$_4$H$_9$ |
| 682 | 3-CH$_3$-4-O-s-C$_4$H$_9$ |
| 683 | 3-CH$_3$-4-O-t-C$_4$H$_9$ |
| 684 | 3-CH$_3$-4-Neopentyloxy |
| 685 | 2-CH$_3$-3-OCH$_3$ |
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 25

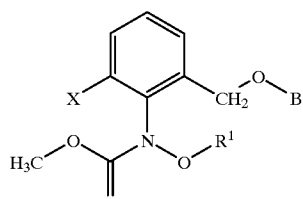

I: $R^1 = CH_3$, $X = CH_3$
II: $R^1 = CH_2\text{—}CH_3$, $X = CH_3$
III: $R^1 = CH_3$, $X = Cl$
IV: $R^1 = CH_2\text{—}CH_3$, $X = Cl$

| No. | B |
|---|---|
| 1 | Pyrrolyl-3 |
| 2 | N—$CH_3$-Pyrrolyl-3 |
| 3 | N—$C_6H_5$-Pyrrolyl-3 |
| 4 | N-(4'-$CH_3$—$C_6H_4$)-Pyrrolyl-3 |
| 5 | N-(3'-$CH_3$—$C_6H_4$)-Pyrrolyl-3 |
| 6 | N-(2'-$CH_3$—$C_6H_4$)-Pyrrolyl-3 |
| 7 | N-(4'-$CH_3O$—$C_6H_4$)-Pyrrolyl-3 |
| 8 | N-(3'-$CH_3O$—$C_6H_4$)-Pyrrolyl-3 |
| 9 | N-(2'-$CH_3O$—$C_6H_4$)-Pyrrolyl-3 |
| 10 | N-(4'-$NO_2$—$C_6H_4$)-Pyrrolyl-3 |
| 11 | N-(3'-$NO_2$—$C_6H_4$)-Pyrrolyl-3 |
| 12 | N-(2'-$NO_2$—$C_6H_4$)-Pyrrolyl-3 |
| 13 | N-(4'-CN—$C_6H_4$)-Pyrrolyl-3 |
| 14 | N-(3'-CN—$C_6H_4$)-Pyrrolyl-3 |
| 15 | N-(2'-CN—$C_6H_4$)-Pyrrolyl-3 |
| 16 | N-(4'-Cl—$C_6H_4$)-Pyrrolyl-3 |
| 17 | N-(3'-Cl—$C_6H_4$)-Pyrrolyl-3 |
| 18 | N-(2'-Cl—$C_6H_4$)-Pyrrolyl-3 |
| 19 | Pyrrolyl-2 |
| 20 | N—$CH_3$-Pyrrolyl-2 |
| 21 | N—$C_6H_5$-Pyrrolyl-2 |
| 22 | N-(4'-$CH_3$—$C_6H_4$)-Pyrrolyl-2 |
| 23 | N-(3'-$CH_3$—$C_6H_4$)-Pyrrolyl-2 |
| 24 | N-(2'-$CH_3$—$C_6H_4$)-Pyrrolyl-2 |
| 25 | N-(4'-$CH_3O$—$C_6H_4$)-Pyrrolyl-2 |
| 26 | N-(3'-$CH_3O$—$C_6H_4$)-Pyrrolyl-2 |
| 27 | N-(2'-$CH_3O$—$C_6H_4$)-Pyrrolyl-2 |
| 28 | N-(4'-$NO_2$—$C_6H_4$)-Pyrrolyl-2 |
| 29 | N-(3'-$NO_2$—$C_6H_4$)-Pyrrolyl-2 |
| 30 | N-(2'-$NO_2$—$C_6H_4$)-Pyrrolyl-2 |
| 31 | N-(4'-CN—$C_6H_4$)-Pyrrolyl-2 |
| 32 | N-(3'-CN—$C_6H_4$)-Pyrrolyl-2 |
| 33 | N-(2'-CN—$C_6H_4$)-Pyrrolyl-2 |
| 34 | N-(4'-Cl—$C_6H_4$)-Pyrrolyl-2 |
| 35 | N-(3'-Cl—$C_6H_4$)-Pyrrolyl-2 |
| 36 | N-(2'-Cl—$C_6H_4$)-Pyrrolyl-2 |
| 37 | Furyl-2 |
| 38 | 5-$CH_3$-Furyl-2 |
| 39 | 5-$C_6H_5$-Furyl-2 |
| 40 | 5-(4'-$CH_3$—$C_6H_4$)-Furyl-2 |
| 41 | 5-(3'-$CH_3$—$C_6H_4$)-Furyl-2 |
| 42 | 5-(2'-$CH_3$—$C_6H_4$)-Furyl-2 |
| 43 | 5-(4'-$CH_3O$—$C_6H_4$)-Furyl-2 |
| 44 | 5-(3'-$CH_3O$—$C_6H_4$)-Furyl-2 |
| 45 | 5-(2'-$CH_3O$—$C_6H_4$)-Furyl-2 |
| 46 | 5-(4'-$NO_2$—$C_6H_4$)-Furyl-2 |
| 47 | 5-(3'-$NO_2$—$C_6H_4$)-Furyl-2 |
| 48 | 5-(2'-$NO_2$—$C_6H_4$)-Furyl-2 |
| 49 | 5-(4'-CN—$C_6H_4$)-Furyl-2 |
| 50 | 5-(3'-CN—$C_6H_4$)-Furyl-2 |
| 51 | 5-(2'-CN—$C_6H_4$)-Furyl-2 |
| 52 | 5-(4'-Cl—$C_6H_4$)-Furyl-2 |
| 53 | 5-(3'-Cl—$C_6H_4$)-Furyl-2 |
| 54 | 5-(2'-Cl—$C_6H_4$)-Furyl-2 |
| 55 | 4-$CH_3$-Furyl-2 |
| 56 | 4-$C_6H_5$-Furyl-2 |
| 57 | 4-(4'-$CH_3$—$C_6H_4$)-Furyl-2 |
| 58 | 4-(3'-$CH_3$—$C_6H_4$)-Furyl-2 |
| 59 | 4-(2'-$CH_3$—$C_6H_4$)-Furyl-2 |
| 60 | 4-(4'-$CH_3O$—$C_6H_4$)-Furyl-2 |
| 61 | 4-(3'-$CH_3O$—$C_6H_4$)-Furyl-2 |
| 62 | 4-(2'-$CH_3O$—$C_6H_4$)-Furyl-2 |
| 63 | 4-(4'-$NO_2$—$C_6H_4$)-Furyl-2 |
| 64 | 4-(3'-$NO_2$—$C_6H_4$)-Furyl-2 |
| 65 | 4-(2'-$NO_2$—$C_6H_4$)-Furyl-2 |
| 66 | 4-(4'-CN—$C_6H_4$)-Furyl-2 |
| 67 | 4-(3'-CN—$C_6H_4$)-Furyl-2 |
| 68 | 4-(2'-CN—$C_6H_4$)-Furyl-2 |
| 69 | 4-(4'-Cl—$C_6H_4$)-Furyl-2 |
| 70 | 4-(3'-Cl—$C_6H_4$)-Furyl-2 |
| 71 | 4-(2'-Cl—$C_6H_4$)-Furyl-2 |
| 72 | Thienyl-2 |
| 73 | 5-$CH_3$-Thienyl-2 |
| 74 | 5-$C_6H_5$-Thienyl-2 |
| 75 | 5-(4'-$CH_3$—$C_6H_4$)-Thienyl-2 |
| 76 | 5-(3'-$CH_3$—$C_6H_4$)-Thienyl-2 |
| 77 | 5-(2'-$CH_3$—$C_6H_4$)-Thienyl-2 |
| 78 | 5-(4'-$CH_3O$—$C_6H_4$)-Thienyl-2 |
| 79 | 5-(3'-$CH_3O$—$C_6H_4$)-Thienyl-2 |
| 80 | 5-(2'-$CH_3O$—$C_6H_4$)-Thienyl-2 |
| 81 | 5-(4'-$NO_2$—$C_6H_4$)-Thienyl-2 |
| 82 | 5-(3'-$NO_2$—$C_6H_4$)-Thienyl-2 |
| 83 | 5-(2'-$NO_2$—$C_6H_4$)-Thienyl-2 |
| 84 | 5-(4'-CN—$C_6H_4$)-Thienyl-2 |
| 85 | 5-(3'-CN—$C_6H_4$)-Thienyl-2 |
| 86 | 5-(2'-CN—$C_6H_4$)-Thienyl-2 |
| 87 | 5-(4'-Cl—$C_6H_4$)-Thienyl-2 |
| 88 | 5-(3'-Cl—$C_6H_4$)-Thienyl-2 |
| 89 | 5-(2'-Cl—$C_6H_4$)-Thienyl-2 |
| 90 | 4-$CH_3$-Thienyl-2 |
| 91 | 4-$C_6H_5$-Thienyl-2 |
| 92 | 4-(4'-$CH_3$—$C_6H_4$)-Thienyl-2 |
| 93 | 4-(3'-$CH_3$—$C_6H_4$)-Thienyl-2 |
| 94 | 4-(2'-$CH_3$—$C_6H_4$)-Thienyl-2 |
| 95 | 4-(4'-$CH_3O$—$C_6H_4$)-Thienyl-2 |
| 96 | 4-(3'-$CH_3O$—$C_6H_4$)-Thienyl-2 |
| 97 | 4-(2'-$CH_3O$—$C_6H_4$)-Thienyl-2 |
| 98 | 4-(4'-$NO_2$—$C_6H_4$)-Thienyl-2 |
| 99 | 4-(3'-$NO_2$—$C_6H_4$)-Thienyl-2 |
| 100 | 4-(2'-$NO_2$—$C_6H_4$)-Thienyl-2 |
| 101 | 4-(4'-CN—$C_6H_4$)-Thienyl-2 |
| 102 | 4-(3'-CN—$C_6H_4$)-Thienyl-2 |
| 103 | 4-(2'-CN—$C_6H_4$)-Thienyl-2 |
| 104 | 4-(4'-Cl—$C_6H_4$)-Thienyl-2 |
| 105 | 4-(3'-Cl—$C_6H_4$)-Thienyl-2 |
| 106 | 4-(2'-Cl—$C_6H_4$)-Thienyl-2 |
| 107 | Thienyl-3 |
| 108 | 5-$CH_3$-Thienyl-3 |
| 109 | 5-$C_6H_5$-Thienyl-3 |
| 110 | 5-(4'-$CH_3$—$C_6H_4$)-Thienyl-3 |
| 111 | 5-(3'-$CH_3$—$C_6H_4$)-Thienyl-3 |
| 112 | 5-(2'-$CH_3$—$C_6H_4$)-Thienyl-3 |
| 113 | 5-(4'-$CH_3O$—$C_6H_4$)-Thienyl-3 |
| 114 | 5-(3'-$CH_3O$—$C_6H_4$)-Thienyl-3 |
| 115 | 5-(2'-$CH_3O$—$C_6H_4$)-Thienyl-3 |
| 116 | 5-(4'-$NO_2$—$C_6H_4$)-Thienyl-3 |
| 117 | 5-(3'-$NO_2$—$C_6H_4$)-Thienyl-3 |
| 118 | 5-(2'-$NO_2$—$C_6H_4$)-Thienyl-3 |
| 119 | 5-(4'-CN—$C_6H_4$)-Thienyl-3 |
| 120 | 5-(3'-CN—$C_6H_4$)-Thienyl-3 |
| 121 | 5-(2'-CN—$C_6H_4$)-Thienyl-3 |
| 122 | 5-(4'-Cl—$C_6H_4$)-Thienyl-3 |
| 123 | 5-(3'-Cl—$C_6H_4$)-Thienyl-3 |
| 124 | 5-(2'-Cl—$C_6H_4$)-Thienyl-3 |
| 125 | Pyrazolyl-4 |
| 126 | N—$CH_3$-Pyrazolyl-4 |
| 127 | N—$C_6H_5$-Pyrazolyl-4 |
| 128 | N-(4'-$CH_3$—$C_6H_4$)-Pyrazolyl-4 |
| 129 | N-(3'-$CH_3$—$C_6H_4$)-Pyrazolyl-4 |
| 130 | N-(2'-$CH_3$—$C_6H_4$)-Pyrazolyl-4 |
| 131 | N-(4'-$CH_3O$—$C_6H_4$)-Pyrazolyl-4 |
| 132 | N-(3'-$CH_3O$—$C_6H_4$)-Pyrazolyl-4 |
| 133 | N-(2'-$CH_3O$—$C_6H_4$)-Pyrazolyl-4 |
| 134 | N-(4'-$NO_2$—$C_6H_4$)-Pyrazolyl-4 |
| 135 | N-(3'-$NO_2$—$C_6H_4$)-Pyrazolyl-4 |
| 136 | N-(2'-$NO_2$—$C_6H_4$)-Pyrazolyl-4 |
| 137 | N-(4'-CN—$C_6H_4$)-Pyrazolyl-4 |
| 138 | N-(3'-CN—$C_6H_4$)-Pyrazolyl-4 |

TABLE 25-continued

| | |
|---|---|
| 139 | N-(2'-CN—$C_6H_4$)-Pyrazolyl-4 |
| 140 | N-(4'-Cl—$C_6H_4$)-Pyrazolyl-4 |
| 141 | N-(3'-Cl—$C_6H_4$)-Pyrazolyl-4 |
| 142 | N-(2'-Cl—$C_6H_4$)-Pyrazolyl-4 |
| 143 | 3-$CH_3$—N-Methylpyrazolyl-4 |
| 144 | 3-$C_6H_5$—N-Methylpyrazolyl-4 |
| 145 | 3-(4'-$CH_3$—$C_6H_4$)—N-Methylpyrazolyl-4 |
| 146 | 3-(3'-$CH_3$—$C_6H_4$)—N-Methylpyrazolyl-4 |
| 147 | 3-(2'-$CH_3$—$C_6H_4$)—N-Methylpyrazolyl-4 |
| 148 | 3-(4'-$CH_3O$—$C_6H_4$)—N-Methylpyrazolyl-4 |
| 149 | 3-(3'-$CH_3O$—$C_6H_4$)—N-Methylpyrazolyl-4 |
| 150 | 3-(2'-$CH_3O$—$C_6H_4$)—N-Methylpyrazolyl-4 |
| 151 | 3-(4'-$NO_2$—$C_6H_4$)—N-Methylpyrazolyl-4 |
| 152 | 3-(3'-$NO_2$—$C_6H_4$)—N-Methylpyrazolyl-4 |
| 153 | 3-(2'-$NO_2$—$C_6H_4$)—N-Methylpyrazolyl-4 |
| 154 | 3-(4'-CN—$C_6H_4$)—N-Methylpyrazolyl-4 |
| 155 | 3-(3'-CN—$C_6H_4$)—N-Methylpyrazolyl-4 |
| 156 | 3-(2'-CN—$C_6H_4$)—N-Methylpyrazolyl-4 |
| 157 | 3-(4'-Cl—$C_6H_4$)—N-Methylpyrazolyl-4 |
| 158 | 3-(3'-Cl—$C_6H_4$)—N-Methylpyrazolyl-4 |
| 159 | 3-(2'-Cl—$C_6H_4$)—N-Methylpyrazolyl-4 |
| 160 | Isoxazolyl-5 |
| 161 | 3-$CH_3$-Isoxazolyl-5 |
| 162 | 3-$C_6H_5$-Isoxazolyl-5 |
| 163 | 3-(4'-$CH_3$—$C_6H_4$)-Isoxazolyl-5 |
| 164 | 3-(3'-$CH_3$—$C_6H_4$)-Isoxazolyl-5 |
| 165 | 3-(2'-$CH_3$—$C_6H_4$)-Isoxazolyl-5 |
| 166 | 3-(4'-$CH_3O$—$C_6H_4$)-Isoxazolyl-5 |
| 167 | 3-(3'-$CH_3O$—$C_6H_4$)-Isoxazolyl-5 |
| 168 | 3-(2'-$CH_3O$—$C_6H_4$)-Isoxazolyl-5 |
| 169 | 3-(4'-$NO_2$—$C_6H_4$)-Isoxazolyl-5 |
| 170 | 3-(3'-$NO_2$—$C_6H_4$)-Isoxazolyl-5 |
| 171 | 3-(2'-$NO_2$—$C_6H_4$)-Isoxazolyl-5 |
| 172 | 3-(4'-CN—$C_6H_4$)-Isoxazolyl-5 |
| 173 | 3-(3'-CN—$C_6H_4$)-Isoxazolyl-5 |
| 174 | 3-(2'-CN—$C_6H_4$)-Isoxazolyl-5 |
| 175 | 3-(4'-Cl—$C_6H_4$)-Isoxazolyl-5 |
| 176 | 3-(3'-Cl—$C_6H_4$)-Isoxazolyl-5 |
| 177 | 3-(2'-Cl—$C_6H_4$)-Isoxazolyl-5 |
| 178 | 4-Chloroisoxazolyl-5 |
| 179 | 3-$CH_3$-4-Chloroisoxazolyl-5 |
| 180 | 3-$C_6H_5$-4-Chloroisoxazolyl-5 |
| 181 | 3-(4'-$CH_3$—$C_6H_4$)-4-Chloroisoxazolyl-5 |
| 182 | 3-(3'-$CH_3$—$C_6H_4$)-4-Chloroisoxazolyl-5 |
| 183 | 3-(2'-$CH_3$—$C_6H_4$)-4-Chloroisoxazolyl-5 |
| 184 | 3-(4'-$CH_3O$—$C_6H_4$)-4-Chloroisoxazolyl-5 |
| 185 | 3-(3'-$CH_3O$—$C_6H_4$)-4-Chloroisoxazolyl-5 |
| 186 | 3-(2'-$CH_3O$—$C_6H_4$)-4-Chloroisoxazolyl-5 |
| 187 | 3-(4'-$NO_2$—$C_6H_4$)-4-Chloroisoxazolyl-5 |
| 188 | 3-(3'-$NO_2$—$C_6H_4$)-4-Chloroisoxazolyl-5 |
| 189 | 3-(2'-$NO_2$—$C_6H_4$)-4-Chloroisoxazolyl-5 |
| 190 | 3-(4'-CN—$C_6H_4$)-4-Chloroisoxazolyl-5 |
| 191 | 3-(3'-CN—$C_6H_4$)-4-Chloroisoxazolyl-5 |
| 192 | 3-(2'-CN—$C_6H_4$)-4-Chloroisoxazolyl-5 |
| 193 | 3-(4'-Cl—$C_6H_4$)-4-Chloroisoxazolyl-5 |
| 194 | 3-(3'-Cl—$C_6H_4$)-4-Chloroisoxazolyl-5 |
| 195 | 3-(2'-Cl—$C_6H_4$)-4-Chloroisoxazolyl-5 |
| 196 | Isoxazolyl-3 |
| 197 | 5-$CH_3$-Isoxazolyl-3 |
| 198 | 5-$C_6H_5$-Isoxazolyl-3 |
| 199 | 5-(4'-$CH_3$—$C_6H_4$)-Isoxazolyl-3 |
| 200 | 5-(3'-$CH_3$—$C_6H_4$)-Isoxazolyl-3 |
| 201 | 5-(2'-$CH_3$—$C_6H_4$)-Isoxazolyl-3 |
| 202 | 5-(4'-$CH_3O$—$C_6H_4$)-Isoxazolyl-3 |
| 203 | 5-(3'-$CH_3O$—$C_6H_4$)-Isoxazolyl-3 |
| 204 | 5-(2'-$CH_3O$—$C_6H_4$)-Isoxazolyl-3 |
| 205 | 5-(4'-$NO_2$—$C_6H_4$)-Isoxazolyl-3 |
| 206 | 5-(3'-$NO_2$—$C_6H_4$)-Isoxazolyl-3 |
| 207 | 5-(2'-$NO_2$—$C_6H_4$)-Isoxazolyl-3 |
| 208 | 5-(4'-CN—$C_6H_4$)-Isoxazolyl-3 |
| 209 | 5-(3'-CN—$C_6H_4$)-Isoxazolyl-3 |
| 210 | 5-(2'-CN—$C_6H_4$)-Isoxazolyl-3 |
| 211 | 5-(4'-Cl—$C_6H_4$)-Isoxazolyl-3 |
| 212 | 5-(3'-Cl—$C_6H_4$)-Isoxazolyl-3 |
| 213 | 5-(2'-Cl—$C_6H_4$)-Isoxazolyl-3 |
| 214 | Isothiazolyl-5 |
| 215 | 3-$CH_3$-Isothiazolyl-5 |
| 216 | 3-$C_6H_5$-Isothiazolyl-5 |
| 217 | 3-(4'-$CH_3$—$C_6H_4$)-Isothiazolyl-5 |
| 218 | 3-(3'-$CH_3$—$C_6H_4$)-Isothiazolyl-5 |
| 219 | 3-(2'-$CH_3$—$C_6H_4$)-Isothiazolyl-5 |
| 220 | 3-(4'-$CH_3O$—$C_6H_4$)-Isothiazolyl-5 |
| 221 | 3-(3'-$CH_3O$—$C_6H_4$)-Isothiazolyl-5 |
| 222 | 3-(2'-$CH_3O$—$C_6H_4$)-Isothiazolyl-5 |
| 223 | 3-(4'-$NO_2$—$C_6H_4$)-Isothiazolyl-5 |
| 224 | 3-(3'-$NO_2$—$C_6H_4$)-Isothiazolyl-5 |
| 225 | 3-(2'-$NO_2$—$C_6H_4$)-Isothiazolyl-5 |
| 226 | 3-(4'-CN—$C_6H_4$)-Isothiazolyl-5 |
| 227 | 3-(3'-CN—$C_6H_4$)-Isothiazolyl-5 |
| 228 | 3-(2'-CN—$C_6H_4$)-Isothiazolyl-5 |
| 229 | 3-(4'-Cl—$C_6H_4$)-Isothiazolyl-5 |
| 230 | 3-(3'-Cl—$C_6H_4$)-Isothiazolyl-5 |
| 231 | 3-(2'-Cl—$C_6H_4$)-Isothiazolyl-5 |
| 232 | Oxazolyl-4 |
| 233 | 2-$CH_3$-Oxazolyl-4 |
| 234 | 2-$C_6H_5$-Oxazolyl-4 |
| 235 | 2-(4'-$CH_3$—$C_6H_4$)-Oxazolyl-4 |
| 236 | 2-(3'-$CH_3$—$C_6H_4$)-Oxazolyl-4 |
| 237 | 2-(2'-$CH_3$—$C_6H_4$)-Oxazolyl-4 |
| 238 | 2-(4'-$CH_3O$—$C_6H_4$)-Oxazolyl-4 |
| 239 | 2-(3'-$CH_3O$—$C_6H_4$)-Oxazolyl-4 |
| 240 | 2-(2'-$CH_3O$—$C_6H_4$)-Oxazolyl-4 |
| 241 | 2-(4'-$NO_2$—$C_6H_4$)-Oxazolyl-4 |
| 242 | 2-(3'-$NO_2$—$C_6H_4$)-Oxazolyl-4 |
| 243 | 2-(2'-$NO_2$—$C_6H_4$)-Oxazolyl-4 |
| 244 | 2-(4'-CN—$C_6H_4$)-Oxazolyl-4 |
| 245 | 2-(3'-CN—$C_6H_4$)-Oxazolyl-4 |
| 246 | 2-(2'-CN—$C_6H_4$)-Oxazolyl-4 |
| 247 | 2-(4'-Cl—$C_6H_4$)-Oxazolyl-4 |
| 248 | 2-(3'-Cl—$C_6H_4$)-Oxazolyl-4 |
| 249 | 2-(2'-Cl—$C_6H_4$)-Oxazolyl-4 |
| 250 | Thiazolyl-4 |
| 251 | 2-$CH_3$-Thiazolyl-4 |
| 252 | 3-$C_6H_5$-Thiazolyl-4 |
| 253 | 2-(4'-$CH_3$—$C_6H_4$)-Thiazolyl-4 |
| 254 | 2-(3'-$CH_3$—$C_6H_4$)-Thiazolyl-4 |
| 255 | 2-(2'-$CH_3$—$C_6H_4$)-Thiazolyl-4 |
| 256 | 2-(4'-$CH_3O$—$C_6H_4$)-Thiazolyl-4 |
| 257 | 2-(3'-$CH_3O$—$C_6H_4$)-Thiazolyl-4 |
| 258 | 2-(2'-$CH_3O$—$C_6H_4$)-Thiazolyl-4 |
| 259 | 2-(4'-$NO_2$—$C_6H_4$)-Thiazolyl-4 |
| 260 | 2-(3'-$NO_2$—$C_6H_4$)-Thiazolyl-4 |
| 261 | 2-(2'-$NO_2$—$C_6H_4$)-Thiazolyl-4 |
| 262 | 2-(4'-CN—$C_6H_4$)-Thiazolyl-4 |
| 263 | 2-(3'-CN—$C_6H_4$)-Thiazolyl-4 |
| 264 | 2-(2'-CN—$C_6H_4$)-Thiazolyl-4 |
| 265 | 2-(4'-Cl—$C_6H_4$)-Thiazolyl-4 |
| 266 | 2-(3'-Cl—$C_6H_4$)-Thiazolyl-4 |
| 267 | 2-(2'-Cl—$C_6H_4$)-Thiazolyl-4 |
| 268 | N—$CH_3$-1,2,4-Triazolyl-5 |
| 269 | 3-$CH_3$—N—$CH_3$-1,2,4-Triazolyl-5 |
| 270 | 3-$C_6H_5$—N—$CH_3$-1,2,4-Triazolyl-5 |
| 271 | 3-(4'-$CH_3$—$C_6H_4$)—N—$CH_3$-1,2,4-Triazolyl-5 |
| 272 | 3-(3'-$CH_3$—$C_6H_4$)—N—$CH_3$-1,2,4-Triazolyl-5 |
| 273 | 3-(2'-$CH_3$—$C_6H_4$)—N—$CH_3$-1,2,4-Triazolyl-5 |
| 274 | 3-(4'-$CH_3O$—$C_6H_4$)—N—$CH_3$-1,2,4-Triazolyl-5 |
| 275 | 3-(3'-$CH_3O$—$C_6H_4$)—N—$CH_3$-1,2,4-Triazolyl-5 |
| 276 | 3-(2'-$CH_3O$—$C_6H_4$)—N—$CH_3$-1,2,4-Triazolyl-5 |
| 277 | 3-(4'-$NO_2$—$C_6H_4$)—N—$CH_3$-1,2,4-Triazolyl-5 |
| 278 | 3-(3'-$NO_2$—$C_6H_4$)—N—$CH_3$-1,2,4-Triazolyl-5 |
| 279 | 3-(2'-$NO_2$—$C_6H_4$)—N—$CH_3$-1,2,4-Triazolyl-5 |
| 280 | 3-(4'-CN—$C_6H_4$)—N—$CH_3$-1,2,4-Triazolyl-5 |
| 281 | 3-(3'-CN—$C_6H_4$)—N—$CH_3$-1,2,4-Triazolyl-5 |
| 282 | 3-(2'-CN—$C_6H_4$)—N—$CH_3$-1,2,4-Triazolyl-5 |
| 283 | 3-(4'-Cl—$C_6H_4$)—N—$CH_3$-1,2,4-Triazolyl-5 |
| 284 | 3-(3'-Cl—$C_6H_4$)—N—$CH_3$-1,2,4-Triazolyl-5 |
| 285 | 3-(2'-Cl—$C_6H_4$)—N—$CH_3$-1,2,4-Triazolyl-5 |
| 286 | 1,3,4-Oxadiazolyl-2 |
| 287 | 5-$CH_3$-1,3,4-Oxadiazolyl-2 |
| 288 | 5-$C_6H_5$-1,3,4-Oxadiazolyl-2 |
| 289 | 5-(4'-$CH_3$—$C_6H_4$)-1,3,4-Oxadiazolyl-2 |
| 290 | 5-(3'-$CH_3$—$C_6H_4$)-1,3,4-Oxadiazolyl-2 |
| 291 | 5-(2'-$CH_3$—$C_6H_4$)-1,3,4-Oxadiazolyl-2 |
| 292 | 5-(4'-$CH_3O$—$C_6H_4$)-1,3,4-Oxadiazolyl-2 |
| 293 | 5-(3'-$CH_3O$—$C_6H_4$)-1,3,4-Oxadiazolyl-2 |
| 294 | 5-(2'-$CH_3O$—$C_6H_4$)-1,3,4-Oxadiazolyl-2 |
| 295 | 5-(4'-$NO_2$—$C_6H_4$)-1,3,4-Oxadiazolyl-2 |
| 296 | 5-(3'-$NO_2$—$C_6H_4$)-1,3,4-Oxadiazolyl-2 |

TABLE 25-continued

| | |
|---|---|
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4,-Thiadiazolyl-3 |
| 343 | 5-(4'-CH$_3$—C$_6$H$_4$)-1-2,4-Thiadiazolyl-3 |
| 344 | 5-(3'-CH$_3$—C$_6$H$_4$)-1-2,4-Thiadiazolyl-3 |
| 345 | 5-(2'-CH$_3$—C$_6$H$_4$)-1-2,4-Thiadiazolyl-3 |
| 346 | 5-(4'-CH$_3$O—C$_6$H$_4$)-1-2,4-Thiadiazolyl-3 |
| 347 | 5-(3'-CH$_3$O—C$_6$H$_4$)-1-2,4-Thiadiazolyl-3 |
| 348 | 5-(2'-CH$_3$O—C$_6$H$_4$)-1-2,4-Thiadiazolyl-3 |
| 349 | 5-(4'-NO$_2$—C$_6$H$_4$)-1-2,4-Thiadiazolyl-3 |
| 350 | 5-(3'-NO$_2$—C$_6$H$_4$)-1-2,4-Thiadiazolyl-3 |
| 351 | 5-(2'-NO$_2$—C$_6$H$_4$)-1-2,4-Thiadiazolyl-3 |
| 352 | 5-(4'-CN—C$_6$H$_4$)-1-2,4-Thiadiazolyl-3 |
| 353 | 5-(3'-CN—C$_6$H$_4$)-1-2,4-Thiadiazolyl-3 |
| 354 | 5-(2'-CN—C$_6$H$_4$)-1-2,4-Thiadiazolyl-3 |
| 355 | 5-(4'-Cl—C$_6$H$_4$)-1-2,4-Thiadiazolyl-3 |
| 356 | 5-(3'-Cl—C$_6$H$_4$)-1-2,4-Thiadiazolyl-3 |
| 357 | 5-(2'-Cl—C$_6$H$_4$)-1-2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |

TABLE 25-continued

| | |
|---|---|
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |
| 385 | 1-Naphthyl |
| 386 | 2-Naphthyl |

TABLE 26

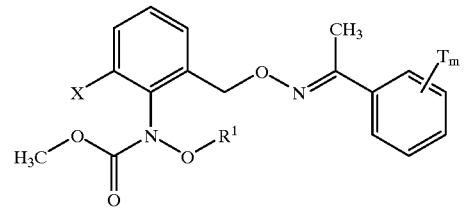

I: $R^1$ = CH$_3$, X = CH$_3$
II: $R^1$ = CH$_2$—CH$_3$, X = CH$_3$
III: $R^1$ = CH$_3$, X = Cl
IV: $R^1$ = CH$_2$—CH$_3$, X = Cl

| No. | $T_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |

TABLE 26-continued

| | |
|---|---|
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C2H5)3 |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 2-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |

TABLE 26-continued

| | |
|---|---|
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH3 |
| 226 | 3-Br, 4-CH3 |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_3$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$——CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)—CH$_3$ |
| 333 | 3-C(=NO-Allyl)—CH$_3$ |
| 334 | 4-C(=NO-Allyl)—CH$_3$ |
| 335 | 2-C(=NO-trans-Chloroallyl)—CH$_3$ |
| 336 | 3-C(=NO-trans-Chloroallyl)—CH$_3$ |
| 337 | 4-C(=NO-trans-Chloroallyl)—CH$_3$ |
| 338 | 2-C(=NO-Propargyl)—CH$_3$ |
| 339 | 3-C(=NO-Propargyl)—CH$_3$ |
| 340 | 4-C(=NO-Propargyl)—CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$^2$—C$^6$H$^5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |

TABLE 26-continued

| | |
|---|---|
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C6H5 |
| 385 | 4-C6H5 |
| 386 | 2-(2'-F—C6H4) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C6H4) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))—C$_6$H$_4$) |
| 424 | 2-(3'-(CH$_3$—C(=NOAllyl))—C$_6$H$_4$) |
| 425 | 2-(4'-(CH$_3$—C(=NOAllyl))—C$_6$H$_4$) |
| 426 | 3-(2'-(CH$_3$—C(=NOAllyl))—C$_6$H$_4$) |
| 427 | 3-(3'-(CH$_3$—C(=NOAllyl))—C$_6$H$_4$) |
| 428 | 3-(4'-(CH$_3$—C(=NOAllyl))—C$_6$H$_4$) |
| 429 | 4-(2'-(CH$_3$—C(=NOAllyl))—C$_6$H$_4$) |
| 430 | 4-(3'-(CH$_3$—C(=NOAllyl))—C$_6$H$_4$) |
| 431 | 4-(4'-(CH$_3$—C(=NOAllyl))—C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF3—C6H4) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C6H5 |
| 476 | 4-O—C6H5 |
| 478 | 2-O—(2'-F—C6H4) |
| 479 | 2-O—(3'-F—C$_6$H$_4$) |
| 480 | 2-O—(4'-F—C$_6$H$_4$) |
| 481 | 3-O—(2'-F—C$_6$H$_4$) |
| 482 | 3-O—(3'-F—C$_6$H$_4$) |
| 483 | 3-O—(4'-F—C$_6$H$_4$) |
| 484 | 4-O—(2'-F—C$_6$H$_4$) |
| 485 | 4-O—(3'-F—C$_6$H$_4$) |
| 486 | 4-O—(4'-F—C$_6$H$_4$) |
| 487 | 2-O—(2'-Cl—C$_6$H$_4$) |
| 488 | 2-O—(3'-Cl—C$_6$H$_4$) |
| 489 | 2-O—(4'-Cl—C$_6$H$_4$) |
| 490 | 3-O—(2'-Cl—C$_6$H$_4$) |
| 491 | 3-O—(3'-Cl—C$_6$H$_4$) |
| 492 | 3-O—(4'-Cl—C$_6$H$_4$) |
| 493 | 3-O—(4'-Cl—C$_6$H$_4$) |
| 494 | 4-O—(2'-Cl—C$_6$H$_4$) |
| 495 | 4-O—(3'-Cl—C$_6$H$_4$) |
| 496 | 4-O—(4'-Cl—C$_6$H$_4$) |
| 497 | 2-O—(2'-CH$_3$—C$_6$H$_4$) |
| 498 | 2-O—(3'-CH$_3$—C$_6$H$_4$) |
| 499 | 2-O—(4'-CH$_3$—C$_6$H$_4$) |
| 500 | 3-O—(2'-CH$_3$—C$_6$H$_4$) |
| 501 | 3-O—(3'-CH$_3$—C$_6$H$_4$) |
| 502 | 3-O—(4'-CH$_3$—C$_6$H$_4$) |
| 503 | 4-O—(2'-CH$_3$—C$_6$H$_4$) |
| 504 | 4-O—(3'-CH$_3$—C$_6$H$_4$) |
| 505 | 4-O—(4'-CH$_3$—C$_6$H$_4$) |
| 506 | 2-O—(2'-CH$_3$—CO—C$_6$H$_4$) |
| 507 | 2-O—(3'-CH$_3$—CO—C$_6$H$_4$) |
| 508 | 2-O—(4'-CH$_3$—CO—C6H4) |
| 509 | 3-O—(2'-CH$_3$—CO—C$_6$H$_4$) |
| 510 | 3-O—(3'-CH$_3$—CO—C$_6$H$_4$) |
| 511 | 3-O—(4'-CH$_3$—CO—C$_6$H$_4$) |
| 512 | 4-O—(2'-CH$_3$—CO—C$_6$H$_4$) |
| 513 | 4-O—(3'-CH$_3$—CO—C$_6$H$_4$) |
| 514 | 4-O—(4'-CH$_3$—CO—C$_6$H$_4$) |
| 515 | 2-O—(2'-(CH$_3$—C(=NOAllyl))—C$_6$H$_4$) |
| 516 | 2-O—(3'-(CH$_3$—C(=NOAllyl))—C$_6$H$_4$) |

TABLE 26-continued

| | |
|---|---|
| 517 | 2-O—(4'-(CH₃—C(=NOAllyl))—C₆H₄) |
| 518 | 3-O—(2'-(CH₃—C(=NOAllyl))—C₆H₄) |
| 519 | 3-O—(3'-(CH₃—C(=NOAllyl))—C₆H₄) |
| 520 | 3-O—(4'-(CH₃—C(=NOAllyl))—C₆H₄) |
| 521 | 4-O—(2'-(CH₃—C(=NOAllyl))—C₆H₄) |
| 522 | 4-O—(3'-(CH₃—C(=NOAllyl))—C₆H₄) |
| 523 | 4-O—(4'-(CH₃—C(=NOAllyl))—C₆H₄) |
| 524 | 2-O—(2'-CH₃O₂C—C₆H₄) |
| 525 | 2-O—(3'-CH₃O₂C—C₆H₄) |
| 526 | 2-O—(4'-CH₃O₂C—C₆H₄) |
| 527 | 3-O—(2'-CH₃O₂C—C₆H₄) |
| 528 | 3-O—(3'-CH₃O₂C—C₆H₄) |
| 529 | 3-O—(4'-CH₃O₂C—C₆H₄) |
| 530 | 4-O—(2'-CH₃O₂C—C₆H₄) |
| 531 | 4-O—(3'-CH₃O₂C—C₆H₄) |
| 532 | 4-O—(4'-CH₃O₂C—C₆H₄) |
| 533 | 2-O—(2'-CH₃O—C₆H₄) |
| 534 | 2-O—(3'-CH₃O—C₆H₄) |
| 535 | 2-O—(4'-CH₃O—C₆H₄) |
| 536 | 3-O—(2'-CH₃O—C₆H₄) |
| 537 | 3-O—(3'-CH₃O—C₆H₄) |
| 538 | 3-O—(4'-CH₃O—C₆H₄) |
| 539 | 4-O—(2'-CH₃O—C₆H₄) |
| 540 | 4-O—(3'-CH₃O—C₆H₄) |
| 541 | 4-O—(4'-CH₃O—C₆H₄) |
| 542 | 2-O—(2'-O₂N—C₆H₄) |
| 543 | 2-O—(3'-O₂N—C₆H₄) |
| 544 | 2-O—(4'-O₂N—C₆H₄) |
| 545 | 3-O—(2'-O₂N—C₆H₄) |
| 546 | 3-O—(3'-O₂N—C₆H₄) |
| 547 | 3-O—(4'-O₂N—C₆H₄) |
| 548 | 4-O—(2'-O₂N—C₆H₄) |
| 549 | 4-O—(3'-O₂N—C₆H₄) |
| 550 | 4-O—(4'-O₂N—C₆H₄) |
| 551 | 2-O—(2'-NC—C₆H₄) |
| 552 | 2-O—(3'-NC—C₆H₄) |
| 553 | 2-O—(4'-NC—C₆H₄) |
| 554 | 3-O—(2'-NC—C₆H₄) |
| 555 | 3-O—(3'-NC—C₆H₄) |
| 556 | 3-O—(4'-NC—C₆H₄) |
| 557 | 4-O—(2'-NC—C₆H₄) |
| 558 | 4-O—(3'-NC—C₆H₄) |
| 559 | 4-O—(4'-NC—C₆H₄) |
| 560 | 2-O—(2'-CF₃—C₆H₄) |
| 561 | 2-O—(3'-CF₃—C₆H₄) |
| 562 | 2-O—(4'-CF₃—C₆H₄) |
| 563 | 3-O—(2'-CF₃—C₆H₄) |
| 564 | 3-O—(3'-CF₃—C₆H₄) |
| 565 | 3-O—(4'-CF₃—C₆H₄) |
| 566 | 4-O—(2'-CF₃—C₆H₄) |
| 567 | 4-O—(3'-CF₃—C₆H₄) |
| 568 | 4-O—(4'-CF₃—C₆H₄) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-CH₃-4-(CH₃—C=N—O—CH₂—CH₂—OCH₃) |
| 642 | 2-CH₃-4-(C₂H₅—C=N—O—CH₂—CH₂—OCH₃) |
| 643 | 2,5-(CH₃)₂-4-(CH₃—C=N—O—CH₂—CH₂—OCH₃) |
| 644 | 2-CH₃-4-(n-C₃H₇—C=N—OCH₃) |
| 645 | 2-CH₃-4-(n-C₃H₇—C=N—OC₂H₅) |
| 646 | 2-CH₃-4-(n-C₃H₇—C=N—O-n-C₃H₇) |
| 647 | 2-CH₃-4-(n-C₃H₇—C=N—O-i-C₃H₇) |
| 648 | 2-CH₃-4-(n-C₃H₇—C=N—O-Allyl) |
| 649 | 2-CH₃-4-(n-C₃H₇—C=N—O-trans-Chloroallyl) |
| 650 | 2-CH₃-4-(n-C₃H₇—C=N—O-Propargyl) |
| 651 | 2-CH₃-4-(n-C₃H₇—C=N—O-n-C₄H₉) |
| 652 | 2-CH₃-4-(n-C₃H₇—C=N—O—CH₂—C₆H₅) |
| 653 | 2-CH₃-4-(i-C₃H₇—C=N—OCH₃) |
| 654 | 2-CH₃-4-(i-C₃H₇—C=N—OC₂H₅) |
| 655 | 2-CH₃-4-(i-C₃H₇—C=N—O-n-C₃H₇) |
| 656 | 2-CH₃-4-(i-C₃H₇—C=N—O-i-C₃H₇) |
| 657 | 2-CH₃-4-(i-C₃H₇—C=N—O-Allyl) |
| 658 | 2-CH₃-4-(i-C₃H₇—C=N—O-trans-Chloroallyl) |
| 659 | 2-CH₃-4-(i-C₃H₇—C=N—O-Propargyl) |
| 660 | 2-CH₃-4-(i-C₃H₇—C=N—O-n-C₄H₉) |
| 661 | 2-CH₃-4-(i-C₃H₇—C=N—O—CH₂—C₆H₅) |
| 662 | 2-O-n-C₄H₉ |
| 663 | 2-O-i-C₄H₉ |
| 664 | 2-O-s-C₄H₉ |
| 665 | 2-O-t-C₄H₉ |
| 666 | 2-Neopentyloxy |
| 667 | 3-O-n-C₄H₉ |
| 668 | 3-O-i-C₄H₉ |
| 669 | 3-O-s-C₄H₉ |
| 670 | 3-O-t-C₄H₉ |
| 671 | 3-Neopentyloxy |
| 672 | 4-O-n-C₄H₉ |
| 673 | 4-O-i-C₄H₉ |
| 674 | 4-O-s-C₄H₉ |

TABLE 26-continued

| | |
|---|---|
| 675 | 4-O-t-$C_4H_9$ |
| 676 | 4-Neopentyloxy |
| 677 | 3-$CH_3$-4-$OCH_3$ |
| 678 | 3-$CH_3$-4-$OC_2H_5$ |
| 679 | 3-$CH_3$-4-O-n-$C_3H_7$ |
| 680 | 3-$CH_3$-4-O-n-$C_4H_9$ |
| 681 | 3-$CH_3$-4-O-i-$C_4H_9$ |
| 682 | 3-$CH_3$-4-O-s-$C_4H_9$ |
| 683 | 3-$CH_3$-4-O-t-$C_4H_9$ |
| 684 | 3-$CH_3$-4-Neopentyloxy |
| 685 | 2-$CH_3$-3-$OCH_3$ |
| 686 | 2-$CH_3$-4-$OCH_3$ |
| 687 | 2-$CH_3$-5-$OCH_3$ |
| 688 | 2-$CH_3$-6-$OCH_3$ |
| 689 | 3-$CH_3$-4-$OCH_3$ |
| 690 | 3-$CH_3$-5-$OCH_3$ |
| 691 | 3-$CH_3$-6-$OCH_3$ |
| 692 | 4-$CH_3$-5-O—$CH_3$ |
| 693 | 4-$CH_3$-6-O—$CH_3$ |
| 694 | 4-$CH_3$-6-$OCH_3$ |
| 695 | 2-$CH_3$-3-O-i-$C_3H_7$ |
| 696 | 2-$CH_3$-4-O-i-$C_3H_7$ |
| 697 | 2-$CH_3$-5-O-i-$C_3H_7$ |
| 698 | 2-$CH_3$-6-O-i-$C_3H_7$ |
| 699 | 3-$CH_3$-4-O-i-$C_3H_7$ |
| 700 | 3-$CH_3$-5-O-i-$C_3H_7$ |
| 701 | 3-$CH_3$-6-O-i-$C_3H_7$ |
| 702 | 4-$CH_3$-5-O-i-$C_3H_7$ |
| 703 | 4-$CH_3$-6-O-i-$C_3H_7$ |
| 704 | 5-$CH_3$-6-O-i-$C_3H_7$ |
| 705 | 2-Cl-3-$OCH_3$ |
| 706 | 2-Cl-4-$OCH_3$ |
| 707 | 2-Cl-5-$OCH_3$ |
| 708 | 2-Cl-6-$OCH_3$ |
| 709 | 3-Cl-4-$OCH_3$ |
| 710 | 3-Cl-5-$OCH_3$ |
| 711 | 3-Cl-6-$OCH_3$ |
| 712 | 4-Cl-5-$OCH_3$ |
| 713 | 4-Cl-6-$OCH_3$ |
| 714 | 5-Cl-6-$OCH_3$ |

TABLE 27

I: $R^1 = CH_3$, X = $CH_3$
II: $R^1 = CH_2$—$CH_3$, X = $CH_3$
III: $R^1 = CH_3$, X = Cl
IV: $R^1 = CH_2$—$CH_3$, X = Cl

| No. | B |
|---|---|
| 1 | Pyrrolyl-3 |
| 2 | N—$CH_3$-Pyrrolyl-3 |
| 3 | N—$C_6H_5$-Pyrrolyl-3 |
| 4 | N-(4'-$CH_3$—$C_6H_4$)-Pyrrolyl-3 |
| 5 | N-(3'-$CH_3$—$C_6H_4$)-Pyrrolyl-3 |
| 6 | N-(2'-$CH_3$—$C_6H_4$)-Pyrrolyl-3 |
| 7 | N-(4'-$CH_3O$—$C_6H_4$)-Pyrrolyl-3 |
| 8 | N-(3'-$CH_3O$—$C_6H_4$)-Pyrrolyl-3 |
| 9 | N-(2'-$CH_3O$—$C_6H_4$)-Pyrrolyl-3 |
| 10 | N-(4'-$NO_2$—$C_6H_4$)-Pyrrolyl-3 |
| 11 | N-(3'-$NO_2$—$C_6H_4$)-Pyrrolyl-3 |
| 12 | N-(2'-$NO_2$—$C_6H_4$)-Pyrrolyl-3 |
| 13 | N-(4'-CN—$C_6H_4$)-Pyrrolyl-3 |
| 14 | N-(3'-CN—$C_6H_4$)-Pyrrolyl-3 |
| 15 | N-(2'-CN—$C_6H_4$)-Pyrrolyl-3 |
| 16 | N-(4'-Cl—$C_6H_4$)-Pyrrolyl-3 |

TABLE 27-continued

| No. | B |
|---|---|
| 17 | N-(3'-Cl—$C_6H_4$)-Pyrrolyl-3 |
| 18 | N-(2'-Cl—$C_6H_4$)-Pyrrolyl-3 |
| 19 | Pyrrolyl-2 |
| 20 | N—$CH_3$-Pyrrolyl-2 |
| 21 | N—$C_6H_5$-Pyrrolyl-2 |
| 22 | N-(4'-$CH_3$—$C_6H_4$)-Pyrrolyl-2 |
| 23 | N-(3'-$CH_3$—$C_6H_4$)-Pyrrolyl-2 |
| 24 | N-(2'-$CH_3$—$C_6H_4$)-Pyrrolyl-2 |
| 25 | N-(4'-$CH_3O$—$C_6H_4$)-Pyrrolyl-2 |
| 26 | N-(3'-$CH_3O$—$C_6H_4$)-Pyrrolyl-2 |
| 27 | N-(2'-$CH_3O$—$C_6H_4$)-Pyrrolyl-2 |
| 28 | N-(4'-$NO_2$—$C_6H_4$)-Pyrrolyl-2 |
| 29 | N-(3'-$NO_2$—$C_6H_4$)-Pyrrolyl-2 |
| 30 | N-(2'-$NO_2$—$C_6H_4$)-Pyrrolyl-2 |
| 31 | N-(4'-CN—$C_6H_4$)-Pyrrolyl-2 |
| 32 | N-(3'-CN—$C_6H_4$)-Pyrrolyl-2 |
| 33 | N-(2'-CN—$C_6H_4$)-Pyrrolyl-2 |
| 34 | N-(4'-Cl—$C_6H_4$)-Pyrrolyl-2 |
| 35 | N-(3'-Cl—$C_6H_4$)-Pyrrolyl-2 |
| 36 | N-(2'-Cl—$C_6H_4$)-Pyrrolyl-2 |
| 37 | Furyl-2 |
| 38 | 5-$CH_3$-Furyl-2 |
| 39 | 5-$C_6H_5$-Furyl-2 |
| 40 | 5-(4'-$CH_3$—$C_6H_4$)-Furyl-2 |
| 41 | 5-(3'-$CH_3$—$C_6H_4$)-Furyl-2 |
| 42 | 5-(2'-$CH_3$—$C_6H_4$)-Furyl-2 |
| 43 | 5-(4'-$CH_3O$—$C_6H_4$)-Furyl-2 |
| 44 | 5-(3'-$CH_3O$—$C_6H_4$)-Furyl-2 |
| 45 | 5-(2'-$CH_3O$—$C_6H_4$)-Furyl-2 |
| 46 | 5-(4'-$NO_2$—$C_6H_4$)-Furyl-2 |
| 47 | 5-(3'-$NO_2$—$C_6H_4$)-Furyl-2 |
| 48 | 5-(2'-$NO_2$—$C_6H_4$)-Furyl-2 |
| 49 | 5-(4'-CN—$C_6H_4$)-Furyl-2 |
| 50 | 5-(3'-CN—$C_6H_4$)-Furyl-2 |
| 51 | 5-(2'-CN—$C_6H_4$)-Furyl-2 |
| 52 | 5-(4'-Cl—$C_6H_4$)-Furyl-2 |
| 53 | 5-(3'-Cl—$C_6H_4$)-Furyl-2 |
| 54 | 5-(2'-Cl—$C_6H_4$)-Furyl-2 |
| 55 | 4-$CH_3$-Furyl-2 |
| 56 | 4-$C_6H_5$-Furyl-2 |
| 57 | 4-(4'-$CH_3$—$C_6H_4$)-Furyl-2 |
| 58 | 4-(3'-$CH_3$—$C_6H_4$)-Furyl-2 |
| 59 | 4-(2'-$CH_3$—$C_6H_4$)-Furyl-2 |
| 60 | 4-(4'-$CH_3O$—$C_6H_4$)-Furyl-2 |
| 61 | 4-(3'-$CH_3O$—$C_6H_4$)-Furyl-2 |
| 62 | 4-(2'-$CH_3O$—$C_6H_4$)-Furyl-2 |
| 63 | 4-(4'-$NO_2$—$C_6H_4$)-Furyl-2 |
| 64 | 4-(3'-$NO_2$—$C_6H_4$)-Furyl-2 |
| 65 | 4-(2'-$NO_2$—$C_6H_4$)-Furyl-2 |
| 66 | 4-(4'-CN—$C_6H_4$)-Furyl-2 |
| 67 | 4-(3'-CN—$C_6H_4$)-Furyl-2 |
| 68 | 4-(2'-CN—$C_6H_4$)-Furyl-2 |
| 69 | 4-(4'-Cl—$C_6H_4$)-Furyl-2 |
| 70 | 4-(3'-Cl—$C_6H_4$)-Furyl-2 |
| 71 | 4-(2'-Cl—$C_6H_4$)-Furyl-2 |
| 72 | Thienyl-2 |
| 73 | 5-$CH_3$-Thienyl-2 |
| 74 | 5-$C_6H_5$-Thienyl-2 |
| 75 | 5-(4'-$CH_3$—$C_6H_4$)-Thienyl-2 |
| 76 | 5-(3'-$CH_3$—$C_6H_4$)-Thienyl-2 |
| 77 | 5-(2'-$CH_3$—$C_6H_4$)-Thienyl-2 |
| 78 | 5-(4'-$CH_3O$—$C_6H_4$)-Thienyl-2 |
| 79 | 5-(3'-$CH_3O$—$C_6H_4$)-Thienyl-2 |
| 80 | 5-(2'-$CH_3O$—$C_6H_4$)-Thienyl-2 |
| 81 | 5-(4'-$NO_2$—$C_6H_4$)-Thienyl-2 |
| 82 | 5-(3'-$NO_2$—$C_6H_4$)-Thienyl-2 |
| 83 | 5-(2'-$NO_2$—$C_6H_4$)-Thienyl-2 |
| 84 | 5-(4'-CN—$C_6H_4$)-Thienyl-2 |
| 85 | 5-(3'-CN—$C_6H_4$)-Thienyl-2 |
| 86 | 5-(2'-CN—$C_6H_4$)-Thienyl-2 |
| 87 | 5-(4'-Cl—$C_6H_4$)-Thienyl-2 |
| 88 | 5-(3'-Cl—$C_6H_4$)-Thienyl-2 |
| 89 | 5-(2'-Cl—$C_6H_4$)-Thienyl-2 |
| 90 | 4-$CH_3$-Thienyl-2 |
| 91 | 4-$C_6H_5$-Thienyl-2 |
| 92 | 4-(4'-$CH_3$—$C_6H_4$)-Thienyl-2 |
| 93 | 4-(3'-$CH_3$—$C_6H_4$)-Thienyl-2 |
| 94 | 4-(2'-$CH_3$—$C_6H_4$)-Thienyl-2 |
| 95 | 4-(4'-$CH_3O$—$C_6H_4$)-Thienyl-2 |

TABLE 27-continued

| | |
|---|---|
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 3-CH$_3$-Oxazolyl-4 |
| 234 | 3-C$_6$H$_5$-Oxazolyl-4 |
| 235 | 3-(4'-CH$_3$—C$_6$H$_4$)-Oxazolyl-4 |
| 236 | 3-(3'-CH$_3$—C$_6$H$_4$)-Oxazolyl-4 |
| 237 | 3-(2'-CH$_3$—C$_6$H$_4$)-Oxazolyl-4 |
| 238 | 3-(4'-CH$_3$O—C$_6$H$_4$)-Oxazolyl-4 |
| 239 | 3-(3'-CH$_3$O—C$_6$H$_4$)-Oxazolyl-4 |
| 240 | 3-(2'-CH$_3$O—C$_6$H$_4$)-Oxazolyl-4 |
| 241 | 3-(4'-NO$_2$—C$_6$H$_4$)-Oxazolyl-4 |
| 242 | 3-(3'-NO$_2$—C$_6$H$_4$)-Oxazolyl-4 |
| 243 | 3-(2'-NO$_2$—C$_6$H$_4$)-Oxazolyl-4 |
| 244 | 3-(4'-CN—C$_6$H$_4$)-Oxazolyl-4 |
| 245 | 3-(3'-CN—C$_6$H$_4$)-Oxazolyl-4 |
| 246 | 3-(2'-CN—C$_6$H$_4$)-Oxazolyl-4 |
| 247 | 3-(4'-Cl—C$_6$H$_4$)-Oxazolyl-4 |
| 248 | 3-(3'-Cl—C$_6$H$_4$)-Oxazolyl-4 |
| 249 | 3-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |

TABLE 27-continued

| | |
|---|---|
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 267 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,3,4-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |
| 385 | 1-Naphthyl |
| 386 | 2-Naphthyl |

TABLE 28

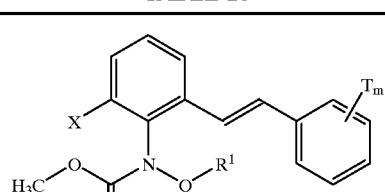

I: $R^1$ = CH$_3$, X = CH$_3$
II: $R^1$ = CH$_2$—CH$_3$, X = CH$_3$
III: $R^1$ = CH$_3$, X = Cl
IV: $R^1$ = CH$_2$—CH$_3$, X = Cl

| No. | T$_m$ |
|---|---|
| 1 | H |
| 2 | 2-F |

TABLE 28-continued

| | |
|---|---|
| 3 | 3-F |
| 4 | 4-F |
| 5 | 2,4-$F_2$ |
| 6 | 2,4,6-$F_3$ |
| 7 | 2,3,4,5,6-$F_5$ |
| 8 | 2,3-$F_2$ |
| 9 | 2-Cl |
| 10 | 3-Cl |
| 11 | 4-Cl |
| 12 | 2,3-$Cl_2$ |
| 13 | 2,4-$Cl_2$ |
| 14 | 2,5-$Cl_2$ |
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |
| 37 | 4-I |
| 38 | 2,4-$I_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-$Cl_2$, 4-Br |
| 66 | 2-$CH_3$ |
| 67 | 3-$CH_3$ |
| 68 | 4-$CH_3$ |
| 69 | 2,3-$(CH_3)_2$ |
| 70 | 2,4-$(CH_3)_2$ |
| 71 | 2,5-$(CH_3)_2$ |
| 72 | 2,6-$(CH_3)_2$ |
| 73 | 3,4-$(CH_3)_2$ |
| 74 | 3,5-$(CH_3)_2$ |
| 75 | 2,3,5-$(CH_3)_3$ |
| 76 | 2,3,4-$(CH_3)_3$ |
| 77 | 2,3,6-$(CH_3)_3$ |
| 78 | 2,4,5-$(CH_3)_3$ |
| 79 | 2,4,6-$(CH_3)_3$ |
| 80 | 3,4,5-$(CH_3)_3$ |
| 81 | 2,3,4,6-$(CH_3)_4$ |
| 82 | 2,3,5,6-$(CH_3)_4$ |
| 83 | 2,3,4,5,6-$(CH_3)_5$ |
| 84 | 2-$C_2H_5$ |
| 85 | 3-$C_2H_5$ |
| 86 | 4-$C_2H_5$ |
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C_2H_5)_3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7)_2$ |
| 98 | 2,6-(i-$C_3H_7)_2$ |
| 99 | 3,5-(i-$C_3H_7)_2$ |
| 100 | 2,4,6-(i-$C_3H_7)_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9)_2$ |
| 108 | 2,4-(t-$C_4H_9)_2$ |
| 109 | 2,5-(t-$C_4H_9)_2$ |
| 110 | 2,6-(t-$C_4H_9)_2$ |
| 111 | 3,4-(t-$C_4H_9)_2$ |
| 112 | 2,4,6-(t-$C_4H_9)_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-$C_4H_9$, 4-$CH_3$ |
| 119 | 2-t-$C_4H_9$, 5-$CH_3$ |
| 120 | 2,6-(t-$C_4H_9)_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9)_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11})_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-$(CH_3)_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$OCH_3$ |

TABLE 28-continued

| | |
|---|---|
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,5-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |

TABLE 28-continued

| | |
|---|---|
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |

TABLE 28-continued

| | |
|---|---|
| 475 | 3-O—$C_6H_5$ |
| 476 | 4-O—$C_6H_5$ |
| 478 | 2-O-(2'-F—$C_6H_4$) |
| 479 | 2-O-(3'-F—$C_6H_4$) |
| 480 | 2-O-(4'-F—$C_6H_4$) |
| 481 | 3-O-(2'-F—$C_6H_4$) |
| 482 | 3-O-(3'-F—$C_6H_4$) |
| 483 | 3-O-(4'-F—$C_6H_4$) |
| 484 | 4-O-(2'-F—$C_6H_4$) |
| 485 | 4-O-(3'-F—$C_6H_4$) |
| 486 | 4-O-(4'-F—$C_6H_4$) |
| 487 | 2-O-(2'-Cl—$C_6H_4$) |
| 488 | 2-O-(3'-Cl—$C_6H_4$) |
| 489 | 2-O-(4'-Cl—$C_6H_4$) |
| 490 | 3-O-(2'-Cl—$C_6H_4$) |
| 491 | 3-O-(3'-Cl—$C_6H_4$) |
| 492 | 3-O-(4'-Cl—$C_6H_4$) |
| 493 | 3-O-(4'-Cl—$C_6H_4$) |
| 494 | 4-O-(2'-Cl—$C_6H_4$) |
| 495 | 4-O-(3'-Cl—$C_6H_4$) |
| 496 | 4-O-(4'-Cl—$C_6H_4$) |
| 497 | 2-O-(2'-Cl—$C_6H_4$) |
| 498 | 2-O-(3'-$CH_3$—$C_6H_4$) |
| 499 | 2-O-(4'-$CH_3$—$C_6H_4$) |
| 500 | 3-O-(2'-$CH_3$—$C_6H_4$) |
| 501 | 3-O-(3'-$CH_3$—$C_6H_4$) |
| 502 | 3-O-(4'-$CH_3$—$C_6H_4$) |
| 503 | 4-O-(2'-$CH_3$—$C_6H_4$) |
| 504 | 4-O-(3'-$CH_3$—$C_6H_4$) |
| 505 | 4-O-(4'-$CH_3$—$C_6H_4$) |
| 506 | 2-O-(2'-$CH_3$—CO—$C_6H_4$) |
| 507 | 2-O-(3'-$CH_3$—CO—$C_6H_4$) |
| 508 | 2-O-(4'-$CH_3$—CO—$C_6H_4$) |
| 509 | 3-O-(2'-$CH_3$—CO—$C_6H_4$) |
| 510 | 3-O-(3'-$CH_3$—CO—$C_6H_4$) |
| 511 | 3-O-(4'-$CH_3$—CO—$C_6H_4$) |
| 512 | 4-O-(2'-$CH_3$—CO—$C_6H_4$) |
| 513 | 4-O-(3'-$CH_3$—CO—$C_6H_4$) |
| 514 | 4-O-(4'-$CH_3$—CO—$C_6H_4$) |
| 515 | 2-O-(2'-($CH_3$—C(=NOAllyl))-$C_6H_4$) |
| 516 | 2-O-(3'-($CH_3$—C(=NOAllyl))-$C_6H_4$) |
| 517 | 2-O-(4'-($CH_3$—C(=NOAllyl))-$C_6H_4$) |
| 518 | 3-O-(2'-($CH_3$—C(=NOAllyl))-$C_6H_4$) |
| 519 | 3-O-(3'-($CH_3$—C(=NOAllyl))-$C_6H_4$) |
| 520 | 3-O-(4'-($CH_3$—C(=NOAllyl))-$C_6H_4$) |
| 521 | 4-O-(2'-($CH_3$—C(=NOAllyl))-$C_6H_4$) |
| 522 | 4-O-(3'-($CH_3$—C(=NOAllyl))-$C_6H_4$) |
| 523 | 4-O-(4'-($CH_3$—C(=NOAllyl))-$C_6H_4$) |
| 524 | 2-O-(2'-$CH_3O_2C$—$C_6H_4$) |
| 525 | 2-O-(3'-$CH_3O_2C$—$C_6H_4$) |
| 526 | 2-O-(4'-$CH_3O_2C$—$C_6H_4$) |
| 527 | 3-O-(2'-$CH_3O_2C$—$C_6H_4$) |
| 528 | 3-O-(3'-$CH_3O_2C$—$C_6H_4$) |
| 529 | 3-O-(4'-$CH_3O_2C$—$C_6H_4$) |
| 530 | 4-O-(2'-$CH_3O_2C$—$C_6H_4$) |
| 531 | 4-O-(3'-$CH_3O_2C$—$C_6H_4$) |
| 532 | 4-O-(4'-$CH_3O_2C$—$C_6H_4$) |
| 533 | 2-O-(2'-$CH_3O$—$C_6H_4$) |
| 534 | 2-O-(3'-$CH_3O$—$C_6H_4$) |
| 535 | 2-O-(4'-$CH_3O$—$C_6H_4$) |
| 536 | 3-O-(2'-$CH_3O$—$C_6H_4$) |
| 537 | 3-O-(3'-$CH_3O$—$C_6H_4$) |
| 538 | 3-O-(4'-$CH_3O$—$C_6H_4$) |
| 539 | 4-O-(2'-$CH_3O$—$C_6H_4$) |
| 540 | 4-O-(3'-$CH_3O$—$C_6H_4$) |
| 541 | 4-O-(4'-$CH_3O$—$C_6H_4$) |
| 542 | 2-O-(2'-$O_2N$—$C_6H_4$) |
| 543 | 2-O-(3'-$O_2N$—$C_6H_4$) |
| 544 | 2-O-(4'-$O_2N$—$C_6H_4$) |
| 545 | 3-O-(2'-$O_2N$—$C_6H_4$) |
| 546 | 3-O-(3'-$O_2N$—$C_6H_4$) |
| 547 | 3-O-(4'-$O_2N$—$C_6H_4$) |
| 548 | 4-O-(2'-$O_2N$—$C_6H_4$) |
| 549 | 4-O-(3'-$O_2N$—$C_6H_4$) |
| 550 | 4-O-(4'-$O_2N$—$C_6H_4$) |
| 551 | 2-O-(2'-NC—$C_6H_4$) |
| 552 | 2-O-(3'-NC—$C_6H_4$) |
| 553 | 2-O-(4'-NC—$C_6H_4$) |
| 554 | 3-O-(2'-NC—$C_6H_4$) |
| 555 | 3-O-(3'-NC—$C_6H_4$) |
| 556 | 3-O-(4'-NC—$C_6H_4$) |
| 557 | 4-O-(2'-NC—$C_6H_4$) |
| 558 | 4-O-(3'-NC—$C_6H_4$) |
| 559 | 4-O-(4'-NC—$C_6H_4$) |
| 560 | 2-O-(2'-$CF_3$—$C_6H_4$) |
| 561 | 2-O-(3'-$CF_3$—$C_6H_4$) |
| 562 | 2-O-(4'-$CF_3$—$C_6H_4$) |
| 563 | 3-O-(2'-$CF_3$—$C_6H_4$) |
| 564 | 3-O-(3'-$CF_3$—$C_6H_4$) |
| 565 | 3-O-(4'-$CF_3$—$C_6H_4$) |
| 566 | 4-O-(2'-$CF_3$—$C_6H_4$) |
| 567 | 4-O-(3'-$CF_3$—$C_6H_4$) |
| 568 | 4-O-(4'-$CF_3$—$C_6H_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |

TABLE 28-continued

| | |
|---|---|
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |

TABLE 29

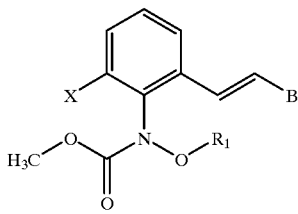

I: $R^1 = CH_3$, $X = CH_3$
II: $R^1 = CH_2-CH_3$, $X = CH_3$
III: $R^1 = CH_3$, $X = Cl$
IV: $R^1 = CH_2-CH_3$, $X = Cl$

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |

TABLE 29-continued

| | |
|---|---|
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N-(4'-CH$_3$—C$_6$H$_4$)-Pyrazolyl-4 |

TABLE 29-continued

| | |
|---|---|
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 3-CH$_3$-Oxazolyl-4 |
| 234 | 3-C$_6$H$_5$-Oxazolyl-4 |
| 235 | 3-(4'-CH$_3$—C$_6$H$_4$)-Oxazolyl-4 |
| 236 | 3-(3'-CH$_3$—C$_6$H$_4$)-Oxazolyl-4 |
| 237 | 3-(2'-CH$_3$—C$_6$H$_4$)-Oxazolyl-4 |
| 238 | 3-(4'-CH$_3$O—C$_6$H$_4$)-Oxazolyl-4 |
| 239 | 3-(3'-CH$_3$O—C$_6$H$_4$)-Oxazolyl-4 |
| 240 | 3-(2'-CH$_3$O—C$_6$H$_4$)-Oxazolyl-4 |
| 241 | 3-(4'-NO$_2$—C$_6$H$_4$)-Oxazolyl-4 |
| 242 | 3-(3'-NO$_2$—C$_6$H$_4$)-Oxazolyl-4 |
| 243 | 3-(2'-NO$_2$—C$_6$H$_4$)-Oxazolyl-4 |
| 244 | 3-(4'-CN—C$_6$H$_4$)-Oxazolyl-4 |
| 245 | 3-(3'-CN—C$_6$H$_4$)-Oxazolyl-4 |
| 246 | 3-(2'-CN—C$_6$H$_4$)-Oxazolyl-4 |
| 247 | 3-(4'-Cl—C$_6$H$_4$)-Oxazolyl-4 |
| 248 | 3-(3'-Cl—C$_6$H$_4$)-Oxazolyl-4 |
| 249 | 3-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 267 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |

TABLE 29-continued

| 287 | 5-CH$_3$-1,3,4-Oxadiazolyl-2 |
| 288 | 5-C$_6$H$_5$-1,3,4-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | Pyridinyl-3 |

TABLE 30

Selected physical data of some compounds

| No. | Compound | IR (cm$^{-1}$) or $^1$H-NMR (ppm) | m.p |
|---|---|---|---|
| 1 | 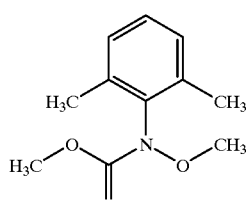 | | 81 |
| 2 | 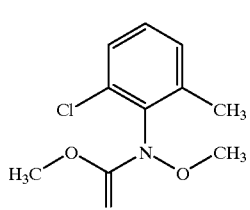 | | 60 |
| 3 | 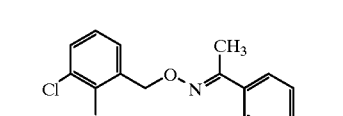 | 3.85(s, broad, 3H); 3.7(s, broad, 3H) | |
| 4 | 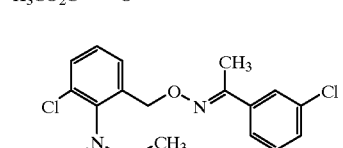 | 3.85(s, broad, 3H); 3.75(s, broad, 3H) | |
| 5 | 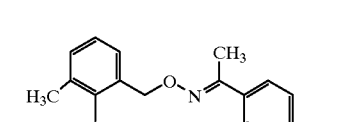 | 3.75(2s, broad, each 3H) | |

TABLE 30-continued

Selected physical data of some compounds

| No. | Compound | IR (cm$^{-1}$) or $^1$H-NMR (ppm) | m.p |
|---|---|---|---|
| 6 | (structure: H$_3$C-phenyl with CH$_2$-O-N=C(CH$_3$)-3,5-dichlorophenyl, N(CO$_2$CH$_3$)(OCH$_3$)) | | 91 |
| 7 | (structure: H$_3$C-phenyl with CH$_2$Br, N(CO$_2$CH$_3$)(OCH$_3$)) | 3.8(s, 3H); 3.75(s, broad, 3H) | |
| 8 | (structure: Cl-phenyl with CH$_2$Br, N(CO$_2$CH$_3$)(OCH$_3$)) | 3.85(s, 3H); 3.8(s, broad, 3H) | |

TABLE 31

Structure: X-phenyl with CH$_2$-S-B substituent, N(C(=O)OCH$_3$)(OR$^1$)

I: R$^1$ = CH$_3$, X = CH$_3$
II: R$^1$ = C$_2$H$_5$, X = CH$_3$
III: R$^1$ = CH$_3$, X = Cl
IV: R$^1$ = C$_2$H$_5$, X = Cl

| No. | B |
|---|---|
| 1 | 2-Pyridyl |
| 2 | 3-Trifluoromethyl-2-pyridyl |
| 3 | 5-Trifluoromethyl-2-pyridyl |
| 4 | 3,5-Bis-(trifluoromethyl)-2-pyridyl |
| 5 | 3,5-Dichloro-2-pyridyl |
| 6 | 3-Chloro-5-trifluoromethyl-2-pyridyl |
| 7 | 3,5-Dichloro-2-pyridyl |
| 8 | 2-Chloro-4-trifluoromethylphenyl |
| 9 | 2-Benzothiazolyl |
| 10 | 5-Chloro-1-methyl-2-benzimidazolyl |
| 11 | 2-Benzoxazolyl |
| 12 | 1-Methyl-5-trifluoromethylimidazo-[5,4-a]-pyridin-2-yl |
| 13 | 5-Chloro-2-pyrimidinyl |
| 14 | 4-Methyl-5-phenyl-2-thiazolin-2-yl |
| 15 | 4-Methyl-5-phenyl-2-oxazolin-2-yl |
| 16 | 7-Trifluoromethyl-4-quinolinyl |

TABLE 57

Selected physical data of some compounds

Structure: X-phenyl with CH$_2$-O-phenyl-T$_m$, N(CO$_2$CH$_3$)(OCH$_3$)

| No. | X | T$_m$ | mp (° C.) | $^1$H-NMR (ppm) or IR (cm$^{-1}$) |
|---|---|---|---|---|
| 1 | Cl | 2-CH$_3$ | | 3.8(s, broad, 6H) |
| 2 | Cl | 2,5-(CH$_3$)$_2$ | | 3.8(s, broad, 6H) |
| 3 | Cl | 2-CH$_3$-4-C(CH$_3$)=N—OCH$_3$ | | 4.0(s, 3H); 3.8 (s, broad, 6H) |
| 4 | Cl | 2,5-(CH$_3$)$_2$-4-C(CH$_3$)=N—O—Allyl | | 3.8(s, broad, 6H) |
| 5 | CH$_3$ | 2-CH$_3$-4-C(CH$_3$)=N—OCH$_3$ | | 4.0(s, 3H); 3.75 (s, broad, 6H) |
| 6 | CH$_3$ | 2-CH$_3$ | | 3.75(s, broad, 6H) |
| 7 | CH$_3$ | 2,5-(CH$_3$)$_2$ | | 3.75(s, broad, 6H) |
| 8 | CH$_3$ | 2,5-(CH$_3$)$_2$-4-C(CH$_3$)=N—O—Allyl | | 3.75(s, broad, 6H) |

Example 11

2-(2'-Methylphenoxymethyl)-trichloroacetanilide (Table 38, No. 1)

a) 2-(2'-Methylphenoxymethyl)-nitrobenzene 75 g (0.347 mol) of 2-nitrobenzyl bromide, 37 g (0.342 mol) of o-cresol and 56 g (0.405 mol) of potassium carbonate in 500 ml of dimethylformamide is stirred for 5 hours at room temperature (20° C.). The reaction mixture is diluted with water and the aqueous phase is extracted three times with ether. The ether phase is dried and evaporated down. The crystalline residue is stirred with methanol and suction filtered. There is obtained 73 g (0.300 mol=88%) of the title compound as a colorless solid.

Mp=83° C.

$^1$H-NMR, (CDCl$_3$; δ (ppm)): 8.15 (d, 1H, I=8 Hz, aromatic); 7.95 (d, 1H, I=8 Hz, 1H, I=8 Hz, aromatic); 7.15 (m, 2H, aromatic); 6.9 (m, 2H, aromatic); 5.45 (s, 2H, O—CH$_2$); 2.35 (s, 3H, CH$_3$).

b) 2-(2'-Methylphenoxymethyl)-aniline 75 g (0.308 mol) of 2-(2'-methylphenoxymethyl)-nitrobenzene (Example 11a) and 10 g of 5% Pt/C (platinum adsorbed on activated carbon) in 50 ml of methanol are stirred vigorously under a hydrogen blanket for 2 hours. A further 2 g of 5% Pt/C is added and the mixture is stirred overnight. The catalyst is filtered off and replaced by 10 g of fresh catalyst. The mixture is stirred overnight and suction filtered, and the filtrate is evaporated down under reduced pressure. The residue is purified by column chromatography with mixtures of hexane and ethyl acetate. There is obtained 61 g (0.286 mol=93%) of the title compound as a colorless solid.

Mp=56° C.

$^1$H-NMR (CDCl$_3$; δ (ppm)): 7.2 (m, 4H, aromatic); 6.95 (d, 1H, I=8 Hz, aromatic); 6,9 (t, 1H, I=6 Hz, aromatic); 6.7 (m, 2H, aromatic); 5.0 (s, 2H, O—CH$_2$); 4.05 (s, broad, 2H, NH$_2$); 2.2 (s, 3H, CH$_3$).

c) 2-(2'-Methylphenoxymethyl)-trichloroacetanilide (Table 38, No. 1)

At 10–15° C., a solution of 6 g of 2-(2'-methylphenoxymethyl)-aniline (Example 1b) in 20 ml of CH$_2$Cl$_2$ is added to a mixture of 6.6 g (36 mmol) of trichloroacetyl chloride and 3 g (38 mmol) of pyridine in 50 ml of CH$_2$Cl$_2$. The mixture is stirred for 1 hour at room temperature, and then extracted with water, dried over MgSO$_4$ and evaporated down. The residue is suction filtered over silica gel and the filtrate which is obtained is evaporated down. The residue crystallizes and is stirred with hexane. There is obtained 7.9 g (22 mmol=78%) of the title compound as a crystalline solid (mp=128° C.).

$^1$H-NMR (CDCl$_3$; δ (ppm)): 9.6 (s, broad, 1H, NH); 8.1 (d, 1H, I=8 Hz, phenyl); 7.5 (t, broad, 1H, phenyl); 7.4 (d, broad, 1H, phenyl); 7.2 (m, 3H, phenyl); 6.95 (m, 2H, phenyl); 5.1 (s, 2H, OCH$_2$); 2.2 (s, 3H, CH$_3$).

Example 12

N-Methyl-N'-(2-(2'-methylphenoxymethyl)-phenyl)-urea (Table 7, No. 2)

In a laboratory autoclave, about 10 ml of methylamine is added to 2 g (5.5 mmol) of the trichloroacetanilide from Example 1c. The autoclave is then closed and the reaction mixture is heated for about 6 hours at 80° C. The reaction mixture is cooled and the autoclave opened. The methylamine is allowed to evaporate off and the solid residue is stirred with methyl tert-butyl ether. The insoluble solid is filtered off and dried under reduced pressure. There is obtained 1.4 g (5.2 mmol=94%) of the title compound as a crystalline solid (mp=144° C.).

$^1$H-NMR (DMSO-d$_6$; δ (ppm)): 8.05 (s, 1H, NH); 7.8 (d, 1H, I=8 Hz, phenyl); 7.4 (d, 1H, I=8 Hz, phenyl); 6.8–7.3 (m, 6H, phenyl); 6.7 (s, 1H, NH); 5.1 (S, 2H, OCH$_2$); 2.65 (d, 3H, I=5 Hz, N—CH$_3$); 2.2 (s, 3H, CH$_3$).

Example 13

2-(2'-Methylphenoxymethyl)-propionyl anilide (Table 38, No. 3)

A mixture of 3 g (14.1 mmol) of the aniline from Example 11b, 1.35 g (17 mmol) of pyridine and 1.4 g (15.5 mmol) of propionyl chloride in 30 ml of methylene chloride is stirred for 1 hour at room temperature. The reaction mixture is then extracted with diluted hydrochloric acid and water, dried over MgSO$_4$ and evaporated down. There is obtained 3.8 g (quantitative yield) of the title compound.

$^1$H-NMR (COCl$_3$; δ (ppm)): 8.25 (s, broad, 1H, NH); 8.15 (d, 1H, I=8 Hz, phenyl); 6.9–7.5 (m, 7H, phenyl); 5.1 (s, 2H, OCH$_2$); 2.35 (q, 2H, I=8 Hz, CH$_2$); 2.25 (s, 3H, CH$_3$); 1.2 (t, 3H, I=8 Hz, CH$_3$).

Example 14

N-Propionyl-2-(2'-methylphenoxymethyl)-propionyl anilide (Table 38, No. 4)

0.41 g (17.1 mmol) of sodium hydride is added in portions to 3.8 g (14 mmol) of the propionyl anilide from Example 13 in 40 ml of dimethylformamide. Upon completion of gas evolution 1.4 g (15.9 mmol) of propionyl chloride is added and the mixture is stirred overnight at room temperature. The reaction mixture is then diluted with water and the aqueous phase is extracted three times with methyl tert-butyl ether. The combined organic phases are extracted with water, dried over MgSO$_4$ and evaporated down. The residue is purified by column chromatography with mixtures of hexane and ethyl acetate. There is obtained 2.6 g (8 mmol= 57%) of the title compound as a yellow oil.

$^1$H-NMR (CDCl$_3$): δ (ppm): 7.6 (m, 1H, phenyl); 7.4 (m, 2H, phenyl); 7.15 (m, 3H, phenyl); 6.85 (m, 2H, phenyl); 4.85 (m, 2H, OCH$_2$); 2.6 (m, 4H, 2×CH$_2$); 2.2 (s, 3H, CH$_3$); 1.1 (t, 6H, I=8 Hz, 2×CH$_3$).

Example 15

N-Methyl-2-(2'-methylphenoxymethyl)-propionyl anilide (Table 38, No. 5)

0.45 g (19 mmol) of sodium hydride is added in portions to 4.0 g (14.8 mmol) of the propionyl anilide from Example 13 in 50 ml of dimethylformamide. Upon completion of gas evolution 3.0 g (21 mmol) of methyl iodide is added and the mixture is stirred for 2 hours at room temperature. The reaction mixture is then diluted with water and the aqueous phase is extracted three times with methyl tert-butyl ether. The combined organic phases are extracted with water, dried over MgSO$_4$ and evaporated down. The residue crystallizes and is stirred with hexane. There is obtained 3.7 g (11.7 mmol=90%) of the title compound as a colorless solid (mp=80° C.).

$^1$H-NMR (CDCl$_3$; δ (ppm): 7.7 (m, 1H, phenyl); 7.4 (m, 2H, phenyl); 7.2 (m, 3H, phenyl); 6.9 (m, 2H, phenyl); 5.0 (s, 2H, OCH$_2$); 3.2 (s, 3H, N—CH$_3$); 2.2 (s, 3H, CH$_3$); 2.0 (m, 2H, CH$_2$); 1.0 (t, 3H, I=8 Hz, CH$_3$).

Example 19

N-Methyl-2-(2'-methylphenoxymethyl)-acetanilide a) N-Methyl-2-(2'-methylphenoxymethyl)-aniline A mixture of 5 g (23 mmol) of 2-(2'-methylphenoxymethyl)-aniline (Example 1b), 5 g (36 mmol) of K$_2$CO$_3$ and 3.4 g (24 mmol) of methyl iodide in 50 ml of dimethylformamide is stirred overnight at room temperature. The reaction mixture is diluted with water and the aqueous phase is extracted three times with methyl tert-butyl ether. The combined organic phases are extracted with water, dried over MgSO$_4$ and evaporated down. The residue is purified chromatographically using mixtures of hexane and methylene chloride. There is obtained 3.0 g (70% purity, about 40% yield) of the title compound as a yellow oil.

$^1$H-NMR (CDCl$_3$; δ in ppm): 6.6–7.4 (m, 8H, phenyl); 5.0 (s, 2H, OCH$_2$); 4.6 (s, broad, 1H, NH); 2.9 (d, 3H, N—CH$_3$); 2.2 (s, 3H, CH$_3$).

b) N-Methyl-2-(2'-methylphenoxymethyl)-acetanilide (Table 7, No. 9)

3 g (approx. 9.3 mmol) of N-methyl-2-(2'-methylphenoxymethyl)-aniline (from Example 5a) is added to a mixture of 1.6 g (16 mmol) of acetoanhydride and 1.3 g (16 mmol) of pyridine in 20 ml of methylene chloride. The mixture is stirred for 1 hour at room temperature and is then extracted with dilute hydrochloric acid and water. The organic phase is evaporated down and the residue is purified by column chromatography with mixtures of hexane and ethyl acetate. There is obtained 2 g (80%) of the title compound as a colorless solid (mp=76° C.).

$^1$H-NMR (CDCl$_3$; δ in ppm): 7.7 (m, 1H, phenyl); 7.4 (m, 2H, phenyl); 7.2 (m, 3H, phenyl); 6.9 (m, 2H, phenyl); 5.0 (s, 2H, OCH$_2$); 3.25 (s, 3H, CH$_3$); 2.25 (s, 3H, CH$_3$); 1.8 (s, 3H, CH$_3$).

The compounds listed in the tables below may be prepared correspondingly.

Compound I from Table 32, No. 1 has for example the following structural formula:

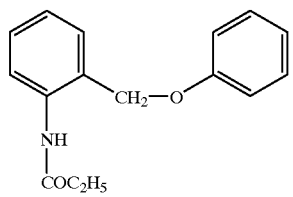

The compounds described in the following tables may be prepared analogously.

TABLE 32

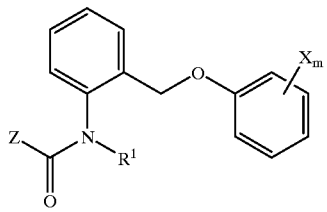

I: $R^1$ = H, Z = $C_2H_5$
II: $R^1$ = $CH_3$, Z = $C_2H_5$
III: $R^1$ = $C_2H_5$, Z = $C_2H_5$
IV: $R^1$ = Allyl, Z = $C_2H_5$
V: $R^1$ = Propargyl, Z = $C_2H_5$
VI: $R^1$ = $CH_2$—$OCH_3$, Z = $C_2H_5$
VII: $R^1$ = CO—$C_2H_5$, Z = $C_2H_5$
VIII: $R^1$ = H, Z = $NH(CH_3)$
IX: $R^1$ = $CH_3$, Z = $NH(CH_3)$
X: $R^1$ = $C_2H_5$, Z = $NH(CH_3)$
XI: $R^1$ = Allyl, Z = $NH(CH_3)$
XII: $R^1$ = Propargyl, Z = $NH(CH_3)$
XIII: $R^1$ = $CH_2$—$OCH_3$, Z = $NH(CH_3)$
XIV: $R^1$ = CO—$C_2H_5$, Z = $NH(CH_3)$

| No. | $X_m$ |
|---|---|
| 1 | H |
| 2 | 2-F |
| 3 | 3-F |
| 4 | 4-F |
| 5 | 2,4-$F_2$ |
| 6 | 2,4,6-$F_3$ |
| 7 | 2,3,4,5,6-$F_5$ |
| 8 | 2,3-$F_2$ |
| 9 | 2-Cl |
| 10 | 3-Cl |
| 11 | 4-Cl |
| 12 | 2,3-$Cl_2$ |
| 13 | 2,4-$Cl_2$ |
| 14 | 2,5-$Cl_2$ |
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |

TABLE 32-continued

| | |
|---|---|
| 37 | 4-I |
| 38 | 2,4-$I_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-$Cl_2$, 4-Br |
| 66 | 2-$CH_3$ |
| 67 | 3-$CH_3$ |
| 68 | 4-$CH_3$ |
| 69 | 2,3-$(CH_3)_2$ |
| 70 | 2,4-$(CH_3)_2$ |
| 71 | 2,5-$(CH_3)_2$ |
| 72 | 2,6-$(CH_3)_2$ |
| 73 | 3,4-$(CH_3)_2$ |
| 74 | 3,5-$(CH_3)_2$ |
| 75 | 2,3,5-$(CH_3)_3$ |
| 76 | 2,3,4-$(CH_3)_3$ |
| 77 | 2,3,6-$(CH_3)_3$ |
| 78 | 2,4,5-$(CH_3)_3$ |
| 79 | 2,4,6-$(CH_3)_3$ |
| 80 | 3,4,5-$(CH_3)_3$ |
| 81 | 2,3,4,6-$(CH_3)_4$ |
| 82 | 2,3,5,6-$(CH_3)_4$ |
| 83 | 2,3,4,5,6-$(CH_3)_5$ |
| 84 | 2-$C_2H_5$ |
| 85 | 3-$C_2H_5$ |
| 86 | 4-$C_2H_5$ |
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C_2H_5)_3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7)_2$ |
| 98 | 2,6-(i-$C_3H_7)_2$ |
| 99 | 3,5-(i-$C_3H_7)_2$ |
| 100 | 2,4,6-(i-$C_3H_7)_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9)_2$ |
| 108 | 2,4-(t-$C_4H_9)_2$ |
| 109 | 2,5-(t-$C_4H_9)_2$ |
| 110 | 2,6-(t-$C_4H_9)_2$ |
| 111 | 3,4-(t-$C_4H_9)_2$ |
| 112 | 2,4,6-(t-$C_4H_9)_3$ |
| 113 | 4-n-$C_9H_{19}$ |
| 114 | 4-n-$C_{12}H_{25}$ |
| 115 | 4-n-$C_{15}H_{31}$ |

TABLE 32-continued

| | |
|---|---|
| 116 | 4-(1,1,3,3-Tetramethylbutyl) |
| 117 | 4-(2,4,4-Trimethylpropyl) |
| 118 | 2-t-$C_4H_9$, 4-$CH_3$ |
| 119 | 2-t-$C_4H_9$, 5-$CH_3$ |
| 120 | 2,6-(t-$C_4H_9$)$_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9$)$_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11}$)$_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-($CH_3$)$_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$OCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-$C_6H_{13}$ |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—($CH_2$)$_3C_6H_5$ |
| 181 | 3-O—($CH_2$)$_3C_6H_5$ |
| 182 | 4-O—($CH_2$)$_3C_6H_5$ |
| 183 | 2,4-($OCH_3$)$_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 2-$CH_3$, 4-Cl |
| 199 | 2-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-$CH_3$, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-($CH_3$)$_2$ |
| 228 | 2-Br, 4,5-($CH_3$)$_2$ |
| 229 | 2-Cl, 3,5-($CH_3$)$_2$ |
| 230 | 2-Br, 3,5-($CH_3$)$_2$ |
| 231 | 2,6-$Cl_2$, 4-$CH_3$ |
| 232 | 2,6-$F_2$, 4-$CH_3$ |
| 233 | 2,5-$Br_2$, 4-$CH_3$ |
| 234 | 2,4-$Br_2$, 6-$CH_3$ |
| 235 | 2,4-$F_2$, 6-$CH_3$ |
| 236 | 2,4-$Br_2$, 6-$CH_3$ |
| 237 | 2,6-($CH_3$)$_2$, 4-F |
| 238 | 2,6-($CH_3$)$_2$, 4-Cl |
| 239 | 2,6-($CH_3$)$_2$, 4-Br |
| 240 | 3,5-($CH_3$)$_2$, 4-F |
| 241 | 3,5-($CH_3$)$_2$, 4-Cl |
| 242 | 3,5-($CH_3$)$_2$, 4-Br |
| 243 | 2,3,6-($CH_3$)$_3$, 4-F |
| 244 | 2,3,6-($CH_3$)$_3$, 4-Cl |
| 245 | 2,3,6-($CH_3$)$_3$, 4-Br |
| 246 | 2,4-($CH_3$)$_2$, 6-F |
| 247 | 2,4-($CH_3$)$_2$, 6-Cl |
| 248 | 2,4-($CH_3$)$_2$, 6-Br |
| 249 | 2-i-$C_3H_7$, 4-Cl, 5-$CH_3$ |
| 250 | 2-Cl, 4-$NO_2$ |
| 251 | 2-$NO_2$, 4-Cl |
| 252 | 2-$OCH_3$, 5-$NO_2$ |
| 253 | 2,4-$Cl_2$, 5-$NO_2$ |
| 254 | 2,4-$Cl_2$, 6-$NO_2$ |
| 255 | 2,6-$Cl_2$, 4-$NO_2$ |
| 256 | 2,6-$Br_2$, 4-$NO_2$ |
| 257 | 2,6-$I_2$, 4-$NO_2$ |
| 258 | 2-$CH_3$, 5-i-$C_3H_7$, 4-Cl |
| 259 | 2-$CO_2CH_3$ |
| 260 | 3-$CO_2CH_3$ |
| 261 | 4-$CO_2CH_3$ |
| 262 | 2-$CO_2$($C_2H_5$) |
| 263 | 3-$CO_2$($C_2H_5$) |
| 264 | 4-$CO_2$($C_2H_5$) |
| 265 | 2-$CO_2$(n-$C_3H_7$) |
| 266 | 3-$CO_2$(n-$C_3H_7$) |
| 267 | 4-$CO_2$(n-$C_3H_7$) |
| 268 | 2-$CO_2$(i-$C_3H_7$) |
| 269 | 3-$CO_2$(i-$C_3H_7$) |
| 270 | 4-$CO_2$(i-$C_3H_7$) |
| 271 | 2-$CO_2$(n-$C_6H_{13}$) |
| 272 | 3-$CO_2$(n-$C_6H_{13}$) |
| 273 | 4-$CO_2$(n-$C_6H_{13}$) |

TABLE 32-continued

| | |
|---|---|
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CO—CH$_2$—CH$_2$—CH$_3$ |
| 305 | 2-Me-4-CO—CH(CH$_3$)$_2$ |
| 306 | 2,5-Me$_2$-4-CHO |
| 307 | 2,5-Me$_2$-4-CO—CH$_3$ |
| 308 | 2,5-Me$_2$-4-CO—CH$_2$—CH$_3$ |
| 309 | 2,5-Me$_2$-4-CH$_2$—CH$_2$—CO—CH$_3$ |
| 310 | 2,5-Me$_2$-4-CO—CH(CH$_3$)$_2$ |
| 311 | 2-Cl-4-CHO |
| 312 | 2-Cl-4-CO—CH$_3$ |
| 313 | 2-Cl-4-CO—CH$_2$—CH$_3$ |
| 314 | 2-Cl-4-CO—CH(CH$_3$)$_2$ |
| 315 | 2,5-Cl$_2$-4-CHO |
| 316 | 2,5-Cl$_2$-4-CO—CH$_3$ |
| 317 | 2,5-Cl$_2$-4-CO—CH$_2$—CH$_3$ |
| 318 | 2,5-Cl$_2$-4-CO—CH$_2$—CH$_2$—CH$_3$ |
| 319 | 2,5-Cl$_2$-4-CO—CH(CH$_3$)$_2$ |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |

TABLE 32-continued

| | |
|---|---|
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |

TABLE 32-continued

| | |
|---|---|
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-$CH_3$-4-($CH_3$—C=N—O—$CH_2$—$CH_2$—$OCH_3$) |
| 642 | 2-$CH_3$-4-($C_2H_5$—C=N—O—$CH_2$—$CH_2$—$OCH_3$) |
| 643 | 2,5-($CH_3$)$_2$-4-($CH_3$—C=N—O—$CH_2$—$CH_2$—$OCH_3$) |
| 644 | 2-$CH_3$-4-(n-$C_3H_7$—C=N—$OCH_3$) |
| 645 | 2-$CH_3$-4-(n-$C_3H_7$—C=N—$OC_2H_5$) |
| 646 | 2-$CH_3$-4-(n-$C_3H_7$—C=N—O-n-$C_3H_7$) |
| 647 | 2-$CH_3$-4-(n-$C_3H_7$—C=N—O-i-$C_3H_7$) |
| 648 | 2-$CH_3$-4-(n-$C_3H_7$—C=N—O-Allyl) |
| 649 | 2-$CH_3$-4-(n-$C_3H_7$—C=N—O-trans-Chloroallyl) |
| 650 | 2-$CH_3$-4-(n-$C_3H_7$—C=N—O-Propargyl) |
| 651 | 2-$CH_3$-4-(n-$C_3H_7$—C=N—O-n-$C_4H_9$) |
| 652 | 2-$CH_3$-4-(n-$C_3H_7$—C=N—O—$CH_2$—$C_6H_5$) |
| 653 | 2-$CH_3$-4-(i-$C_3H_7$—C=N—$OCH_3$) |
| 654 | 2-$CH_3$-4-(i-$C_3H_7$—C=N—$OC_2H_5$) |
| 655 | 2-$CH_3$-4-(i-$C_3H_7$—C=N—O-n-$C_3H_7$) |
| 656 | 2-$CH_3$-4-(i-$C_3H_7$—C=N—O-i-$C_3H_7$) |
| 657 | 2-$CH_3$-4-(i-$C_3H_7$—C=N—O-Allyl) |
| 658 | 2-$CH_3$-4-(i-$C_3H_7$—C=N—O-trans-Chloroallyl) |
| 659 | 2-$CH_3$-4-(i-$C_3H_7$—C=N—O-Propargyl) |
| 660 | 2-$CH_3$-4-(i-$C_3H_7$—C=N—O-n-$C_4H_9$) |
| 661 | 2-$CH_3$-4-(i-$C_3H_7$—C=N—O—$CH_2$—$C_6H_5$) |
| 662 | 2-O-n-$C_4H_9$ |
| 663 | 2-O-i-$C_4H_9$ |
| 664 | 2-O-s-$C_4H_9$ |
| 665 | 2-O-t-$C_4H_9$ |
| 666 | 2-Neopentyloxy |
| 667 | 3-O-n-$C_4H_9$ |
| 668 | 3-O-i-$C_4H_9$ |
| 669 | 3-O-s-$C_4H_9$ |
| 670 | 3-O-t-$C_4H_9$ |
| 671 | 3-Neopentyloxy |
| 672 | 4-O-n-$C_4H_9$ |
| 673 | 4-O-i-$C_4H_9$ |
| 674 | 4-O-s-$C_4H_9$ |
| 675 | 4-O-t-$C_4H_9$ |
| 676 | 4-Neopentyloxy |
| 677 | 3-$CH_3$-4-$OCH_3$ |
| 678 | 3-$CH_3$-4-$OC_2H_5$ |
| 679 | 3-$CH_3$-4-O-n-$C_3H_7$ |
| 680 | 3-$CH_3$-4-O-n-$C_4H_9$ |
| 681 | 3-$CH_3$-4-O-i-$C_4H_9$ |
| 682 | 3-$CH_3$-4-O-s-$C_4H_9$ |
| 683 | 3-$CH_3$-4-O-t-$C_4H_9$ |
| 684 | 3-$CH_3$-4-Neopentyloxy |
| 685 | 2-$CH_3$-3-$OCH_3$ |
| 686 | 2-$CH_3$-4-$OCH_3$ |
| 687 | 2-$CH_3$-5-$OCH_3$ |
| 688 | 2-$CH_3$-6-$OCH_3$ |
| 689 | 3-$CH_3$-4-$OCH_3$ |
| 690 | 3-$CH_3$-5-$OCH_3$ |
| 691 | 3-$CH_3$-6-$OCH_3$ |
| 692 | 4-$CH_3$-5-O—$CH_3$ |
| 693 | 4-$CH_3$-6-O—$CH_3$ |
| 694 | 4-$CH_3$-6-$OCH_3$ |
| 695 | 2-$CH_3$-3-O-i-$C_3H_7$ |
| 696 | 2-$CH_3$-4-O-i-$C_3H_7$ |
| 697 | 2-$CH_3$-5-O-i-$C_3H_7$ |
| 698 | 2-$CH_3$-6-O-i-$C_3H_7$ |
| 699 | 3-$CH_3$-4-O-i-$C_3H_7$ |
| 700 | 3-$CH_3$-5-O-i-$C_3H_7$ |
| 701 | 3-$CH_3$-6-O-i-$C_3H_7$ |
| 702 | 4-$CH_3$-5-O-i-$C_3H_7$ |
| 703 | 4-$CH_3$-6-O-i-$C_3H_7$ |
| 704 | 5-$CH_3$-6-O-i-$C_3H_7$ |
| 705 | 2-Cl-3-$OCH_3$ |
| 706 | 2-Cl-4-$OCH_3$ |
| 707 | 2-Cl-5-$OCH_3$ |
| 708 | 2-Cl-6-$OCH_3$ |
| 709 | 3-Cl-4-$OCH_3$ |
| 710 | 3-Cl-5-$OCH_3$ |
| 711 | 3-Cl-6-$OCH_3$ |
| 712 | 4-Cl-5-$OCH_3$ |
| 713 | 4-Cl-6-$OCH_3$ |
| 714 | 5-Cl-6-$OCH_3$ |

TABLE 33

I: $R^1$ = H, Z = $C_2H_5$
II: $R^1$ = $CH_3$, Z = $C_2H_5$
III: $R^1$ = $C_2H_5$, Z = $C_2H_5$
IV: $R^1$ = Allyl, Z = $C_2H_5$
V: $R^1$ = Propargyl, Z = $C_2H_5$
VI: $R^1$ = $CH_2$—$OCH_3$, Z = $C_2H_5$
VII: $R^1$ = CO—$C_2H_5$, Z = $C_2H_5$
VIII: $R^1$ = H, Z = $NH(CH_3)$
IX: $R^1$ = $CH_3$, Z = $NH(CH_3)$
X: $R^1$ = $C_2H_5$, Z = $NH(CH_3)$
XI: $R^1$ = Allyl, Z = $NH(CH_3)$
XII: $R^1$ = Propargyl, Z = $NH(CH_3)$
XIII: $R^1$ = $CH_2$—$OCH_3$, Z = $NH(CH_3)$
XIV: $R^1$ = CO—$C_2H_5$, Z = $NH(CH_3)$

| No. | $X_m$ |
|---|---|
| 1 | H |
| 2 | 2-F |

TABLE 33-continued

| | |
|---|---|
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |

TABLE 33-continued

| | |
|---|---|
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |

TABLE 33-continued

| | |
|---|---|
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,5-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CO—CH$_2$—CH$_3$ |
| 304 | 2-Me-4-CO—CH$_2$—CH$_2$—CH$_3$ |
| 305 | 2-Me-4-CO—CH(CH$_3$)$_2$ |
| 306 | 2,5-Me$_2$-4-CHO |
| 307 | 2,5-Me$_2$-4-CO—CH$_3$ |
| 308 | 2,5-Me$_2$-4-CO—CH$_2$—CH$_3$ |
| 309 | 2,5-Me$_2$-4-CH$_2$—CH$_2$—CO—CH$_3$ |
| 310 | 2,5-Me$_2$-4-CO—CH(CH$_3$)$_2$ |
| 311 | 2-Cl-4-CHO |
| 312 | 2-Cl-4-CO—CH$_3$ |
| 313 | 2-Cl-4-CO—CH$_2$—CH$_3$ |
| 314 | 2-Cl-4-CO—CH(CH$_3$)$_2$ |
| 315 | 2,5-Cl$_2$-4-CHO |

TABLE 33-continued

| | |
|---|---|
| 316 | 2,5-Cl$_2$-4-CO—CH$_3$ |
| 317 | 2,5-Cl$_2$-4-CO—CH$_2$—CH$_3$ |
| 318 | 2,5-Cl$_2$-4-CO—CH$_2$—CH$_2$—CH$_3$ |
| 319 | 2,5-Cl$_2$-4-CO—CH(CH$_3$)$_2$ |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |

TABLE 33-continued

| | |
|---|---|
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |

TABLE 33-continued

| | |
|---|---|
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-$CH_3$-4-($CH_3$—C=N—O—$CH_2$—$CH_2$—$OCH_3$) |
| 642 | 2-$CH_3$-4-($C_2H_5$—C=N—O—$CH_2$—$CH_2$—$OCH_3$) |
| 643 | 2,5-$(CH_3)_2$-4-($CH_3$—C=N—O—$CH_2$—$CH_2$—$OCH_3$) |
| 644 | 2-$CH_3$-4-(n-$C_3H_7$—C=N—$OCH_3$) |
| 645 | 2-$CH_3$-4-(n-$C_3H_7$—C=N—$OC_2H_5$) |
| 646 | 2-$CH_3$-4-(n-$C_3H_7$—C=N—O-n-$C_3H_7$) |
| 647 | 2-$CH_3$-4-(n-$C_3H_7$—C=N—O-i-$C_3H_7$) |
| 648 | 2-$CH_3$-4-(n-$C_3H_7$—C=N—O-Allyl) |
| 649 | 2-$CH_3$-4-(n-$C_3H_7$—C=N—O-trans-Chloroallyl) |
| 650 | 2-$CH_3$-4-(n-$C_3H_7$—C=N—O-Propargyl) |
| 651 | 2-$CH_3$-4-(n-$C_3H_7$—C=N—O-n-$C_4H_9$) |
| 652 | 2-$CH_3$-4-(n-$C_3H_7$—C=N—O—$CH_2$—$C_6H_5$) |
| 653 | 2-$CH_3$-4-(i-$C_3H_7$—C=N—$OCH_3$) |
| 654 | 2-$CH_3$-4-(i-$C_3H_7$—C=N—$OC_2H_5$) |
| 655 | 2-$CH_3$-4-(i-$C_3H_7$—C=N—O-n-$C_3H_7$) |
| 656 | 2-$CH_3$-4-(i-$C_3H_7$—C=N—O-i-$C_3H_7$) |
| 657 | 2-$CH_3$-4-(i-$C_3H_7$—C=N—O-Allyl) |
| 658 | 2-$CH_3$-4-(i-$C_3H_7$—C=N—O-trans-Chloroallyl) |
| 659 | 2-$CH_3$-4-(i-$C_3H_7$—C=N—O-Propargyl) |
| 660 | 2-$CH_3$-4-(i-$C_3H_7$—C=N—O-n-$C_4H_9$) |
| 661 | 2-$CH_3$-4-(i-$C_3H_7$—C=N—O—$CH_2$—$C_6H_5$) |
| 662 | 2-O-n-$C_4H_9$ |
| 663 | 2-O-i-$C_4H_9$ |
| 664 | 2-O-s-$C_4H_9$ |
| 665 | 2-O-t-$C_4H_9$ |
| 666 | 2-Neopentyloxy |
| 667 | 3-O-n-$C_4H_9$ |
| 668 | 3-O-i-$C_4H_9$ |
| 669 | 3-O-s-$C_4H_9$ |
| 670 | 3-O-t-$C_4H_9$ |
| 671 | 3-Neopentyloxy |
| 672 | 4-O-n-$C_4H_9$ |
| 673 | 4-O-i-$C_4H_9$ |
| 674 | 4-O-s-$C_4H_9$ |
| 675 | 4-O-t-$C_4H_9$ |
| 676 | 4-Neopentyloxy |
| 677 | 3-$CH_3$-4-$OCH_3$ |
| 678 | 3-$CH_3$-4-$OC_2H_5$ |
| 679 | 3-$CH_3$-4-O-n-$C_3H_7$ |
| 680 | 3-$CH_3$-4-O-n-$C_4H_9$ |
| 681 | 3-$CH_3$-4-O-i-$C_4H_9$ |
| 682 | 3-$CH_3$-4-O-s-$C_4H_9$ |
| 683 | 3-$CH_3$-4-O-t-$C_4H_9$ |
| 684 | 3-$CH_3$-4-Neopentyloxy |
| 685 | 2-$CH_3$-3-$OCH_3$ |
| 686 | 2-$CH_3$-4-$OCH_3$ |
| 687 | 2-$CH_3$-5-$OCH_3$ |
| 688 | 2-$CH_3$-6-$OCH_3$ |
| 689 | 3-$CH_3$-4-$OCH_3$ |
| 690 | 3-$CH_3$-5-$OCH_3$ |
| 691 | 3-$CH_3$-6-$OCH_3$ |
| 692 | 4-$CH_3$-5-O—$CH_3$ |
| 693 | 4-$CH_3$-6-O—$CH_3$ |
| 694 | 4-$CH_3$-6-$OCH_3$ |
| 695 | 2-$CH_3$-3-O-i-$C_3H_7$ |
| 696 | 2-$CH_3$-4-O-i-$C_3H_7$ |
| 697 | 2-$CH_3$-5-O-i-$C_3H_7$ |
| 698 | 2-$CH_3$-6-O-i-$C_3H_7$ |
| 699 | 3-$CH_3$-4-O-i-$C_3H_7$ |
| 700 | 3-$CH_3$-5-O-i-$C_3H_7$ |
| 701 | 3-$CH_3$-6-O-i-$C_3H_7$ |
| 702 | 4-$CH_3$-5-O-i-$C_3H_7$ |
| 703 | 4-$CH_3$-6-O-i-$C_3H_7$ |
| 704 | 5-$CH_3$-6-O-i-$C_3H_7$ |
| 705 | 2-Cl-3-$OCH_3$ |
| 706 | 2-Cl-4-$OCH_3$ |
| 707 | 2-Cl-5-$OCH_3$ |
| 708 | 2-Cl-6-$OCH_3$ |
| 709 | 3-Cl-4-$OCH_3$ |

TABLE 33-continued

| | |
|---|---|
| 710 | 3-Cl-5-$OCH_3$ |
| 711 | 3-Cl-6-$OCH_3$ |
| 712 | 4-Cl-5-$OCH_3$ |
| 713 | 4-Cl-6-$OCH_3$ |
| 714 | 5-Cl-6-$OCH_3$ |

TABLE 34

I: $R^1$ = H, Z = $C_2H_5$
II: $R^1$ = $CH_3$, Z = $C_2H_5$
III: $R^1$ = $C_2H_5$, Z = $C_2H_5$
IV: $R^1$ = Allyl, Z = $C_2H_5$
V: $R^1$ = Propargyl, Z = $C_2H_5$
VI: $R^1$ = $CH_2$—$OCH_3$, Z = $C_2H_5$
VII: $R^1$ = CO—$C_2H_5$, Z = $C_2H_5$
VIII: $R^1$ = H, Z = NH($CH_3$)
IX: $R^1$ = $CH_3$, Z = NH($CH_3$)
X: $R^1$ = $C_2H_5$, Z = NH($CH_3$)
XI: $R^1$ = Allyl, Z = NH($CH_3$)
XII: $R^1$ = Propargyl, Z = NH($CH_3$)
XIII: $R^1$ = $CH_2$—$OCH_3$, Z = NH($CH_3$)
XIV: $R^1$ = CO—$C_2H_5$, Z = NH($CH_3$)

| No. | $X_m$ |
|---|---|
| 1 | H |
| 2 | 2-F |
| 3 | 3-F |
| 4 | 4-F |
| 5 | 2,4-$F_2$ |
| 6 | 2,4,6-$F_3$ |
| 7 | 2,3,4,5,6-$F_5$ |
| 8 | 2,3-$F_2$ |
| 9 | 2-Cl |
| 10 | 3-Cl |
| 11 | 4-Cl |
| 12 | 2,3-$Cl_2$ |
| 13 | 2,4-$Cl_2$ |
| 14 | 2,5-$Cl_2$ |
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |
| 37 | 4-I |
| 38 | 2,4-$I_2$ |
| 39 | 2-Cl, 3-F |
| 40 | 2-Cl, 4-F |
| 41 | 2-Cl, 5-F |

TABLE 34-continued

| | |
|---|---|
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |

TABLE 34-continued

| | | |
|---|---|---|
| 200 | 2-CH$_3$, 6-Cl | |
| 201 | 2-CH$_3$, 3-F | |
| 202 | 2-CH$_3$, 4-F | |
| 203 | 2-CH$_3$, 5-F | |
| 204 | 2-CH$_3$, 6-F | |
| 205 | 2-CH$_3$, 3-Br | |
| 206 | 2-CH$_3$, 4-Br | |
| 207 | 2-CH$_3$, 5-Br | |
| 208 | 2-CH$_3$, 6-Br | |
| 209 | 2-Cl, 3-CH$_3$ | |
| 210 | 2-Cl, 4-CH$_3$ | |
| 211 | 2-Cl, 5-CH$_3$ | |
| 212 | 2-F, 3-CH$_3$ | |
| 213 | 2-F, 4-CH$_3$ | |
| 214 | 2-F, 5-CH$_3$ | |
| 215 | 2-Br, 3-CH$_3$ | |
| 216 | 2-Br, 4-CH$_3$ | |
| 217 | 2-Br, 5-CH$_3$ | |
| 218 | 3-CH$_3$, 4-Cl | |
| 219 | 3-CH$_3$, 5-Cl | |
| 220 | 3-CH$_3$, 4-F | |
| 221 | 3-CH$_3$, 5-F | |
| 222 | 3-CH$_3$, 4-Br | |
| 223 | 3-CH$_3$, 5-Br | |
| 224 | 3-F, 4-CH$_3$ | |
| 225 | 3-Cl, 4-CH$_3$ | |
| 226 | 3-Br, 4-CH$_3$ | |
| 227 | 2-Cl, 4,5-(CH$_3$)$_2$ | |
| 228 | 2-Br, 4,5-(CH$_3$)$_2$ | |
| 229 | 2-Cl, 3,5-(CH$_3$)$_2$ | |
| 230 | 2-Br, 3,5-(CH$_3$)$_2$ | |
| 231 | 2,6-Cl$_2$, 4-CH$_3$ | |
| 232 | 2,6-F$_2$, 4-CH$_3$ | |
| 233 | 2,5-Br$_2$, 4-CH$_3$ | |
| 234 | 2,4-Br$_2$, 6-CH$_3$ | |
| 235 | 2,4-F$_2$, 6-CH$_3$ | |
| 236 | 2,4-Br$_2$, 6-CH$_3$ | |
| 237 | 2,6-(CH$_3$)$_2$, 4-F | |
| 238 | 2,6-(CH$_3$)$_2$, 4-Cl | |
| 239 | 2,6-(CH$_3$)$_2$, 4-Br | |
| 240 | 3,5-(CH$_3$)$_2$, 4-F | |
| 241 | 3,5-(CH$_3$)$_2$, 4-Cl | |
| 242 | 3,5-(CH$_3$)$_2$, 4-Br | |
| 243 | 2,3,6-(CH$_3$)$_3$, 4-F | |
| 244 | 2,3,6-(CH$_3$)$_3$, 4-Cl | |
| 245 | 2,3,6-(CH$_3$)$_3$, 4-Br | |
| 246 | 2,4-(CH$_3$)$_2$, 6-F | |
| 247 | 2,4-(CH$_3$)$_2$, 6-Cl | |
| 248 | 2,4-(CH$_3$)$_2$, 6-Br | |
| 249 | 2-i-C$_3$H$_7$, 4-Cl, 5-CH$_3$ | |
| 250 | 2-Cl, 4-NO$_2$ | |
| 251 | 2-NO$_2$, 4-Cl | |
| 252 | 2-OCH$_3$, 5-NO$_2$ | |
| 253 | 2,4-Cl$_2$, 5-NO$_2$ | |
| 254 | 2,4-Cl$_2$, 6-NO$_2$ | |
| 255 | 2,6-Cl$_2$, 4-NO$_2$ | |
| 256 | 2,6-Br$_2$, 4-NO$_2$ | |
| 257 | 2,6-I$_2$, 4-NO$_2$ | |
| 258 | 2-CH$_3$, 5-i-C$_3$H$_7$, 4-Cl | |
| 259 | 2-CO$_2$CH$_3$ | |
| 260 | 3-CO$_2$CH$_3$ | |
| 261 | 4-CO$_2$CH$_3$ | |
| 262 | 2-CO$_2$(C$_2$H$_5$) | |
| 263 | 3-CO$_2$(C$_2$H$_5$) | |
| 264 | 4-CO$_2$(C$_2$H$_5$) | |
| 265 | 2-CO$_2$(n-C$_3$H$_7$) | |
| 266 | 3-CO$_2$(n-C$_3$H$_7$) | |
| 267 | 4-CO$_2$(n-C$_3$H$_7$) | |
| 268 | 2-CO$_2$(i-C$_3$H$_7$) | |
| 269 | 3-CO$_2$(i-C$_3$H$_7$) | |
| 270 | 4-CO$_2$(i-C$_3$H$_7$) | |
| 271 | 2-CO$_2$(n-C$_6$H$_{13}$) | |
| 272 | 3-CO$_2$(n-C$_6$H$_{13}$) | |
| 273 | 4-CO$_2$(n-C$_6$H$_{13}$) | |
| 274 | 2-CH$_2$—OCH$_3$ | |
| 275 | 3-CH$_2$—OCH$_3$ | |
| 276 | 4-CH$_2$—OCH$_3$ | |
| 277 | 2-CH$_2$O(C$_2$H$_5$) | |
| 278 | 3-CH$_2$O(C$_2$H$_5$) | |
| 279 | 4-CH$_2$O(C$_2$H$_5$) | |
| 280 | 2-CH$_2$O(n-C$_3$H$_7$) | |
| 281 | 3-CH$_2$O(n-C$_3$H$_7$) | |
| 282 | 4-CH$_2$O(n-C$_3$H$_7$) | |
| 283 | 2-CH$_2$O(i-C$_3$H$_7$) | |
| 284 | 3-CH$_2$O(i-C$_3$H$_7$) | |
| 285 | 4-CH$_2$O(i-C$_3$H$_7$) | |
| 286 | 2-CHO | |
| 287 | 3-CHO | |
| 288 | 4-CHO | |
| 289 | 2-CO—CH$_3$ | |
| 290 | 3-CO—CH$_3$ | |
| 291 | 4-CO—CH$_3$ | |
| 292 | 2-CO—CH$_2$—CH$_3$ | |
| 293 | 3-CO—CH$_2$—CH$_3$ | |
| 294 | 4-CO—CH$_2$—CH$_3$ | |
| 295 | 2-CO—CH$_2$—CH$_2$—CH$_3$ | |
| 296 | 3-CO—CH$_2$—CH$_2$—CH$_3$ | |
| 297 | 4-CO—CH$_2$—CH$_2$—CH$_3$ | |
| 298 | 2-CO—CH(CH$_3$)—CH$_3$ | |
| 299 | 3-CO—CH(CH$_3$)—CH$_3$ | |
| 300 | 4-CO—CH(CH$_3$)—CH$_3$ | |
| 301 | 2-Me-4-CHO | |
| 302 | 2-Me-4-CO—CH$_3$ | |
| 303 | 2-Me-4-CO—CH$_2$—CH$_3$ | |
| 304 | 2-Me-4-CO—CH$_2$—CH$_2$—CH$_3$ | |
| 305 | 2-Me-4-CO—CH(CH$_3$)$_2$ | |
| 306 | 2,5-Me$_2$-4-CHO | |
| 307 | 2,5-Me$_2$-4-CO—CH$_3$ | |
| 308 | 2,5-Me$_2$-4-CO—CH$_2$—CH$_3$ | |
| 309 | 2,5-Me$_2$-4-CH$_2$—CH$_2$—CO—CH$_3$ | |
| 310 | 2,5-Me$_2$-4-CO—CH(CH$_3$)$_2$ | |
| 311 | 2-Cl-4-CHO | |
| 312 | 2-Cl-4-CO—CH$_3$ | |
| 313 | 2-Cl-4-CO—CH$_2$—CH$_3$ | |
| 314 | 2-Cl-4-CO—CH(CH$_3$)$_2$ | |
| 315 | 2,5-Cl$_2$-4-CHO | |
| 316 | 2,5-Cl$_2$-4-CO—CH$_3$ | |
| 317 | 2,5-Cl$_2$-4-CO—CH$_2$—CH$_3$ | |
| 318 | 2,5-Cl$_2$-4-CO—CH$_2$—CH$_2$—CH$_3$ | |
| 319 | 2,5-Cl$_2$-4-CO—CH(CH$_3$)$_2$ | |
| 320 | 2-C(=NOCH$_3$)—CH$_3$ | |
| 321 | 3-C(=NOCH$_3$)—CH$_3$ | |
| 322 | 4-C(=NOCH$_3$)—CH$_3$ | |
| 323 | 2-C(=NOC$_2$H$_5$)—CH$_3$ | |
| 324 | 3-C(=NOC$_2$H$_5$)—CH$_3$ | |
| 325 | 4-C(=NOC$_2$H$_5$)—CH$_3$ | |
| 326 | 2-C(=NO-n-C$_3$H$_7$)—CH$_3$ | |
| 327 | 3-C(=NO-n-C$_3$H$_7$)—CH$_3$ | |
| 328 | 4-C(=NO-n-C$_3$H$_7$)—CH$_3$ | |
| 329 | 2-C(=NO-i-C$_3$H$_7$)—CH$_3$ | |
| 330 | 3-C(=NO-i-C$_3$H$_7$)—CH$_3$ | |
| 331 | 4-C(=NO-i-C$_3$H$_7$)—CH$_3$ | |
| 332 | 2-C(=NO-Allyl)-CH$_3$ | |
| 333 | 3-C(=NO-Allyl)-CH$_3$ | |
| 334 | 4-C(=NO-Allyl)-CH$_3$ | |
| 335 | 2-C(=NO-trans-Chloroallyl)-CH$_3$ | |
| 336 | 3-C(=NO-trans-Chloroallyl)-CH$_3$ | |
| 337 | 4-C(=NO-trans-Chloroallyl)-CH$_3$ | |
| 338 | 2-C(=NO-Propargyl)-CH$_3$ | |
| 339 | 3-C(=NO-Propargyl)-CH$_3$ | |
| 340 | 4-C(=NO-Propargyl)-CH$_3$ | |
| 341 | 2-C(=NO-n-C$_4$H$_9$)—CH$_3$ | |
| 342 | 3-C(=NO-n-C$_4$H$_9$)—CH$_3$ | |
| 343 | 4-C(=NO-n-C$_4$H$_9$)—CH$_3$ | |
| 344 | 2-C(=NO—CH$_2$—C$_6$H$_5$)—CH$_3$ | |
| 345 | 3-C(=NO—CH$_2$—C$_6$H$_5$)—CH$_3$ | |
| 346 | 4-C(=NO—CH$_2$—C$_6$H$_5$)—CH$_3$ | |
| 347 | 2-CH$_3$-4-CH=NOCH$_3$ | |
| 348 | 2-CH$_3$-4-CH=NOC$_2$H$_5$ | |
| 349 | 2-CH$_3$-4-CH=NO-n-C$_3$H$_7$ | |
| 350 | 2-CH$_3$-4-CH=NO-i-C$_3$H$_7$ | |
| 351 | 2-CH$_3$-4-CH=NO-Allyl | |
| 352 | 2-CH$_3$-4-CH=NO-(trans-Chloroallyl) | |
| 353 | 2-CH$_3$-4-CH=NO-Propargyl | |
| 354 | 2-CH$_3$-4-CH=NO-n-C$_4$H$_9$ | |
| 355 | 2-CH$_3$-4-CH=NO—CH$_2$—C$_6$H$_5$ | |
| 356 | 2-CH$_3$-4-(CH$_3$—C=NOCH$_3$) | |
| 357 | 2-CH$_3$-4-(CH$_3$—C=NOC$_2$H$_5$) | |

TABLE 34-continued

| | |
|---|---|
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |

TABLE 34-continued

| | |
|---|---|
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-CH$_3$-4-(CH$_3$—C=N—O—CH$_2$—CH$_2$—OCH$_3$) |
| 642 | 2-CH$_3$-4-(C$_2$H$_5$—C=N—O—CH$_2$—CH$_2$—OCH$_3$) |
| 643 | 2,5-(CH$_3$)$_2$-4-(CH$_3$—C=N—O—CH$_2$—CH$_2$—OCH$_3$) |
| 644 | 2-CH$_3$-4-(n-C$_3$H$_7$—C=N—OCH$_3$) |
| 645 | 2-CH$_3$-4-(n-C$_3$H$_7$—C=N—OC$_2$H$_5$) |
| 646 | 2-CH$_3$-4-(n-C$_3$H$_7$—C=N—O-n-C$_3$H$_7$) |
| 647 | 2-CH$_3$-4-(n-C$_3$H$_7$—C=N—O-i-C$_3$H$_7$) |
| 648 | 2-CH$_3$-4-(n-C$_3$H$_7$—C=N—O-Allyl) |
| 649 | 2-CH$_3$-4-(n-C$_3$H$_7$—C=N—O-trans-Chloroallyl) |
| 650 | 2-CH$_3$-4-(n-C$_3$H$_7$—C=N—O-Propargyl) |
| 651 | 2-CH$_3$-4-(n-C$_3$H$_7$—C=N—O-n-C$_4$H$_9$) |
| 652 | 2-CH$_3$-4-(n-C$_3$H$_7$—C=N—O—CH$_2$—C$_6$H$_5$) |
| 653 | 2-CH$_3$-4-(i-C$_3$H$_7$—C=N—OCH$_3$) |
| 654 | 2-CH$_3$-4-(i-C$_3$H$_7$—C=N—OC$_2$H$_5$) |
| 655 | 2-CH$_3$-4-(i-C$_3$H$_7$—C=N—O-n-C$_3$H$_7$) |
| 656 | 2-CH$_3$-4-(i-C$_3$H$_7$—C=N—O-i-C$_3$H$_7$) |
| 657 | 2-CH$_3$-4-(i-C$_3$H$_7$—C=N—O-Allyl) |
| 658 | 2-CH$_3$-4-(i-C$_3$H$_7$—C=N—O-trans-Chloroallyl) |
| 659 | 2-CH$_3$-4-(i-C$_3$H$_7$—C=N—O-Propargyl) |
| 660 | 2-CH$_3$-4-(i-C$_3$H$_7$—C=N—O-n-C$_4$H$_9$) |
| 661 | 2-CH$_3$-4-(i-C$_3$H$_7$—C=N—O—CH$_2$—C$_6$H$_5$) |
| 662 | 2-O-n-C$_4$H$_9$ |
| 663 | 2-O-i-C$_4$H$_9$ |
| 664 | 2-O-s-C$_4$H$_9$ |
| 665 | 2-O-t-C$_4$H$_9$ |
| 666 | 2-Neopentyloxy |
| 667 | 3-O-n-C$_4$H$_9$ |
| 668 | 3-O-i-C$_4$H$_9$ |
| 669 | 3-O-s-C$_4$H$_9$ |
| 670 | 3-O-t-C$_4$H$_9$ |
| 671 | 3-Neopentyloxy |
| 672 | 4-O-n-C$_4$H$_9$ |

TABLE 34-continued

| | |
|---|---|
| 673 | 4-O-i-C$_4$H$_9$ |
| 674 | 4-O-s-C$_4$H$_9$ |
| 675 | 4-O-t-C$_4$H$_9$ |
| 676 | 4-Neopentyloxy |
| 677 | 3-CH$_3$-4-OCH$_3$ |
| 678 | 3-CH$_3$-4-OC$_2$H$_5$ |
| 679 | 3-CH$_3$-4-O-n-C$_3$H$_7$ |
| 680 | 3-CH$_3$-4-O-n-C$_4$H$_9$ |
| 681 | 3-CH$_3$-4-O-i-C$_4$H$_9$ |
| 682 | 3-CH$_3$-4-O-s-C$_4$H$_9$ |
| 683 | 3-CH$_3$-4-O-t-C$_4$H$_9$ |
| 684 | 3-CH$_3$-4-Neopentyloxy |
| 685 | 2-CH$_3$-3-OCH$_3$ |
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 35

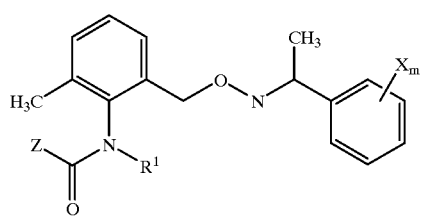

I: R$^1$ = H, Z = C$_2$H$_5$
II: R$^1$ = CH$_3$, Z = C$_2$H$_5$
III: R$^1$ = C$_2$H$_5$, Z = C$_2$H$_5$
IV: R$^1$ = Allyl, Z = C$_2$H$_5$
V: R$^1$ = Propargyl, Z = C$_2$H$_5$
VI: R$^1$ = CH$_2$—OCH$_3$, Z = C$_2$H$_5$
VII: R$^1$ = CO—C$_2$H$_5$, Z = C$_2$H$_5$
VIII: R$^1$ = H, Z = NH(CH$_3$)
IX: R$^1$ = CH$_3$, Z = NH(CH$_3$)
X: R$^1$ = C$_2$H$_5$, Z = NH(CH$_3$)
XI: R$^1$ = Allyl, Z = NH(CH$_3$)
XII: R$^1$ = Propargyl, Z = NH(CH$_3$)
XIII: R$^1$ = CH$_2$—OCH$_3$, Z = NH(CH$_3$)
XIV: R$^1$ = CO—C$_2$H$_5$, Z = NH(CH$_3$)

| No. | X$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |

TABLE 35-continued

| | |
|---|---|
| 84 | 2-$C_2H_5$ |
| 85 | 3-$C_2H_5$ |
| 86 | 4-$C_2H_5$ |
| 87 | 2,4-$(C_2H_5)_2$ |
| 88 | 2,6-$(C_2H_5)_2$ |
| 89 | 3,5-$(C_2H_5)_2$ |
| 90 | 2,4,6-$(C_2H_5)_3$ |
| 91 | 2-n-$C_3H_7$ |
| 92 | 3-n-$C_3H_7$ |
| 93 | 4-n-$C_3H_7$ |
| 94 | 2-i-$C_3H_7$ |
| 95 | 3-i-$C_3H_7$ |
| 96 | 4-i-$C_3H_7$ |
| 97 | 2,4-(i-$C_3H_7)_2$ |
| 98 | 2,6-(i-$C_3H_7)_2$ |
| 99 | 3,5-(i-$C_3H_7)_2$ |
| 100 | 2,4,6-(i-$C_3H_7)_3$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 2,3-(t-$C_4H_9)_2$ |
| 108 | 2,4-(t-$C_4H_9)_2$ |
| 109 | 2,5-(t-$C_4H_9)_2$ |
| 110 | 2,6-(t-$C_4H_9)_2$ |
| 111 | 3,4-(t-$C_4H_9)_2$ |
| 112 | 2,4,6-(t-$C_4H_9)_3$ |
| 113 | 4-n-$C_9H_{19}$ |
| 114 | 4-n-$C_{12}H_{25}$ |
| 115 | 4-n-$C_{15}H_{31}$ |
| 116 | 4-(1,1,3,3-Tetramethylbutyl) |
| 117 | 4-(2,4,4-Trimethylpropyl) |
| 118 | 2-t-$C_4H_9$, 4-$CH_3$ |
| 119 | 2-t-$C_4H_9$, 5-$CH_3$ |
| 120 | 2,6-(t-$C_4H_9)_2$, 4-$CH_3$ |
| 121 | 2-$CH_3$, 4-t-$C_4H_9$ |
| 122 | 2-$CH_3$, 6-t-$C_4H_9$ |
| 123 | 2-$CH_3$, 4-i-$C_3H_7$ |
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9)_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11})_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-$(CH_3)_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$OCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-$C_6H_{13}$ |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—$(CH_2)_3C_6H_5$ |
| 181 | 3-O—$(CH_2)_3C_6H_5$ |
| 182 | 4-O—$(CH_2)_3C_6H_5$ |
| 183 | 2,4-$(OCH_3)_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 2-$CH_3$, 4-Cl |
| 199 | 2-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-$CH_3$, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-$(CH_3)_2$ |
| 228 | 2-Br, 4,5-$(CH_3)_2$ |
| 229 | 2-Cl, 3,5-$(CH_3)_2$ |
| 230 | 2-Br, 3,5-$(CH_3)_2$ |
| 231 | 2,6-$Cl_2$, 4-$CH_3$ |
| 232 | 2,6-$F_2$, 4-$CH_3$ |
| 233 | 2,6-$Br_2$, 4-$CH_3$ |
| 234 | 2,4-$Br_2$, 6-$CH_3$ |
| 235 | 2,4-$F_2$, 6-$CH_3$ |
| 236 | 2,4-$Br_2$, 6-$CH_3$ |
| 237 | 2,6-$(CH_3)_2$, 4-F |
| 238 | 2,6-$(CH_3)_2$, 4-Cl |
| 239 | 2,6-$(CH_3)_2$, 4-Br |
| 240 | 3,5-$(CH_3)_2$, 4-F |
| 241 | 3,5-$(CH_3)_2$, 4-Cl |

TABLE 35-continued

| | |
|---|---|
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CO—CH$_2$—CH$_3$ |
| 304 | 2-Me-4-CO—CH$_2$—CH$_2$—CH$_3$ |
| 305 | 2-Me-4-CO—CH(CH$_3$)$_2$ |
| 306 | 2,5-Me$_2$-4-CHO |
| 307 | 2,5-Me$_2$-4-CO—CH$_3$ |
| 308 | 2,5-Me$_2$-4-CO—CH$_2$—CH$_3$ |
| 309 | 2,5-Me$_2$-4-CH$_2$—CH$_2$—CO—CH$_3$ |
| 310 | 2,5-Me$_2$-4-CO—CH(CH$_3$)$_2$ |
| 311 | 2-Cl-4-CHO |
| 312 | 2-Cl-4-CO—CH$_3$ |
| 313 | 2-Cl-4-CO—CH$_2$—CH$_3$ |
| 314 | 2-Cl-4-CO—CH(CH$_3$)$_2$ |
| 315 | 2,5-Cl$_2$-4-CHO |
| 316 | 2,5-Cl$_2$-4-CO—CH$_3$ |
| 317 | 2,5-Cl$_2$-4-CO—CH$_2$—CH$_3$ |
| 318 | 2,5-Cl$_2$-4-CO—CH$_2$—CH$_2$—CH$_3$ |
| 319 | 2,5-Cl$_2$-4-CO—CH(CH$_3$)$_2$ |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |

TABLE 35-continued

| | |
|---|---|
| 400 | 3-(4'-Cl—$C_6H_4$) |
| 401 | 4-(2'-Cl—$C_6H_4$) |
| 402 | 4-(3'-Cl—$C_6H_4$) |
| 403 | 4-(4'-Cl—$C_6H_4$) |
| 405 | 2-(2'-$CH_3$—$C_6H_4$) |
| 406 | 2-(3'-$CH_3$—$C_6H_4$) |
| 407 | 2-(4'-$CH_3$—$C_6H_4$) |
| 408 | 3-(2'-$CH_3$—$C_6H_4$) |
| 409 | 3-(3'-$CH_3$—$C_6H_4$) |
| 410 | 3-(4'-$CH_3$—$C_6H_4$) |
| 411 | 4-(2'-$CH_3$—$C_6H_4$) |
| 412 | 4-(3'-$CH_3$—$C_6H_4$) |
| 413 | 4-(4'-$CH_3$—$C_6H_4$) |
| 414 | 2-(2'-$CH_3$—CO—$C_6H_4$) |
| 415 | 2-(3'-$CH_3$—CO—$C_6H_4$) |
| 416 | 2-(4'-$CH_3$—CO—$C_6H_4$) |
| 417 | 3-(2'-$CH_3$—CO—$C_6H_4$) |
| 418 | 3-(3'-$CH_3$—CO—$C_6H_4$) |
| 419 | 3-(4'-$CH_3$—CO—$C_6H_4$) |
| 420 | 4-(2'-$CH_3$—CO—$C_6H_4$) |
| 421 | 4-(3'-$CH_3$—CO—$C_6H_4$) |
| 422 | 4-(4'-$CH_3$—CO—$C_6H_4$) |
| 423 | 2-(2'-($CH_3$—C(=NOAllyl))-$C_6H_4$) |
| 424 | 2-(3'-($CH_3$—C(=NOAllyl))-$C_6H_4$) |
| 425 | 2-(4'-($CH_3$—C(=NOAllyl))-$C_6H_4$) |
| 426 | 3-(2'-($CH_3$—C(=NOAllyl))-$C_6H_4$) |
| 427 | 3-(3'-($CH_3$—C(=NOAllyl))-$C_6H_4$) |
| 428 | 3-(4'-($CH_3$—C(=NOAllyl))-$C_6H_4$) |
| 429 | 4-(2'-($CH_3$—C(=NOAllyl))-$C_6H_4$) |
| 430 | 4-(3'-($CH_3$—C(=NOAllyl))-$C_6H_4$) |
| 431 | 4-(4'-($CH_3$—C(=NOAllyl))-$C_6H_4$) |
| 432 | 2-(2'-$CH_3O_2C$—$C_6H_4$) |
| 433 | 2-(3'-$CH_3O_2C$—$C_6H_4$) |
| 434 | 2-(4'-$CH_3O_2C$—$C_6H_4$) |
| 435 | 3-(2'-$CH_3O_2C$—$C_6H_4$) |
| 436 | 3-(3'-$CH_3O_2C$—$C_6H_4$) |
| 437 | 3-(4'-$CH_3O_2C$—$C_6H_4$) |
| 438 | 4-(2'-$CH_3O_2C$—$C_6H_4$) |
| 439 | 4-(3'-$CH_3O_2C$—$C_6H_4$) |
| 440 | 4-(4'-$CH_3O_2C$—$C_6H_4$) |
| 441 | 2-(2'-$CH_3O$—$C_6H_4$) |
| 442 | 2-(3'-$CH_3O$—$C_6H_4$) |
| 443 | 2-(4'-$CH_3O$—$C_6H_4$) |
| 444 | 3-(2'-$CH_3O$—$C_6H_4$) |
| 445 | 3-(3'-$CH_3O$—$C_6H_4$) |
| 446 | 3-(4'-$CH_3O$—$C_6H_4$) |
| 447 | 4-(2'-$CH_3O$—$C_6H_4$) |
| 448 | 4-(3'-$CH_3O$—$C_6H_4$) |
| 449 | 4-(4'-$CH_3O$—$C_6H_4$) |
| 450 | 2-(2'-$O_2N$—$C_6H_4$) |
| 451 | 2-(3'-$O_2N$—$C_6H_4$) |
| 452 | 2-(4'-$O_2N$—$C_6H_4$) |
| 453 | 3-(2'-$O_2N$—$C_6H_4$) |
| 454 | 3-(3'-$O_2N$—$C_6H_4$) |
| 455 | 3-(4'-$O_2N$—$C_6H_4$) |
| 456 | 4-(2'-$O_2N$—$C_6H_4$) |
| 457 | 4-(3'-$O_2N$—$C_6H_4$) |
| 458 | 4-(4'-$O_2N$—$C_6H_4$) |
| 459 | 2-(2'-NC—$C_6H_4$) |
| 460 | 2-(3'-NC—$C_6H_4$) |
| 461 | 2-(4'-NC—$C_6H_4$) |
| 462 | 3-(2'-NC—$C_6H_4$) |
| 463 | 3-(3'-NC—$C_6H_4$) |
| 464 | 3-(4'-NC—$C_6H_4$) |
| 465 | 4-(2'-NC—$C_6H_4$) |
| 466 | 4-(3'-NC—$C_6H_4$) |
| 467 | 4-(4'-NC—$C_6H_4$) |
| 468 | 2-(2'-$CF_3$—$C_6H_4$) |
| 469 | 2-(3'-$CF_3$—$C_6H_4$) |
| 470 | 2-(4'-$CF_3$—$C_6H_4$) |
| 471 | 3-(2'-$CF_3$—$C_6H_4$) |
| 472 | 3-(3'-$CF_3$—$C_6H_4$) |
| 473 | 3-(4'-$CF_3$—$C_6H_4$) |
| 474 | 4-(2'-$CF_3$—$C_6H_4$) |
| 475 | 4-(3'-$CF_3$—$C_6H_4$) |
| 476 | 4-(4'-$CF_3$—$C_6H_4$) |
| 477 | 2-O—$C_6H_5$ |
| 475 | 3-O—$C_6H_5$ |
| 476 | 4-O—$C_6H_5$ |
| 478 | 2-O-(2'-F—$C_6H_4$) |
| 479 | 2-O-(3'-F—$C_6H_4$) |
| 480 | 2-O-(4'-F—$C_6H_4$) |
| 481 | 3-O-(2'-F—$C_6H_4$) |
| 482 | 3-O-(3'-F—$C_6H_4$) |
| 483 | 3-O-(4'-F—$C_6H_4$) |
| 484 | 4-O-(2'-F—$C_6H_4$) |
| 485 | 4-O-(3'-F—$C_6H_4$) |
| 486 | 4-O-(4'-F—$C_6H_4$) |
| 487 | 2-O-(2'-Cl—$C_6H_4$) |
| 488 | 2-O-(3'-Cl—$C_6H_4$) |
| 489 | 2-O-(4'-Cl—$C_6H_4$) |
| 490 | 3-O-(2'-Cl—$C_6H_4$) |
| 491 | 3-O-(3'-Cl—$C_6H_4$) |
| 492 | 3-O-(4'-Cl—$C_6H_4$) |
| 493 | 3-O-(4'-Cl—$C_6H_4$) |
| 494 | 4-O-(2'-Cl—$C_6H_4$) |
| 495 | 4-O-(3'-Cl—$C_6H_4$) |
| 496 | 4-O-(4'-Cl—$C_6H_4$) |
| 497 | 2-O-(2'-$CH_3$—$C_6H_4$) |
| 498 | 2-O-(3'-$CH_3$—$C_6H_4$) |
| 499 | 2-O-(4'-$CH_3$—$C_6H_4$) |
| 500 | 3-O-(2'-$CH_3$—$C_6H_4$) |
| 501 | 3-O-(3'-$CH_3$—$C_6H_4$) |
| 502 | 3-O-(4'-$CH_3$—$C_6H_4$) |
| 503 | 4-O-(2'-$CH_3$—$C_6H_4$) |
| 504 | 4-O-(3'-$CH_3$—$C_6H_4$) |
| 505 | 4-O-(4'-$CH_3$—$C_6H_4$) |
| 506 | 2-O-(2'-$CH_3$—CO—$C_6H_4$) |
| 507 | 2-O-(3'-$CH_3$—CO—$C_6H_4$) |
| 508 | 2-O-(4'-$CH_3$—CO—$C_6H_4$) |
| 509 | 3-O-(2'-$CH_3$—CO—$C_6H_4$) |
| 510 | 3-O-(3'-$CH_3$—CO—$C_6H_4$) |
| 511 | 3-O-(4'-$CH_3$—CO—$C_6H_4$) |
| 512 | 4-O-(2'-$CH_3$—CO—$C_6H_4$) |
| 513 | 4-O-(3'-$CH_3$—CO—$C_6H_4$) |
| 514 | 4-O-(4'-$CH_3$—CO—$C_6H_4$) |
| 515 | 2-O-(2'-($CH_3$—C(=NOAllyl))-$C_6H_4$) |
| 516 | 2-O-(3'-($CH_3$—C(=NOAllyl))-$C_6H_4$) |
| 517 | 2-O-(4'-($CH_3$—C(=NOAllyl))-$C_6H_4$) |
| 518 | 3-O-(2'-($CH_3$—C(=NOAllyl))-$C_6H_4$) |
| 519 | 3-O-(3'-($CH_3$—C(=NOAllyl))-$C_6H_4$) |
| 520 | 3-O-(4'-($CH_3$—C(=NOAllyl))-$C_6H_4$) |
| 521 | 4-O-(2'-($CH_3$—C(=NOAllyl))-$C_6H_4$) |
| 522 | 4-O-(3'-($CH_3$—C(=NOAllyl))-$C_6H_4$) |
| 523 | 4-O-(4'-($CH_3$—C(=NOAllyl))-$C_6H_4$) |
| 524 | 2-O-(2'-$CH_3O_2C$—$C_6H_4$) |
| 525 | 2-O-(3'-$CH_3O_2C$—$C_6H_4$) |
| 526 | 2-O-(4'-$CH_3O_2C$—$C_6H_4$) |
| 527 | 3-O-(2'-$CH_3O_2C$—$C_6H_4$) |
| 528 | 3-O-(3'-$CH_3O_2C$—$C_6H_4$) |
| 529 | 3-O-(4'-$CH_3O_2C$—$C_6H_4$) |
| 530 | 4-O-(2'-$CH_3O_2C$—$C_6H_4$) |
| 531 | 4-O-(3'-$CH_3O_2C$—$C_6H_4$) |
| 532 | 4-O-(4'-$CH_3O_2C$—$C_6H_4$) |
| 533 | 2-O-(2'-$CH_3O$—$C_6H_4$) |
| 534 | 2-O-(3'-$CH_3O$—$C_6H_4$) |
| 535 | 2-O-(4'-$CH_3O$—$C_6H_4$) |
| 536 | 3-O-(2'-$CH_3O$—$C_6H_4$) |
| 537 | 3-O-(3'-$CH_3O$—$C_6H_4$) |
| 538 | 3-O-(4'-$CH_3O$—$C_6H_4$) |
| 539 | 4-O-(2'-$CH_3O$—$C_6H_4$) |
| 540 | 4-O-(3'-$CH_3O$—$C_6H_4$) |
| 541 | 4-O-(4'-$CH_3O$—$C_6H_4$) |
| 542 | 2-O-(2'-$O_2N$—$C_6H_4$) |
| 543 | 2-O-(3'-$O_2N$—$C_6H_4$) |
| 544 | 2-O-(4'-$O_2N$—$C_6H_4$) |
| 545 | 3-O-(2'-$O_2N$—$C_6H_4$) |
| 546 | 3-O-(3'-$O_2N$—$C_6H_4$) |
| 547 | 3-O-(4'-$O_2N$—$C_6H_4$) |
| 548 | 4-O-(2'-$O_2N$—$C_6H_4$) |
| 549 | 4-O-(3'-$O_2N$—$C_6H_4$) |
| 550 | 4-O-(4'-$O_2N$—$C_6H_4$) |
| 551 | 2-O-(2'-NC—$C_6H_4$) |
| 552 | 2-O-(3'-NC—$C_6H_4$) |
| 553 | 2-O-(4'-NC—$C_6H_4$) |
| 554 | 3-O-(2'-NC—$C_6H_4$) |
| 555 | 3-O-(3'-NC—$C_6H_4$) |
| 556 | 3-O-(4'-NC—$C_6H_4$) |

TABLE 35-continued

| | |
|---|---|
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-CH$_3$-4-(CH$_3$—C=N—O—CH$_2$—CH$_2$—OCH$_3$) |
| 642 | 2-CH$_3$-4-(C$_2$H$_5$—C=N—O—CH$_2$—CH$_2$—OCH$_3$) |
| 643 | 2,5-(CH$_3$)$_2$-4-(CH$_3$—C=N—O—CH$_2$—CH$_2$—OCH$_3$) |
| 644 | 2-CH$_3$-4-(n-C$_3$H$_7$—C=N—OCH$_3$) |
| 645 | 2-CH$_3$-4-(n-C$_3$H$_7$—C=N—OC$_2$H$_5$) |
| 646 | 2-CH$_3$-4-(n-C$_3$H$_7$—C=N—O-n-C$_3$H$_7$) |
| 647 | 2-CH$_3$-4-(n-C$_3$H$_7$—C=N—O-i-C$_3$H$_7$) |
| 648 | 2-CH$_3$-4-(n-C$_3$H$_7$—C=N—O-Allyl) |
| 649 | 2-CH$_3$-4-(n-C$_3$H$_7$—C=N—O-trans-Chloroallyl) |
| 650 | 2-CH$_3$-4-(n-C$_3$H$_7$—C=N—O-Propargyl) |
| 651 | 2-CH$_3$-4-(n-C$_3$H$_7$—C=N—O-n-C$_4$H$_9$) |
| 652 | 2-CH$_3$-4-(n-C$_3$H$_7$—C=N—O—CH$_2$—C$_6$H$_5$) |
| 653 | 2-CH$_3$-4-(i-C$_3$H$_7$—C=N—OCH$_3$) |
| 654 | 2-CH$_3$-4-(i-C$_3$H$_7$—C=N—OC$_2$H$_5$) |
| 655 | 2-CH$_3$-4-(i-C$_3$H$_7$—C=N—O-n-C$_3$H$_7$) |
| 656 | 2-CH$_3$-4-(i-C$_3$H$_7$—C=N—O-i-C$_3$H$_7$) |
| 657 | 2-CH$_3$-4-(i-C$_3$H$_7$—C=N—O-Allyl) |
| 658 | 2-CH$_3$-4-(i-C$_3$H$_7$—C=N—O-trans-Chloroallyl) |
| 659 | 2-CH$_3$-4-(i-C$_3$H$_7$—C=N—O-Propargyl) |
| 660 | 2-CH$_3$-4-(i-C$_3$H$_7$—C=N—O-n-C$_4$H$_9$) |
| 661 | 2-CH$_3$-4-(i-C$_3$H$_7$—C=N—O—CH$_2$—C$_6$H$_5$) |
| 662 | 2-O-n-C$_4$H$_9$ |
| 663 | 2-O-i-C$_4$H$_9$ |
| 664 | 2-O-s-C$_4$H$_9$ |
| 665 | 2-O-t-C$_4$H$_9$ |
| 666 | 2-Neopentyloxy |
| 667 | 3-O-n-C$_4$H$_9$ |
| 668 | 3-O-i-C$_4$H$_9$ |
| 669 | 3-O-s-C$_4$H$_9$ |
| 670 | 3-O-t-C$_4$H$_9$ |
| 671 | 3-Neopentyloxy |
| 672 | 4-O-n-C$_4$H$_9$ |
| 673 | 4-O-i-C$_4$H$_9$ |
| 674 | 4-O-s-C$_4$H$_9$ |
| 675 | 4-O-t-C$_4$H$_9$ |
| 676 | 4-Neopentyloxy |
| 677 | 3-CH$_3$-4-OCH$_3$ |
| 678 | 3-CH$_3$-4-OC$_2$H$_5$ |
| 679 | 3-CH$_3$-4-O-n-C$_3$H$_7$ |
| 680 | 3-CH$_3$-4-O-n-C$_4$H$_9$ |
| 681 | 3-CH$_3$-4-O-i-C$_4$H$_9$ |
| 682 | 3-CH$_3$-4-O-s-C$_4$H$_9$ |
| 683 | 3-CH$_3$-4-O-t-C$_4$H$_9$ |
| 684 | 3-CH$_3$-4-Neopentyloxy |
| 685 | 2-CH$_3$-3-OCH$_3$ |
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |

TABLE 35-continued

| 713 | 4-Cl-6-OCH$_3$ |
| 714 | 5-Cl-6-OCH$_3$ |

TABLE 36

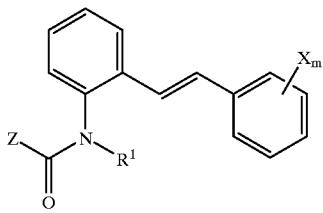

I: $R^1$ = H, Z = $C_2H_5$
II: $R^1$ = $CH_3$, Z = $C_2H_5$
III: $R^1$ = $C_2H_5$, Z = $C_2H_5$
IV: $R^1$ = Allyl, Z = $C_2H_5$
V: $R^1$ = Propargyl, Z = $C_2H_5$
VI: $R^1$ = $CH_2$—$OCH_3$, Z = $C_2H_5$
VII: $R^1$ = CO—$C_2H_5$, Z = $C_2H_5$
VIII: $R^1$ = H, Z = NH($CH_3$)
IX: $R^1$ = $CH_3$, Z = NH($CH_3$)
X: $R^1$ = $C_2H_5$, Z = NH($CH_3$)
XI: $R^1$ = Allyl, Z = NH($CH_3$)
XII: $R^1$ = Propargyl, Z = NH($CH_3$)
XIII: $R^1$ = $CH_2$—$OCH_3$, Z = NH($CH_3$)
XIV: $R^1$ = CO—$C_2H_5$, Z = NH($CH_3$)

| No. | $X_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |

TABLE 36-continued

| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |

TABLE 36-continued

| | |
|---|---|
| 124 | 2-$CH_3$, 5-i-$C_3H_7$ |
| 125 | 3-$CH_3$, 4-i-$C_3H_7$ |
| 126 | 2-i-$C_3H_7$, 5-$CH_3$ |
| 127 | 2,4-(t-$C_4H_9$)$_2$, 6-i-$C_3H_7$ |
| 128 | 2-Allyl |
| 129 | 3-Allyl |
| 130 | 4-Allyl |
| 131 | 2-Allyl, 6-$CH_3$ |
| 132 | 2-cyclo-$C_6H_{11}$ |
| 133 | 3-cyclo-$C_6H_{11}$ |
| 134 | 4-cyclo-$C_6H_{11}$ |
| 135 | 2,4-(cyclo-$C_6H_{11}$)$_2$, 6-$CH_3$ |
| 136 | 2-$CH_3$, 4-cyclo-$C_6H_{11}$ |
| 137 | 2-$CH_2$—$C_6H_5$ |
| 138 | 3-$CH_2$—$C_6H_5$ |
| 139 | 4-$CH_2$—$C_6H_5$ |
| 140 | 2-$CH_2$—$C_6H_5$, 4-$CH_3$ |
| 141 | 2-$CH_3$, 4-$CH_2$—$C_6H_5$ |
| 142 | 2-$C_6H_5$ |
| 143 | 3-$C_6H_5$ |
| 144 | 4-$C_6H_5$ |
| 145 | 4-(2-i-$C_3H_7$—$C_6H_4$) |
| 146 | 4-$C_6H_5$, 2,6-($CH_3$)$_2$ |
| 147 | 2-Cl, 4-$C_6H_5$ |
| 148 | 2-Br, 4-$C_6H_5$ |
| 149 | 2-$C_6H_5$, 4-Cl |
| 150 | 2-$C_6H_5$, 4-Br |
| 151 | 2-$CH_2C_6H_5$, 4-Cl |
| 152 | 2-$CH_2C_6H_5$, 4-Br |
| 153 | 2-Cl, 4-$CH_2C_6H_5$ |
| 154 | 2-Br, 4-$CH_2C_6H_5$ |
| 155 | 2-cyclo-$C_6H_{11}$, 4-Cl |
| 156 | 2-cyclo-$C_6H_{11}$, 4-Br |
| 157 | 2-Cl, 4-cyclo-$C_6H_{11}$ |
| 158 | 2-Br, 4-cyclo-$C_6H_{11}$ |
| 159 | 2-$OCH_3$ |
| 160 | 3-$OCH_3$ |
| 161 | 4-$OCH_3$ |
| 162 | 2-$OC_2H_5$ |
| 163 | 3-O—$C_2H_5$ |
| 164 | 4-O—$C_2H_5$ |
| 165 | 2-O-n-$C_3H_7$ |
| 166 | 3-O-n-$C_3H_7$ |
| 167 | 4-O-n-$C_3H_7$ |
| 168 | 2-O-i-$C_3H_7$ |
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-$C_6H_{13}$ |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—($CH_2$)$_3C_6H_5$ |
| 181 | 3-O—($CH_2$)$_3C_6H_5$ |
| 182 | 4-O—($CH_2$)$_3C_6H_5$ |
| 183 | 2,4-($OCH_3$)$_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 2-$CH_3$, 4-Cl |
| 199 | 2-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-$CH_3$, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-($CH_3$)$_2$ |
| 228 | 2-Br, 4,5-($CH_3$)$_2$ |
| 229 | 2-Cl, 3,5-($CH_3$)$_2$ |
| 230 | 2-Br, 3,5-($CH_3$)$_2$ |
| 231 | 2,6-$Cl_2$, 4-$CH_3$ |
| 232 | 2,6-$F_2$, 4-$CH_3$ |
| 233 | 2,6-$Br_2$, 4-$CH_3$ |
| 234 | 2,4-$Br_2$, 6-$CH_3$ |
| 235 | 2,4-$F_2$, 6-$CH_3$ |
| 236 | 2,4-$Br_2$, 6-$CH_3$ |
| 237 | 2,6-($CH_3$)$_2$, 4-F |
| 238 | 2,6-($CH_3$)$_2$, 4-Cl |
| 239 | 2,6-($CH_3$)$_2$, 4-Br |
| 240 | 3,5-($CH_3$)$_2$, 4-F |
| 241 | 3,5-($CH_3$)$_2$, 4-Cl |
| 242 | 3,5-($CH_3$)$_2$, 4-Br |
| 243 | 2,3,6-($CH_3$)$_3$, 4-F |
| 244 | 2,3,6-($CH_3$)$_3$, 4-Cl |
| 245 | 2,3,6-($CH_3$)$_3$, 4-Br |
| 246 | 2,4-($CH_3$)$_2$, 6-F |
| 247 | 2,4-($CH_3$)$_2$, 6-Cl |
| 248 | 2,4-($CH_3$)$_2$, 6-Br |
| 249 | 2-i-$C_3H_7$, 4-Cl, 5-$CH_3$ |
| 250 | 2-Cl, 4-$NO_2$ |
| 251 | 2-$NO_2$, 4-Cl |
| 252 | 2-$OCH_3$, 5-$NO_2$ |
| 253 | 2,4-$Cl_2$, 5-$NO_2$ |
| 254 | 2,4-$Cl_2$, 6-$NO_2$ |
| 255 | 2,6-$Cl_2$, 4-$NO_2$ |
| 256 | 2,6-$Br_2$, 4-$NO_2$ |
| 257 | 2,6-$I_2$, 4-$NO_2$ |
| 258 | 2-$CH_3$, 5-i-$C_3H_7$, 4-Cl |
| 259 | 2-$CO_2CH_3$ |
| 260 | 3-$CO_2CH_3$ |
| 261 | 4-$CO_2CH_3$ |
| 262 | 2-$CO_2$($C_2H_5$) |
| 263 | 3-$CO_2$($C_2H_5$) |
| 264 | 4-$CO_2$($C_2H_5$) |
| 265 | 2-$CO_2$(n-$C_3H_7$) |
| 266 | 3-$CO_2$(n-$C_3H_7$) |
| 267 | 4-$CO_2$(n-$C_3H_7$) |
| 268 | 2-$CO_2$(i-$C_3H_7$) |
| 269 | 3-$CO_2$(i-$C_3H_7$) |
| 270 | 4-$CO_2$(i-$C_3H_7$) |
| 271 | 2-$CO_2$(n-$C_6H_{13}$) |
| 272 | 3-$CO_2$(n-$C_6H_{13}$) |
| 273 | 4-$CO_2$(n-$C_6H_{13}$) |
| 274 | 2-$CH_2$—$OCH_3$ |
| 275 | 3-$CH_2$—$OCH_3$ |
| 276 | 4-$CH_2$—$OCH_3$ |
| 277 | 2-$CH_2O$($C_2H_5$) |
| 278 | 3-$CH_2O$($C_2H_5$) |
| 279 | 4-$CH_2O$($C_2H_5$) |
| 280 | 2-$CH_2O$(n-$C_3H_7$) |
| 281 | 3-$CH_2O$(n-$C_3H_7$) |

TABLE 36-continued

| | |
|---|---|
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CO—CH$_2$—CH$_3$ |
| 304 | 2-Me-4-CO—CH$_2$—CH$_2$—CH$_3$ |
| 305 | 2-Me-4-CO—CH(CH$_3$)$_2$ |
| 306 | 2,5-Me$_2$-4-CHO |
| 307 | 2,5-Me$_2$-4-CO—CH$_3$ |
| 308 | 2,5-Me$_2$-4-CO—CH$_2$—CH$_3$ |
| 309 | 2,5-Me$_2$-4-CH$_2$—CH$_2$—CO—CH$_3$ |
| 310 | 2,5-Me$_2$-4-CO—CH(CH$_3$)$_2$ |
| 311 | 2-Cl-4-CHO |
| 312 | 2-Cl-4-CO—CH$_3$ |
| 313 | 2-Cl-4-CO—CH$_2$—CH$_3$ |
| 314 | 2-Cl-4-CO—CH(CH$_3$)$_2$ |
| 315 | 2,5-Cl$_2$-4-CHO |
| 316 | 2,5-Cl$_2$-4-CO—CH$_3$ |
| 317 | 2,5-Cl$_2$-4-CO—CH$_2$—CH$_3$ |
| 318 | 2,5-Cl$_2$-4-CO—CH$_2$—CH$_2$—CH$_3$ |
| 319 | 2,5-Cl$_2$-4-CO—CH(CH$_3$)$_2$ |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |

TABLE 36-continued

| | |
|---|---|
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_4$) |
| 561 | 2-O-(3'-CF$_3$—C$_6$H$_4$) |
| 562 | 2-O-(4'-CF$_3$—C$_6$H$_4$) |
| 563 | 3-O-(2'-CF$_3$—C$_6$H$_4$) |
| 564 | 3-O-(3'-CF$_3$—C$_6$H$_4$) |
| 565 | 3-O-(4'-CF$_3$—C$_6$H$_4$) |
| 566 | 4-O-(2'-CF$_3$—C$_6$H$_4$) |
| 567 | 4-O-(3'-CF$_3$—C$_6$H$_4$) |
| 568 | 4-O-(4'-CF$_3$—C$_6$H$_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |

TABLE 36-continued

| | |
|---|---|
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |

TABLE 37

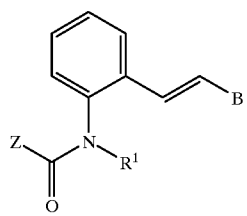

I: $R^1$ = H, Z = $C_2H_5$
II: $R^1$ = $CH_3$, Z = $C_2H_5$
III: $R^1$ = $C_2H_5$, Z = $C_2H_5$
IV: $R^1$ = Allyl, Z = $C_2H_5$
V: $R^1$ = Propargyl, Z = $C_2H_5$
VI: $R^1$ = $CH_2$—$OCH_3$, Z = $C_2H_5$
VII: $R^1$ = CO—$C_2H_5$, Z = $C_2H_5$
VIII: $R^1$ = H, Z = $NH(CH_3)$
IX: $R^1$ = $CH_3$, Z = $NH(CH_3)$
X: $R^1$ = $C_2H_5$, Z = $NH(CH_3)$
XI: $R^1$ = Allyl, Z = $NH(CH_3)$
XII: $R^1$ = Propargyl, Z = $NH(CH_3)$
XIII: $R^1$ = $CH_2$—$OCH_3$, Z = $NH(CH_3)$
XIV: $R^1$ = CO—$C_2H_5$, Z = $NH(CH_3)$

| No. | B |
|---|---|
| 1 | Pyrrolyl-3 |
| 2 | N—$CH_3$-Pyrrolyl-3 |

TABLE 37-continued

| | |
|---|---|
| 3 | N—$C_6H_5$-Pyrrolyl-3 |
| 4 | N-(4'-$CH_3$—$C_6H_4$)-Pyrrolyl-3 |
| 5 | N-(3'-$CH_3$—$C_6H_4$)-Pyrrolyl-3 |
| 6 | N-(2'-$CH_3$—$C_6H_4$)-Pyrrolyl-3 |
| 7 | N-(4'-$CH_3O$—$C_6H_4$)-Pyrrolyl-3 |
| 8 | N-(3'-$CH_3O$—$C_6H_4$)-Pyrrolyl-3 |
| 9 | N-(2'-$CH_3O$—$C_6H_4$)-Pyrrolyl-3 |
| 10 | N-(4'-$NO_2$—$C_6H_4$)-Pyrrolyl-3 |
| 11 | N-(3'-$NO_2$—$C_6H_4$)-Pyrrolyl-3 |
| 12 | N-(2'-$NO_2$—$C_6H_4$)-Pyrrolyl-3 |
| 13 | N-(4'-CN—$C_6H_4$)-Pyrrolyl-3 |
| 14 | N-(3'-CN—$C_6H_4$)-Pyrrolyl-3 |
| 15 | N-(2'-CN—$C_6H_4$)-Pyrrolyl-3 |
| 16 | N-(4'-Cl—$C_6H_4$)-Pyrrolyl-3 |
| 17 | N-(3'-Cl—$C_6H_4$)-Pyrrolyl-3 |
| 18 | N-(2'-Cl—$C_6H_4$)-Pyrrolyl-3 |
| 19 | Pyrrolyl-2 |
| 20 | N—$CH_3$-Pyrrolyl-2 |
| 21 | N—$C_6H_5$-Pyrrolyl-2 |
| 22 | N-(4'-$CH_3$—$C_6H_4$)-Pyrrolyl-2 |
| 23 | N-(3'-$CH_3$—$C_6H_4$)-Pyrrolyl-2 |
| 24 | N-(2'-$CH_3$—$C_6H_4$)-Pyrrolyl-2 |
| 25 | N-(4'-$CH_3O$—$C_6H_4$)-Pyrrolyl-2 |
| 26 | N-(3'-$CH_3O$—$C_6H_4$)-Pyrrolyl-2 |
| 27 | N-(2'-$CH_3O$—$C_6H_4$)-Pyrrolyl-2 |
| 28 | N-(4'-$NO_2$—$C_6H_4$)-Pyrrolyl-2 |
| 29 | N-(3'-$NO_2$—$C_6H_4$)-Pyrrolyl-2 |
| 30 | N-(2'-$NO_2$—$C_6H_4$)-Pyrrolyl-2 |
| 31 | N-(4'-CN—$C_6H_4$)-Pyrrolyl-2 |
| 32 | N-(3'-CN—$C_6H_4$)-Pyrrolyl-2 |
| 33 | N-(2'-CN—$C_6H_4$)-Pyrrolyl-2 |
| 34 | N-(4'-Cl—$C_6H_4$)-Pyrrolyl-2 |
| 35 | N-(3'-Cl—$C_6H_4$)-Pyrrolyl-2 |
| 36 | N-(2'-Cl—$C_6H_4$)-Pyrrolyl-2 |
| 37 | Furyl-2 |
| 38 | 5-$CH_3$-Furyl-2 |
| 39 | 5-$C_6H_5$-Furyl-2 |
| 40 | 5-(4'-$CH_3$—$C_6H_4$)-Furyl-2 |
| 41 | 5-(3'-$CH_3$—$C_6H_4$)-Furyl-2 |
| 42 | 5-(2'-$CH_3$—$C_6H_4$)-Furyl-2 |
| 43 | 5-(4'-$CH_3O$—$C_6H_4$)-Furyl-2 |
| 44 | 5-(3'-$CH_3O$—$C_6H_4$)-Furyl-2 |
| 45 | 5-(2'-$CH_3O$—$C_6H_4$)-Furyl-2 |
| 46 | 5-(4'-$NO_2$—$C_6H_4$)-Furyl-2 |
| 47 | 5-(3'-$NO_2$—$C_6H_4$)-Furyl-2 |
| 48 | 5-(2'-$NO_2$—$C_6H_4$)-Furyl-2 |
| 49 | 5-(4'-CN—$C_6H_4$)-Furyl-2 |
| 50 | 5-(3'-CN—$C_6H_4$)-Furyl-2 |
| 51 | 5-(2'-CN—$C_6H_4$)-Furyl-2 |
| 52 | 5-(4'-Cl—$C_6H_4$)-Furyl-2 |
| 53 | 5-(3'-Cl—$C_6H_4$)-Furyl-2 |
| 54 | 5-(2'-Cl—$C_6H_4$)-Furyl-2 |
| 55 | 4-$CH_3$-Furyl-2 |
| 56 | 4-$C_6H_5$-Furyl-2 |
| 57 | 4-(4'-$CH_3$—$C_6H_4$)-Furyl-2 |
| 58 | 4-(3'-$CH_3$—$C_6H_4$)-Furyl-2 |
| 59 | 4-(2'-$CH_3$—$C_6H_4$)-Furyl-2 |
| 60 | 4-(4'-$CH_3O$—$C_6H_4$)-Furyl-2 |
| 61 | 4-(3'-$CH_3O$—$C_6H_4$)-Furyl-2 |
| 62 | 4-(2'-$CH_3O$—$C_6H_4$)-Furyl-2 |
| 63 | 4-(4'-$NO_2$—$C_6H_4$)-Furyl-2 |
| 64 | 4-(3'-$NO_2$—$C_6H_4$)-Furyl-2 |
| 65 | 4-(2'-$NO_2$—$C_6H_4$)-Furyl-2 |
| 66 | 4-(4'-CN—$C_6H_4$)-Furyl-2 |
| 67 | 4-(3'-CN—$C_6H_4$)-Furyl-2 |
| 68 | 4-(2'-CN—$C_6H_4$)-Furyl-2 |
| 69 | 4-(4'-Cl—$C_6H_4$)-Furyl-2 |
| 70 | 4-(3'-Cl—$C_6H_4$)-Furyl-2 |
| 71 | 4-(2'-Cl—$C_6H_4$)-Furyl-2 |
| 72 | Thienyl-2 |
| 73 | 5-$CH_3$-Thienyl-2 |
| 74 | 5-$C_6H_5$-Thienyl-2 |
| 75 | 5-(4'-$CH_3$—$C_6H_4$)-Thienyl-2 |
| 76 | 5-(3'-$CH_3$—$C_6H_4$)-Thienyl-2 |
| 77 | 5-(2'-$CH_3$—$C_6H_4$)-Thienyl-2 |
| 78 | 5-(4'-$CH_3O$—$C_6H_4$)-Thienyl-2 |
| 79 | 5-(3'-$CH_3O$—$C_6H_4$)-Thienyl-2 |
| 80 | 5-(2'-$CH_3O$—$C_6H_4$)-Thienyl-2 |
| 81 | 5-(4'-$NO_2$—$C_6H_4$)-Thienyl-2 |

TABLE 37-continued

| | |
|---|---|
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 3-CH$_3$-Oxazolyl-4 |
| 234 | 3-C$_6$H$_5$-Oxazolyl-4 |
| 235 | 3-(4'-CH$_3$—C$_6$H$_4$)-Oxazolyl-4 |
| 236 | 3-(3'-CH$_3$—C$_6$H$_4$)-Oxazolyl-4 |
| 237 | 3-(2'-CH$_3$—C$_6$H$_4$)-Oxazolyl-4 |
| 238 | 3-(4'-CH$_3$O—C$_6$H$_4$)-Oxazolyl-4 |
| 239 | 3-(3'-CH$_3$O—C$_6$H$_4$)-Oxazolyl-4 |

TABLE 37-continued

| | |
|---|---|
| 240 | 3-(2'-CH$_3$O—C$_6$H$_4$)-Oxazolyl-4 |
| 241 | 3-(4'-NO$_2$—C$_6$H$_4$)-Oxazolyl-4 |
| 242 | 3-(3'-NO$_2$—C$_6$H$_4$)-Oxazolyl-4 |
| 243 | 3-(2'-NO$_2$—C$_6$H$_4$)-Oxazolyl-4 |
| 244 | 3-(4'-CN—C$_6$H$_4$)-Oxazolyl-4 |
| 245 | 3-(3'-CN—C$_6$H$_4$)-Oxazolyl-4 |
| 246 | 3-(2'-CN—C$_6$H$_4$)-Oxazolyl-4 |
| 247 | 3-(4'-Cl—C$_6$H$_4$)-Oxazolyl-4 |
| 248 | 3-(3'-Cl—C$_6$H$_4$)-Oxazolyl-4 |
| 249 | 3-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 267 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,3,4-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |

TABLE 38

Selected physical data of some compounds

| No. | Compound | IR (cm⁻¹) or ¹H-NMR (ppm) | mp (° C.) |
|---|---|---|---|
| 1 | Cl₃C-C(=O)-NH-[2-(2-methylphenoxymethyl)phenyl] | | 128 |
| 2 | H₃C-NH-C(=O)-NH-[2-(2-methylphenoxymethyl)phenyl] | | 144 |
| 3 | H₃C-CH₂-C(=O)-NH-[2-(2-methylphenoxymethyl)phenyl] | | — |
| 4 | (H₃C-CH₂-C(=O))₂N-[2-(2-methylphenoxymethyl)phenyl] | | — |
| 5 | H₃C-CH₂-C(=O)-N(CH₃)-[2-(2-methylphenoxymethyl)phenyl] | | 80 |
| 6 | (H₃C-CH₂-C(=O))₂N-[2-(2-methylphenoxymethyl)phenyl] | | 75 |
| 7 | H₂N-C(=O)-NH-[2-(2-methylphenoxymethyl)phenyl] | | 188 |

TABLE 38-continued

Selected physical data of some compounds

| No. | Compound | IR (cm⁻¹) or ¹H-NMR (ppm) | mp (° C.) |
|---|---|---|---|
| 8 | (H₃C)₂N-C(=O)-NH-[2-(2-methylphenoxymethyl)phenyl] | | 115 |
| 9 | H₃C-C(=O)-N(CH₃)-[2-(2-methylphenoxymethyl)phenyl] | | 76 |
| 10 | Cl₃C-C(=O)-N(CH₃)-[2-(2-methylphenoxymethyl)phenyl] | | 96 |
| 11 | F₃C-C(=O)-N(CH₃)-[2-(2-methylphenoxymethyl)phenyl] | 3.3 (s, 3H); 2.25(s, 3H) | |

TABLE 58

Selected physical data of some compounds

[Structure: 2-methyl-6-(phenoxymethyl-Xm)phenyl group with N(R¹)-C(=O)-CH₂-CH₃ substituent]

| No. | Xₘ | R¹ | IR (cm⁻¹) or ¹H-NMR (ppm) | mp (° C.) |
|---|---|---|---|---|
| 1 | 2-CH₃ | H | | 120 |
| 2 | 2-CH₃ | CH₃ | | oil |
| 3 | 2-CH₃ | C₂H₅ | | oil |

TABLE 58-continued

Selected physical data of some compounds

![structure: H3C-phenyl with CH3, N(R1)-C(=O)-CH2-CH3, and CH2-O-phenyl-Xm]

| No. | X_m | R¹ | IR (cm⁻¹) or ¹H-NMR (ppm) | mp (° C.) |
|---|---|---|---|---|
| 4 | 2-CH₃ | Allyl | | oil |
| 5 | 2-CH₃ | Propargyl | | oil |
| 6 | 2-CH₃ | CH₂—OCH₃ | | oil |
| 7 | 2,5-(CH₃)₂ | H | | 170 |
| 8 | 2,5-(CH₃)₂ | CH₃ | | oil |
| 9 | 2,5-(CH₃)₂ | C₂H₅ | | oil |
| 10 | 2,5-(CH₃)₂ | Allyl | | oil |
| 11 | 2,5-(CH₃)₂ | Propargyl | | oil |
| 12 | 2,5-(CH₃)₂ | CH₂—OCH₃ | | oil |
| 13 | 2-CH₃-4-C(CH₃)=N—OCH₃ | H | | 125 |
| 14 | 2-CH₃-4-C(CH₃)=N—OCH₃ | CH₃ | | oil |
| 15 | 2-CH₃-4-C(CH₃)=N—OCH₃ | C₂H₅ | | oil |
| 16 | 2-CH₃-4-C(CH₃)=N—OCH₃ | Allyl | | 87 |
| 17 | 2-CH₃-4-C(CH₃)=N—OCH₃ | Propargyl | | oil |
| 18 | 2-CH₃-4-C(CH₃)=N—OCH₃ | CH₂—OCH₃ | | oil |
| 19 | 2,5-(CH₃)₂-4-C(CH₃)=N—O-Allyl | H | | 85 |
| 20 | 2,5-(CH₃)₂-4-C(CH₃)=N—O-Allyl | CH₃ | | oil |
| 21 | 2,5-(CH₃)₂-4-C(CH₃)=N—O-Allyl | C₂H₅ | | oil |
| 22 | 2,5-(CH₃)₂-4-C(CH₃)=N—O-Allyl | Allyl | | 87 |
| 23 | 2,5-(CH₃)₂-4-C(CH₃)=N—O-Allyl | Propargyl | | oil |
| 24 | 2,5-(CH₃)₂-4-C(CH₃)=N—O-Allyl | CH₂—OCH₃ | | oil |

TABLE 59

Selected physical data of some compounds

![structure: H3C-phenyl with CH3, N(R1)-C(=O)-CH2-CH3, and CH2-O-N(=CH-CH3?)-phenyl-Xm]

| No. | X_m | R¹ | IR (cm⁻¹) or ¹H-NMR (ppm) | mp (° C.) |
|---|---|---|---|---|
| 1 | 4-CH₃ | H | | 118 |
| 2 | 4-CH₃ | CH₃ | | oil |
| 3 | 4-CH₃ | C₂H₅ | | oil |
| 4 | 4-CH₃ | Allyl | | oil |
| 5 | 4-CH₃ | Propargyl | | oil |
| 6 | 4-CH₃ | CH₂—OCH₃ | | oil |
| 7 | 3,5-Cl₂ | H | | 160 |
| 8 | 3,5-Cl₂ | CH₃ | | oil |
| 9 | 3,5-Cl₂ | C₂H₅ | | oil |
| 10 | 3,5-Cl₂ | Allyl | | 85 |
| 11 | 3,5-Cl₂ | Propargyl | | oil |
| 12 | 3,5-Cl₂ | CH₂—OCH₃ | | oil |

TABLE 39

![structure: phenyl with X, A-Phenyl, N(R1)-C(=O)-Z]

| No. | X | R¹ | X | A |
|---|---|---|---|---|
| 1 | H | H | CH₃ | —CH₂O— |
| 2 | H | H | CH₃ | —CH₂O—N=C(CH₃)— |
| 3 | H | H | CH₃ | —CH=CH— |
| 4 | H | H | NH₂ | —CH₂O— |
| 5 | H | H | NH₂ | —CH₂O—N=C(CH₃)— |
| 6 | H | H | NH₂ | —CH=CH— |
| 7 | H | H | N(CH₃)₂ | —CH₂O— |
| 8 | H | H | N(CH₃)₂ | —CH₂O—N=C(CH₃)— |
| 9 | H | H | N(CH₃)₂ | —CH=CH— |
| 10 | H | H | CCl₃ | —CH₂O— |
| 11 | H | H | CCl₃ | —CH₂O—N=C(CH₃)— |
| 12 | H | H | CCl₃ | —CH=CH— |
| 13 | H | H | CF₃ | —CH₂O— |
| 14 | H | H | CF₃ | —CH₂O—N=C(CH₃)— |
| 15 | H | H | CF₃ | —CH=CH— |
| 16 | H | Propargyl | CH₃ | —CH₂O— |
| 17 | H | Propargyl | CH₃ | —CH₂O—N=C(CH₃)— |
| 18 | H | Propargyl | CH₃ | —CH=CH— |
| 19 | H | Propargyl | NH₂ | —CH₂O— |
| 20 | H | Propargyl | NH₂ | —CH₂O—N=C(CH₃)— |
| 21 | H | Propargyl | NH₂ | —CH=CH— |
| 22 | H | Propargyl | N(CH₃)₂ | —CH₂O— |
| 23 | H | Propargyl | N(CH₃)₂ | —CH₂O—N=C(CH₃)— |
| 24 | H | Propargyl | N(CH₃)₂ | —CH=CH— |
| 25 | H | Propargyl | CCl₃ | —CH₂O— |
| 26 | H | Propargyl | CCl₃ | —CH₂O—N=C(CH₃)— |
| 27 | H | Propargyl | CCl₃ | —CH=CH— |
| 28 | H | Propargyl | CF₃ | —CH₂O— |
| 29 | H | Propargyl | CF₃ | —CH₂O—N=C(CH₃)— |
| 30 | H | Propargyl | CF₃ | —CH=CH— |
| 31 | CH₃ | H | CH₃ | —CH₂O— |
| 32 | CH₃ | H | CH₃ | —CH₂O—N=C(CH₃)— |
| 33 | CH₃ | H | CH₃ | —CH=CH— |
| 34 | CH₃ | H | NH₂ | —CH₂O— |
| 35 | CH₃ | H | NH₂ | —CH₂O—N=C(CH₃)— |
| 36 | CH₃ | H | NH₂ | —CH=CH— |
| 37 | CH₃ | H | N(CH₃)₂ | —CH₂O— |
| 38 | CH₃ | H | N(CH₃)₂ | —CH₂O—N=C(CH₃)— |
| 39 | CH₃ | H | N(CH₃)₂ | —CH=CH— |
| 40 | CH₃ | H | CCl₃ | —CH₂O— |
| 41 | CH₃ | H | CCl₃ | —CH₂O—N=C(CH₃)— |
| 42 | CH₃ | H | CCl₃ | —CH=CH— |
| 43 | CH₃ | H | CF₃ | —CH₂O— |
| 44 | CH₃ | H | CF₃ | —CH₂O—N=C(CH₃)— |
| 45 | CH₃ | H | CF₃ | —CH=CH— |
| 46 | CH₃ | Propargyl | CH₃ | —CH₂O— |
| 47 | CH₃ | Propargyl | CH₃ | —CH₂O—N=C(CH₃)— |
| 48 | CH₃ | Propargyl | CH₃ | —CH=CH— |
| 49 | CH₃ | Propargyl | NH₂ | —CH₂O— |
| 50 | CH₃ | Propargyl | NH₂ | —CH₂O—N=C(CH₃)— |
| 51 | CH₃ | Propargyl | NH₂ | —CH=CH— |
| 52 | CH₃ | Propargyl | N(CH₃)₂ | —CH₂O— |
| 53 | CH₃ | Propargyl | N(CH₃)₂ | —CH₂O—N=C(CH₃)— |
| 54 | CH₃ | Propargyl | N(CH₃)₂ | —CH=CH— |
| 55 | CH₃ | Propargyl | CCl₃ | —CH₂O— |
| 56 | CH₃ | Propargyl | CCl₃ | —CH₂O—N=C(CH₃)— |
| 57 | CH₃ | Propargyl | CCl₃ | —CH=CH— |
| 58 | CH₃ | Propargyl | CF₃ | —CH₂O— |
| 59 | CH₃ | Propargyl | CF₃ | —CH₂O—N=C(CH₃)— |
| 60 | CH₃ | Propargyl | CF₃ | —CH=CH— |
| 61 | Cl | H | CH₃ | —CH₂O— |
| 62 | Cl | H | CH₃ | —CH₂O—N=C(CH₃)— |
| 63 | Cl | H | CH₃ | —CH=CH— |
| 64 | Cl | H | NH₂ | —CH₂O— |
| 65 | Cl | H | NH₂ | —CH₂O—N=C(CH₃)— |

TABLE 39-continued

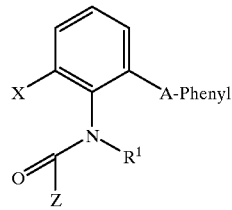

| No. | X | R¹ | X | A |
|---|---|---|---|---|
| 66 | Cl | H | NH₂ | —CH=CH— |
| 67 | Cl | H | N(CH₃)₂ | —CH₂O— |
| 68 | Cl | H | N(CH₃)₂ | —CH₂O—N=C(CH₃)— |
| 69 | Cl | H | N(CH₃)₂ | —CH=CH— |
| 70 | Cl | H | CCl₃ | —CH₂O— |
| 71 | Cl | H | CCl₃ | —CH₂O—N=C(CH₃)— |
| 72 | Cl | H | CCl₃ | —CH=CH— |
| 73 | Cl | H | CF₃ | —CH₂O— |
| 74 | Cl | H | CF₃ | —CH₂O—N=C(CH₃)— |
| 75 | Cl | H | CF₃ | —CH=CH— |
| 76 | Cl | Propargyl | CH₃ | —CH₂O— |
| 77 | Cl | Propargyl | CH₃ | —CH₂O—N=C(CH₃)— |
| 78 | Cl | Propargyl | CH₃ | —CH=CH— |
| 79 | Cl | Propargyl | NH₂ | —CH₂O— |
| 80 | Cl | Propargyl | NH₂ | —CH₂O—N=C(CH₃)— |
| 81 | Cl | Propargyl | NH₂ | —CH=CH— |
| 82 | Cl | Propargyl | N(CH₃)₂ | —CH₂O— |
| 83 | Cl | Propargyl | N(CH₃)₂ | —CH₂O—N=C(CH₃)— |
| 84 | Cl | Propargyl | N(CH₃)₂ | —CH=CH— |
| 85 | Cl | Propargyl | CCl₃ | —CH₂O— |
| 86 | Cl | Propargyl | CCl₃ | —CH₂O—N=C(CH₃)— |
| 87 | Cl | Propargyl | CCl₃ | —CH=CH— |
| 88 | Cl | Propargyl | CF₃ | —CH₂O— |
| 89 | Cl | Propargyl | CF₃ | —CH₂O—N=C(CH₃)— |
| 90 | Cl | Propargyl | CF₃ | —CH=CH— |

TABLE 40

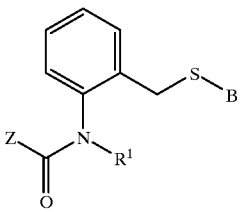

I: R¹ = H, Z = C₂H₅
II: R¹ = CH₃, Z = C₂H₅
III: R¹ = C₂H₅, Z = C₂H₅
IV: R¹ = Allyl, Z = C₂H₅
V: R¹ = Propargyl, Z = C₂H₅
VI: R¹ = CH₂—OCH₃, Z = C₂H₅
VII: R¹ = CO—C₂H₅, Z = C₂H₅
VIII: R¹ = H, Z = NH(CH₃)
IX: R¹ = CH₃, Z = NH(CH₃)
X: R¹ = C₂H₅, Z = NH(CH₃)
XI: R¹ = Allyl, Z = NH(CH₃)
XII: R¹ = Propargyl, Z = NH(CH₃)
XIII: R¹ = CH₂—OCH₃, Z = NH(CH₃)
XIV: R¹ = CO—C₂H₅, Z = NH(CH₃)

| No. | B |
|---|---|
| 1 | 2-Pyridyl |
| 2 | 3-Trifluoromethyl-2-pyridyl |
| 3 | 5-Trifluoromethyl-2-pyridyl |
| 4 | 3,5-Bis-(trifluoromethyl)-2-pyridyl |
| 5 | 3,5-Dichloro-2-pyridyl |
| 6 | 3-Chloroo-5-trifluoromethyl-2-pyridyl |
| 7 | 3,5-Dichloro-2-pyridyl |
| 8 | 2-Chloro-4-trifluoromethylphenyl |

TABLE 40-continued

| 9 | 2-Benzothiazolyl |
| 10 | 5-Chloroo-1-methyl-2-benzimidazolyl |
| 11 | 2-Benzoxazolyl |
| 12 | 1-Methyl-5-trifluoromethylimidazo-[5,4-a]-pyridin-2-yl |
| 13 | 5-Chloroo-2-pyrimidinyl |
| 14 | 4-Methyl-5-phenyl-2-thiazolin-2-yl |
| 15 | 4-Methyl-5-phenyl-2-oxazolin-2-yl |
| 16 | 7-Trifluoromethyl-4-quinolinyl |

Example 16

Methyl N-[2-(3",4"-dichlorophenyl-1'-methyliminooxymethyl-4')-6-methylphenyl]-carbamate (Table 47, No. 2)

a) 2-(Methanesulfonyloxymethyl)-6-methyl-nitrobenzene

At 10–15° C., 27 g (0.23 mol) of methanesulfonyl chloride dissolved in 20 ml of CH₂Cl₂ is dripped into a mixture of 34 g (0.2 mol) of 3-methyl-2-nitrobenzyl alcohol and 27 g (0.27 mol) of triethylamine in 100 ml of CH₂Cl₂. The reaction mixture is stirred for 1 hour at room temperature and is then extracted with water. The organic phase is dried over MgSO₄ and evaporated down. There is obtained as residue 48 g of the title compound as a yellow oil, containing about 10% of the corresponding benzyl chloride as impurity. The crude product is used for the next reaction without any further purification.

¹H-NMR(COCl₃; δ in ppm): 7.3–7.6 (m, 3H, phenyl); 5.3 (S, 2H, OCH₂); 3.0 (S, 3H, CH₃—SO₃); 2.4 (S, 3H, CH₃).

b) 2-(3",4"-Dichlorophenyl-1'-methyl-iminooxymethyl-4')-6-methyl-nitrobenzene

At room temperature, 1.8 g (75 mmol) of sodium hydride is added in portions to a solution of 13 g (64 mmol) of 3,4-dichloroacetophenonoxime in 100 ml of dimethylformamide. Upon conclusion of gas evolution, a solution of 16 g (65 mmol) of the mesylate from Example 1a in 30 ml of dimethylformamide is dripped in at 25–30° C., and the mixture is then stirred for 1 hour at room temperature. The reaction mixture is diluted with water and the aqueous phase is then extracted three times with methyl tert-butyl ether. The combined organic phases are washed with water, dried over MGSO₄ and evaporated down. The residue crystallizes and is stirred with methanol. The mother liquor is purified by column chromatography with mixtures of cyclohexane and ethyl acetate. There is obtained a total of 20.4 g (58 mmol=90%) of the title compound as pale yellow crystals.

¹H-NMR(CDCl₃; δ in ppm): 7.7 (S, broad, 1H, phenyl); 7.2–7.6 (m, 5H, phenyl); 5.3 (S, 2H, OCH₂); 2.4 (S, 3H, CH₃); 2.2 (S, 3H, CH₃).

c) 2-(3",4"-Dichlorophenyl-1'-methyl-iminooxymethyl-4')-6-methyl-aniline

At 20–30° C., 53 g of 21.8% strength Na₂[Fe(CO)₄] solution (1 kg of the solution contains 633 g of water, 218 g of Na₂[Fe(CO)₄], 108 g of Na₂CO₃ and 41 g of NaOH) is added dropwise to 19 g (52.8 mmol) of the nitrobenzene from Example 16b in 150 ml of methanol. The brown suspension is stirred for 2 hours at room temperature, and the reaction mixture is then diluted with methylene chloride and the mixture is suction filtered using kieselguhr. The residue is again washed with CH₂Cl₂ and the combined extracts are extracted with water, dried over MgSO₄ and evaporated down. The brown residue is purified by column chromatography with mixtures of cyclohexane and ethyl acetate. There is obtained 14.3 g (44.3 mmol=82%) of the title compound as a beige solid.

$^1$H-NMR(CDCl$_3$; δ in ppm): 7.7 (S, 1H, phenyl); 7.5 (m, 2H, phenyl); 7.1 (t, broad, 2H, phenyl); 6.7 (t, 1H, I=8 Hz, phenyl); 5.2 (S, 2H, OCH$_2$); 4.15 (S, 2H, NH$_2$; 2.2 (S, 3H, CH$_3$).

d) Methyl N-[2-(3",4"-dichlorophenyl-1'-methyl-iminooxymethyl-4'-6-methylphenyl]-carbamate (Table 47, No. 2)

At 20–30° C., 4.8 g (50 mmol) of methyl chloroformate and subsequently 4.8 g (60 mmol) of pyridine are dripped into a solution of 14.3 g (44 mmol) of the aniline from Example 1c in 150 ml of CH$_2$Cl$_2$. The mixture is stirred overnight at room temperature and is then extracted with dilute hydrochloric acid and water. The reaction mixture is suction filtered using silica gel, dried over MgSO$_4$ and evaporated down. The residue crystallizes and is stirred with cyclohexane. There is obtained 13.8 g (36 mmol=82%) of the title compound as a colorless solid (mp=109° C.).

$^1$H-NMR(CDCl$_3$; δ in ppm): 7.8 (S, 1H, phenyl); 7.6 (S, broad, 1H, NH); 7.4 (S, 2H, phenyl); 7.2 (m, 3H, phenyl); 5.2 (S, 2H, OCH$_2$); 3.8 (S, 3H, OCH$_3$); 2.3 (S, 3H, CH$_3$); 2.2 (S, 3H, CH$_3$).

Example 17

Methyl N-[2-(3",4"-dichlorophenyl-1'-methyl-iminooxymethyl-4')-6-methylphenyl]-N-propargyl-carbamate (Table 47, No. 13)

At 25–30° C., 0.15 g (6.3 mmol) of sodium hydride is added in portions to a solution of 1.9 g (5 mmol) of the carbamate from Example 16d in 20 ml of dimethylformamide. When no more gas evolves, 0.75 g (6.3 mmol) of propargyl bromide is added and the whole is stirred overnight at room temperature. The reaction mixture is diluted with water and the aqueous phase is extracted three times with methyl tert-butyl ether. The combined organic phases are extracted with water, dried over MgSO$_4$ and evaporated down. There is obtained 1.4 g (3.3 mmol=67%) of the title compound as a yellow oil.

$^1$H-NMR (CDCl$_3$; δ in ppm): 7.75 (S, broad, 1H, phenyl); 7.2–7.6 (m, 5H, phenyl); 5.2 (dd, 2H, I=12 Hz, OCH$_2$); 4.4 (dd, broad, I=16 Hz, NCH$_2$); (S, 3H, OCH$_3$); 2.3 (S, 3H, CH$_3$); 2.25 (S, broad, 1H, C≡CH); 2.2 (S, 3H, CH$_3$); the $^1$H-NMR spectrum also contains signals of about 20% of the amide rotamer.

The compounds described in the following tables may be prepared analogously.

TABLE 41

I: R$^1$ = H, CH$_3$
II: R$^1$ = CH$_3$, X = CH$_3$
III: R$^1$ = C$_2$H$_5$, X = CH$_3$
IV: R$^1$ = Allyl, X = CH$_3$
V: R$^1$ = Propargyl, X = CH$_3$
VI: R$^1$ = CH$_2$—OCH$_3$, X = CH$_3$
VII: R$^1$ = CO$_2$CH$_3$, X = CH$_3$
VIII: R$^1$ = H, X = Cl
IX: R$^1$ = CH$_3$, X = Cl TABLE 41-continued X: R$^1$ = C$_2$H$_5$, X = Cl
XI: R$^1$ = Allyl, X = Cl
XII: R$^1$ = Propargyl, X = Cl
XIII: R$^1$ = CH$_2$—OCH$_3$, X = Cl
XIV: R$^1$ = CO$_2$CH$_3$, X = Cl Compound I from Table 41 has for instance the following structural formula:

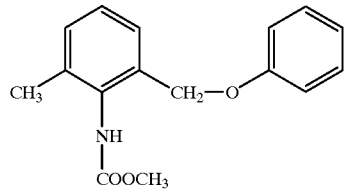

| No. | T$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |

TABLE 41-continued

| | |
|---|---|
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |

TABLE 41-continued

| | |
|---|---|
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |

TABLE 41-continued

| | |
|---|---|
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-Cl—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))-C$_6$H$_4$) |
| 516 | 2-O-(3'-(CH$_3$—C(=NOAllyl))-C$_6$H$_4$) |
| 517 | 2-O-(4'-(CH$_3$—C(=NOAllyl))-C$_6$H$_4$) |
| 518 | 3-O-(2'-(CH$_3$—C(=NOAllyl))-C$_6$H$_4$) |
| 519 | 3-O-(3'-(CH$_3$—C(=NOAllyl))-C$_6$H$_4$) |
| 520 | 3-O-(4'-(CH$_3$—C(=NOAllyl))-C$_6$H$_4$) |
| 521 | 4-O-(2'-(CH$_3$—C(=NOAllyl))-C$_6$H$_4$) |
| 522 | 4-O-(3'-(CH$_3$—C(=NOAllyl))-C$_6$H$_4$) |
| 523 | 4-O-(4'-(CH$_3$—C(=NOAllyl))-C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |

TABLE 41-continued

| | | |
|---|---|---|
| 532 | 4-O-(4'-CH$_3$O$_2$C—C$_6$H$_4$) | |
| 533 | 2-O-(2'-CH$_3$O—C$_6$H$_4$) | |
| 534 | 2-O-(3'-CH$_3$O—C$_6$H$_4$) | |
| 535 | 2-O-(4'-CH$_3$O—C$_6$H$_4$) | |
| 536 | 3-O-(2'-CH$_3$O—C$_6$H$_4$) | |
| 537 | 3-O-(3'-CH$_3$O—C$_6$H$_4$) | |
| 538 | 3-O-(4'-CH$_3$O—C$_6$H$_4$) | |
| 539 | 4-O-(2'-CH$_3$O—C$_6$H$_4$) | |
| 540 | 4-O-(3'-CH$_3$O—C$_6$H$_4$) | |
| 541 | 4-O-(4'-CH$_3$O—C$_6$H$_4$) | |
| 542 | 2-O-(2'-O$_2$N—C$_6$H$_4$) | |
| 543 | 2-O-(3'-O$_2$N—C$_6$H$_4$) | |
| 544 | 2-O-(4'-O$_2$N—C$_6$H$_4$) | |
| 545 | 3-O-(2'-O$_2$N—C$_6$H$_4$) | |
| 546 | 3-O-(3'-O$_2$N—C$_6$H$_4$) | |
| 547 | 3-O-(4'-O$_2$N—C$_6$H$_4$) | |
| 548 | 4-O-(2'-O$_2$N—C$_6$H$_4$) | |
| 549 | 4-O-(3'-O$_2$N—C$_6$H$_4$) | |
| 550 | 4-O-(4'-O$_2$N—C$_6$H$_4$) | |
| 551 | 2-O-(2'-NC—C$_6$H$_4$) | |
| 552 | 2-O-(3'-NC—C$_6$H$_4$) | |
| 553 | 2-O-(4'-NC—C$_6$H$_4$) | |
| 554 | 3-O-(2'-NC—C$_6$H$_4$) | |
| 555 | 3-O-(3'-NC—C$_6$H$_4$) | |
| 556 | 3-O-(4'-NC—C$_6$H$_4$) | |
| 557 | 4-O-(2'-NC—C$_6$H$_4$) | |
| 558 | 4-O-(3'-NC—C$_6$H$_4$) | |
| 559 | 4-O-(4'-NC—C$_6$H$_4$) | |
| 560 | 2-O-(2'-CF$_3$—C$_6$H$_4$) | |
| 561 | 2-O-(3'-CF$_3$—C$_6$H$_4$) | |
| 562 | 2-O-(4'-CF$_3$—C$_6$H$_4$) | |
| 563 | 3-O-(2'-CF$_3$—C$_6$H$_4$) | |
| 564 | 3-O-(3'-CF$_3$—C$_6$H$_4$) | |
| 565 | 3-O-(4'-CF$_3$—C$_6$H$_4$) | |
| 566 | 4-O-(2'-CF$_3$—C$_6$H$_4$) | |
| 567 | 4-O-(3'-CF$_3$—C$_6$H$_4$) | |
| 568 | 4-O-(4'-CF$_3$—C$_6$H$_4$) | |
| 569 | 2-Pyridinyl-2' | |
| 570 | 2-Pyridinyl-3' | |
| 571 | 2-Pyridinyl-4' | |
| 572 | 3-Pyridinyl-2' | |
| 573 | 3-Pyridinyl-3' | |
| 574 | 3-Pyridinyl-4' | |
| 575 | 4-Pyridinyl-2' | |
| 576 | 4-Pyridinyl-3' | |
| 577 | 4-Pyridinyl-4' | |
| 578 | 2-Pyrimidinyl-2' | |
| 579 | 2-Pyrimidinyl-3' | |
| 580 | 2-Pyrimidinyl-4' | |
| 581 | 3-Pyrimidinyl-2' | |
| 582 | 3-Pyrimidinyl-3' | |
| 583 | 3-Pyrimidinyl-4' | |
| 584 | 4-Pyrimidinyl-2' | |
| 585 | 4-Pyrimidinyl-3' | |
| 586 | 4-Pyrimidinyl-4' | |
| 587 | 2-Pyrazolyl-1' | |
| 588 | 2-Pyrazolyl-3' | |
| 589 | 2-Pyrazolyl-4' | |
| 590 | 3-Pyrazolyl-1' | |
| 591 | 3-Pyrazolyl-3' | |
| 592 | 3-Pyrazolyl-4' | |
| 593 | 4-Pyrazolyl-1' | |
| 594 | 4-Pyrazolyl-3' | |
| 595 | 4-Pyrazolyl-4' | |
| 596 | 2-Isoxazolyl-3' | |
| 597 | 2-Isoxazolyl-4' | |
| 598 | 2-Isoxazolyl-5' | |
| 599 | 3-Isoxazolyl-3' | |
| 600 | 3-Isoxazolyl-4' | |
| 601 | 3-Isoxazolyl-5' | |
| 602 | 4-Isoxazolyl-3' | |
| 603 | 4-Isoxazolyl-4' | |
| 604 | 4-Isoxazolyl-5' | |
| 605 | 2-Isothiazolyl-3' | |
| 606 | 2-Isothiazolyl-4' | |
| 607 | 2-Isothiazolyl-5' | |
| 608 | 3-Isothiazolyl-3' | |
| 609 | 3-Isothiazolyl-4' | |
| 610 | 3-Isothiazolyl-5' | |
| 611 | 4-Isothiazolyl-3' | |
| 612 | 4-Isothiazolyl-4' | |
| 613 | 4-Isothiazolyl-5' | |
| 614 | 2-Imidazolyl-1' | |
| 615 | 2-Imidazolyl-2' | |
| 616 | 2-Imidazolyl-4' | |
| 617 | 3-Imidazolyl-1' | |
| 618 | 3-Imidazolyl-2' | |
| 619 | 3-Imidazolyl-4' | |
| 620 | 4-Imidazolyl-1' | |
| 621 | 4-Imidazolyl-2' | |
| 622 | 4-Imidazolyl-4' | |
| 623 | 2-Oxazolyl-2' | |
| 624 | 2-Oxazolyl-4' | |
| 625 | 2-Oxazolyl-5' | |
| 626 | 3-Oxazolyl-2' | |
| 627 | 3-Oxazolyl-4' | |
| 628 | 3-Oxazolyl-5' | |
| 629 | 4-Oxazolyl-2' | |
| 630 | 4-Oxazolyl-4' | |
| 631 | 4-Oxazolyl-5' | |
| 632 | 2-Thiazolyl-2' | |
| 633 | 2-Thiazolyl-4' | |
| 634 | 2-Thiazolyl-5' | |
| 635 | 3-Thiazolyl-2' | |
| 636 | 3-Thiazolyl-4' | |
| 637 | 3-Thiazolyl-5' | |
| 638 | 4-Thiazolyl-2' | |
| 639 | 4-Thiazolyl-4' | |
| 640 | 4-Thiazolyl-5' | |
| 641 | 2-CH$_3$-4-(CH$_3$—C=N—O—CH$_2$—CH$_2$—OCH$_3$) | |
| 642 | 2-CH$_3$-4-(C$_2$H$_5$—C=N—O—CH$_2$—CH$_2$—OCH$_3$) | |
| 643 | 2,5-(CH$_3$)$_2$-4-(CH$_3$—C=N—O—CH$_2$—CH$_2$—OCH$_3$) | |
| 644 | 2-CH$_3$-4-(n-C$_3$H$_7$—C=N—OCH$_3$) | |
| 645 | 2-CH$_3$-4-(n-C$_3$H$_7$—C=N—OC$_2$H$_5$) | |
| 646 | 2-CH$_3$-4-(n-C$_3$H$_7$—C=N—O-n-C$_3$H$_7$) | |
| 647 | 2-CH$_3$-4-(n-C$_3$H$_7$—C=N—O-i-C$_3$H$_7$) | |
| 648 | 2-CH$_3$-4-(n-C$_3$H$_7$—C=N—O-Allyl) | |
| 649 | 2-CH$_3$-4-(n-C$_3$H$_7$—C=N—O-trans-Chloroallyl) | |
| 650 | 2-CH$_3$-4-(n-C$_3$H$_7$—C=N—O-Propargyl) | |
| 651 | 2-CH$_3$-4-(n-C$_3$H$_7$—C=N—O-n-C$_4$H$_9$) | |
| 652 | 2-CH$_3$-4-(n-C$_3$H$_7$—C=N—O—CH$_2$—C$_6$H$_5$) | |
| 653 | 2-CH$_3$-4-(i-C$_3$H$_7$—C=N—OCH$_3$) | |
| 654 | 2-CH$_3$-4-(i-C$_3$H$_7$—C=N—OC$_2$H$_5$) | |
| 655 | 2-CH$_3$-4-(i-C$_3$H$_7$—C=N—O-n-C$_3$H$_7$) | |
| 656 | 2-CH$_3$-4-(i-C$_3$H$_7$—C=N—O-i-C$_3$H$_7$) | |
| 657 | 2-CH$_3$-4-(i-C$_3$H$_7$—C=N—O-Allyl) | |
| 658 | 2-CH$_3$-4-(i-C$_3$H$_7$—C=N—O-trans-Chloroallyl) | |
| 659 | 2-CH$_3$-4-(i-C$_3$H$_7$—C=N—O-Propargyl) | |
| 660 | 2-CH$_3$-4-(i-C$_3$H$_7$—C=N—O-n-C$_4$H$_9$) | |
| 661 | 2-CH$_3$-4-(i-C$_3$H$_7$—C=N—O—CH$_2$—C$_6$H$_5$) | |
| 662 | 2-O-n-C$_4$H$_9$ | |
| 663 | 2-O-i-C$_4$H$_9$ | |
| 664 | 2-O-s-C$_4$H$_9$ | |
| 665 | 2-O-t-C$_4$H$_9$ | |
| 666 | 2-Neopentyloxy | |
| 667 | 3-O-n-C$_4$H$_9$ | |
| 668 | 3-O-i-C$_4$H$_9$ | |
| 669 | 3-O-s-C$_4$H$_9$ | |
| 670 | 3-O-t-C$_4$H$_9$ | |
| 671 | 3-Neopentyloxy | |
| 672 | 4-O-n-C$_4$H$_9$ | |
| 673 | 4-O-i-C$_4$H$_9$ | |
| 674 | 4-O-s-C$_4$H$_9$ | |
| 675 | 4-O-t-C$_4$H$_9$ | |
| 676 | 4-Neopentyloxy | |
| 677 | 3-CH$_3$-4-OCH$_3$ | |
| 678 | 3-CH$_3$-4-OC$_2$H$_5$ | |
| 679 | 3-CH$_3$-4-O-n-C$_3$H$_7$ | |
| 680 | 3-CH$_3$-4-O-n-C$_4$H$_9$ | |
| 681 | 3-CH$_3$-4-O-i-C$_4$H$_9$ | |
| 682 | 3-CH$_3$-4-O-s-C$_4$H$_9$ | |
| 683 | 3-CH$_3$-4-O-t-C$_4$H$_9$ | |
| 684 | 3-CH$_3$-4-Neopentyloxy | |
| 685 | 2-CH$_3$-3-OCH$_3$ | |
| 686 | 2-CH$_3$-4-OCH$_3$ | |
| 687 | 2-CH$_3$-5-OCH$_3$ | |
| 688 | 2-CH$_3$-6-OCH$_3$ | |
| 689 | 3-CH$_3$-4-OCH$_3$ | |

TABLE 41-continued

| | |
|---|---|
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 42

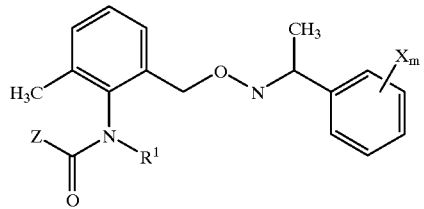

| No. | B |
|---|---|
| 1 | Pyrrolyl-3 |
| 2 | N—CH$_3$-Pyrrolyl-3 |
| 3 | N—C$_2$H$_6$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N-CH$_3$-Pyrrolyl-2 |
| 21 | N-C$_6$H$_5$-Pyrrolyl-2 |
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |

TABLE 42-continued

| | |
|---|---|
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |

TABLE 42-continued

| | |
|---|---|
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N-CH$_3$-Pyrazolyl-4 |
| 127 | N-C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$-N-Methylpyrazolyl-4 |
| 144 | 3-C$_6$H$_5$-N-Methylpyrazolyl-4 |
| 145 | 3-(4'-CH$_3$—C$_6$H$_4$)-N-Methylpyrazolyl-4 |
| 146 | 3-(3'-CH$_3$—C$_6$H$_4$)-N-Methylpyrazolyl-4 |
| 147 | 3-(2'-CH$_3$—C$_6$H$_4$)-N-Methylpyrazolyl-4 |
| 148 | 3-(4'-CH$_3$O—C$_6$H$_4$)-N-Methylpyrazolyl-4 |
| 149 | 3-(3'-CH$_3$O—C$_6$H$_4$)-N-Methylpyrazolyl-4 |
| 150 | 3-(2'-CH$_3$O—C$_6$H$_4$)-N-Methylpyrazolyl-4 |
| 151 | 3-(4'-NO$_2$—C$_6$H$_4$)-N-Methylpyrazolyl-4 |
| 152 | 3-(3'-NO$_2$—C$_6$H$_4$)-N-Methylpyrazolyl-4 |
| 153 | 3-(2'-NO$_2$—C$_6$H$_4$)-N-Methylpyrazolyl-4 |
| 154 | 3-(4'-CN—C$_6$H$_4$)-N-Methylpyrazolyl-4 |
| 155 | 3-(3'-CN—C$_6$H$_4$)-N-Methylpyrazolyl-4 |
| 156 | 3-(2'-CN—C$_6$H$_4$)-N-Methylpyrazolyl-4 |
| 157 | 3-(4'-Cl—C$_6$H$_4$)-N-Methylpyrazolyl-4 |
| 158 | 3-(3'-Cl—C$_6$H$_4$)-N-Methylpyrazolyl-4 |
| 159 | 3-(2'-Cl—C$_6$H$_4$)-N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 3-CH$_3$-Oxazolyl-4 |
| 234 | 3-C$_6$H$_5$-Oxazolyl-4 |
| 235 | 3-(4'-CH$_3$—C$_6$H$_4$)-Oxazolyl-4 |
| 236 | 3-(3'-CH$_3$—C$_6$H$_4$)-Oxazolyl-4 |
| 237 | 3-(2'-CH$_3$—C$_6$H$_4$)-Oxazolyl-4 |
| 238 | 3-(4'-CH$_3$O—C$_6$H$_4$)-Oxazolyl-4 |
| 239 | 3-(3'-CH$_3$O—C$_6$H$_4$)-Oxazolyl-4 |
| 240 | 3-(2'-CH$_3$O—C$_6$H$_4$)-Oxazolyl-4 |
| 241 | 3-(4'-NO$_2$—C$_6$H$_4$)-Oxazolyl-4 |
| 242 | 3-(3'-NO$_2$—C$_6$H$_4$)-Oxazolyl-4 |
| 243 | 3-(2'-NO$_2$—C$_6$H$_4$)-Oxazolyl-4 |
| 244 | 3-(4'-CN—C$_6$H$_4$)-Oxazolyl-4 |
| 245 | 3-(3'-CN—C$_6$H$_4$)-Oxazolyl-4 |
| 246 | 3-(2'-CN—C$_6$H$_4$)-Oxazolyl-4 |
| 247 | 3-(4'-Cl—C$_6$H$_4$)-Oxazolyl-4 |
| 248 | 3-(3'-Cl—C$_6$H$_4$)-Oxazolyl-4 |
| 249 | 3-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 257 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Thiazolyl-5 |
| 270 | 3-C$_6$H$_5$—N—CH$_3$-1,2,4-Thiazolyl-5 |
| 271 | 3-(4'-CH$_3$—C$_6$H$_4$)—N—CH$_3$-1,2,4-Thiazolyl-5 |
| 272 | 3-(3'-CH$_3$—C$_6$H$_4$)—N—CH$_3$-1,2,4-Thiazolyl-5 |

TABLE 42-continued

| | |
|---|---|
| 273 | 3-(2'-CH$_3$—C$_6$H$_4$)—N—CH$_3$-1,2,4-Thiazolyl-5 |
| 274 | 3-(4'-CH$_3$O—C$_6$H$_4$)—N—CH$_3$-1,2,4-Thiazolyl-5 |
| 275 | 3-(3'-CH$_3$O—C$_6$H$_4$)—N—CH$_3$-1,2,4-Thiazolyl-5 |
| 276 | 3-(2'-CH$_3$O—C$_6$H$_4$)—N—CH$_3$-1,2,4-Thiazolyl-5 |
| 277 | 3-(4'-NO$_2$—C$_6$H$_4$)—N—CH$_3$-1,2,4-Thiazolyl-5 |
| 278 | 3-(3'-NO$_2$—C$_6$H$_4$)—N—CH$_3$-1,2,4-Thiazolyl-5 |
| 279 | 3-(2'-NO$_2$—C$_6$H$_4$)—N—CH$_3$-1,2,4-Thiazolyl-5 |
| 280 | 3-(4'-CN—C$_6$H$_4$)—N—CH$_3$-1,2,4-Thiazolyl-5 |
| 281 | 3-(3'-CN—C$_6$H$_4$)—N—CH$_3$-1,2,4-Thiazolyl-5 |
| 282 | 3-(2'-CN—C$_6$H$_4$)—N—CH$_3$-1,2,4-Thiazolyl-5 |
| 283 | 3-(4'-Cl—C$_6$H$_4$)—N—CH$_3$-1,2,4-Thiazolyl-5 |
| 284 | 3-(3'-Cl—C$_6$H$_4$)—N—CH$_3$-1,2,4-Thiazolyl-5 |
| 285 | 3-(2'-Cl—C$_6$H$_4$)—N—CH$_3$-1,2,4-Thiazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,3,4-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | 1-Naphthyl |
| 385 | 2-Naphthyl |

TABLE 43

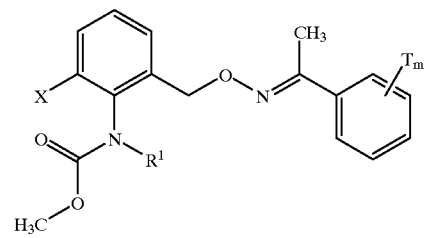

I:    R$^1$ = H, X = CH$_3$
II:   R$^1$ = CH$_3$, X = CH$_3$
III:  R$^1$ = C$_2$H$_5$, X = CH$_3$
IV:   R$^1$ = Allyl, X = CH$_3$
V:    R$^1$ = Propargyl, X = CH$_3$
VI:   R$^1$ = CH$_2$—OCH$_3$, X = CH$_3$
VII:  R$^1$ = CO$_2$CH$_3$, X = CH$_3$
VIII: R$^1$ = H, X = Cl
IX:   R$^1$ = CH$_3$, X = Cl
X:    R$^1$ = C$_2$H$_5$, X = Cl
XI:   R$^1$ = Allyl, X = Cl
XII:  R$^1$ = Propargyl, X = Cl
XIII: R$^1$ = CH$_2$—OCH$_3$, X = Cl
XIV:  R$^1$ = CO$_2$CH$_3$, X = Cl

| No. | T$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |

TABLE 43-continued

| | |
|---|---|
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4,-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |

TABLE 43-continued

| | |
|---|---|
| 169 | 3-O-i-$C_3H_7$ |
| 170 | 4-O-i-$C_3H_7$ |
| 171 | 2-O-n-$C_6H_{13}$ |
| 172 | 3-O-n-$C_6H_{13}$ |
| 173 | 4-O-n-$C_6H_{13}$ |
| 174 | 2-O-n-$C_8H_{17}$ |
| 175 | 3-O-n-$C_8H_{17}$ |
| 176 | 4-O-n-$C_8H_{17}$ |
| 177 | 2-O—$CH_2C_6H_5$ |
| 178 | 3-O—$CH_2C_6H_5$ |
| 179 | 4-O—$CH_2C_6H_5$ |
| 180 | 2-O—$(CH_2)_3C_6H_5$ |
| 181 | 3-O—$(CH_2)_3C_6H_5$ |
| 182 | 4-O—$(CH_2)_3C_6H_5$ |
| 183 | 2,4-$(OCH_3)_2$ |
| 184 | 2-$CF_3$ |
| 185 | 3-$CF_3$ |
| 186 | 4-$CF_3$ |
| 187 | 2-$OCF_3$ |
| 188 | 3-$OCF_3$ |
| 189 | 4-$OCF_3$ |
| 190 | 3-$OCH_2CHF_2$ |
| 191 | 2-$NO_2$ |
| 192 | 3-$NO_2$ |
| 193 | 4-$NO_2$ |
| 194 | 2-CN |
| 195 | 3-CN |
| 196 | 4-CN |
| 197 | 2-$CH_3$, 3-Cl |
| 198 | 2-$CH_3$, 4-Cl |
| 199 | 2-$CH_3$, 5-Cl |
| 200 | 2-$CH_3$, 6-Cl |
| 201 | 2-$CH_3$, 3-F |
| 202 | 2-$CH_3$, 4-F |
| 203 | 2-$CH_3$, 5-F |
| 204 | 2-$CH_3$, 6-F |
| 205 | 2-$CH_3$, 3-Br |
| 206 | 2-$CH_3$, 4-Br |
| 207 | 2-$CH_3$, 5-Br |
| 208 | 2-$CH_3$, 6-Br |
| 209 | 2-Cl, 3-$CH_3$ |
| 210 | 2-Cl, 4-$CH_3$ |
| 211 | 2-Cl, 5-$CH_3$ |
| 212 | 2-F, 3-$CH_3$ |
| 213 | 2-F, 4-$CH_3$ |
| 214 | 2-F, 5-$CH_3$ |
| 215 | 2-Br, 3-$CH_3$ |
| 216 | 2-Br, 4-$CH_3$ |
| 217 | 2-Br, 5-$CH_3$ |
| 218 | 3-$CH_3$, 4-Cl |
| 219 | 3-$CH_3$, 5-Cl |
| 220 | 3-$CH_3$, 4-F |
| 221 | 3-$CH_3$, 5-F |
| 222 | 3-$CH_3$, 4-Br |
| 223 | 3-$CH_3$, 5-Br |
| 224 | 3-F, 4-$CH_3$ |
| 225 | 3-Cl, 4-$CH_3$ |
| 226 | 3-Br, 4-$CH_3$ |
| 227 | 2-Cl, 4,5-$(CH_3)_2$ |
| 228 | 2-Br, 4,5-$(CH_3)_2$ |
| 229 | 2-Cl, 3,5-$(CH_3)_2$ |
| 230 | 2-Br, 3,5-$(CH_3)_2$ |
| 231 | 2,6-$Cl_2$, 4-$CH_3$ |
| 232 | 2,6-$F_2$, 4-$CH_3$ |
| 233 | 2,6-$Br_2$, 4-$CH_3$ |
| 234 | 2,4-$Br_2$, 6-$CH_3$ |
| 235 | 2,4-$F_2$, 6-$CH_3$ |
| 236 | 2,4-$Br_2$, 6-$CH_3$ |
| 237 | 2,6-$(CH_3)_2$, 4-F |
| 238 | 2,6-$(CH_3)_2$, 4-Cl |
| 239 | 2,6-$(CH_3)_2$, 4-Br |
| 240 | 3,5-$(CH_3)_2$, 4-F |
| 241 | 3,5-$(CH_3)_2$, 4-Cl |
| 242 | 3,5-$(CH_3)_2$, 4-Br |
| 243 | 2,3,6-$(CH_3)_3$, 4-F |
| 244 | 2,3,6-$(CH_3)_3$, 4-Cl |
| 245 | 2,3,6-$(CH_3)_3$, 4-Br |
| 246 | 2,4-$(CH_3)_2$, 6-F |
| 247 | 2,4-$(CH_3)_2$, 6-Cl |
| 248 | 2,4-$(CH_3)_2$, 6-Br |
| 249 | 2-i-$C_3H_7$, 4-Cl, 5-$CH_3$ |
| 250 | 2-Cl, 4-$NO_2$ |
| 251 | 2-$NO_2$, 4-Cl |
| 252 | 2-$OCH_3$, 5-$NO_2$ |
| 253 | 2,4-$Cl_2$, 5-$NO_2$ |
| 254 | 2,4-$Cl_2$, 6-$NO_2$ |
| 255 | 2,6-$Cl_2$, 4-$NO_2$ |
| 256 | 2,6-$Br_2$, 4-$NO_2$ |
| 257 | 2,6-$I_2$, 4-$NO_2$ |
| 258 | 2-$CH_3$, 5-i-$C_3H_7$, 4-Cl |
| 259 | 2-$CO_2CH_3$ |
| 260 | 3-$CO_2CH_3$ |
| 261 | 4-$CO_2CH_3$ |
| 262 | 2-$CO_2(C_2H_5)$ |
| 263 | 3-$CO_2(C_2H_5)$ |
| 264 | 4-$CO_2(C_2H_5)$ |
| 265 | 2-$CO_2$(n-$C_3H_7$) |
| 266 | 3-$CO_2$(n-$C_3H_7$) |
| 267 | 4-$CO_2$(n-$C_3H_7$) |
| 268 | 2-$CO_2$(i-$C_3H_7$) |
| 269 | 3-$CO_2$(i-$C_3H_7$) |
| 270 | 4-$CO_2$(i-$C_3H_7$) |
| 271 | 2-$CO_2$(n-$C_6H_{13}$) |
| 272 | 3-$CO_2$(n-$C_6H_{13}$) |
| 273 | 4-$CO_2$(n-$C_6H_{13}$) |
| 274 | 2-$CH_2$—$OCH_3$ |
| 275 | 3-$CH_2$—$OCH_3$ |
| 276 | 4-$CH_2$—$OCH_3$ |
| 277 | 2-$CH_2O(C_2H_5)$ |
| 278 | 3-$CH_2O(C_2H_5)$ |
| 279 | 4-$CH_2O(C_2H_5)$ |
| 280 | 2-$CH_2O$(n-$C_3H_7$) |
| 281 | 3-$CH_2O$(n-$C_3H_7$) |
| 282 | 4-$CH_2O$(n-$C_3H_7$) |
| 283 | 2-$CH_2O$(i-$C_3H_7$) |
| 284 | 3-$CH_2O$(i-$C_3H_7$) |
| 285 | 4-$CH_2O$(i-$C_3H_7$) |
| 286 | 2-CHO |
| 287 | 3-CHO |
| 288 | 4-CHO |
| 289 | 2-CO—$CH_3$ |
| 290 | 3-CO—$CH_3$ |
| 291 | 4-CO—$CH_3$ |
| 292 | 2-CO—$CH_2$—$CH_3$ |
| 293 | 3-CO—$CH_2$—$CH_3$ |
| 294 | 4-CO—$CH_2$—$CH_3$ |
| 295 | 2-CO—$CH_2$—$CH_2$—$CH_3$ |
| 296 | 3-CO—$CH_2$—$CH_2$—$CH_3$ |
| 297 | 4-CO—$CH_2$—$CH_2$—$CH_3$ |
| 298 | 2-CO—$CH(CH_3)$—$CH_3$ |
| 299 | 3-CO—$CH(CH_3)$—$CH_3$ |
| 300 | 4-CO—$CH(CH_3)$—$CH_3$ |
| 301 | 2-Me-4-CHO |
| 302 | 2-Me-4-$CH_3$—CO |
| 303 | 2-Me-4-$CH_3$—$CH_2$—CO |
| 304 | 2-Me-4-$CH_3$—$CH_2$—$CH_2$—CO |
| 305 | 2-Me-4-$CH_3$—$CH(CH_3)$—CO |
| 306 | 2,5-$Me_2$-4-CHO |
| 307 | 2,5-$Me_2$-4-$CH_3$—CO |
| 308 | 2,5-$Me_2$-4-$CH_3$—$CH_2$—CO |
| 309 | 2,5-$Me_2$-4-$CH_3$—$CH_2$—$CH_2$—CO |
| 310 | 2,5-$Me_2$-4-$CH_3$—$CH(CH_3)$—CO |
| 311 | 2-Cl-4-CHO |
| 312 | 2-Cl-4-$CH_3$—CO |
| 313 | 2-Cl-4-$CH_3$—$CH_2$—CO |
| 314 | 2-Cl-4-$CH_3$—$CH(CH_3)$—CO |
| 315 | 2,5-$Cl_2$-4-CHO |
| 316 | 2,5-$Cl_2$-4-$CH_3$—CO |
| 317 | 2,5-$Cl_2$-4-$CH_3$—$CH_2$—CO |
| 318 | 2,5-$Cl_2$-4-$CH_3$—$CH_2$—$CH_2$—CO |
| 319 | 2,5-$Cl_2$-4-$CH_3$——$CH(CH_3)$—CO |
| 320 | 2-C(=$NOCH_3$)—$CH_3$ |
| 321 | 3-C(=$NOCH_3$)—$CH_3$ |
| 322 | 4-C(=$NOCH_3$)—$CH_3$ |
| 323 | 2-C(=$NOC_2H_5$)—$CH_3$ |
| 324 | 3-C(=$NOC_2H_5$)—$CH_3$ |
| 325 | 4-C(=$NOC_2H_5$)—$CH_3$ |
| 326 | 2-C(=NO-n-$C_3H_7$)—$CH_3$ |

TABLE 43-continued

| | |
|---|---|
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)-CH$_3$ |
| 333 | 3-C(=NO-Allyl)-CH$_3$ |
| 334 | 4-C(=NO-Allyl)-CH$_3$ |
| 335 | 2-C(=NO-trans-Chloroallyl)-CH$_3$ |
| 336 | 3-C(=NO-trans-Chloroallyl)-CH$_3$ |
| 337 | 4-C(=NO-trans-Chloroallyl)-CH$_3$ |
| 338 | 2-C(=NO-Propargyl)-CH$_3$ |
| 339 | 3-C(=NO-Propargyl)-CH$_3$ |
| 340 | 4-C(=NO-Propargyl)-CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Propargyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |

TABLE 43-continued

| | |
|---|---|
| 484 | 4-O-(2'-F—$C_6H_4$) |
| 485 | 4-O-(3'-F—$C_6H_4$) |
| 486 | 4-O-(4'-F—$C_6H_4$) |
| 487 | 2-O-(2'-Cl—$C_6H_4$) |
| 488 | 2-O-(3'-Cl—$C_6H_4$) |
| 489 | 2-O-(4'-Cl—$C_6H_4$) |
| 490 | 3-O-(2'-Cl—$C_6H_4$) |
| 491 | 3-O-(3'-Cl—$C_6H_4$) |
| 492 | 3-O-(4'-Cl—$C_6H_4$) |
| 493 | 3-O-(4'-Cl—$C_6H_4$) |
| 494 | 4-O-(2'-Cl—$C_6H_4$) |
| 495 | 4-O-(3'-Cl—$C_6H_4$) |
| 496 | 4-O-(4'-Cl—$C_6H_4$) |
| 497 | 2-O-(2'-$CH_3$—$C_6H_4$) |
| 498 | 2-O-(3'-$CH_3$—$C_6H_4$) |
| 499 | 2-O-(4'-$CH_3$—$C_6H_4$) |
| 500 | 3-O-(2'-$CH_3$—$C_6H_4$) |
| 501 | 3-O-(3'-$CH_3$—$C_6H_4$) |
| 502 | 3-O-(4'-$CH_3$—$C_6H_4$) |
| 503 | 4-O-(2'-$CH_3$—$C_6H_4$) |
| 504 | 4-O-(3'-$CH_3$—$C_6H_4$) |
| 505 | 4-O-(4'-$CH_3$—$C_6H_4$) |
| 506 | 2-O-(2'-$CH_3$—CO—$C_6H_4$) |
| 507 | 2-O-(3'-$CH_3$—CO—$C_6H_4$) |
| 508 | 2-O-(4'-$CH_3$—CO—$C_6H_4$) |
| 509 | 3-O-(2'-$CH_3$—CO—$C_6H_4$) |
| 510 | 3-O-(3'-$CH_3$—CO—$C_6H_4$) |
| 511 | 3-O-(4'-$CH_3$—CO—$C_6H_4$) |
| 512 | 4-O-(2'-$CH_3$—CO—$C_6H_4$) |
| 513 | 4-O-(3'-$CH_3$—CO—$C_6H_4$) |
| 514 | 4-O-(4'-$CH_3$—CO—$C_6H_4$) |
| 515 | 2-O-(2'-($CH_3$—C(=NOAllyl))-$C_6H_4$) |
| 516 | 2-O-(3'-($CH_3$—C(=NOAllyl))-$C_6H_4$) |
| 517 | 2-O-(4'-($CH_3$—C(=NOAllyl))-$C_6H_4$) |
| 518 | 3-O-(2'-($CH_3$—C(=NOAllyl))-$C_6H_4$) |
| 519 | 3-O-(3'-($CH_3$—C(=NOAllyl))-$C_6H_4$) |
| 520 | 3-O-(4'-($CH_3$—C(=NOAllyl))-$C_6H_4$) |
| 521 | 4-O-(2'-($CH_3$—C(=NOAllyl))-$C_6H_4$) |
| 522 | 4-O-(3'-($CH_3$—C(=NOAllyl))-$C_6H_4$) |
| 523 | 4-O-(4'-($CH_3$—C(=NOAllyl))-$C_6H_4$) |
| 524 | 2-O-(2'-$CH_3O_2C$—$C_6H_4$) |
| 525 | 2-O-(3'-$CH_3O_2C$—$C_6H_4$) |
| 526 | 2-O-(4'-$CH_3O_2C$—$C_6H_4$) |
| 527 | 3-O-(2'-$CH_3O_2C$—$C_6H_4$) |
| 528 | 3-O-(3'-$CH_3O_2C$—$C_6H_4$) |
| 529 | 3-O-(4'-$CH_3O_2C$—$C_6H_4$) |
| 530 | 4-O-(2'-$CH_3O_2C$—$C_6H_4$) |
| 531 | 4-O-(3'-$CH_3O_2C$—$C_6H_4$) |
| 532 | 4-O-(4'-$CH_3O_2C$—$C_6H_4$) |
| 533 | 2-O-(2'-$CH_3O$—$C_6H_4$) |
| 534 | 2-O-(3'-$CH_3O$—$C_6H_4$) |
| 535 | 2-O-(4'-$CH_3O$—$C_6H_4$) |
| 536 | 3-O-(2'-$CH_3O$—$C_6H_4$) |
| 537 | 3-O-(3'-$CH_3O$—$C_6H_4$) |
| 538 | 3-O-(4'-$CH_3O$—$C_6H_4$) |
| 539 | 4-O-(2'-$CH_3O$—$C_6H_4$) |
| 540 | 4-O-(3'-$CH_3O$—$C_6H_4$) |
| 541 | 4-O-(4'-$CH_3O$—$C_6H_4$) |
| 542 | 2-O-(2'-$O_2N$—$C_6H_4$) |
| 543 | 2-O-(3'-$O_2N$—$C_6H_4$) |
| 544 | 2-O-(4'-$O_2N$—$C_6H_4$) |
| 545 | 3-O-(2'-$O_2N$—$C_6H_4$) |
| 546 | 3-O-(3'-$O_2N$—$C_6H_4$) |
| 547 | 3-O-(4'-$O_2N$—$C_6H_4$) |
| 548 | 4-O-(2'-$O_2N$—$C_6H_4$) |
| 549 | 4-O-(3'-$O_2N$—$C_6H_4$) |
| 550 | 4-O-(4'-$O_2N$—$C_6H_4$) |
| 551 | 2-O-(2'-NC—$C_6H_4$) |
| 552 | 2-O-(3'-NC—$C_6H_4$) |
| 553 | 2-O-(4'-NC—$C_6H_4$) |
| 554 | 3-O-(2'-NC—$C_6H_4$) |
| 555 | 3-O-(3'-NC—$C_6H_4$) |
| 556 | 3-O-(4'-NC—$C_6H_4$) |
| 557 | 4-O-(2'-NC—$C_6H_4$) |
| 558 | 4-O-(3'-NC—$C_6H_4$) |
| 559 | 4-O-(4'-NC—$C_6H_4$) |
| 560 | 2-O-(2'-$CF_3$—$C_6H_4$) |
| 561 | 2-O-(3'-$CF_3$—$C_6H_4$) |
| 562 | 2-O-(4'-$CF_3$—$C_6H_4$) |

TABLE 43-continued

| | |
|---|---|
| 563 | 3-O-(2'-$CF_3$—$C_6H_4$) |
| 564 | 3-O-(3'-$CF_3$—$C_6H_4$) |
| 565 | 3-O-(4'-$CF_3$—$C_6H_4$) |
| 566 | 4-O-(2'-$CF_3$—$C_6H_4$) |
| 567 | 4-O-(3'-$CF_3$—$C_6H_4$) |
| 568 | 4-O-(4'-$CF_3$—$C_6H_4$) |
| 569 | 2-Pyridinyl-2' |
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |
| 641 | 2-$CH_3$-4-($CH_3$—C=N—O—$CH_2$—$CH_2$—$OCH_3$) |

TABLE 43-continued

| | |
|---|---|
| 642 | 2-CH$_3$-4-(C$_2$H$_5$—C=N—O—CH$_2$—CH$_2$—OCH$_3$) |
| 643 | 2,5-(CH$_3$)$_2$-4-(CH$_3$—C=N—O—CH$_2$—CH$_2$—OCH$_3$) |
| 644 | 2-CH$_3$-4-(n-C$_3$H$_7$—C=N—OCH$_3$) |
| 645 | 2-CH$_3$-4-(n-C$_3$H$_7$—C=N—OC$_2$H$_5$) |
| 646 | 2-CH$_3$-4-(n-C$_3$H$_7$—C=N—O-n-C$_3$H$_7$) |
| 647 | 2-CH$_3$-4-(n-C$_3$H$_7$—C=N—O-i-C$_3$H$_7$) |
| 648 | 2-CH$_3$-4-(n-C$_3$H$_7$—C=N—O-Allyl) |
| 649 | 2-CH$_3$-4-(n-C$_3$H$_7$—C=N—O-trans-Chloroallyl) |
| 650 | 2-CH$_3$-4-(n-C$_3$H$_7$—C=N—O-Propargyl) |
| 651 | 2-CH$_3$-4-(n-C$_3$H$_7$—C=N—O-n-C$_4$H$_9$) |
| 652 | 2-CH$_3$-4-(n-C$_3$H$_7$—C=N—O—CH$_2$—C$_6$H$_5$) |
| 653 | 2-CH$_3$-4-(i-C$_3$H$_7$—C=N—OCH$_3$) |
| 654 | 2-CH$_3$-4-(i-C$_3$H$_7$—C=N—OC$_2$H$_5$) |
| 655 | 2-CH$_3$-4-(i-C$_3$H$_7$—C=N—O-n-C$_3$H$_7$) |
| 656 | 2-CH$_3$-4-(i-C$_3$H$_7$—C=N—O-i-C$_3$H$_7$) |
| 657 | 2-CH$_3$-4-(i-C$_3$H$_7$—C=N—O-Allyl) |
| 658 | 2-CH$_3$-4-(i-C$_3$H$_7$—C=N—O-trans-Chloroallyl) |
| 659 | 2-CH$_3$-4-(i-C$_3$H$_7$—C=N—O-Propargyl) |
| 660 | 2-CH$_3$-4-(i-C$_3$H$_7$—C=N—O-n-C$_4$H$_9$) |
| 661 | 2-CH$_3$-4-(i-C$_3$H$_7$—C=N—O—CH$_2$—C$_6$H$_5$) |
| 662 | 2-O-n-C$_4$H$_9$ |
| 663 | 2-O-i-C$_4$H$_9$ |
| 664 | 2-O-s-C$_4$H$_9$ |
| 665 | 2-O-t-C$_4$H$_9$ |
| 666 | 2-Neopentyloxy |
| 667 | 3-O-n-C$_4$H$_9$ |
| 668 | 3-O-i-C$_4$H$_9$ |
| 669 | 3-O-s-C$_4$H$_9$ |
| 670 | 3-O-t-C$_4$H$_9$ |
| 671 | 3-Neopentyloxy |
| 672 | 4-O-n-C$_4$H$_9$ |
| 673 | 4-O-i-C$_4$H$_9$ |
| 674 | 4-O-s-C$_4$H$_9$ |
| 675 | 4-O-t-C$_4$H$_9$ |
| 676 | 4-Neopentyloxy |
| 677 | 3-CH$_3$-4-OCH$_3$ |
| 678 | 3-CH$_3$-4-OC$_2$H$_5$ |
| 679 | 3-CH$_3$-4-O-n-C$_3$H$_7$ |
| 680 | 3-CH$_3$-4-O-n-C$_4$H$_9$ |
| 681 | 3-CH$_3$-4-O-i-C$_4$H$_9$ |
| 682 | 3-CH$_3$-4-O-s-C$_4$H$_9$ |
| 683 | 3-CH$_3$-4-O-t-C$_4$H$_9$ |
| 684 | 3-CH$_3$-4-Neopentyloxy |
| 685 | 2-CH$_3$-3-OCH$_3$ |
| 686 | 2-CH$_3$-4-OCH$_3$ |
| 687 | 2-CH$_3$-5-OCH$_3$ |
| 688 | 2-CH$_3$-6-OCH$_3$ |
| 689 | 3-CH$_3$-4-OCH$_3$ |
| 690 | 3-CH$_3$-5-OCH$_3$ |
| 691 | 3-CH$_3$-6-OCH$_3$ |
| 692 | 4-CH$_3$-5-O—CH$_3$ |
| 693 | 4-CH$_3$-6-O—CH$_3$ |
| 694 | 4-CH$_3$-6-OCH$_3$ |
| 695 | 2-CH$_3$-3-O-i-C$_3$H$_7$ |
| 696 | 2-CH$_3$-4-O-i-C$_3$H$_7$ |
| 697 | 2-CH$_3$-5-O-i-C$_3$H$_7$ |
| 698 | 2-CH$_3$-6-O-i-C$_3$H$_7$ |
| 699 | 3-CH$_3$-4-O-i-C$_3$H$_7$ |
| 700 | 3-CH$_3$-5-O-i-C$_3$H$_7$ |
| 701 | 3-CH$_3$-6-O-i-C$_3$H$_7$ |
| 702 | 4-CH$_3$-5-O-i-C$_3$H$_7$ |
| 703 | 4-CH$_3$-6-O-i-C$_3$H$_7$ |
| 704 | 5-CH$_3$-6-O-i-C$_3$H$_7$ |
| 705 | 2-Cl-3-OCH$_3$ |
| 706 | 2-Cl-4-OCH$_3$ |
| 707 | 2-Cl-5-OCH$_3$ |
| 708 | 2-Cl-6-OCH$_3$ |
| 709 | 3-Cl-4-OCH$_3$ |
| 710 | 3-Cl-5-OCH$_3$ |
| 711 | 3-Cl-6-OCH$_3$ |
| 712 | 4-Cl-5-OCH$_3$ |
| 713 | 4-Cl-6-OCH$_3$ |
| 714 | 5-Cl-6-OCH$_3$ |

TABLE 44

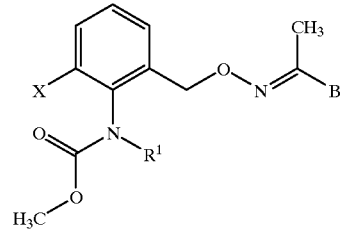

I: $R^1$ = H, X = CH$_3$
II: $R^1$ = CH$_3$, X = CH$_3$
III: $R^1$ = C$_2$H$_5$, X = CH$_3$
IV: $R^1$ = Allyl, X = CH$_3$
V: $R^1$ = Propargyl, X = CH$_3$
VI: $R^1$ = CH$_2$—OCH$_3$, X = CH$_3$
VII: $R^1$ = CO$_2$CH$_3$, X = CH$_3$
VIII: $R^1$ = H, X = Cl
IX: $R^1$ = CH$_3$, X = Cl
X: $R^1$ = C$_2$H$_5$, X = Cl
XI: $R^1$ = Allyl, X = Cl
XII: $R^1$ = Propargyl, X = Cl
XIII: $R^1$ = CH$_2$—OCH$_3$, X = Cl
XIV: $R^1$ = CO$_2$CH$_3$, X = Cl

| No. | B |
|---|---|
| 1 | Pyrrolyl-3 |
| 2 | N—CH$_3$-Pyrrolyl-3 |
| 3 | N—C$_6$H$_5$-Pyrrolyl-3 |
| 4 | N-(4'-CH$_3$—C$_6$H$_4$)-Pyrrolyl-3 |
| 5 | N-(3'-CH$_3$—C$_6$H$_4$)-Pyrrolyl-3 |
| 6 | N-(2'-CH$_3$—C$_6$H$_4$)-Pyrrolyl-3 |
| 7 | N-(4'-CH$_3$O—C$_6$H$_4$)-Pyrrolyl-3 |
| 8 | N-(3'-CH$_3$O—C$_6$H$_4$)-Pyrrolyl-3 |
| 9 | N-(2'-CH$_3$O—C$_6$H$_4$)-Pyrrolyl-3 |
| 10 | N-(4'-NO$_2$—C$_6$H$_4$)-Pyrrolyl-3 |
| 11 | N-(3'-NO$_2$—C$_6$H$_4$)-Pyrrolyl-3 |
| 12 | N-(2'-NO$_2$—C$_6$H$_4$)-Pyrrolyl-3 |
| 13 | N-(4'-CN—C$_6$H$_4$)-Pyrrolyl-3 |
| 14 | N-(3'-CN—C$_6$H$_4$)-Pyrrolyl-3 |
| 15 | N-(2'-CN—C$_6$H$_4$)-Pyrrolyl-3 |
| 16 | N-(4'-Cl—C$_6$H$_4$)-Pyrrolyl-3 |
| 17 | N-(3'-Cl—C$_6$H$_4$)-Pyrrolyl-3 |
| 18 | N-(2'-Cl—C$_6$H$_4$)-Pyrrolyl-3 |
| 19 | Pyrrolyl-2 |
| 20 | N—CH$_3$-Pyrrolyl-2 |
| 21 | N—C$_6$H$_5$-Pyrrolyl-2 |
| 22 | N-(4'-CH$_3$—C$_6$H$_4$)-Pyrrolyl-2 |
| 23 | N-(3'-CH$_3$—C$_6$H$_4$)-Pyrrolyl-2 |
| 24 | N-(2'-CH$_3$—C$_6$H$_4$)-Pyrrolyl-2 |
| 25 | N-(4'-CH$_3$O—C$_6$H$_4$)-Pyrrolyl-2 |
| 26 | N-(3'-CH$_3$O—C$_6$H$_4$)-Pyrrolyl-2 |
| 27 | N-(2'-CH$_3$O—C$_6$H$_4$)-Pyrrolyl-2 |
| 28 | N-(4'-NO$_2$—C$_6$H$_4$)-Pyrrolyl-2 |
| 29 | N-(3'-NO$_2$—C$_6$H$_4$)-Pyrrolyl-2 |
| 30 | N-(2'-NO$_2$—C$_6$H$_4$)-Pyrrolyl-2 |
| 31 | N-(4'-CN—C$_6$H$_4$)-Pyrrolyl-2 |
| 32 | N-(3'-CN—C$_6$H$_4$)-Pyrrolyl-2 |
| 33 | N-(2'-CN—C$_6$H$_4$)-Pyrrolyl-2 |
| 34 | N-(4'-Cl—C$_6$H$_4$)-Pyrrolyl-2 |
| 35 | N-(3'-Cl—C$_6$H$_4$)-Pyrrolyl-2 |
| 36 | N-(2'-Cl—C$_6$H$_4$)-Pyrrolyl-2 |
| 37 | Furyl-2 |
| 38 | 5-CH$_3$-Furyl-2 |
| 39 | 5-C$_6$H$_5$-Furyl-2 |
| 40 | 5-(4'-CH$_3$—C$_6$H$_4$)-Furyl-2 |
| 41 | 5-(3'-CH$_3$—C$_6$H$_4$)-Furyl-2 |
| 42 | 5-(2'-CH$_3$—C$_6$H$_4$)-Furyl-2 |
| 43 | 5-(4'-CH$_3$O—C$_6$H$_4$)-Furyl-2 |
| 44 | 5-(3'-CH$_3$O—C$_6$H$_4$)-Furyl-2 |
| 45 | 5-(2'-CH$_3$O—C$_6$H$_4$)-Furyl-2 |

TABLE 44-continued

| | |
|---|---|
| 46 | 5-(4'-NO$_2$—C$_6$H$_4$)-Furyl-2 |
| 47 | 5-(3'-NO$_2$—C$_6$H$_4$)-Furyl-2 |
| 48 | 5-(2'-NO$_2$—C$_6$H$_4$)-Furyl-2 |
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N—CH$_3$-Pyrazolyl-4 |
| 127 | N—C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |

TABLE 44-continued

| | |
|---|---|
| 204 | 5-(2'-CH₃O—C₆H₄)-Isoxazolyl-3 |
| 205 | 5-(4'-NO₂—C₆H₄)-Isoxazolyl-3 |
| 206 | 5-(3'-NO₂—C₆H₄)-Isoxazolyl-3 |
| 207 | 5-(2'-NO₂—C₆H₄)-Isoxazolyl-3 |
| 208 | 5-(4'-CN—C₆H₄)-Isoxazolyl-3 |
| 209 | 5-(3'-CN—C₆H₄)-Isoxazolyl-3 |
| 210 | 5-(2'-CN—C₆H₄)-Isoxazolyl-3 |
| 211 | 5-(4'-Cl—C₆H₄)-Isoxazolyl-3 |
| 212 | 5-(3'-Cl—C₆H₄)-Isoxazolyl-3 |
| 213 | 5-(2'-Cl—C₆H₄)-Isoxazolyl-3 |
| 214 | Isothiazolyl-5 |
| 215 | 3-CH₃-Isothiazolyl-5 |
| 216 | 3-C₆H₅-Isothiazolyl-5 |
| 217 | 3-(4'-CH₃—C₆H₄)-Isothiazolyl-5 |
| 218 | 3-(3'-CH₃—C₆H₄)-Isothiazolyl-5 |
| 219 | 3-(2'-CH₃—C₆H₄)-Isothiazolyl-5 |
| 220 | 3-(4'-CH₃O—C₆H₄)-Isothiazolyl-5 |
| 221 | 3-(3'-CH₃O—C₆H₄)-Isothiazolyl-5 |
| 222 | 3-(2'-CH₃O—C₆H₄)-Isothiazolyl-5 |
| 223 | 3-(4'-NO₂—C₆H₄)-Isothiazolyl-5 |
| 224 | 3-(3'-NO₂—C₆H₄)-Isothiazolyl-5 |
| 225 | 3-(2'-NO₂—C₆H₄)-Isothiazolyl-5 |
| 226 | 3-(4'-CN—C₆H₄)-Isothiazolyl-5 |
| 227 | 3-(3'-CN—C₆H₄)-Isothiazolyl-5 |
| 228 | 3-(2'-CN—C₆H₄)-Isothiazolyl-5 |
| 229 | 3-(4'-Cl—C₆H₄)-Isothiazolyl-5 |
| 230 | 3-(3'-Cl—C₆H₄)-Isothiazolyl-5 |
| 231 | 3-(2'-Cl—C₆H₄)-Isothiazolyl-5 |
| 232 | Oxazolyl-4 |
| 233 | 3-CH₃-Oxazolyl-4 |
| 234 | 3-C₆H₅-Oxazolyl-4 |
| 235 | 3-(4'-CH₃—C₆H₄)-Oxazolyl-4 |
| 236 | 3-(3'-CH₃—C₆H₄)-Oxazolyl-4 |
| 237 | 3-(2'-CH₃—C₆H₄)-Oxazolyl-4 |
| 238 | 3-(4'-CH₃O—C₆H₄)-Oxazolyl-4 |
| 239 | 3-(3'-CH₃O—C₆H₄)-Oxazolyl-4 |
| 240 | 3-(2'-CH₃O—C₆H₄)-Oxazolyl-4 |
| 241 | 3-(4'-NO₂—C₆H₄)-Oxazolyl-4 |
| 242 | 3-(3'-NO₂—C₆H₄)-Oxazolyl-4 |
| 243 | 3-(2'-NO₂—C₆H₄)-Oxazolyl-4 |
| 244 | 3-(4'-CN—C₆H₄)-Oxazolyl-4 |
| 245 | 3-(3'-CN—C₆H₄)-Oxazolyl-4 |
| 246 | 3-(2'-CN—C₆H₄)-Oxazolyl-4 |
| 247 | 3-(4'-Cl—C₆H₄)-Oxazolyl-4 |
| 248 | 3-(3'-Cl—C₆H₄)-Oxazolyl-4 |
| 249 | 3-(2'-Cl—C₆H₄)-Oxazolyl-4 |
| 250 | Thiazolyl-4 |
| 251 | 2-CH₃-Thiazolyl-4 |
| 252 | 2-C₆H₅-Thiazolyl-4 |
| 253 | 2-(4'-CH₃—C₆H₄)-Thiazolyl-4 |
| 254 | 2-(3'-CH₃—C₆H₄)-Thiazolyl-4 |
| 255 | 2-(2'-CH₃—C₆H₄)-Thiazolyl-4 |
| 256 | 2-(4'-CH₃O—C₆H₄)-Thiazolyl-4 |
| 257 | 2-(3'-CH₃O—C₆H₄)-Thiazolyl-4 |
| 258 | 2-(2'-CH₃O—C₆H₄)-Thiazolyl-4 |
| 259 | 2-(4'-NO₂—C₆H₄)-Thiazolyl-4 |
| 260 | 2-(3'-NO₂—C₆H₄)-Thiazolyl-4 |
| 261 | 2-(2'-NO₂—C₆H₄)-Thiazolyl-4 |
| 262 | 2-(4'-CN—C₆H₄)-Thiazolyl-4 |
| 263 | 2-(3'-CN—C₆H₄)-Thiazolyl-4 |
| 264 | 2-(2'-CN—C₆H₄)-Thiazolyl-4 |
| 265 | 2-(4'-Cl—C₆H₄)-Thiazolyl-4 |
| 266 | 2-(3'-Cl—C₆H₄)-Thiazolyl-4 |
| 267 | 2-(2'-Cl—C₆H₄)-Thiazolyl-4 |
| 268 | N—CH₃-1,2,4-Triazolyl-5 |
| 269 | 3-CH₃—N—CH₃-1,2,4-Triazolyl-5 |
| 270 | 3-C₆H₅—N—CH₃-1,2,4-Triazolyl-5 |
| 271 | 3-(4'-CH₃—C₆H₄)—N—CH₃-1,2,4-Triazolyl-5 |
| 272 | 3-(3'-CH₃—C₆H₄)—N—CH₃-1,2,4-Triazolyl-5 |
| 273 | 3-(2'-CH₃—C₆H₄)—N—CH₃-1,2,4-Triazolyl-5 |
| 274 | 3-(4'-CH₃O—C₆H₄)—N—CH₃-1,2,4-Triazolyl-5 |
| 275 | 3-(3'-CH₃O—C₆H₄)—N—CH₃-1,2,4-Triazolyl-5 |
| 276 | 3-(2'-CH₃O—C₆H₄)—N—CH₃-1,2,4-Triazolyl-5 |
| 277 | 3-(4'-NO₂—C₆H₄)—N—CH₃-1,2,4-Triazolyl-5 |
| 278 | 3-(3'-NO₂—C₆H₄)—N—CH₃-1,2,4-Triazolyl-5 |
| 279 | 3-(2'-NO₂—C₆H₄)—N—CH₃-1,2,4-Triazolyl-5 |
| 280 | 3-(4'-CN—C₆H₄)—N—CH₃-1,2,4-Triazolyl-5 |
| 281 | 3-(3'-CN—C₆H₄)—N—CH₃-1,2,4-Triazolyl-5 |
| 282 | 3-(2'-CN—C₆H₄)—N—CH₃-1,2,4-Triazolyl-5 |
| 283 | 3-(4'-Cl—C₆H₄)—N—CH₃-1,2,4-Triazolyl-5 |
| 284 | 3-(3'-Cl—C₆H₄)—N—CH₃-1,2,4-Triazolyl-5 |
| 285 | 3-(2'-Cl—C₆H₄)—N—CH₃-1,2,4-Triazolyl-5 |
| 286 | 1,3,4-Oxadiazolyl-2 |
| 287 | 5-CH₃-1,3,4-Oxadiazolyl-2 |
| 288 | 5-C₆H₅-1,3,4-Oxadiazolyl-2 |
| 289 | 5-(4'-CH₃—C₆H₄)-1,3,4-Oxadiazolyl-2 |
| 290 | 5-(3'-CH₃—C₆H₄)-1,3,4-Oxadiazolyl-2 |
| 291 | 5-(2'-CH₃—C₆H₄)-1,3,4-Oxadiazolyl-2 |
| 292 | 5-(4'-CH₃O—C₆H₄)-1,3,4-Oxadiazolyl-2 |
| 293 | 5-(3'-CH₃O—C₆H₄)-1,3,4-Oxadiazolyl-2 |
| 294 | 5-(2'-CH₃O—C₆H₄)-1,3,4-Oxadiazolyl-2 |
| 295 | 5-(4'-NO₂—C₆H₄)-1,3,4-Oxadiazolyl-2 |
| 296 | 5-(3'-NO₂—C₆H₄)-1,3,4-Oxadiazolyl-2 |
| 297 | 5-(2'-NO₂—C₆H₄)-1,3,4-Oxadiazolyl-2 |
| 298 | 5-(4'-CN—C₆H₄)-1,3,4-Oxadiazolyl-2 |
| 299 | 5-(3'-CN—C₆H₄)-1,3,4-Oxadiazolyl-2 |
| 300 | 5-(2'-CN—C₆H₄)-1,3,4-Oxadiazolyl-2 |
| 301 | 5-(4'-Cl—C₆H₄)-1,3,4-Oxadiazolyl-2 |
| 302 | 5-(3'-Cl—C₆H₄)-1,3,4-Oxadiazolyl-2 |
| 303 | 5-(2'-Cl—C₆H₄)-1,3,4-Oxadiazolyl-2 |
| 304 | 1,2,4-Oxadiazolyl-3 |
| 305 | 5-CH₃-1,2,4-Oxadiazolyl-3 |
| 306 | 5-C₆H₅-1,2,4-Oxadiazolyl-3 |
| 307 | 5-(4'-CH₃—C₆H₄)-1,2,4-Oxadiazolyl-3 |
| 308 | 5-(3'-CH₃—C₆H₄)-1,2,4-Oxadiazolyl-3 |
| 309 | 5-(2'-CH₃—C₆H₄)-1,2,4-Oxadiazolyl-3 |
| 310 | 5-(4'-CH₃O—C₆H₄)-1,2,4-Oxadiazolyl-3 |
| 311 | 5-(3'-CH₃O—C₆H₄)-1,2,4-Oxadiazolyl-3 |
| 312 | 5-(2'-CH₃O—C₆H₄)-1,2,4-Oxadiazolyl-3 |
| 313 | 5-(4'-NO₂—C₆H₄)-1,2,4-Oxadiazolyl-3 |
| 314 | 5-(3'-NO₂—C₆H₄)-1,2,4-Oxadiazolyl-3 |
| 315 | 5-(2'-NO₂—C₆H₄)-1,2,4-Oxadiazolyl-3 |
| 316 | 5-(4'-CN—C₆H₄)-1,2,4-Oxadiazolyl-3 |
| 317 | 5-(3'-CN—C₆H₄)-1,2,4-Oxadiazolyl-3 |
| 318 | 5-(2'-CN—C₆H₄)-1,2,4-Oxadiazolyl-3 |
| 319 | 5-(4'-Cl—C₆H₄)-1,2,4-Oxadiazolyl-3 |
| 320 | 5-(3'-Cl—C₆H₄)-1,2,4-Oxadiazolyl-3 |
| 321 | 5-(2'-Cl—C₆H₄)-1,2,4-Oxadiazolyl-3 |
| 322 | 1,2,4-Oxadiazolyl-5 |
| 323 | 3-CH₃-1,2,4-Oxadiazolyl-5 |
| 324 | 3-C₆H₅-1,2,4-Oxadiazolyl-5 |
| 325 | 3-(4'-CH₃—C₆H₄)-1,2,4-Oxadiazolyl-5 |
| 326 | 3-(3'-CH₃—C₆H₄)-1,2,4-Oxadiazolyl-5 |
| 327 | 3-(2'-CH₃—C₆H₄)-1,2,4-Oxadiazolyl-5 |
| 328 | 3-(4'-CH₃O—C₆H₄)-1,2,4-Oxadiazolyl-5 |
| 329 | 3-(3'-CH₃O—C₆H₄)-1,2,4-Oxadiazolyl-5 |
| 330 | 3-(2'-CH₃O—C₆H₄)-1,2,4-Oxadiazolyl-5 |
| 331 | 3-(4'-NO₂—C₆H₄)-1,2,4-Oxadiazolyl-5 |
| 332 | 3-(3'-NO₂—C₆H₄)-1,2,4-Oxadiazolyl-5 |
| 333 | 3-(2'-NO₂—C₆H₄)-1,2,4-Oxadiazolyl-5 |
| 334 | 3-(4'-CN—C₆H₄)-1,2,4-Oxadiazolyl-5 |
| 335 | 3-(3'-CN—C₆H₄)-1,2,4-Oxadiazolyl-5 |
| 336 | 3-(2'-CN—C₆H₄)-1,2,4-Oxadiazolyl-5 |
| 337 | 3-(4'-Cl—C₆H₄)-1,2,4-Oxadiazolyl-5 |
| 338 | 3-(3'-Cl—C₆H₄)-1,2,4-Oxadiazolyl-5 |
| 339 | 3-(2'-Cl—C₆H₄)-1,2,4-Oxadiazolyl-5 |
| 340 | 1,2,4-Thiadiazolyl-3 |
| 341 | 5-CH₃-1,2,4-Thiadiazolyl-3 |
| 342 | 5-C₆H₅-1,2,4-Thiadiazolyl-3 |
| 343 | 5-(4'-CH₃—C₆H₄)-1,2,4-Thiadiazolyl-3 |
| 344 | 5-(3'-CH₃—C₆H₄)-1,2,4-Thiadiazolyl-3 |
| 345 | 5-(2'-CH₃—C₆H₄)-1,2,4-Thiadiazolyl-3 |
| 346 | 5-(4'-CH₃O—C₆H₄)-1,2,4-Thiadiazolyl-3 |
| 347 | 5-(3'-CH₃O—C₆H₄)-1,2,4-Thiadiazolyl-3 |
| 348 | 5-(2'-CH₃O—C₆H₄)-1,2,4-Thiadiazolyl-3 |
| 349 | 5-(4'-NO₂—C₆H₄)-1,2,4-Thiadiazolyl-3 |
| 350 | 5-(3'-NO₂—C₆H₄)-1,2,4-Thiadiazolyl-3 |
| 351 | 5-(2'-NO₂—C₆H₄)-1,2,4-Thiadiazolyl-3 |
| 352 | 5-(4'-CN—C₆H₄)-1,2,4-Thiadiazolyl-3 |
| 353 | 5-(3'-CN—C₆H₄)-1,2,4-Thiadiazolyl-3 |
| 354 | 5-(2'-CN—C₆H₄)-1,2,4-Thiadiazolyl-3 |
| 355 | 5-(4'-Cl—C₆H₄)-1,2,4-Thiadiazolyl-3 |
| 356 | 5-(3'-Cl—C₆H₄)-1,2,4-Thiadiazolyl-3 |
| 357 | 5-(2'-Cl—C₆H₄)-1,2,4-Thiadiazolyl-3 |
| 358 | 1,3,4-Thiadiazolyl-2 |
| 359 | 5-CH₃-1,3,4-Thiadiazolyl-2 |
| 360 | 5-C₆H₅-1,3,4-Thiadiazolyl-2 |
| 361 | 5-(4'-CH₃—C₆H₄)-1,3,4-Thiadiazolyl-2 |

TABLE 44-continued

| | |
|---|---|
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |
| 384 | 1-Naphthyl |
| 385 | 2-Naphthyl |

TABLE 45

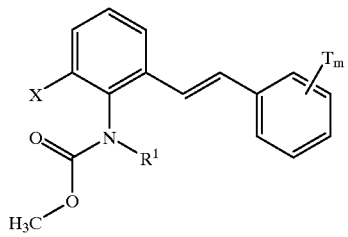

I: $R^1$ = H, X = CH$_3$
II: $R^1$ = CH$_3$, X = CH$_3$
III: $R^1$ = C$_2$H$_5$, X = CH$_3$
IV: $R^1$ = Allyl, X = CH$_3$
V: $R^1$ = Propargyl, X = CH$_3$
VII: $R^1$ = CO$_2$CH$_3$, X = CH$_3$
VIII: $R^1$ = H, X = Cl
IX: $R^1$ = CH$_3$, X = Cl
X: $R^1$ = C$_2$H$_5$, X = Cl
XI: $R^1$ = Allyl, X = Cl
XII: $R^1$ = Propargyl, X = Cl
XIII: $R^1$ = CH$_2$—OCH$_3$, X = Cl
XIV: $R^1$ = CO$_2$CH$_3$, X = Cl

| No. | T$_m$ |
|---|---|
| 1 | H |
| 2 | 2-F |
| 3 | 3-F |
| 4 | 4-F |
| 5 | 2,4-F$_2$ |
| 6 | 2,4,6-F$_3$ |
| 7 | 2,3,4,5,6-F$_5$ |
| 8 | 2,3-F$_2$ |
| 9 | 2-Cl |
| 10 | 3-Cl |
| 11 | 4-Cl |
| 12 | 2,3-Cl$_2$ |
| 13 | 2,4-Cl$_2$ |
| 14 | 2,5-Cl$_2$ |
| 15 | 2,6-Cl$_2$ |
| 16 | 3,4-Cl$_2$ |
| 17 | 3,5-Cl$_2$ |

TABLE 45-continued

| No. | T$_m$ |
|---|---|
| 18 | 2,3,4-Cl$_3$ |
| 19 | 2,3,5-Cl$_3$ |
| 20 | 2,3,6-Cl$_3$ |
| 21 | 2,4,5-Cl$_3$ |
| 22 | 2,4,6-Cl$_3$ |
| 23 | 3,4,5-Cl$_3$ |
| 24 | 2,3,4,6-Cl$_4$ |
| 25 | 2,3,5,6-Cl$_4$ |
| 26 | 2,3,4,5,6-Cl$_5$ |
| 27 | 2-Br |
| 28 | 3-Br |
| 29 | 4-Br |
| 30 | 2,4-Br$_2$ |
| 31 | 2,5-Br$_2$ |
| 32 | 2,6-Br$_2$ |
| 33 | 2,4,6-Br$_3$ |
| 34 | 2,3,4,5,6-Br$_5$ |
| 35 | 2-I |
| 36 | 3-I |
| 37 | 4-I |
| 38 | 2,4-I$_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 3-F |
| 51 | 2-Br, 4-F |
| 52 | 2-Br, 5-F |
| 53 | 2-Br, 6-F |
| 54 | 2-F, 3-Cl |
| 55 | 2-F, 4-Cl |
| 56 | 2-F, 5-Cl |
| 57 | 3-Cl, 4-F |
| 58 | 3-Cl, 5-F |
| 59 | 3-Cl, 4-Br |
| 60 | 3-Cl, 5-Br |
| 61 | 3-F, 4-Cl |
| 62 | 3-F, 4-Br |
| 63 | 3-Br, 4-Cl |
| 64 | 3-Br, 4-F |
| 65 | 2,6-Cl$_2$, 4-Br |
| 66 | 2-CH$_3$ |
| 67 | 3-CH$_3$ |
| 68 | 4-CH$_3$ |
| 69 | 2,3-(CH$_3$)$_2$ |
| 70 | 2,4-(CH$_3$)$_2$ |
| 71 | 2,5-(CH$_3$)$_2$ |
| 72 | 2,6-(CH$_3$)$_2$ |
| 73 | 3,4-(CH$_3$)$_2$ |
| 74 | 3,5-(CH$_3$)$_2$ |
| 75 | 2,3,5-(CH$_3$)$_3$ |
| 76 | 2,3,4-(CH$_3$)$_3$ |
| 77 | 2,3,6-(CH$_3$)$_3$ |
| 78 | 2,4,5-(CH$_3$)$_3$ |
| 79 | 2,4,6-(CH$_3$)$_3$ |
| 80 | 3,4,5-(CH$_3$)$_3$ |
| 81 | 2,3,4,6-(CH$_3$)$_4$ |
| 82 | 2,3,5,6-(CH$_3$)$_4$ |
| 83 | 2,3,4,5,6-(CH$_3$)$_5$ |
| 84 | 2-C$_2$H$_5$ |
| 85 | 3-C$_2$H$_5$ |
| 86 | 4-C$_2$H$_5$ |
| 87 | 2,4-(C$_2$H$_5$)$_2$ |
| 88 | 2,6-(C$_2$H$_5$)$_2$ |
| 89 | 3,5-(C$_2$H$_5$)$_2$ |
| 90 | 2,4,6-(C$_2$H$_5$)$_3$ |
| 91 | 2-n-C$_3$H$_7$ |
| 92 | 3-n-C$_3$H$_7$ |
| 93 | 4-n-C$_3$H$_7$ |
| 94 | 2-i-C$_3$H$_7$ |
| 95 | 3-i-C$_3$H$_7$ |
| 96 | 4-i-C$_3$H$_7$ |

TABLE 45-continued

| | |
|---|---|
| 97 | 2,4-(i-C$_3$H$_7$)$_2$ |
| 98 | 2,6-(i-C$_3$H$_7$)$_2$ |
| 99 | 3,5-(i-C$_3$H$_7$)$_2$ |
| 100 | 2,4,6-(i-C$_3$H$_7$)$_3$ |
| 101 | 2-s-C$_4$H$_9$ |
| 102 | 3-s-C$_4$H$_9$ |
| 103 | 4-s-C$_4$H$_9$ |
| 104 | 2-t-C$_4$H$_9$ |
| 105 | 3-t-C$_4$H$_9$ |
| 106 | 4-t-C$_4$H$_9$ |
| 107 | 2,3-(t-C$_4$H$_9$)$_2$ |
| 108 | 2,4-(t-C$_4$H$_9$)$_2$ |
| 109 | 2,5-(t-C$_4$H$_9$)$_2$ |
| 110 | 2,6-(t-C$_4$H$_9$)$_2$ |
| 111 | 3,4-(t-C$_4$H$_9$)$_2$ |
| 112 | 2,4,6-(t-C$_4$H$_9$)$_3$ |
| 113 | 4-n-C$_9$H$_{19}$ |
| 114 | 4-n-C$_{12}$H$_{25}$ |
| 115 | 4-n-C$_{15}$H$_{31}$ |
| 116 | 4-(1,1,3,3-Tetramethylbutyl) |
| 117 | 4-(2,4,4-Trimethylpropyl) |
| 118 | 2-t-C$_4$H$_9$, 4-CH$_3$ |
| 119 | 2-t-C$_4$H$_9$, 5-CH$_3$ |
| 120 | 2,6-(t-C$_4$H$_9$)$_2$, 4-CH$_3$ |
| 121 | 2-CH$_3$, 4-t-C$_4$H$_9$ |
| 122 | 2-CH$_3$, 6-t-C$_4$H$_9$ |
| 123 | 2-CH$_3$, 4-i-C$_3$H$_7$ |
| 124 | 2-CH$_3$, 5-i-C$_3$H$_7$ |
| 125 | 3-CH$_3$, 4-i-C$_3$H$_7$ |
| 126 | 2-i-C$_3$H$_7$, 5-CH$_3$ |
| 127 | 2,4-(t-C$_4$H$_9$)$_2$, 6-i-C$_3$H$_7$ |
| 128 | 2-Allyl |
| 129 | 3-Allyl |
| 130 | 4-Allyl |
| 131 | 2-Allyl, 6-CH$_3$ |
| 132 | 2-cyclo-C$_6$H$_{11}$ |
| 133 | 3-cyclo-C$_6$H$_{11}$ |
| 134 | 4-cyclo-C$_6$H$_{11}$ |
| 135 | 2,4-(cyclo-C$_6$H$_{11}$)$_2$, 6-CH$_3$ |
| 136 | 2-CH$_3$, 4-cyclo-C$_6$H$_{11}$ |
| 137 | 2-CH$_2$—C$_6$H$_5$ |
| 138 | 3-CH$_2$—C$_6$H$_5$ |
| 139 | 4-CH$_2$—C$_6$H$_5$ |
| 140 | 2-CH$_2$—C$_6$H$_5$, 4-CH$_3$ |
| 141 | 2-CH$_3$, 4-CH$_2$—C$_6$H$_5$ |
| 142 | 2-C$_6$H$_5$ |
| 143 | 3-C$_6$H$_5$ |
| 144 | 4-C$_6$H$_5$ |
| 145 | 4-(2-i-C$_3$H$_7$—C$_6$H$_4$) |
| 146 | 4-C$_6$H$_5$, 2,6-(CH$_3$)$_2$ |
| 147 | 2-Cl, 4-C$_6$H$_5$ |
| 148 | 2-Br, 4-C$_6$H$_5$ |
| 149 | 2-C$_6$H$_5$, 4-Cl |
| 150 | 2-C$_6$H$_5$, 4-Br |
| 151 | 2-CH$_2$C$_6$H$_5$, 4-Cl |
| 152 | 2-CH$_2$C$_6$H$_5$, 4-Br |
| 153 | 2-Cl, 4-CH$_2$C$_6$H$_5$ |
| 154 | 2-Br, 4-CH$_2$C$_6$H$_5$ |
| 155 | 2-cyclo-C$_6$H$_{11}$, 4-Cl |
| 156 | 2-cyclo-C$_6$H$_{11}$, 4-Br |
| 157 | 2-Cl, 4-cyclo-C$_6$H$_{11}$ |
| 158 | 2-Br, 4-cyclo-C$_6$H$_{11}$ |
| 159 | 2-OCH$_3$ |
| 160 | 3-OCH$_3$ |
| 161 | 4-OCH$_3$ |
| 162 | 2-OC$_2$H$_5$ |
| 163 | 3-O—C$_2$H$_5$ |
| 164 | 4-O—C$_2$H$_5$ |
| 165 | 2-O-n-C$_3$H$_7$ |
| 166 | 3-O-n-C$_3$H$_7$ |
| 167 | 4-O-n-C$_3$H$_7$ |
| 168 | 2-O-i-C$_3$H$_7$ |
| 169 | 3-O-i-C$_3$H$_7$ |
| 170 | 4-O-i-C$_3$H$_7$ |
| 171 | 2-O-n-C$_6$H$_{13}$ |
| 172 | 3-O-n-C$_6$H$_{13}$ |
| 173 | 4-O-n-C$_6$H$_{13}$ |
| 174 | 2-O-n-C$_8$H$_{17}$ |
| 175 | 3-O-n-C$_8$H$_{17}$ |
| 176 | 4-O-n-C$_8$H$_{17}$ |
| 177 | 2-O—CH$_2$C$_6$H$_5$ |
| 178 | 3-O—CH$_2$C$_6$H$_5$ |
| 179 | 4-O—CH$_2$C$_6$H$_5$ |
| 180 | 2-O—(CH$_2$)$_3$C$_6$H$_5$ |
| 181 | 3-O—(CH$_2$)$_3$C$_6$H$_5$ |
| 182 | 4-O—(CH$_2$)$_3$C$_6$H$_5$ |
| 183 | 2,4-(OCH$_3$)$_2$ |
| 184 | 2-CF$_3$ |
| 185 | 3-CF$_3$ |
| 186 | 4-CF$_3$ |
| 187 | 2-OCF$_3$ |
| 188 | 3-OCF$_3$ |
| 189 | 4-OCF$_3$ |
| 190 | 3-OCH$_2$CHF$_2$ |
| 191 | 2-NO$_2$ |
| 192 | 3-NO$_2$ |
| 193 | 4-NO$_2$ |
| 194 | 2-CN |
| 195 | 3-CN |
| 196 | 4-CN |
| 197 | 2-CH$_3$, 3-Cl |
| 198 | 2-CH$_3$, 4-Cl |
| 199 | 2-CH$_3$, 5-Cl |
| 200 | 2-CH$_3$, 6-Cl |
| 201 | 2-CH$_3$, 3-F |
| 202 | 2-CH$_3$, 4-F |
| 203 | 2-CH$_3$, 5-F |
| 204 | 2-CH$_3$, 6-F |
| 205 | 2-CH$_3$, 3-Br |
| 206 | 2-CH$_3$, 4-Br |
| 207 | 2-CH$_3$, 5-Br |
| 208 | 2-CH$_3$, 6-Br |
| 209 | 2-Cl, 3-CH$_3$ |
| 210 | 2-Cl, 4-CH$_3$ |
| 211 | 2-Cl, 5-CH$_3$ |
| 212 | 2-F, 3-CH$_3$ |
| 213 | 2-F, 4-CH$_3$ |
| 214 | 2-F, 5-CH$_3$ |
| 215 | 2-Br, 3-CH$_3$ |
| 216 | 2-Br, 4-CH$_3$ |
| 217 | 2-Br, 5-CH$_3$ |
| 218 | 3-CH$_3$, 4-Cl |
| 219 | 3-CH$_3$, 5-Cl |
| 220 | 3-CH$_3$, 4-F |
| 221 | 3-CH$_3$, 5-F |
| 222 | 3-CH$_3$, 4-Br |
| 223 | 3-CH$_3$, 5-Br |
| 224 | 3-F, 4-CH$_3$ |
| 225 | 3-Cl, 4-CH$_3$ |
| 226 | 3-Br, 4-CH$_3$ |
| 227 | 2-Cl, 4,5-(CH$_3$)$_2$ |
| 228 | 2-Br, 4,5-(CH$_3$)$_2$ |
| 229 | 2-Cl, 3,5-(CH$_3$)$_2$ |
| 230 | 2-Br, 3,5-(CH$_3$)$_2$ |
| 231 | 2,6-Cl$_2$, 4-CH$_3$ |
| 232 | 2,6-F$_2$, 4-CH$_3$ |
| 233 | 2,6-Br$_2$, 4-CH$_3$ |
| 234 | 2,4-Br$_2$, 6-CH$_3$ |
| 235 | 2,4-F$_2$, 6-CH$_3$ |
| 236 | 2,4-Br$_2$, 6-CH$_3$ |
| 237 | 2,6-(CH$_3$)$_2$, 4-F |
| 238 | 2,6-(CH$_3$)$_2$, 4-Cl |
| 239 | 2,6-(CH$_3$)$_2$, 4-Br |
| 240 | 3,5-(CH$_3$)$_2$, 4-F |
| 241 | 3,5-(CH$_3$)$_2$, 4-Cl |
| 242 | 3,5-(CH$_3$)$_2$, 4-Br |
| 243 | 2,3,6-(CH$_3$)$_3$, 4-F |
| 244 | 2,3,6-(CH$_3$)$_3$, 4-Cl |
| 245 | 2,3,6-(CH$_3$)$_3$, 4-Br |
| 246 | 2,4-(CH$_3$)$_2$, 6-F |
| 247 | 2,4-(CH$_3$)$_2$, 6-Cl |
| 248 | 2,4-(CH$_3$)$_2$, 6-Br |
| 249 | 2-i-C$_3$H$_7$, 4-Cl, 5-CH$_3$ |
| 250 | 2-Cl, 4-NO$_2$ |
| 251 | 2-NO$_2$, 4-Cl |
| 252 | 2-OCH$_3$, 5-NO$_2$ |
| 253 | 2,4-Cl$_2$, 5-NO$_2$ |
| 254 | 2,4-Cl$_2$, 6-NO$_2$ |

TABLE 45-continued

| | |
|---|---|
| 255 | 2,6-Cl$_2$, 4-NO$_2$ |
| 256 | 2,6-Br$_2$, 4-NO$_2$ |
| 257 | 2,6-I$_2$, 4-NO$_2$ |
| 258 | 2-CH$_3$, 5-i-C$_3$H$_7$, 4-Cl |
| 259 | 2-CO$_2$CH$_3$ |
| 260 | 3-CO$_2$CH$_3$ |
| 261 | 4-CO$_2$CH$_3$ |
| 262 | 2-CO$_2$(C$_2$H$_5$) |
| 263 | 3-CO$_2$(C$_2$H$_5$) |
| 264 | 4-CO$_2$(C$_2$H$_5$) |
| 265 | 2-CO$_2$(n-C$_3$H$_7$) |
| 266 | 3-CO$_2$(n-C$_3$H$_7$) |
| 267 | 4-CO$_2$(n-C$_3$H$_7$) |
| 268 | 2-CO$_2$(i-C$_3$H$_7$) |
| 269 | 3-CO$_2$(i-C$_3$H$_7$) |
| 270 | 4-CO$_2$(i-C$_3$H$_7$) |
| 271 | 2-CO$_2$(n-C$_6$H$_{13}$) |
| 272 | 3-CO$_2$(n-C$_6$H$_{13}$) |
| 273 | 4-CO$_2$(n-C$_6$H$_{13}$) |
| 274 | 2-CH$_2$—OCH$_3$ |
| 275 | 3-CH$_2$—OCH$_3$ |
| 276 | 4-CH$_2$—OCH$_3$ |
| 277 | 2-CH$_2$O(C$_2$H$_5$) |
| 278 | 3-CH$_2$O(C$_2$H$_5$) |
| 279 | 4-CH$_2$O(C$_2$H$_5$) |
| 280 | 2-CH$_2$O(n-C$_3$H$_7$) |
| 281 | 3-CH$_2$O(n-C$_3$H$_7$) |
| 282 | 4-CH$_2$O(n-C$_3$H$_7$) |
| 283 | 2-CH$_2$O(i-C$_3$H$_7$) |
| 284 | 3-CH$_2$O(i-C$_3$H$_7$) |
| 285 | 4-CH$_2$O(i-C$_3$H$_7$) |
| 286 | 2-CHO |
| 287 | 3-CHO |
| 288 | 4-CHO |
| 289 | 2-CO—CH$_3$ |
| 290 | 3-CO—CH$_3$ |
| 291 | 4-CO—CH$_3$ |
| 292 | 2-CO—CH$_2$—CH$_3$ |
| 293 | 3-CO—CH$_2$—CH$_3$ |
| 294 | 4-CO—CH$_2$—CH$_3$ |
| 295 | 2-CO—CH$_2$—CH$_2$—CH$_3$ |
| 296 | 3-CO—CH$_2$—CH$_2$—CH$_3$ |
| 297 | 4-CO—CH$_2$—CH$_2$—CH$_3$ |
| 298 | 2-CO—CH(CH$_3$)—CH$_3$ |
| 299 | 3-CO—CH(CH$_3$)—CH$_3$ |
| 300 | 4-CO—CH(CH$_3$)—CH$_3$ |
| 301 | 2-Me-4-CHO |
| 302 | 2-Me-4-CH$_3$—CO |
| 303 | 2-Me-4-CH$_3$—CH$_2$—CO |
| 304 | 2-Me-4-CH$_3$—CH$_2$—CH$_2$—CO |
| 305 | 2-Me-4-CH$_3$—CH(CH$_3$)—CO |
| 306 | 2,5-Me$_2$-4-CHO |
| 307 | 2,5-Me$_2$-4-CH$_3$—CO |
| 308 | 2,5-Me$_2$-4-CH$_3$—CH$_2$—CO |
| 309 | 2,5-Me$_2$-4-CH$_3$—CH$_2$—CH$_2$—CO |
| 310 | 2,5-Me$_2$-4-CH$_3$—CH(CH$_3$)—CO |
| 311 | 2-Cl-4-CHO |
| 312 | 2-Cl-4-CH$_3$—CO |
| 313 | 2-Cl-4-CH$_3$—CH$_2$—CO |
| 314 | 2-Cl-4-CH$_3$—CH(CH$_3$)—CO |
| 315 | 2,5-Cl$_2$-4-CHO |
| 316 | 2,5-Cl$_2$-4-CH$_3$—CO |
| 317 | 2,5-Cl$_2$-4-CH$_3$—CH$_2$—CO |
| 318 | 2,5-Cl$_2$-4-CH$_3$—CH$_2$—CH$_2$—CO |
| 319 | 2,5-Cl$_2$-4-CH$_3$—CH(CH$_3$)—CO |
| 320 | 2-C(=NOCH$_3$)—CH$_3$ |
| 321 | 3-C(=NOCH$_3$)—CH$_3$ |
| 322 | 4-C(=NOCH$_3$)—CH$_3$ |
| 323 | 2-C(=NOC$_2$H$_5$)—CH$_3$ |
| 324 | 3-C(=NOC$_2$H$_5$)—CH$_3$ |
| 325 | 4-C(=NOC$_2$H$_5$)—CH$_3$ |
| 326 | 2-C(=NO-n-C$_3$H$_7$)—CH$_3$ |
| 327 | 3-C(=NO-n-C$_3$H$_7$)—CH$_3$ |
| 328 | 4-C(=NO-n-C$_3$H$_7$)—CH$_3$ |
| 329 | 2-C(=NO-i-C$_3$H$_7$)—CH$_3$ |
| 330 | 3-C(=NO-i-C$_3$H$_7$)—CH$_3$ |
| 331 | 4-C(=NO-i-C$_3$H$_7$)—CH$_3$ |
| 332 | 2-C(=NO-Allyl)—CH$_3$ |
| 333 | 3-C(=NO-Allyl)—CH$_3$ |
| 334 | 4-C(=NO-Allyl)—CH$_3$ |
| 335 | 2-C(=NO-trans-Chloroallyl)—CH$_3$ |
| 336 | 3-C(=NO-trans-Chloroallyl)—CH$_3$ |
| 337 | 4-C(=NO-trans-Chloroallyl)—CH$_3$ |
| 338 | 2-C(=NO-Propargyl)—CH$_3$ |
| 339 | 3-C(=NO-Propargyl)—CH$_3$ |
| 340 | 4-C(=NO-Propargyl)—CH$_3$ |
| 341 | 2-C(=NO-n-C$_4$H$_9$)—CH$_3$ |
| 342 | 3-C(=NO-n-C$_4$H$_9$)—CH$_3$ |
| 343 | 4-C(=NO-n-C$_4$H$_9$)—CH$_3$ |
| 344 | 2-C(=NO—CH$_2$—C$_6$H$_5$)—CH$_3$ |
| 345 | 3-C(=NO—CH$_2$—C$_6$H$_5$)—CH$_3$ |
| 346 | 4-C(=NO—CH$_2$—C$_6$H$_5$)—CH$_3$ |
| 347 | 2-CH$_3$-4-CH=NOCH$_3$ |
| 348 | 2-CH$_3$-4-CH=NOC$_2$H$_5$ |
| 349 | 2-CH$_3$-4-CH=NO-n-C$_3$H$_7$ |
| 350 | 2-CH$_3$-4-CH=NO-i-C$_3$H$_7$ |
| 351 | 2-CH$_3$-4-CH=NO-Allyl |
| 352 | 2-CH$_3$-4-CH=NO-(trans-Chloroallyl) |
| 353 | 2-CH$_3$-4-CH=NO-Propargyl |
| 354 | 2-CH$_3$-4-CH=NO-n-C$_4$H$_9$ |
| 355 | 2-CH$_3$-4-CH=NO—CH$_2$—C$_6$H$_5$ |
| 356 | 2-CH$_3$-4-(CH$_3$—C=NOCH$_3$) |
| 357 | 2-CH$_3$-4-(CH$_3$—C=NOC$_2$H$_5$) |
| 358 | 2-CH$_3$-4-(CH$_3$—C=NO-n-C$_3$H$_7$) |
| 359 | 2-CH$_3$-4-(CH$_3$—C=NO-i-C$_3$H$_7$) |
| 360 | 2-CH$_3$-4-(CH$_3$—C=NO-Allyl) |
| 361 | 2-CH$_3$-4-(CH$_3$—C=NO-trans-Chloroallyl) |
| 362 | 2-CH$_3$-4-(CH$_3$—C=NO-Propargyl) |
| 363 | 2-CH$_3$-4-(CH$_3$—C=NO-n-C$_4$H$_9$) |
| 364 | 2-CH$_3$-4-(CH$_3$—C=NO—CH$_2$—C$_6$H$_5$) |
| 365 | 2-CH$_3$-4-(C$_2$H$_5$—C=NO—CH$_3$) |
| 366 | 2-CH$_3$-4-(C$_2$H$_5$—C=NO—C$_2$H$_5$) |
| 367 | 2-CH$_3$-4-(C$_2$H$_5$—C=NO-n-C$_3$H$_7$) |
| 368 | 2-CH$_3$-4-(C$_2$H$_5$—C=NO-i-C$_3$H$_7$) |
| 369 | 2-CH$_3$-4-(C$_2$H$_5$—C=NO-Allyl) |
| 370 | 2-CH$_3$-4-(C$_2$H$_5$—C=NO-trans-Chloroallyl) |
| 371 | 2-CH$_3$-4-(C$_2$H$_5$—C=NO-Propargyl) |
| 372 | 2-CH$_3$-4-(C$_2$H$_5$—C=NO-n-C$_4$H$_9$) |
| 373 | 2-CH$_3$-4-(C$_2$H$_5$—C=NO—CH$_2$—C$_6$H$_5$) |
| 374 | 2,5-(CH$_3$)$_2$-4-(CH$_3$—C=NOCH$_3$) |
| 375 | 2,5-(CH$_3$)$_2$-4-(CH$_3$—C=NOC$_2$H$_5$) |
| 376 | 2,5-(CH$_3$)$_2$-4-(CH$_3$—C=NO-n-C$_3$H$_7$) |
| 377 | 2,5-(CH$_3$)$_2$-4-(CH$_3$—C=NO-i-C$_3$H$_7$) |
| 378 | 2,5-(CH$_3$)$_2$-4-(CH$_3$—C=NO-Allyl) |
| 379 | 2,5-(CH$_3$)$_2$-4-(CH$_3$—C=NO-trans-Chloroallyl) |
| 380 | 2,5-(CH$_3$)$_2$-4-(CH$_3$—C=NO-Proparyl) |
| 381 | 2,5-(CH$_3$)$_2$-4-(CH$_3$—C=NO-n-C$_4$H$_9$) |
| 382 | 2,5-(CH$_3$)$_2$-4-(CH$_3$—C=NO—CH$_2$—C$_6$H$_5$) |
| 383 | 2-C$_6$H$_5$ |
| 384 | 3-C$_6$H$_5$ |
| 385 | 4-C$_6$H$_5$ |
| 386 | 2-(2'-F—C$_6$H$_4$) |
| 387 | 2-(3'-F—C$_6$H$_4$) |
| 388 | 2-(4'-F—C$_6$H$_4$) |
| 389 | 3-(2'-F—C$_6$H$_4$) |
| 390 | 3-(3'-F—C$_6$H$_4$) |
| 391 | 3-(4'-F—C$_6$H$_4$) |
| 392 | 4-(2'-F—C$_6$H$_4$) |
| 393 | 4-(3'-F—C$_6$H$_4$) |
| 394 | 4-(4'-F—C$_6$H$_4$) |
| 395 | 2-(2'-Cl—C$_6$H$_4$) |
| 396 | 2-(3'-Cl—C$_6$H$_4$) |
| 397 | 2-(4'-Cl—C$_6$H$_4$) |
| 398 | 3-(2'-Cl—C$_6$H$_4$) |
| 399 | 3-(3'-Cl—C$_6$H$_4$) |
| 400 | 3-(4'-Cl—C$_6$H$_4$) |
| 401 | 4-(2'-Cl—C$_6$H$_4$) |
| 402 | 4-(3'-Cl—C$_6$H$_4$) |
| 403 | 4-(4'-Cl—C$_6$H$_4$) |
| 405 | 2-(2'-CH$_3$—C$_6$H$_4$) |
| 406 | 2-(3'-CH$_3$—C$_6$H$_4$) |
| 407 | 2-(4'-CH$_3$—C$_6$H$_4$) |
| 408 | 3-(2'-CH$_3$—C$_6$H$_4$) |
| 409 | 3-(3'-CH$_3$—C$_6$H$_4$) |
| 410 | 3-(4'-CH$_3$—C$_6$H$_4$) |
| 411 | 4-(2'-CH$_3$—C$_6$H$_4$) |
| 412 | 4-(3'-CH$_3$—C$_6$H$_4$) |
| 413 | 4-(4'-CH$_3$—C$_6$H$_4$) |

TABLE 45-continued

| | |
|---|---|
| 414 | 2-(2'-CH$_3$—CO—C$_6$H$_4$) |
| 415 | 2-(3'-CH$_3$—CO—C$_6$H$_4$) |
| 416 | 2-(4'-CH$_3$—CO—C$_6$H$_4$) |
| 417 | 3-(2'-CH$_3$—CO—C$_6$H$_4$) |
| 418 | 3-(3'-CH$_3$—CO—C$_6$H$_4$) |
| 419 | 3-(4'-CH$_3$—CO—C$_6$H$_4$) |
| 420 | 4-(2'-CH$_3$—CO—C$_6$H$_4$) |
| 421 | 4-(3'-CH$_3$—CO—C$_6$H$_4$) |
| 422 | 4-(4'-CH$_3$—CO—C$_6$H$_4$) |
| 423 | 2-(2'-(CH$_3$—C(=NOAllyl))-C$_6$H$_4$) |
| 424 | 2-(3'-(CH$_3$—C(=NOAllyl))-C$_6$H$_4$) |
| 425 | 2-(4'-(CH$_3$—C(=NOAllyl))-C$_6$H$_4$) |
| 426 | 3-(2'-(CH$_3$—C(=NOAllyl))-C$_6$H$_4$) |
| 427 | 3-(3'-(CH$_3$—C(=NOAllyl))-C$_6$H$_4$) |
| 428 | 3-(4'-(CH$_3$—C(=NOAllyl))-C$_6$H$_4$) |
| 429 | 4-(2'-(CH$_3$—C(=NOAllyl))-C$_6$H$_4$) |
| 430 | 4-(3'-(CH$_3$—C(=NOAllyl))-C$_6$H$_4$) |
| 431 | 4-(4'-(CH$_3$—C(=NOAllyl))-C$_6$H$_4$) |
| 432 | 2-(2'-CH$_3$O$_2$C—C$_6$H$_4$) |
| 433 | 2-(3'-CH$_3$O$_2$C—C$_6$H$_4$) |
| 434 | 2-(4'-CH$_3$O$_2$C—C$_6$H$_4$) |
| 435 | 3-(2'-CH$_3$O$_2$C—C$_6$H$_4$) |
| 436 | 3-(3'-CH$_3$O$_2$C—C$_6$H$_4$) |
| 437 | 3-(4'-CH$_3$O$_2$C—C$_6$H$_4$) |
| 438 | 4-(2'-CH$_3$O$_2$C—C$_6$H$_4$) |
| 439 | 4-(3'-CH$_3$O$_2$C—C$_6$H$_4$) |
| 440 | 4-(4'-CH$_3$O$_2$C—C$_6$H$_4$) |
| 441 | 2-(2'-CH$_3$O—C$_6$H$_4$) |
| 442 | 2-(3'-CH$_3$O—C$_6$H$_4$) |
| 443 | 2-(4'-CH$_3$O—C$_6$H$_4$) |
| 444 | 3-(2'-CH$_3$O—C$_6$H$_4$) |
| 445 | 3-(3'-CH$_3$O—C$_6$H$_4$) |
| 446 | 3-(4'-CH$_3$O—C$_6$H$_4$) |
| 447 | 4-(2'-CH$_3$O—C$_6$H$_4$) |
| 448 | 4-(3'-CH$_3$O—C$_6$H$_4$) |
| 449 | 4-(4'-CH$_3$O—C$_6$H$_4$) |
| 450 | 2-(2'-O$_2$N—C$_6$H$_4$) |
| 451 | 2-(3'-O$_2$N—C$_6$H$_4$) |
| 452 | 2-(4'-O$_2$N—C$_6$H$_4$) |
| 453 | 3-(2'-O$_2$N—C$_6$H$_4$) |
| 454 | 3-(3'-O$_2$N—C$_6$H$_4$) |
| 455 | 3-(4'-O$_2$N—C$_6$H$_4$) |
| 456 | 4-(2'-O$_2$N—C$_6$H$_4$) |
| 457 | 4-(3'-O$_2$N—C$_6$H$_4$) |
| 458 | 4-(4'-O$_2$N—C$_6$H$_4$) |
| 459 | 2-(2'-NC—C$_6$H$_4$) |
| 460 | 2-(3'-NC—C$_6$H$_4$) |
| 461 | 2-(4'-NC—C$_6$H$_4$) |
| 462 | 3-(2'-NC—C$_6$H$_4$) |
| 463 | 3-(3'-NC—C$_6$H$_4$) |
| 464 | 3-(4'-NC—C$_6$H$_4$) |
| 465 | 4-(2'-NC—C$_6$H$_4$) |
| 466 | 4-(3'-NC—C$_6$H$_4$) |
| 467 | 4-(4'-NC—C$_6$H$_4$) |
| 468 | 2-(2'-CF$_3$—C$_6$H$_4$) |
| 469 | 2-(3'-CF$_3$—C$_6$H$_4$) |
| 470 | 2-(4'-CF$_3$—C$_6$H$_4$) |
| 471 | 3-(2'-CF$_3$—C$_6$H$_4$) |
| 472 | 3-(3'-CF$_3$—C$_6$H$_4$) |
| 473 | 3-(4'-CF$_3$—C$_6$H$_4$) |
| 474 | 4-(2'-CF$_3$—C$_6$H$_4$) |
| 475 | 4-(3'-CF$_3$—C$_6$H$_4$) |
| 476 | 4-(4'-CF$_3$—C$_6$H$_4$) |
| 477 | 2-O—C$_6$H$_5$ |
| 475 | 3-O—C$_6$H$_5$ |
| 476 | 4-O—C$_6$H$_5$ |
| 478 | 2-O-(2'-F—C$_6$H$_4$) |
| 479 | 2-O-(3'-F—C$_6$H$_4$) |
| 480 | 2-O-(4'-F—C$_6$H$_4$) |
| 481 | 3-O-(2'-F—C$_6$H$_4$) |
| 482 | 3-O-(3'-F—C$_6$H$_4$) |
| 483 | 3-O-(4'-F—C$_6$H$_4$) |
| 484 | 4-O-(2'-F—C$_6$H$_4$) |
| 485 | 4-O-(3'-F—C$_6$H$_4$) |
| 486 | 4-O-(4'-F—C$_6$H$_4$) |
| 487 | 2-O-(2'-Cl—C$_6$H$_4$) |
| 488 | 2-O-(3'-Cl—C$_6$H$_4$) |
| 489 | 2-O-(4'-Cl—C$_6$H$_4$) |
| 490 | 3-O-(2'-Cl—C$_6$H$_4$) |
| 491 | 3-O-(3'-Cl—C$_6$H$_4$) |
| 492 | 3-O-(4'-Cl—C$_6$H$_4$) |
| 493 | 3-O-(4'-Cl—C$_6$H$_4$) |
| 494 | 4-O-(2'-Cl—C$_6$H$_4$) |
| 495 | 4-O-(3'-Cl—C$_6$H$_4$) |
| 496 | 4-O-(4'-Cl—C$_6$H$_4$) |
| 497 | 2-O-(2'-CH$_3$—C$_6$H$_4$) |
| 498 | 2-O-(3'-CH$_3$—C$_6$H$_4$) |
| 499 | 2-O-(4'-CH$_3$—C$_6$H$_4$) |
| 500 | 3-O-(2'-CH$_3$—C$_6$H$_4$) |
| 501 | 3-O-(3'-CH$_3$—C$_6$H$_4$) |
| 502 | 3-O-(4'-CH$_3$—C$_6$H$_4$) |
| 503 | 4-O-(2'-CH$_3$—C$_6$H$_4$) |
| 504 | 4-O-(3'-CH$_3$—C$_6$H$_4$) |
| 505 | 4-O-(4'-CH$_3$—C$_6$H$_4$) |
| 506 | 2-O-(2'-CH$_3$—CO—C$_6$H$_4$) |
| 507 | 2-O-(3'-CH$_3$—CO—C$_6$H$_4$) |
| 508 | 2-O-(4'-CH$_3$—CO—C$_6$H$_4$) |
| 509 | 3-O-(2'-CH$_3$—CO—C$_6$H$_4$) |
| 510 | 3-O-(3'-CH$_3$—CO—C$_6$H$_4$) |
| 511 | 3-O-(4'-CH$_3$—CO—C$_6$H$_4$) |
| 512 | 4-O-(2'-CH$_3$—CO—C$_6$H$_4$) |
| 513 | 4-O-(3'-CH$_3$—CO—C$_6$H$_4$) |
| 514 | 4-O-(4'-CH$_3$—CO—C$_6$H$_4$) |
| 515 | 2-O-(2'-(CH$_3$—C(=NOAllyl))—C$_6$H$_4$) |
| 516 | 2-O-(3'-(CH$_3$—C(=NOAllyl))—C$_6$H$_4$) |
| 517 | 2-O-(4'-(CH$_3$—C(=NOAllyl))—C$_6$H$_4$) |
| 518 | 3-O-(2'-(CH$_3$—C(=NOAllyl))—C$_6$H$_4$) |
| 519 | 3-O-(3'-(CH$_3$—C(=NOAllyl))—C$_6$H$_4$) |
| 520 | 3-O-(4'-(CH$_3$—C(=NOAllyl))—C$_6$H$_4$) |
| 521 | 4-O-(2'-(CH$_3$—C(=NOAllyl))—C$_6$H$_4$) |
| 522 | 4-O-(3'-(CH$_3$—C(=NOAllyl))—C$_6$H$_4$) |
| 523 | 4-O-(4'-(CH$_3$—C(=NOAllyl))—C$_6$H$_4$) |
| 524 | 2-O-(2'-CH$_3$O$_2$C—C$_6$H$_4$) |
| 525 | 2-O-(3'-CH$_3$O$_2$C—C$_6$H$_4$) |
| 526 | 2-O-(4'-CH$_3$O$_2$C—C$_6$H$_4$) |
| 527 | 3-O-(2'-CH$_3$O$_2$C—C$_6$H$_4$) |
| 528 | 3-O-(3'-CH$_3$O$_2$C—C$_6$H$_4$) |
| 529 | 3-O-(4'-CH$_3$O$_2$C—C$_6$H$_4$) |
| 530 | 4-O-(2'-CH$_3$O$_2$C—C$_6$H$_4$) |
| 531 | 4-O-(3'-CH$_3$O$_2$C—C$_6$H$_4$) |
| 532 | 4-O-(4'-CH$_3$O$_2$C—C$_6$H$_4$) |
| 533 | 2-O-(2'-CH$_3$O—C$_6$H$_4$) |
| 534 | 2-O-(3'-CH$_3$O—C$_6$H$_4$) |
| 535 | 2-O-(4'-CH$_3$O—C$_6$H$_4$) |
| 536 | 3-O-(2'-CH$_3$O—C$_6$H$_4$) |
| 537 | 3-O-(3'-CH$_3$O—C$_6$H$_4$) |
| 538 | 3-O-(4'-CH$_3$O—C$_6$H$_4$) |
| 539 | 4-O-(2'-CH$_3$O—C$_6$H$_4$) |
| 540 | 4-O-(3'-CH$_3$O—C$_6$H$_4$) |
| 541 | 4-O-(4'-CH$_3$O—C$_6$H$_4$) |
| 542 | 2-O-(2'-O$_2$N—C$_6$H$_4$) |
| 543 | 2-O-(3'-O$_2$N—C$_6$H$_4$) |
| 544 | 2-O-(4'-O$_2$N—C$_6$H$_4$) |
| 545 | 3-O-(2'-O$_2$N—C$_6$H$_4$) |
| 546 | 3-O-(3'-O$_2$N—C$_6$H$_4$) |
| 547 | 3-O-(4'-O$_2$N—C$_6$H$_4$) |
| 548 | 4-O-(2'-O$_2$N—C$_6$H$_4$) |
| 549 | 4-O-(3'-O$_2$N—C$_6$H$_4$) |
| 550 | 4-O-(4'-O$_2$N—C$_6$H$_4$) |
| 551 | 2-O-(2'-NC—C$_6$H$_4$) |
| 552 | 2-O-(3'-NC—C$_6$H$_4$) |
| 553 | 2-O-(4'-NC—C$_6$H$_4$) |
| 554 | 3-O-(2'-NC—C$_6$H$_4$) |
| 555 | 3-O-(3'-NC—C$_6$H$_4$) |
| 556 | 3-O-(4'-NC—C$_6$H$_4$) |
| 557 | 4-O-(2'-NC—C$_6$H$_4$) |
| 558 | 4-O-(3'-NC—C$_6$H$_4$) |
| 559 | 4-O-(4'-NC—C$_6$H$_4$) |
| 560 | 2-O-(2'-CF$_3$—C$_6$H$_5$) |
| 561 | 2-O-(3'-CF$_3$—C$_6$H$_5$) |
| 562 | 2-O-(4'-CF$_3$—C$_6$H$_5$) |
| 563 | 3-O-(2'-CF$_3$—C$_6$H$_5$) |
| 564 | 3-O-(3'-CF$_3$—C$_6$H$_5$) |
| 565 | 3-O-(4'-CF$_3$—C$_6$H$_5$) |
| 566 | 4-O-(2'-CF$_3$—C$_6$H$_5$) |
| 567 | 4-O-(3'-CF$_3$—C$_6$H$_5$) |
| 568 | 4-O-(4'-CF$_3$—C$_6$H$_5$) |
| 569 | 2-Pyridinyl-2' |

TABLE 45-continued

| | |
|---|---|
| 570 | 2-Pyridinyl-3' |
| 571 | 2-Pyridinyl-4' |
| 572 | 3-Pyridinyl-2' |
| 573 | 3-Pyridinyl-3' |
| 574 | 3-Pyridinyl-4' |
| 575 | 4-Pyridinyl-2' |
| 576 | 4-Pyridinyl-3' |
| 577 | 4-Pyridinyl-4' |
| 578 | 2-Pyrimidinyl-2' |
| 579 | 2-Pyrimidinyl-3' |
| 580 | 2-Pyrimidinyl-4' |
| 581 | 3-Pyrimidinyl-2' |
| 582 | 3-Pyrimidinyl-3' |
| 583 | 3-Pyrimidinyl-4' |
| 584 | 4-Pyrimidinyl-2' |
| 585 | 4-Pyrimidinyl-3' |
| 586 | 4-Pyrimidinyl-4' |
| 587 | 2-Pyrazolyl-1' |
| 588 | 2-Pyrazolyl-3' |
| 589 | 2-Pyrazolyl-4' |
| 590 | 3-Pyrazolyl-1' |
| 591 | 3-Pyrazolyl-3' |
| 592 | 3-Pyrazolyl-4' |
| 593 | 4-Pyrazolyl-1' |
| 594 | 4-Pyrazolyl-3' |
| 595 | 4-Pyrazolyl-4' |
| 596 | 2-Isoxazolyl-3' |
| 597 | 2-Isoxazolyl-4' |
| 598 | 2-Isoxazolyl-5' |
| 599 | 3-Isoxazolyl-3' |
| 600 | 3-Isoxazolyl-4' |
| 601 | 3-Isoxazolyl-5' |
| 602 | 4-Isoxazolyl-3' |
| 603 | 4-Isoxazolyl-4' |
| 604 | 4-Isoxazolyl-5' |
| 605 | 2-Isothiazolyl-3' |
| 606 | 2-Isothiazolyl-4' |
| 607 | 2-Isothiazolyl-5' |
| 608 | 3-Isothiazolyl-3' |
| 609 | 3-Isothiazolyl-4' |
| 610 | 3-Isothiazolyl-5' |
| 611 | 4-Isothiazolyl-3' |
| 612 | 4-Isothiazolyl-4' |
| 613 | 4-Isothiazolyl-5' |
| 614 | 2-Imidazolyl-1' |
| 615 | 2-Imidazolyl-2' |
| 616 | 2-Imidazolyl-4' |
| 617 | 3-Imidazolyl-1' |
| 618 | 3-Imidazolyl-2' |
| 619 | 3-Imidazolyl-4' |
| 620 | 4-Imidazolyl-1' |
| 621 | 4-Imidazolyl-2' |
| 622 | 4-Imidazolyl-4' |
| 623 | 2-Oxazolyl-2' |
| 624 | 2-Oxazolyl-4' |
| 625 | 2-Oxazolyl-5' |
| 626 | 3-Oxazolyl-2' |
| 627 | 3-Oxazolyl-4' |
| 628 | 3-Oxazolyl-5' |
| 629 | 4-Oxazolyl-2' |
| 630 | 4-Oxazolyl-4' |
| 631 | 4-Oxazolyl-5' |
| 632 | 2-Thiazolyl-2' |
| 633 | 2-Thiazolyl-4' |
| 634 | 2-Thiazolyl-5' |
| 635 | 3-Thiazolyl-2' |
| 636 | 3-Thiazolyl-4' |
| 637 | 3-Thiazolyl-5' |
| 638 | 4-Thiazolyl-2' |
| 639 | 4-Thiazolyl-4' |
| 640 | 4-Thiazolyl-5' |

TABLE 46

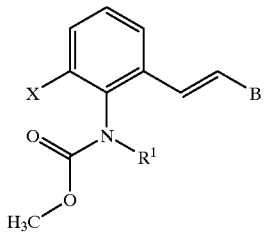

I:    $R^1 = H, X = CH_3$
II:    $R^1 = CH_3, X = CH_3$
III:    $R^1 = C_2H_5, X = CH_3$
IV:    $R^1 = Allyl, X = CH_3$
V:    $R^1 = Propargyl, X = CH_3$
VI:    $R^1 = CH_2-OCH_3, X = CH_3$
VII:    $R^1 = CO_2CH_3, X = CH_3$
VIII:    $R^1 = H, X = Cl$
IX:    $R^1 = CH_3, X = Cl$
X:    $R^1 = C_2H_5, X = Cl$
XI:    $R^1 = Allyl, X = Cl$
XII:    $R^1 = Propargyl, X = Cl$
XIII:    $R^1 = CH_2-OCH_3, X = Cl$
XIV:    $R^1 = CO_2CH_3, X = Cl$

| No. | B |
|---|---|
| 1 | Pyrrolyl-3 |
| 2 | N—$CH_3$-Pyrrolyl-3 |
| 3 | N—$C_6H_5$-Pyrrolyl-3 |
| 4 | N-(4'-$CH_3$—$C_6H_4$)-Pyrrolyl-3 |
| 5 | N-(3'-$CH_3$—$C_6H_4$)-Pyrrolyl-3 |
| 6 | N-(2'-$CH_3$—$C_6H_4$)-Pyrrolyl-3 |
| 7 | N-(4'-$CH_3O$—$C_6H_4$)-Pyrrolyl-3 |
| 8 | N-(3'-$CH_3O$—$C_6H_4$)-Pyrrolyl-3 |
| 9 | N-(2'-$CH_3O$—$C_6H_4$)-Pyrrolyl-3 |
| 10 | N-(4'-$NO_2$—$C_6H_4$)-Pyrrolyl-3 |
| 11 | N-(3'-$NO_2$—$C_6H_4$)-Pyrrolyl-3 |
| 12 | N-(2'-$NO_2$—$C_6H_4$)-Pyrrolyl-3 |
| 13 | N-(4'-CN—$C_6H_4$)-Pyrrolyl-3 |
| 14 | N-(3'-CN—$C_6H_4$)-Pyrrolyl-3 |
| 15 | N-(2'-CN—$C_6H_4$)-Pyrrolyl-3 |
| 16 | N-(4'-Cl—$C_6H_4$)-Pyrrolyl-3 |
| 17 | N-(3'-Cl—$C_6H_4$)-Pyrrolyl-3 |
| 18 | N-(2'-Cl—$C_6H_4$)-Pyrrolyl-3 |
| 19 | Pyrrolyl-2 |
| 20 | N—$CH_3$-Pyrrolyl-2 |
| 21 | N—$C_6H_5$-Pyrrolyl-2 |
| 22 | N-(4'-$CH_3$—$C_6H_4$)-Pyrrolyl-2 |
| 23 | N-(3'-$CH_3$—$C_6H_4$)-Pyrrolyl-2 |
| 24 | N-(2'-$CH_3$—$C_6H_4$)-Pyrrolyl-2 |
| 25 | N-(4'-$CH_3O$—$C_6H_4$)-Pyrrolyl-2 |
| 26 | N-(3'-$CH_3O$—$C_6H_4$)-Pyrrolyl-2 |
| 27 | N-(2'-$CH_3O$—$C_6H_4$)-Pyrrolyl-2 |
| 28 | N-(4'-$NO_2$—$C_6H_4$)-Pyrrolyl-2 |
| 29 | N-(3'-$NO_2$—$C_6H_4$)-Pyrrolyl-2 |
| 30 | N-(2'-$NO_2$—$C_6H_4$)-Pyrrolyl-2 |
| 31 | N-(4'-CN—$C_6H_4$)-Pyrrolyl-2 |
| 32 | N-(3'-CN—$C_6H_4$)-Pyrrolyl-2 |
| 33 | N-(2'-CN—$C_6H_4$)-Pyrrolyl-2 |
| 34 | N-(4'-Cl—$C_6H_4$)-Pyrrolyl-2 |
| 35 | N-(3'-Cl—$C_6H_4$)-Pyrrolyl-2 |
| 36 | N-(2'-Cl—$C_6H_4$)-Pyrrolyl-2 |
| 37 | Furyl-2 |
| 38 | 5-$CH_3$-Furyl-2 |
| 39 | 5-$C_6H_5$-Furyl-2 |
| 40 | 5-(4'-$CH_3$—$C_6H_4$)-Furyl-2 |
| 41 | 5-(3'-$CH_3$—$C_6H_4$)-Furyl-2 |
| 42 | 5-(2'-$CH_3$—$C_6H_4$)-Furyl-2 |
| 43 | 5-(4'-$CH_3O$—$C_6H_4$)-Furyl-2 |
| 44 | 5-(3'-$CH_3O$—$C_6H_4$)-Furyl-2 |
| 45 | 5-(2'-$CH_3O$—$C_6H_4$)-Furyl-2 |
| 46 | 5-(4'-$NO_2$—$C_6H_4$)-Furyl-2 |
| 47 | 5-(3'-$NO_2$—$C_6H_4$)-Furyl-2 |
| 48 | 5-(2'-$NO_2$—$C_6H_4$)-Furyl-2 |

TABLE 46-continued

| | |
|---|---|
| 49 | 5-(4'-CN—C$_6$H$_4$)-Furyl-2 |
| 50 | 5-(3'-CN—C$_6$H$_4$)-Furyl-2 |
| 51 | 5-(2'-CN—C$_6$H$_4$)-Furyl-2 |
| 52 | 5-(4'-Cl—C$_6$H$_4$)-Furyl-2 |
| 53 | 5-(3'-Cl—C$_6$H$_4$)-Furyl-2 |
| 54 | 5-(2'-Cl—C$_6$H$_4$)-Furyl-2 |
| 55 | 4-CH$_3$-Furyl-2 |
| 56 | 4-C$_6$H$_5$-Furyl-2 |
| 57 | 4-(4'-CH$_3$—C$_6$H$_4$)-Furyl-2 |
| 58 | 4-(3'-CH$_3$—C$_6$H$_4$)-Furyl-2 |
| 59 | 4-(2'-CH$_3$—C$_6$H$_4$)-Furyl-2 |
| 60 | 4-(4'-CH$_3$O—C$_6$H$_4$)-Furyl-2 |
| 61 | 4-(3'-CH$_3$O—C$_6$H$_4$)-Furyl-2 |
| 62 | 4-(2'-CH$_3$O—C$_6$H$_4$)-Furyl-2 |
| 63 | 4-(4'-NO$_2$—C$_6$H$_4$)-Furyl-2 |
| 64 | 4-(3'-NO$_2$—C$_6$H$_4$)-Furyl-2 |
| 65 | 4-(2'-NO$_2$—C$_6$H$_4$)-Furyl-2 |
| 66 | 4-(4'-CN—C$_6$H$_4$)-Furyl-2 |
| 67 | 4-(3'-CN—C$_6$H$_4$)-Furyl-2 |
| 68 | 4-(2'-CN—C$_6$H$_4$)-Furyl-2 |
| 69 | 4-(4'-Cl—C$_6$H$_4$)-Furyl-2 |
| 70 | 4-(3'-Cl—C$_6$H$_4$)-Furyl-2 |
| 71 | 4-(2'-Cl—C$_6$H$_4$)-Furyl-2 |
| 72 | Thienyl-2 |
| 73 | 5-CH$_3$-Thienyl-2 |
| 74 | 5-C$_6$H$_5$-Thienyl-2 |
| 75 | 5-(4'-CH$_3$—C$_6$H$_4$)-Thienyl-2 |
| 76 | 5-(3'-CH$_3$—C$_6$H$_4$)-Thienyl-2 |
| 77 | 5-(2'-CH$_3$—C$_6$H$_4$)-Thienyl-2 |
| 78 | 5-(4'-CH$_3$O—C$_6$H$_4$)-Thienyl-2 |
| 79 | 5-(3'-CH$_3$O—C$_6$H$_4$)-Thienyl-2 |
| 80 | 5-(2'-CH$_3$O—C$_6$H$_4$)-Thienyl-2 |
| 81 | 5-(4'-NO$_2$—C$_6$H$_4$)-Thienyl-2 |
| 82 | 5-(3'-NO$_2$—C$_6$H$_4$)-Thienyl-2 |
| 83 | 5-(2'-NO$_2$—C$_6$H$_4$)-Thienyl-2 |
| 84 | 5-(4'-CN—C$_6$H$_4$)-Thienyl-2 |
| 85 | 5-(3'-CN—C$_6$H$_4$)-Thienyl-2 |
| 86 | 5-(2'-CN—C$_6$H$_4$)-Thienyl-2 |
| 87 | 5-(4'-Cl—C$_6$H$_4$)-Thienyl-2 |
| 88 | 5-(3'-Cl—C$_6$H$_4$)-Thienyl-2 |
| 89 | 5-(2'-Cl—C$_6$H$_4$)-Thienyl-2 |
| 90 | 4-CH$_3$-Thienyl-2 |
| 91 | 4-C$_6$H$_5$-Thienyl-2 |
| 92 | 4-(4'-CH$_3$—C$_6$H$_4$)-Thienyl-2 |
| 93 | 4-(3'-CH$_3$—C$_6$H$_4$)-Thienyl-2 |
| 94 | 4-(2'-CH$_3$—C$_6$H$_4$)-Thienyl-2 |
| 95 | 4-(4'-CH$_3$O—C$_6$H$_4$)-Thienyl-2 |
| 96 | 4-(3'-CH$_3$O—C$_6$H$_4$)-Thienyl-2 |
| 97 | 4-(2'-CH$_3$O—C$_6$H$_4$)-Thienyl-2 |
| 98 | 4-(4'-NO$_2$—C$_6$H$_4$)-Thienyl-2 |
| 99 | 4-(3'-NO$_2$—C$_6$H$_4$)-Thienyl-2 |
| 100 | 4-(2'-NO$_2$—C$_6$H$_4$)-Thienyl-2 |
| 101 | 4-(4'-CN—C$_6$H$_4$)-Thienyl-2 |
| 102 | 4-(3'-CN—C$_6$H$_4$)-Thienyl-2 |
| 103 | 4-(2'-CN—C$_6$H$_4$)-Thienyl-2 |
| 104 | 4-(4'-Cl—C$_6$H$_4$)-Thienyl-2 |
| 105 | 4-(3'-Cl—C$_6$H$_4$)-Thienyl-2 |
| 106 | 4-(2'-Cl—C$_6$H$_4$)-Thienyl-2 |
| 107 | Thienyl-3 |
| 108 | 5-CH$_3$-Thienyl-3 |
| 109 | 5-C$_6$H$_5$-Thienyl-3 |
| 110 | 5-(4'-CH$_3$—C$_6$H$_4$)-Thienyl-3 |
| 111 | 5-(3'-CH$_3$—C$_6$H$_4$)-Thienyl-3 |
| 112 | 5-(2'-CH$_3$—C$_6$H$_4$)-Thienyl-3 |
| 113 | 5-(4'-CH$_3$O—C$_6$H$_4$)-Thienyl-3 |
| 114 | 5-(3'-CH$_3$O—C$_6$H$_4$)-Thienyl-3 |
| 115 | 5-(2'-CH$_3$O—C$_6$H$_4$)-Thienyl-3 |
| 116 | 5-(4'-NO$_2$—C$_6$H$_4$)-Thienyl-3 |
| 117 | 5-(3'-NO$_2$—C$_6$H$_4$)-Thienyl-3 |
| 118 | 5-(2'-NO$_2$—C$_6$H$_4$)-Thienyl-3 |
| 119 | 5-(4'-CN—C$_6$H$_4$)-Thienyl-3 |
| 120 | 5-(3'-CN—C$_6$H$_4$)-Thienyl-3 |
| 121 | 5-(2'-CN—C$_6$H$_4$)-Thienyl-3 |
| 122 | 5-(4'-Cl—C$_6$H$_4$)-Thienyl-3 |
| 123 | 5-(3'-Cl—C$_6$H$_4$)-Thienyl-3 |
| 124 | 5-(2'-Cl—C$_6$H$_4$)-Thienyl-3 |
| 125 | Pyrazolyl-4 |
| 126 | N-CH$_3$-Pyrazolyl-4 |
| 127 | N-C$_6$H$_5$-Pyrazolyl-4 |
| 128 | N-(4'-CH$_3$—C$_6$H$_4$)-Pyrazolyl-4 |
| 129 | N-(3'-CH$_3$—C$_6$H$_4$)-Pyrazolyl-4 |
| 130 | N-(2'-CH$_3$—C$_6$H$_4$)-Pyrazolyl-4 |
| 131 | N-(4'-CH$_3$O—C$_6$H$_4$)-Pyrazolyl-4 |
| 132 | N-(3'-CH$_3$O—C$_6$H$_4$)-Pyrazolyl-4 |
| 133 | N-(2'-CH$_3$O—C$_6$H$_4$)-Pyrazolyl-4 |
| 134 | N-(4'-NO$_2$—C$_6$H$_4$)-Pyrazolyl-4 |
| 135 | N-(3'-NO$_2$—C$_6$H$_4$)-Pyrazolyl-4 |
| 136 | N-(2'-NO$_2$—C$_6$H$_4$)-Pyrazolyl-4 |
| 137 | N-(4'-CN—C$_6$H$_4$)-Pyrazolyl-4 |
| 138 | N-(3'-CN—C$_6$H$_4$)-Pyrazolyl-4 |
| 139 | N-(2'-CN—C$_6$H$_4$)-Pyrazolyl-4 |
| 140 | N-(4'-Cl—C$_6$H$_4$)-Pyrazolyl-4 |
| 141 | N-(3'-Cl—C$_6$H$_4$)-Pyrazolyl-4 |
| 142 | N-(2'-Cl—C$_6$H$_4$)-Pyrazolyl-4 |
| 143 | 3-CH$_3$—N-Methylpyrazolyl-4 |
| 144 | 3-C$_6$H$_5$—N-Methylpyrazolyl-4 |
| 145 | 3-(4'-CH$_3$—C$_6$H$_4$)—N-Methylpyrazolyl-4 |
| 146 | 3-(3'-CH$_3$—C$_6$H$_4$)—N-Methylpyrazolyl-4 |
| 147 | 3-(2'-CH$_3$—C$_6$H$_4$)—N-Methylpyrazolyl-4 |
| 148 | 3-(4'-CH$_3$O—C$_6$H$_4$)—N-Methylpyrazolyl-4 |
| 149 | 3-(3'-CH$_3$O—C$_6$H$_4$)—N-Methylpyrazolyl-4 |
| 150 | 3-(2'-CH$_3$O—C$_6$H$_4$)—N-Methylpyrazolyl-4 |
| 151 | 3-(4'-NO$_2$—C$_6$H$_4$)—N-Methylpyrazolyl-4 |
| 152 | 3-(3'-NO$_2$—C$_6$H$_4$)—N-Methylpyrazolyl-4 |
| 153 | 3-(2'-NO$_2$—C$_6$H$_4$)—N-Methylpyrazolyl-4 |
| 154 | 3-(4'-CN—C$_6$H$_4$)—N-Methylpyrazolyl-4 |
| 155 | 3-(3'-CN—C$_6$H$_4$)—N-Methylpyrazolyl-4 |
| 156 | 3-(2'-CN—C$_6$H$_4$)—N-Methylpyrazolyl-4 |
| 157 | 3-(4'-Cl—C$_6$H$_4$)—N-Methylpyrazolyl-4 |
| 158 | 3-(3'-Cl—C$_6$H$_4$)—N-Methylpyrazolyl-4 |
| 159 | 3-(2'-Cl—C$_6$H$_4$)—N-Methylpyrazolyl-4 |
| 160 | Isoxazolyl-5 |
| 161 | 3-CH$_3$-Isoxazolyl-5 |
| 162 | 3-C$_6$H$_5$-Isoxazolyl-5 |
| 163 | 3-(4'-CH$_3$—C$_6$H$_4$)-Isoxazolyl-5 |
| 164 | 3-(3'-CH$_3$—C$_6$H$_4$)-Isoxazolyl-5 |
| 165 | 3-(2'-CH$_3$—C$_6$H$_4$)-Isoxazolyl-5 |
| 166 | 3-(4'-CH$_3$O—C$_6$H$_4$)-Isoxazolyl-5 |
| 167 | 3-(3'-CH$_3$O—C$_6$H$_4$)-Isoxazolyl-5 |
| 168 | 3-(2'-CH$_3$O—C$_6$H$_4$)-Isoxazolyl-5 |
| 169 | 3-(4'-NO$_2$—C$_6$H$_4$)-Isoxazolyl-5 |
| 170 | 3-(3'-NO$_2$—C$_6$H$_4$)-Isoxazolyl-5 |
| 171 | 3-(2'-NO$_2$—C$_6$H$_4$)-Isoxazolyl-5 |
| 172 | 3-(4'-CN—C$_6$H$_4$)-Isoxazolyl-5 |
| 173 | 3-(3'-CN—C$_6$H$_4$)-Isoxazolyl-5 |
| 174 | 3-(2'-CN—C$_6$H$_4$)-Isoxazolyl-5 |
| 175 | 3-(4'-Cl—C$_6$H$_4$)-Isoxazolyl-5 |
| 176 | 3-(3'-Cl—C$_6$H$_4$)-Isoxazolyl-5 |
| 177 | 3-(2'-Cl—C$_6$H$_4$)-Isoxazolyl-5 |
| 178 | 4-Chloroisoxazolyl-5 |
| 179 | 3-CH$_3$-4-Chloroisoxazolyl-5 |
| 180 | 3-C$_6$H$_5$-4-Chloroisoxazolyl-5 |
| 181 | 3-(4'-CH$_3$—C$_6$H$_4$)-4-Chloroisoxazolyl-5 |
| 182 | 3-(3'-CH$_3$—C$_6$H$_4$)-4-Chloroisoxazolyl-5 |
| 183 | 3-(2'-CH$_3$—C$_6$H$_4$)-4-Chloroisoxazolyl-5 |
| 184 | 3-(4'-CH$_3$O—C$_6$H$_4$)-4-Chloroisoxazolyl-5 |
| 185 | 3-(3'-CH$_3$O—C$_6$H$_4$)-4-Chloroisoxazolyl-5 |
| 186 | 3-(2'-CH$_3$O—C$_6$H$_4$)-4-Chloroisoxazolyl-5 |
| 187 | 3-(4'-NO$_2$—C$_6$H$_4$)-4-Chloroisoxazolyl-5 |
| 188 | 3-(3'-NO$_2$—C$_6$H$_4$)-4-Chloroisoxazolyl-5 |
| 189 | 3-(2'-NO$_2$—C$_6$H$_4$)-4-Chloroisoxazolyl-5 |
| 190 | 3-(4'-CN—C$_6$H$_4$)-4-Chloroisoxazolyl-5 |
| 191 | 3-(3'-CN—C$_6$H$_4$)-4-Chloroisoxazolyl-5 |
| 192 | 3-(2'-CN—C$_6$H$_4$)-4-Chloroisoxazolyl-5 |
| 193 | 3-(4'-Cl—C$_6$H$_4$)-4-Chloroisoxazolyl-5 |
| 194 | 3-(3'-Cl—C$_6$H$_4$)-4-Chloroisoxazolyl-5 |
| 195 | 3-(2'-Cl—C$_6$H$_4$)-4-Chloroisoxazolyl-5 |
| 196 | Isoxazolyl-3 |
| 197 | 5-CH$_3$-Isoxazolyl-3 |
| 198 | 5-C$_6$H$_5$-Isoxazolyl-3 |
| 199 | 5-(4'-CH$_3$—C$_6$H$_4$)-Isoxazolyl-3 |
| 200 | 5-(3'-CH$_3$—C$_6$H$_4$)-Isoxazolyl-3 |
| 201 | 5-(2'-CH$_3$—C$_6$H$_4$)-Isoxazolyl-3 |
| 202 | 5-(4'-CH$_3$O—C$_6$H$_4$)-Isoxazolyl-3 |
| 203 | 5-(3'-CH$_3$O—C$_6$H$_4$)-Isoxazolyl-3 |
| 204 | 5-(2'-CH$_3$O—C$_6$H$_4$)-Isoxazolyl-3 |
| 205 | 5-(4'-NO$_2$—C$_6$H$_4$)-Isoxazolyl-3 |
| 206 | 5-(3'-NO$_2$—C$_6$H$_4$)-Isoxazolyl-3 |

TABLE 46-continued

| | |
|---|---|
| 207 | 5-(2'-NO$_2$—C$_6$H$_4$)-Isoxazolyl-3 |
| 208 | 5-(4'-CN—C$_6$H$_4$)-Isoxazolyl-3 |
| 209 | 5-(3'-CN—C$_6$H$_4$)-Isoxazolyl-3 |
| 210 | 5-(2'-CN—C$_6$H$_4$)-Isoxazolyl-3 |
| 211 | 5-(4'-Cl—C$_6$H$_4$)-Isoxazolyl-3 |
| 212 | 5-(3'-Cl—C$_6$H$_4$)-Isoxazolyl-3 |
| 213 | 5-(2'-Cl—C$_6$H$_4$)-Isoxazolyl-3 |
| 214 | Isothiazolyl-5 |
| 215 | 3-CH$_3$-Isothiazolyl-5 |
| 216 | 3-C$_6$H$_5$-Isothiazolyl-5 |
| 217 | 3-(4'-CH$_3$—C$_6$H$_4$)-Isothiazolyl-5 |
| 218 | 3-(3'-CH$_3$—C$_6$H$_4$)-Isothiazolyl-5 |
| 219 | 3-(2'-CH$_3$—C$_6$H$_4$)-Isothiazolyl-5 |
| 220 | 3-(4'-CH$_3$O—C$_6$H$_4$)-Isothiazolyl-5 |
| 221 | 3-(3'-CH$_3$O—C$_6$H$_4$)-Isothiazolyl-5 |
| 222 | 3-(2'-CH$_3$O—C$_6$H$_4$)-Isothiazolyl-5 |
| 223 | 3-(4'-NO$_2$—C$_6$H$_4$)-Isothiazolyl-5 |
| 224 | 3-(3'-NO$_2$—C$_6$H$_4$)-Isothiazolyl-5 |
| 225 | 3-(2'-NO$_2$—C$_6$H$_4$)-Isothiazolyl-5 |
| 226 | 3-(4'-CN—C$_6$H$_4$)-Isothiazolyl-5 |
| 227 | 3-(3'-CN—C$_6$H$_4$)-Isothiazolyl-5 |
| 228 | 3-(2'-CN—C$_6$H$_4$)-Isothiazolyl-5 |
| 229 | 3-(4'-Cl—C$_6$H$_4$)-Isothiazolyl-5 |
| 230 | 3-(3'-Cl—C$_6$H$_4$)-Isothiazolyl-5 |
| 231 | 3-(2'-Cl—C$_6$H$_4$)-Isothiazolyl-5 |
| 232 | Oxazolyl-4 |
| 233 | 3-CH$_3$-Oxazolyl-4 |
| 234 | 3-C$_6$H$_5$-Oxazolyl-4 |
| 235 | 3-(4'-CH$_3$—C$_6$H$_4$)-Oxazolyl-4 |
| 236 | 3-(3'-CH$_3$—C$_6$H$_4$)-Oxazolyl-4 |
| 237 | 3-(2'-CH$_3$—C$_6$H$_4$)-Oxazolyl-4 |
| 238 | 3-(4'-CH$_3$O—C$_6$H$_4$)-Oxazolyl-4 |
| 239 | 3-(3'-CH$_3$O—C$_6$H$_4$)-Oxazolyl-4 |
| 240 | 3-(2'-CH$_3$O—C$_6$H$_4$)-Oxazolyl-4 |
| 241 | 3-(4'-NO$_2$—C$_6$H$_4$)-Oxazolyl-4 |
| 242 | 3-(3'-NO$_2$—C$_6$H$_4$)-Oxazolyl-4 |
| 243 | 3-(2'-NO$_2$—C$_6$H$_4$)-Oxazolyl-4 |
| 244 | 3-(4'-CN—C$_6$H$_4$)-Oxazolyl-4 |
| 245 | 3-(3'-CN—C$_6$H$_4$)-Oxazolyl-4 |
| 246 | 3-(2'-CN—C$_6$H$_4$)-Oxazolyl-4 |
| 247 | 3-(4'-Cl—C$_6$H$_4$)-Oxazolyl-4 |
| 248 | 3-(3'-Cl—C$_6$H$_4$)-Oxazolyl-4 |
| 249 | 3-(2'-Cl—C$_6$H$_4$)-Oxazolyl-4 |
| 250 | Thiazolyl-4 |
| 251 | 2-CH$_3$-Thiazolyl-4 |
| 252 | 2-C$_6$H$_5$-Thiazolyl-4 |
| 253 | 2-(4'-CH$_3$—C$_6$H$_4$)-Thiazolyl-4 |
| 254 | 2-(3'-CH$_3$—C$_6$H$_4$)-Thiazolyl-4 |
| 255 | 2-(2'-CH$_3$—C$_6$H$_4$)-Thiazolyl-4 |
| 256 | 2-(4'-CH$_3$O—C$_6$H$_4$)-Thiazolyl-4 |
| 257 | 2-(3'-CH$_3$O—C$_6$H$_4$)-Thiazolyl-4 |
| 258 | 2-(2'-CH$_3$O—C$_6$H$_4$)-Thiazolyl-4 |
| 259 | 2-(4'-NO$_2$—C$_6$H$_4$)-Thiazolyl-4 |
| 260 | 2-(3'-NO$_2$—C$_6$H$_4$)-Thiazolyl-4 |
| 261 | 2-(2'-NO$_2$—C$_6$H$_4$)-Thiazolyl-4 |
| 262 | 2-(4'-CN—C$_6$H$_4$)-Thiazolyl-4 |
| 263 | 2-(3'-CN—C$_6$H$_4$)-Thiazolyl-4 |
| 264 | 2-(2'-CN—C$_6$H$_4$)-Thiazolyl-4 |
| 265 | 2-(4'-Cl—C$_6$H$_4$)-Thiazolyl-4 |
| 266 | 2-(3'-Cl—C$_6$H$_4$)-Thiazolyl-4 |
| 267 | 2-(2'-Cl—C$_6$H$_4$)-Thiazolyl-4 |
| 268 | N—CH$_3$-1,2,4-Triazolyl-5 |
| 269 | 3-CH$_3$—N—CH$_3$-1,2,4-Triazolyl-5 |
| 270 | 3-C$_6$H$_5$—N—CH$_3$-1,2,4-Triazolyl-5 |
| 271 | 3-(4'-CH$_3$—C$_6$H$_4$)—N—CH$_3$-1,2,4-Triazolyl-5 |
| 272 | 3-(3'-CH$_3$—C$_6$H$_4$)—N—CH$_3$-1,2,4-Triazolyl-5 |
| 273 | 3-(2'-CH$_3$—C$_6$H$_4$)—N—CH$_3$-1,2,4-Triazolyl-5 |
| 274 | 3-(4'-CH$_3$O—C$_6$H$_4$)—N—CH$_3$-1,2,4-Triazolyl-5 |
| 275 | 3-(3'-CH$_3$O—C$_6$H$_4$)—N—CH$_3$-1,2,4-Triazolyl-5 |
| 276 | 3-(2'-CH$_3$O—C$_6$H$_4$)—N—CH$_3$-1,2,4-Triazolyl-5 |
| 277 | 3-(4'-NO$_2$—C$_6$H$_4$)—N—CH$_3$-1,2,4-Triazolyl-5 |
| 278 | 3-(3'-NO$_2$—C$_6$H$_4$)—N—CH$_3$-1,2,4-Triazolyl-5 |
| 279 | 3-(2'-NO$_2$—C$_6$H$_4$)—N—CH$_3$-1,2,4-Triazolyl-5 |
| 280 | 3-(4'-CN—C$_6$H$_4$)—N—CH$_3$-1,2,4-Triazolyl-5 |
| 281 | 3-(3'-CN—C$_6$H$_4$)—N—CH$_3$-1,2,4-Triazolyl-5 |
| 282 | 3-(2'-CN—C$_6$H$_4$)—N—CH$_3$-1,2,4-Triazolyl-5 |
| 283 | 3-(4'-Cl—C$_6$H$_4$)—N—CH$_3$-1,2,4-Triazolyl-5 |
| 284 | 3-(3'-Cl—C$_6$H$_4$)—N—CH$_3$-1,2,4-Triazolyl-5 |
| 285 | 3-(2'-Cl—C$_6$H$_4$)—N—CH$_3$-1,2,4-Triazolyl-5 |
| 286 | 1,3,4-Oxadiazolyl-2 |
| 287 | 5-CH$_3$-1,3,4-Oxadiazolyl-2 |
| 288 | 5-C$_6$H$_5$-1,3,4-Oxadiazolyl-2 |
| 289 | 5-(4'-CH$_3$—C$_6$H$_4$)-1,3,4-Oxadiazolyl-2 |
| 290 | 5-(3'-CH$_3$—C$_6$H$_4$)-1,3,4-Oxadiazolyl-2 |
| 291 | 5-(2'-CH$_3$—C$_6$H$_4$)-1,3,4-Oxadiazolyl-2 |
| 292 | 5-(4'-CH$_3$O—C$_6$H$_4$)-1,3,4-Oxadiazolyl-2 |
| 293 | 5-(3'-CH$_3$O—C$_6$H$_4$)-1,3,4-Oxadiazolyl-2 |
| 294 | 5-(2'-CH$_3$O—C$_6$H$_4$)-1,3,4-Oxadiazolyl-2 |
| 295 | 5-(4'-NO$_2$—C$_6$H$_4$)-1,3,4-Oxadiazolyl-2 |
| 296 | 5-(3'-NO$_2$—C$_6$H$_4$)-1,3,4-Oxadiazolyl-2 |
| 297 | 5-(2'-NO$_2$—C$_6$H$_4$)-1,3,4-Oxadiazolyl-2 |
| 298 | 5-(4'-CN—C$_6$H$_4$)-1,3,4-Oxadiazolyl-2 |
| 299 | 5-(3'-CN—C$_6$H$_4$)-1,3,4-Oxadiazolyl-2 |
| 300 | 5-(2'-CN—C$_6$H$_4$)-1,3,4-Oxadiazolyl-2 |
| 301 | 5-(4'-Cl—C$_6$H$_4$)-1,3,4-Oxadiazolyl-2 |
| 302 | 5-(3'-Cl—C$_6$H$_4$)-1,3,4-Oxadiazolyl-2 |
| 303 | 5-(2'-Cl—C$_6$H$_4$)-1,3,4-Oxadiazolyl-2 |
| 304 | 1,2,4-Oxadiazolyl-3 |
| 305 | 5-CH$_3$-1,2,4-Oxadiazolyl-3 |
| 306 | 5-C$_6$H$_5$-1,2,4-Oxadiazolyl-3 |
| 307 | 5-(4'-CH$_3$—C$_6$H$_4$)-1,2,4-Oxadiazolyl-3 |
| 308 | 5-(3'-CH$_3$—C$_6$H$_4$)-1,2,4-Oxadiazolyl-3 |
| 309 | 5-(2'-CH$_3$—C$_6$H$_4$)-1,2,4-Oxadiazolyl-3 |
| 310 | 5-(4'-CH$_3$O—C$_6$H$_4$)-1,2,4-Oxadiazolyl-3 |
| 311 | 5-(3'-CH$_3$O—C$_6$H$_4$)-1,2,4-Oxadiazolyl-3 |
| 312 | 5-(2'-CH$_3$O—C$_6$H$_4$)-1,2,4-Oxadiazolyl-3 |
| 313 | 5-(4'-NO$_2$—C$_6$H$_4$)-1,2,4-Oxadiazolyl-3 |
| 314 | 5-(3'-NO$_2$—C$_6$H$_4$)-1,2,4-Oxadiazolyl-3 |
| 315 | 5-(2'-NO$_2$—C$_6$H$_4$)-1,2,4-Oxadiazolyl-3 |
| 316 | 5-(4'-CN—C$_6$H$_4$)-1,2,4-Oxadiazolyl-3 |
| 317 | 5-(3'-CN—C$_6$H$_4$)-1,2,4-Oxadiazolyl-3 |
| 318 | 5-(2'-CN—C$_6$H$_4$)-1,2,4-Oxadiazolyl-3 |
| 319 | 5-(4'-Cl—C$_6$H$_4$)-1,2,4-Oxadiazolyl-3 |
| 320 | 5-(3'-Cl—C$_6$H$_4$)-1,2,4-Oxadiazolyl-3 |
| 321 | 5-(2'-Cl—C$_6$H$_4$)-1,2,4-Oxadiazolyl-3 |
| 322 | 1,2,4-Oxadiazolyl-5 |
| 323 | 3-CH$_3$-1,2,4-Oxadiazolyl-5 |
| 324 | 3-C$_6$H$_5$-1,2,4-Oxadiazolyl-5 |
| 325 | 3-(4'-CH$_3$—C$_6$H$_4$)-1,2,4-Oxadiazolyl-5 |
| 326 | 3-(3'-CH$_3$—C$_6$H$_4$)-1,2,4-Oxadiazolyl-5 |
| 327 | 3-(2'-CH$_3$—C$_6$H$_4$)-1,2,4-Oxadiazolyl-5 |
| 328 | 3-(4'-CH$_3$O—C$_6$H$_4$)-1,2,4-Oxadiazolyl-5 |
| 329 | 3-(3'-CH$_3$O—C$_6$H$_4$)-1,2,4-Oxadiazolyl-5 |
| 330 | 3-(2'-CH$_3$O—C$_6$H$_4$)-1,2,4-Oxadiazolyl-5 |
| 331 | 3-(4'-NO$_2$—C$_6$H$_4$)-1,2,4-Oxadiazolyl-5 |
| 332 | 3-(3'-NO$_2$—C$_6$H$_4$)-1,2,4-Oxadiazolyl-5 |
| 333 | 3-(2'-NO$_2$—C$_6$H$_4$)-1,2,4-Oxadiazolyl-5 |
| 334 | 3-(4'-CN—C$_6$H$_4$)-1,2,4-Oxadiazolyl-5 |
| 335 | 3-(3'-CN—C$_6$H$_4$)-1,2,4-Oxadiazolyl-5 |
| 336 | 3-(2'-CN—C$_6$H$_4$)-1,2,4-Oxadiazolyl-5 |
| 337 | 3-(4'-Cl—C$_6$H$_4$)-1,2,4-Oxadiazolyl-5 |
| 338 | 3-(3'-Cl—C$_6$H$_4$)-1,2,4-Oxadiazolyl-5 |
| 339 | 3-(2'-Cl—C$_6$H$_4$)-1,2,4-Oxadiazolyl-5 |
| 340 | 1,2,4-Thiadiazolyl-3 |
| 341 | 5-CH$_3$-1,2,4-Thiadiazolyl-3 |
| 342 | 5-C$_6$H$_5$-1,2,4-Thiadiazolyl-3 |
| 343 | 5-(4'-CH$_3$—C$_6$H$_4$)-1,2,4-Thiadiazolyl-3 |
| 344 | 5-(3'-CH$_3$—C$_6$H$_4$)-1,2,4-Thiadiazolyl-3 |
| 345 | 5-(2'-CH$_3$—C$_6$H$_4$)-1,2,4-Thiadiazolyl-3 |
| 346 | 5-(4'-CH$_3$O—C$_6$H$_4$)-1,2,4-Thiadiazolyl-3 |
| 347 | 5-(3'-CH$_3$O—C$_6$H$_4$)-1,2,4-Thiadiazolyl-3 |
| 348 | 5-(2'-CH$_3$O—C$_6$H$_4$)-1,2,4-Thiadiazolyl-3 |
| 349 | 5-(4'-NO$_2$—C$_6$H$_4$)-1,2,4-Thiadiazolyl-3 |
| 350 | 5-(3'-NO$_2$—C$_6$H$_4$)-1,2,4-Thiadiazolyl-3 |
| 351 | 5-(2'-NO$_2$—C$_6$H$_4$)-1,2,4-Thiadiazolyl-3 |
| 352 | 5-(4'-CN—C$_6$H$_4$)-1,2,4-Thiadiazolyl-3 |
| 353 | 5-(3'-CN—C$_6$H$_4$)-1,2,4-Thiadiazolyl-3 |
| 354 | 5-(2'-CN—C$_6$H$_4$)-1,2,4-Thiadiazolyl-3 |
| 355 | 5-(4'-Cl—C$_6$H$_4$)-1,2,4-Thiadiazolyl-3 |
| 356 | 5-(3'-Cl—C$_6$H$_4$)-1,2,4-Thiadiazolyl-3 |
| 357 | 5-(2'-Cl—C$_6$H$_4$)-1,2,4-Thiadiazolyl-3 |
| 358 | 1,3,4-Thiadiazolyl-2 |
| 359 | 5-CH$_3$-1,3,4-Thiadiazolyl-2 |
| 360 | 5-C$_6$H$_5$-1,3,4-Thiadiazolyl-2 |
| 361 | 5-(4'-CH$_3$—C$_6$H$_4$)-1,3,4-Thiadiazolyl-2 |
| 362 | 5-(3'-CH$_3$—C$_6$H$_4$)-1,3,4-Thiadiazolyl-2 |
| 363 | 5-(2'-CH$_3$—C$_6$H$_4$)-1,3,4-Thiadiazolyl-2 |
| 364 | 5-(4'-CH$_3$O—C$_6$H$_4$)-1,3,4-Thiadiazolyl-2 |

TABLE 46-continued

| | |
|---|---|
| 365 | 5-(3'-CH$_3$O—C$_6$H$_4$)-1,3,4-Thiadiazolyl-2 |
| 366 | 5-(2'-CH$_3$O—C$_6$H$_4$)-1,3,4-Thiadiazolyl-2 |
| 367 | 5-(4'-NO$_2$—C$_6$H$_4$)-1,3,4-Thiadiazolyl-2 |
| 368 | 5-(3'-NO$_2$—C$_6$H$_4$)-1,3,4-Thiadiazolyl-2 |
| 369 | 5-(2'-NO$_2$—C$_6$H$_4$)-1,3,4-Thiadiazolyl-2 |
| 370 | 5-(4'-CN—C$_6$H$_4$)-1,3,4-Thiadiazolyl-2 |
| 371 | 5-(3'-CN—C$_6$H$_4$)-1,3,4-Thiadiazolyl-2 |
| 372 | 5-(2'-CN—C$_6$H$_4$)-1,3,4-Thiadiazolyl-2 |
| 373 | 5-(4'-Cl—C$_6$H$_4$)-1,3,4-Thiadiazolyl-2 |
| 374 | 5-(3'-Cl—C$_6$H$_4$)-1,3,4-Thiadiazolyl-2 |
| 375 | 5-(2'-Cl—C$_6$H$_4$)-1,3,4-Thiadiazolyl-2 |
| 376 | Pyridinyl-2 |
| 377 | Pyridinyl-4 |
| 378 | Pyridazinyl-3 |
| 379 | Pyridazinyl-4 |
| 380 | Pyridazinyl-2 |
| 381 | Pyrimidinyl-4 |
| 382 | Pyrimidinyl-5 |
| 383 | Pyrimidinyl-2 |

TABLE 47

Selected physical data of some compounds

| No. | X$_m$ | R$^1$ | IR (cm$^{-1}$) or $^1$H-NMR (ppm) | mp |
|---|---|---|---|---|
| 1 | 4-Cl | H | | 133 |
| 2 | 3,4-Cl$_2$ | H | | 109 |
| 3 | 4-t-C$_4$H$_9$ | H | | 86 |
| 4 | 4-CH$_3$ | H | | 117 |
| 5 | 4-CF$_3$ | H | | 103 |
| 6 | 3-Br | H | | 99 |
| 7 | 3-Cl | H | | 93 |
| 8 | 3-CF$_3$ | H | | 88 |
| 9 | 3,5-Cl$_2$ | H | | 100 |
| 10 | 3,4-(CH$_3$)$_2$ | H | | 127 |
| 11 | 3,4-Cl$_2$ | CH$_3$ | | 74 |
| 12 | 3,4-Cl$_2$ | Allyl | 3.65(S, 3H); 2.2(S, 6H) | |
| 13 | 3,4-Cl$_2$ | Propargyl | 3.65(S, 3H); 2.3(S, 3H); 2.2(S, 3H) | |
| 14 | 3,4-Cl$_2$ | CH$_2$—OCH$_3$ | 3.65(S, 3H); 2.3(S, 3H); 2.2(S, 3H) | |
| 15 | 3,4-Cl$_2$ | CO—OCH$_3$ | | 137 |
| 16 | 4-t-C$_4$H$_9$ | CH$_3$ | 3.65(S, 3H); 2.25(S, 3H); 2.2(S, 3H) | |
| 17 | 4-t-C$_4$H$_9$ | Allyl | | 69 |
| 18 | 4-t-C$_4$H$_9$ | Propargyl | | 117 |
| 19 | 4-t-C$_4$H$_9$ | CH$_2$—OCH$_3$ | 3.65(S, 3H); 2.25(S, 3H); 2.2(S, 3H) | 117 |
| 20 | 4-t-C$_4$H$_9$ | CO—OCH$_3$ | 3.65; 2.1 | 119 |
| 21 | 4-CH$_3$ | CH$_3$ | | 69 |
| 22 | 4-CH$_3$ | Allyl | 3.65(S, 3H); 2.25(S, 3H); 2.2(S, 3H) | |
| 23 | 4-CH$_3$ | Propargyl | 3.65(S, 3H); 2.3(S, 3H); 2.2(S, 3H) | |
| 24 | 4-CH$_3$ | CH$_2$—OCH$_3$ | 3.65(S, 3H); 2.3(S, 3H); 2.2(S, 3H) | |
| 25 | 4-CH$_3$ | CO—OCH$_3$ | | 97 |
| 26 | 4-CF$_3$ | CH$_3$ | | 76 |
| 27 | 4-CF$_3$ | Allyl | 3.65(S, 3H); 2.3(S, 3H); 2.25(S, 3H) | |
| 28 | 4-CF$_3$ | Propargyl | 3.65(S, 3H); 2.3(S, 3H); 2.25(S, 3H) | |
| 29 | 4-CF$_3$ | CH$_2$—OCH$_3$ | 3.65(S, 3H); 2.25(S, 6H) | |
| 30 | 4-CF$_3$ | CO—OCH$_3$ | | 103 |
| 31 | 4-Cl | CH$_3$ | | 106 |
| 32 | 4-Cl | Allyl | 3.65(S, 3H); 2.2(2S, each 3H) | |
| 33 | 4-Cl | Propargyl | 3.65(S, 3H); 2.3(S, 3H; 2.2(S, 3H) | |
| 34 | 4-Cl | CH$_2$—OCH$_3$ | 3.65(S, 3H); 2.25(S, 3H; 2.2(S, 3H) | |
| 35 | 4-Cl | CO—OCH$_3$ | | 109 |
| 36 | 3-Br | CH$_3$ | | 75 |
| 37 | 3-Br | Allyl | 3.65(S, 3H); 2.2(2S, each 3H | |
| 38 | 3-Br | Propargyl | 3.65(S, 3H); 2.3(S, 3H); 2.2(S, 3H) | |
| 39 | 3-Br | CH$_2$—OCH$_3$ | | 72 |
| 40 | 3-Br | CO—OCH$_3$ | | 131 |
| 41 | 3-Cl | CH$_3$ | | 84 |
| 42 | 3-Cl | Allyl | 3.65(S, 3H); 2.25(S, 3H); 2.2(S, 3H) | |
| 43 | 3-Cl | Propargyl | 3.65(S, 3H); 2.3(S, 3H); 2.2(S, 3H) | |
| 44 | 3-Cl | CH$_2$—OCH$_3$ | | 66 |
| 45 | 3-Cl | CO—OCH$_3$ | | 123 |
| 46 | 3-CF$_3$ | CH$_3$ | | 63 |
| 47 | 3-CF$_3$ | Allyl | | 64 |
| 48 | 3-CF$_3$ | Propargyl | 3.65(S, 3H); 2.3(S, 3H); 2.25(S, 3H) | |
| 49 | 3-CF$_3$ | CH$_2$—OCH$_3$ | | 89 |
| 50 | 3-CF$_3$ | CO—OCH$_3$ | | 136 |
| 51 | 4-Br | CO—OCH$_3$ | | 103 |
| 52 | 4-Br | H | | 108 |
| 53 | 4-Br | Propargyl | 1710, 1486, 1469, 1447, 1376, 1299, 1252, 1026, 1008, 774 | |
| 54 | 4-Br | CH$_2$—OCH$_3$ | 1715, 1468, 1445, 1370, 1301, 1274, 1090, 1059, 1008, 775 | |
| 55 | 3,4-(CH$_3$)$_2$ | CH$_3$ | | oil |
| 56 | 3,4-(CH$_3$)$_2$ | Allyl | | oil |
| 57 | 3,4-(CH$_3$)$_2$ | Propargyl | | oil |
| 58 | 3,4-(CH$_3$)$_2$ | CH$_2$—OCH$_3$ | | oil |
| 59 | 3,4-(CH$_3$)$_2$ | CO—OCH$_3$ | | 135 |
| 60 | 3,5-Cl$_2$ | CH$_3$ | | 95 |
| 61 | 3,5-Cl$_2$ | Allyl | | 97 |
| 62 | 3,5-Cl$_2$ | Propargyl | | 100 |
| 63 | 3,5-Cl$_2$ | CH$_2$—OCH$_3$ | | 112 |
| 64 | 3,5-Cl$_2$ | CO—OCH$_3$ | | 160 |

TABLE 48

Selected physical data of some compounds

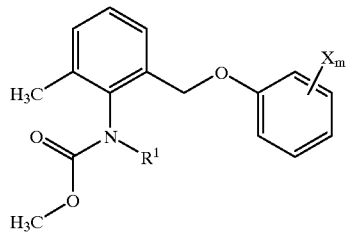

| No. | $X_m$ | $R^1$ | IR (cm$^{-1}$) or $^1$H-NMR (ppm) | mp |
|---|---|---|---|---|
| 1 | 2-CH$_3$-4-C(CH$_3$)=N—OCH$_3$ | H | | 82 |
| 2 | 2,4-(CH$_3$)$_2$ | H | | 131 |
| 3 | 2,5-(CH$_3$)$_2$ | H | | 124 |
| 4 | 2-CH$_3$-4-C(CH$_3$)=N—OC$_2$H$_5$ | H | | 102 |
| 5 | 2,5-(CH$_3$)$_2$-4-C(CH$_3$)=N—OC$_2$H$_5$ | H | | 116 |
| 6 | 2,5-(CH$_3$)$_2$-4-C(CH$_3$)=N—OCH$_3$ | H | | 122 |
| 7 | 2-CH$_3$-4-C(CH$_3$)=N—OCH$_3$ | CH$_3$ | 4.0(S, 3H); 3.65(S, 3H) | |
| 8 | 2-CH$_3$-4-C(CH$_3$)=N—OCH$_3$ | Allyl | | 101 |
| 9 | 2-CH$_3$-4-C(CH$_3$)=N—OCH$_3$ | Propargyl | 4.0(S, 3H); 3.65(S, 3H) | |
| 10 | 2-CH$_3$-4-C(CH$_3$)=N—OCH$_3$ | CH$_2$—OCH$_3$ | 4.0(S, 3H); 3.65(S, 3H) | |
| 11 | 2-CH$_3$-4-C(CH$_3$)=N—OCH$_3$ | CO—OCH$_3$ | | 122 |
| 12 | 2,4-(CH$_3$)$_2$ | CH$_3$ | 3.65(S, 3H); 2.25(2s, each 3H) | |
| 13 | 2,4-(CH$_3$)$_2$ | Allyl | | 59 |
| 14 | 2,4-(CH$_3$)$_2$ | Propargyl | 3.65(S, 3H); 2.25(3s, each 3H) | |
| 15 | 2,4-(CH$_3$)$_2$ | CH$_2$—OCH$_3$ | | 76 |
| 16 | 2,4-(CH$_3$)$_2$ | CO—OCH$_3$ | | 133 |
| 17 | 2,5-(CH$_3$)$_2$ | CH$_3$ | 3.65(S, 3H); 2.3(S, 3H) | |
| 18 | 2,5-(CH$_3$)$_2$ | Allyl | | 56 |
| 19 | 2,5-(CH$_3$)$_2$ | Propargyl | | 80 |
| 20 | 2,5-(CH$_3$)$_2$ | CH$_2$—OCH$_3$ | 3.65(S, 3H); 2.3(S, 3H) | 80 |
| 21 | 2,5-(CH$_3$)$_2$ | CH$_2$—OCH$_3$ | | 140 |
| 22 | 2-CH$_3$ | H | | 107 |
| 23 | 2-CH$_3$ | Propargyl | | oil |
| 24 | 2-CH$_3$ | CO—OCH$_3$ | | 135 |
| 25 | 2-CH$_3$ | CH$_2$—OCH$_3$ | | oil |
| 26 | 2-CH$_3$-4-C(CH$_3$)=N—O—Allyl | H | | 97 |
| 27 | 2-CH$_3$-4-C(CH$_3$)=N—O—Allyl | Propargyl | | oil |
| 28 | 2-CH$_3$-4-C(CH$_3$)=N—O—Allyl | CO—OCH$_3$ | | 130 |
| 29 | 2-CH$_3$-4-C(CH$_3$)=N—O—Allyl | CH$_2$—OCH$_3$ | | oil |
| 30 | 2-CH$_3$-4-C(CH$_3$)=N—O—C$_2$H$_5$ | CH$_3$ | | oil |
| 31 | 2-CH$_3$-4-C(CH$_3$)=N—O—C$_2$H$_5$ | Allyl | | 75 |
| 32 | 2-CH$_3$-4-C(CH$_3$)=N—O—C$_2$H$_5$ | Propargyl | | 77 |
| 33 | 2-CH$_3$-4-C(CH$_3$)=N—O—C$_2$H$_5$ | CH$_2$—OCH$_3$ | | oil |
| 34 | 2-CH$_3$-4-C(CH$_3$)=N—O—C$_2$H$_5$ | CO—OCH$_3$ | | oil |
| 35 | 2,5-(CH$_3$)$_2$-4-C(CH$_3$)=N—OCH$_3$ | CH$_3$ | | oil |
| 36 | 2,5-(CH$_3$)$_2$-4-C(CH$_3$)=N—OCH$_3$ | Allyl | | 104 |
| 37 | 2,5-(CH$_3$)$_2$-4-C(CH$_3$)=N—OCH$_3$ | Propargyl | | oil |
| 38 | 2,5-(CH$_3$)$_2$-4-C(CH$_3$)=N—OCH$_3$ | CH$_2$—OCH$_3$ | | oil |
| 39 | 2,5-(CH$_3$)$_2$-4-C(CH$_3$)=N—OCH$_3$ | CO—OCH$_3$ | | 158 |
| 40 | 2,5-(CH$_3$)$_2$-4-C(CH$_3$)=N—OC$_2$H$_5$ | CH$_3$ | | oil |
| 41 | 2,5-(CH$_3$)$_2$-4-C(CH$_3$)=N—OC$_2$H$_5$ | Allyl | | 71 |
| 42 | 2,5-(CH$_3$)$_2$-4-C(CH$_3$)=N—OC$_2$H$_5$ | Propargyl | | oil |
| 43 | 2,5-(CH$_3$)$_2$-4-C(CH$_3$)=N—OC$_2$H$_5$ | CH$_2$—OCH$_3$ | | oil |
| 44 | 2,5-(CH$_3$)$_2$-4-C(CH$_3$)=N—OC$_2$H$_5$ | CO—OCH$_3$ | | 128 |

TABLE 49

Structure: X and CH2-S-B substituents on benzene ring with N(R1)-C(=O)-O-CH3

- I: R¹ = H, X = CH₃
- II: R¹ = CH₃, X = CH₃
- III: R¹ = C₂H₅, X = CH₃
- IV: R¹ = Allyl, X = CH₃
- V: R¹ = Propargyl, X = CH₃
- VI: R¹ = CH₂—OCH₃, X = CH₃
- VII: R¹ = CO₂CH₃, X = CH₃
- VIII: R¹ = H, X = Cl
- IX: R¹ = CH₃, X = Cl
- X: R¹ = C₂H₅, X = Cl
- XI: R¹ = Allyl, X = Cl
- XII: R¹ = Propargyl, X = Cl
- XIII: R¹ = CH₂—OCH₃, X = Cl
- XIV: R¹ = CO₂CH₃, X = Cl

| No. | B |
|---|---|
| 1 | 2-Pyridyl |
| 2 | 3-Trifluoromethyl-2-pyridyl |
| 3 | 5-Trifluoromethyl-2-pyridyl |
| 4 | 3,5-Bis-(trifluoromethyl)-2-pyridyl |
| 5 | 3,5-Dichloro-2-pyridyl |
| 6 | 3-Chloro-5-trifluoromethyl-2-pyridyl |
| 7 | 3,5-Dichloro-2-pyridyl |
| 8 | 2-Chloro-4-trifluoromethylphenyl |
| 9 | 2-Benzothiazolyl |
| 10 | 5-Chloro-1-methyl-2-benzimidazolyl |
| 11 | 2-Benzoxazolyl |
| 12 | 1-Methyl-5-trifluoromethylimide-azo[5,4-a]-pyridin-2-yl |
| 13 | 5-Chloro-2-pyrimidinyl |
| 14 | 4-Methyl-5-phenyl-2-thiazolin-2-yl |
| 15 | 4-Methyl-5-phenyl-2-oxazolin-2-yl |
| 16 | 7-Trifluoromethyl-4-quinolinyl |

TABLE 50

Selected physical data of some compounds

| No. | X_m | IR (cm⁻¹) or ¹H-NMR (ppm) | mp |
|---|---|---|---|
| 1 | 4-NO₂ | | 112 |
| 2 | 3,4-Cl₂ | 3.8(s, 3H); 3.75(s, 3H) | |
| 3 | 2,4-(CH₃)₂ | 3.75(s, 3H); 3.7(s, 3H) | |
| 4 | H | 3.75(2s, each 3H) | |
| 5 | 4-i-C₃H₇ | 3.8(s, 3H); 3.75(s, 3H) | |
| 6 | 3,4-(CH₃)₂ | 3.8(s, 3H); 3.75(s, 3H) | |
| 7 | 3-CH₃-4-OCH₃ | 3.85(s, 3H); 3.8(s, 3H); 3.75(s, 3H) | |
| 8 | 3-CH₃-4-O-i-C₃H₇ | 3.8(2s, each 3H) | |
| 9 | 4-CF₃ | 3.8(s, 3H); 3.75(s, 3H) | |
| 10 | 3-CH₃ | 3.8(2s, each 3H) | |
| 11 | 3-CF₃ | 3.8(s, 3H); 3.75(s, 3H) | |
| 12 | 4-F | 3.8(s, 3H); 3.75(s, 3H) | |
| 13 | 4-Br | 3.8(s, 3H); 3.75(s, 3H) | |
| 14 | 3-Br | 3.8(s, 3H); 3.75(s, 3H) | |
| 15 | 4-t-Bu | 3.8(s, 3H); 3.75(s, 3H) | |
| 16 | 4-OCH₃ | 3.85(s, 3H); 3.8(s, 3H); 3.75(s, 3H) | |
| 17 | 2-CH₃ | 3.8(s, 3H); 3.75(s, 3H) | |
| 18 | 3-Cl | 3.8(s, 3H); 3.75(s, 3H) | |
| 19 | 4-CN | 3.8(s, 3H); 3.75(s, 3H) | |
| 20 | 4-C₂H₅ | 3.8(s, 3H); 3.75(s, 3H) | |

TABLE 51

Selected physical data of some compounds

| No. | X_m | IR(cm⁻¹) or ¹H-NMR (ppm) | mp |
|---|---|---|---|
| 1 | 4-Cl | 3.8(s, 3H); 3.75(s, 3H) | |
| 2 | 2-Cl | 3.8(s, 3H); 3.75(s, 3H) | |
| 3 | 2,5-(CH₃)₂-4-C(C₂H₅)=N—O-Allyl | 3.8(s, 3H); 3.75(s, 3H) | |
| 4 | 2,5-(CH₃)₂-4-C(C₂H₅)=N—O—CH₃ | 3.9(s, 3H); 3.8(s, 3H); 3.75(s, 3H) | |
| 5 | 2-CH₃-4-C(C₂H₅)=N—O-trans-Cl-Allyl | 3.8(s, 3H); 3.75(s, 3H) | |
| 6 | 2-CH₃-4-C(C₂H₅)=N—O-Allyl | 3.8(s, 3H); 3.75(s, 3H) | |
| 7 | 2-CH₃-4-Cl | 3.8(s, 3H); 3.75(s, 3H) | |
| 8 | 2-Cl-4-CH₃ | 3.8(s, 3H); 3.75(s, 3H) | |
| 9 | 2-Cl-5-CH₃ | 3.8(s, 3H); 3.75(s, 3H) | |
| 10 | 2-CH₃-4-C(C₂H₅)=N—O-C₂H₅ | 4.2(q, 2H); 3.8(s, 3H); 3.75(s, 3H) | |
| 11 | 2-CH₃-4-C(C₂H₅)=N—O—CH₃ | 3.95(s, 3H); 3.8(s, 3H); 3.75(s, 3H) | |
| 12 | 2,5-(CH₃)₂-4-C(CH₃)=N—O-trans-Cl-Allyl | 3.8(s, 3H); 3.75(s, 3H) | |
| 13 | 2,5-(CH₃)₂-4-C(CH₃)=N—O—C₂H₅ | 4.2(t, 2H); 3.8(s, 3H); 3.75(s, 3H) | |
| 14 | 2,5-(CH₃)₂-4-C(CH₃)=N—O—CH₃ | 3.95(s, 3H); 3.8(s, 3H); 3.75(s, 3H) | |
| 15 | 2-CH₃-4-C(CH₃)=N—O-trans-Cl-Allyl | 3.8(s, 3H); 3.75(s, 3H) | |

TABLE 51-continued

Selected physical data of some compounds

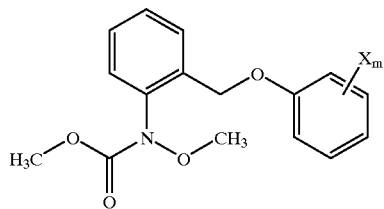

| No. | $X_m$ | IR(cm$^{-1}$) or $^1$H-NMR (ppm) | mp |
|---|---|---|---|
| 16 | 2-CH$_3$-4-C(CH$_3$)=N—O—C$_2$H$_5$ | 4.2(t, 2H); 3.8(s, 3H); 3.75(s, 3H) | |
| 17 | 2,5-(CH$_3$)$_2$-4-C(C$_2$H$_5$)=N—O—C$_2$H$_5$ | 4.2(t, 2H); 3.8(s, 3H); 3.75(s, 3H) | |

TABLE 60

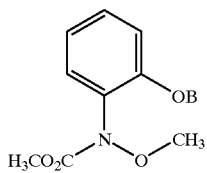

| No. | B |
|---|---|
| 1 | Phenyl |
| 2 | 3-Phenoxyphenyl |
| 3 | 3-(2-Cyanophenoxy)-phenyl |
| 4 | 4-Chlorophenyl |
| 5 | 3-Trifluoromethylphenyl |
| 6 | 3-tert.-Butoxyphenyl |
| 7 | 3,5-Dichlorophenyl |
| 8 | 3,5-Diethylphenyl |
| 9 | 2-Pyridyl |
| 10 | 4-Pyrimidinyl |
| 11 | 6-Phenoxy-pyrimidin-4-yl |
| 12 | 6-Chloropyrimidin-4-yl |
| 13 | 6-(2-Fluorophenoxy)-pyrimidin-4-yl |
| 14 | 6-(2-Methylphenoxy)-pyrimidin-4-yl |
| 15 | 6-(2-Cyanophenoxy)-pyrimidin-4-yl |
| 16 | 6-(2,6-Difluorophenoxy)-pyrimidin-4-yl |

The novel compounds are suitable as fungicides. The fungicidal compounds according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients, or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are given below.

I. A solution of 90 parts by weight of the compound from Table 7, No. 1 (7/1) and 10 parts by weight of N-methyl-α-pyrrolidone, which is suitable for application in the form of very fine drops.

II. A mixture of 20 parts by weight of compound 7/2, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, a dispersion is obtained.

III. An aqueous dispersion of 20 parts by weight of compound 7/3, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound 7/4, 25 parts by weight of cyclohexanol, 65 parts by weight of a mineral oil fraction having a boiling point between 210 and 280° C., and 10 parts by weight of the adduct of 40 moles of ethylene oxide and 1 mole of castor oil.

V. A hammer-milled mixture of 80 parts by weight of compound 7/5, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound 7/6 and 97 parts by weight of particulate kaolin. The dust contains 3 wt % of the active ingredient.

VII. An intimate mixture of 30 parts by weight of compound 7/7, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound 7/8, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound 7/9, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the fungi, or the seeds, plants, materials or soil to be protected against fungus attack with a fungicidally effective amount of the active ingredients.

The agents may be applied before or after infection of the materials, plants or seed by the fungi.

The compounds I are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

*Puccinia* species in cereals,

*Rhizoctonia solani* in cotton,

*Ustilago* species in cereals and sugar cane,

*Venturia inaequalis* (scab) in apples,

*Helminthosporium* species in cereals,

*Septoria nodorum* in wheat,

*Botrytis cinerea* (gray mold) in strawberries and grapes,

*Cercospora arachidicola* in groundnuts,

*Pseudocercosporella herpotrichoides* in wheat and barley,

*Pyricularia oryzae* in rice,

*Phytophthora infestans* in potatoes and tomatoes,

*Fusarium* and *Verticillium* species in various plants,

*Plasmopara viticola* in grapes,

*Alternaria* species in fruit and vegetables.

The novel compounds may also be used for protecting materials (timber), for instance against *Paecilomyces variotii*.

The fungicidal agents generally contain from 0.1 to 95, an preferably from 0.5 to 90, wt % of active ingredient.

The application rates depend on the effect desired, and are from 0.02 to 3 kg of active ingredient per hectare.

When the active ingredients are used for treating seed, amounts of from 0.001 to 50, and preferably from 0.01 to 10, g per kg of seed are generally needed.

When the agents according to the invention are used as fungicides, they may be present together with other active ingredients, e.g., herbicides, insecticides, growth regulators, other fungicides, and fertilizers.

When they are mixed with other fungicides, the spectrum of fungicidal action is in many cases increased.

USE EXAMPLES

The active ingredients used for comparison purposes were isopropyl N-phenylcarbamate (A)—known from GB 574 995 isopropyl N-3-chlorophenylcarbamate (B)—known from GB 574 995—and methyl N-3,4-dichlorophenylcarbamate (C)—known from BE 612 550.

Example 1
Action on Wheat Mildew

Leaves of pot-grown wheat seedlings of the "Frühgold" variety were sprayed with aqueous liquors containing (dry basis) 80% of active ingredient and 20% of emulsifier, and dusted, 24 hours after the sprayed-on layer had dried, with spores of wheat mildew (*Erysiphe graminis* var. *tritici*). The plants were then set up in the greenhouse at from 20 to 22° C. and a relative humidity of from 75 to 80%. The extent of mildew spread was assessed after 7 days.

The results show that active ingredients nos. 1, 2, 3, 4, 8, 9, 20, 23, 31, 33, 34, 35, 36, 42, 43, 44, 47, 48, 52, 53, 54, 55, 56, 57, 60, 61, 62, 63, 64, 67, 69, 70, 71, 72, 74, 78, 79, 85, 87, 89, 90, 91, 92, 93, 94, 95, 104, 105, 106 and 107 from Table 7 have, when applied as spray liquors containing 250 ppm of active ingredient, a better fungicidal action (95%) than prior art comparative agents A (45%), B (45%) and C (45%).

Example 2
Action on *Pyricularia oryzae* (Protective)

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in climatic cabinets at 22 to 24° C. and 95 to 99% relative humidity. The extent of fungus attack was assessed after 6 days.

The results show that active ingredients nos. 1, 2, 12, 18, 19, 22, 29, 39, 40, 42, 47, 49, 50, 52, 53, 54, 60, 61, 62, 63, 69, 70, 71, 72, 73, 74, 81, 83, 85, 87, 89, 90, 91, 92, 94, 95, 104, 105, 106 and 107 from Table 7 have, when applied as spray liquors containing 250 ppm of active ingredient, a better fungicidal action (95%) than prior art comparative agents A (30%), B (30%) and C (30%).

Example 3
Action on Wheat Mildew

Leaves of pot-grown wheat seedlings of the "Frühgold" variety were sprayed with aqueous liquors containing (dry basis) 80% of active ingredient and 20% of emulsifier, and dusted, 24 hours after the sprayed-on layer had dried, with spores of wheat mildew (*Erysiphe graminis* var. *tritici*). The plants were then set up in the greenhouse at from 20 to 22° C. and a relative humidity of from 75 to 80%. The extent of mildew spread was assessed after 7 days.

The results show that active ingredient no. 3 from Table 14, nos. 3 and 4 from Table 21, nos. 1, 3, 4, 5, 6, 7, 8, 9, 10, 11, 15, 17, 18, 19, 20, 21, 22, 23, 24, 25, 26, 27, 28, 29, 30, 31, 32, 33, 34, 35, 36, 37, 38, 39, 40 41, 42, 43 and 44 from Table 48, nos. 7, 8, 9, 10, 11, 13, 14, 15, 16, 17, 18, 20 and 23 from Table 14, nos. 1, 2, 3, 4, 5, 6, 7, 8, 9, 10, 11, 12, 13, 14, 15, 16, 17, 18 and 19 from Table 52, and nos. 1, 2, 3, 4, 5, 6, 7, 8, 9, 10, 11, 12, 13, 14, 15, 16 and 17 from Table 53 have, when applied as spray liquors containing 250 ppm of active ingredient, a better fungicidal action (100%) than prior art comparative agents A, B and C (15%).

Example 4
Action on *Pyricularia oryzae* (Protective)

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in climatic cabinets at 22 to 24° C. and 95 to 99% relative humidity. The extent of fungus attack was assessed after 6 days.

The results show that active ingredient nos. 3, 7, 8, 9, 10, 11, 13, 14, 15, 16, 17, 18, 20, 21, 22 and 24 from Table 14, nos. 1, 2, 3, 4, 5, 6, 7, 8, 9, 10, 11, 12, 13, 14, 15, 16, 17, 18, 19 and 20 from Table 52, nos. 1, 2, 3, 4, 5, 6, 7, 8, 9, 10, 11, 12, 13, 14, 15, 16 and 17 from Table 53, nos. 3 and 4 from Table 21, nos. 4 and 5 from Table 38, nos. 4, 7, 10, 16, 20, 21, 22, 23, 24, 25, 41, 42, 55, 56, 57, 58 and 59 from Table 47, and nos. 1, 4, 5, 6, 7, 8, 11, 20, 21, 22, 23, 24, 25, 26, 27, 28, 29, 30, 31, 32, 33, 34, 35, 36, 37, 38, 39, 40, 41, 42, 43 and 44 from Table 48 have, when applied as spray liquors containing 250 ppm of active ingredient, a better fungicidal action (100%) than prior art comparative agents A, B and C (0%).

Use Example 5
Action on *Botrytis cinerea*

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22 to 24° C. in a chamber of high humidity. After 5 days, the disease had spread to such a great extent on the untreated plants that the necroses covered the major portion of the leaves.

| Active ingredient | Percentage leaf attack after spraying with aqueous formulations containing 500 ppm of active ingredient |
| --- | --- |
| Table 30, active ingr. no. 2 | 5 |
| Comparative substance A | 100 |
| Comparative substance B | 100 |
| Comparative substance C | 100 |
| Untreated | 100 |

Use Example 6
Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20 to 30° C. To accelerate and intensify the sporangiophore discharge, the plants were then again placed in the moist chamber for 16 hours. The extent of fungus attack was then assessed on the undersides of the leaves.

| Active ingredient | Percentage leaf attack after applying aqueous formulations containing 500 ppm of active ingredient |
| --- | --- |
| Table 21, active ingr. no. 3 | 5 |
| Table 21, active ingr. no. 4 | 0 |
| Table 30, active ingr. no. 1 | 15 |
| Comparative substance A | 65 |
| Comparative substance B | 40 |
| Comparative substance C | 25 |
| Untreated | 65 |

What is claimed is:

1. An intermediate of the formula VI

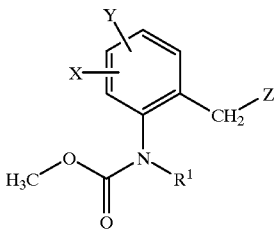

VI where X and Y are identical or different and each is hydrogen, F, Cl, Br, $CF_3$, CN, $NO_2$, alkoxy, alkenyloxy, alkynyloxy, alkyl, alkenyl or alkynyl or may be condensed together to form a phenyl ring, $R^1$ is hydrogen, alkyl, alkenyl, alkynyl, cyclopropyl, cyclopropylmethyl, cyclobutyl, $—CH_2—CN$, $—CH_2—O—CH_3$, $—CO_2CH_3$ or $—S—R^5$, wherein $R^5$ is alkyl, cyclopropyl, cyclopropylmethyl or cyclobutyl, Z is $O—(C_1-C_4)$-alkyl.

2. An intermediate of the formula XI

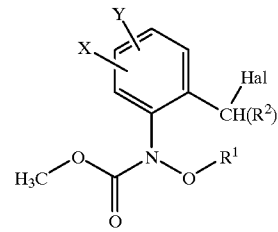

XI where X and Y are identical or different and each is hydrogen, F, Cl, Br, $CF_3$, CN, $NO_2$, alkoxy, alkenyloxy, alkynyloxy, alkyl, alkenyl or alkynyl or may together be condensed to form a substituted or unsubstituted aromatic or heteroaromatic, alicyclic or heterocyclic, partially or completely hydrogenated ring, R¹ is substituted or unsubstituted alkyl, alkenyl, alkynyl, cycloalkyl, cycloalkenyl or —CO₂-alkyl, R² is hydrogen, alkyl, alkenyl, alkynyl or cycloalkyl, and Hal is halogen.

3. An intermediate of the formula XII

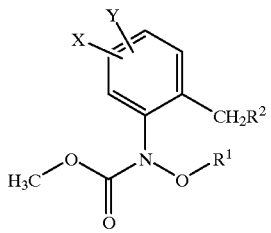

XII where X and Y are identical or different and each is hydrogen, F, Cl, Br, CF₃, CN, NO₂, alkoxy, alkenyloxy, alkynyloxy, alkyl, alkenyl or alkynyl or may together be condensed to form a substituted or unsubstituted aromatic or heteroaromatic, alicyclic or heterocyclic, partially or completely hydrogenated ring, R¹ is substituted or unsubstituted alkyl, alkenyl, alkynyl, cycloalkyl, cycloalkenyl or —CO₂-alkyl, and R² is hydrogen, alkyl, alkenyl, alkynyl or cycloalkyl.

4. An intermediate of the formula XIII

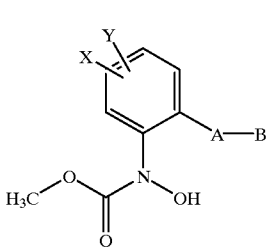

XIII where X and Y are identical or different and each is hydrogen, F, Cl, Br, CF₃, CN, NO₂, alkoxy, alkenyloxy, alkynyloxy, alkyl, alkenyl or alkynyl or may together be condensed to form a substituted or unsubstituted aromatic or heteroaromatic, alicyclic or heterocyclic, partially or completely hydrogenated ring, A is —O—, —S—, —CR²=CR³—, CHR²—O—, —CHR²—S—, —CHR²—O—N=C(R⁴)—, —CR²=N—O—, —O—N=C(R⁴)—, —C≡C—, —CHR²—CHR³—, —CHR²—O—CO—, —O—CHR²— or a single bond, B is substituted or unsubstituted alkyl, alkenyl, alkynyl, cycloalkyl, cycloalkenyl, cycloalkynyl, aryl, hetaryl, heterocyclyl or hydrogen, and R² and R³ are identical or different and each is hydrogen, alkyl, alkenyl, alkynyl or cycloalkyl, and R⁴ is hydrogen, cyano, alkyl, alkenyl, alkynyl, cycloalkyl or alkoxy, wherein B is not hydrogen when A is a single bond.

5. An intermediate of the formula XXXI

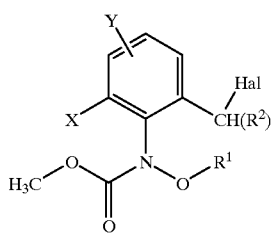

XXXI where X and Y are identical or different and each is F, Cl, Br, CF₃, CN, NO₂, alkoxy, alkenyloxy, alkynyloxy, alkyl, alkenyl or alkynyl or may together be condensed to form a substituted or unsubstituted aromatic or heteroaromatic, alicyclic or heterocyclic, partially or completely hydrogenated ring, or Y is hydrogen, R¹ is substituted or unsubstituted alkyl, alkenyl, alkynyl, cycloalkyl, cycloalkenyl or —CO₂-alkyl, R² is hydrogen, alkyl, alkenyl, alkynyl or cycloalkyl, and Hal is halogen.

6. An intermediate of the formula XXXII

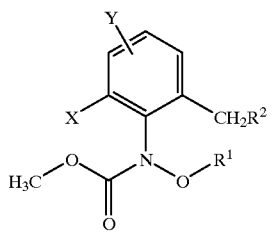

XXXII where X and Y are identical or different and each is F, Cl, Br, CF₃, CN, NO₂, alkoxy, alkenyloxy, alkynyloxy, alkyl, alkenyl or alkynyl or may together be condensed to form a substituted or unsubstituted aromatic or heteroaromatic, alicyclic or heterocyclic, partially or completely hydrogenated ring, or Y is hydrogen, R¹ is substituted or unsubstituted alkyl, alkenyl, alkynyl, cycloalkyl, cycloalkenyl or —CO₂-alkyl, and R² is hydrogen, alkyl, alkenyl, alkynyl or cycloalkyl.

7. An intermediate of the formula XXXIII

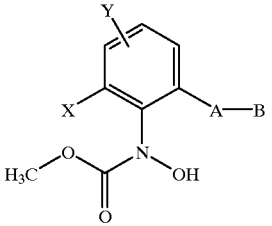

XXXIII where X and Y are identical or different and each is F, Cl, Br, CF₃, CN, NO₂, alkoxy, alkenyloxy, alkynyloxy, alkyl, alkenyl or alkynyl or may together be condensed to form a substituted or unsubstituted aromatic or heteroaromatic, alicyclic or heterocyclic, partially or completely hydrogenated ring, or Y is hydrogen, A is —O—, —S—, —CR²=CR³—, —CHR²—O—, —CHR²—S—, —CHR²—O—N=C(R⁴)—, —$CR^2$=N—O—, —O—N=$C(R^4)$—, —C≡C—, —$CHR^2$—$CHR^3$—, —$CHR^2$—O—CO—, —O—$CHR^2$— or a single bond, B is substituted or unsubstituted alkyl, alkenyl, alkynyl, cycloalkyl, cycloalkenyl, cycloalkynyl, aryl, hetaryl, heterocyclyl or hydrogen, and $R^2$ and $R^3$ are identical or different and each is hydrogen, alkyl, alkenyl, alkynyl or cycloalkyl, and $R^4$ is hydrogen, cyano, alkyl, alkenyl, alkynyl, cycloalkyl or alkoxy.

* * * * *